US011229450B2

(12) United States Patent
Shelton, IV et al.

(10) Patent No.: US 11,229,450 B2
(45) Date of Patent: Jan. 25, 2022

(54) MODULAR BATTERY POWERED HANDHELD SURGICAL INSTRUMENT WITH MOTOR DRIVE

(71) Applicant: Cilag GmbH International, Zug (CH)

(72) Inventors: Frederick E. Shelton, IV, Hillsboro, OH (US); David C. Yates, Morrow, OH (US); Kevin L. Houser, Springboro, OH (US); Jeffrey D. Messerly, Cincinnati, OH (US); Jason L. Harris, Lebanon, OH (US); Adam D. Hensel, Gahanna, OH (US)

(73) Assignee: Cilag GmbH International, Zug (CH)

( * ) Notice: Subject to any disclaimer, the term of this patent is extended or adjusted under 35 U.S.C. 154(b) by 1323 days.

(21) Appl. No.: 15/382,292

(22) Filed: Dec. 16, 2016

(65) Prior Publication Data

US 2017/0202572 A1    Jul. 20, 2017

Related U.S. Application Data

(60) Provisional application No. 62/330,669, filed on May 2, 2016, provisional application No. 62/279,635, filed on Jan. 15, 2016.

(51) Int. Cl.
*A61B 17/32*    (2006.01)
*A61B 18/14*    (2006.01)
(Continued)

(52) U.S. Cl.
CPC ............. *A61B 17/320092* (2013.01); *A61B 17/320068* (2013.01); *A61B 18/1206* (2013.01);
(Continued)

(58) Field of Classification Search
CPC ..... A61B 17/320068; A61B 17/320092; A61B 18/1206; A61B 18/1445; A61B 18/1447;
(Continued)

(56) References Cited

U.S. PATENT DOCUMENTS

| 969,528 A | 9/1910 | Disbrow |
|---|---|---|
| 1,570,025 A | 1/1926 | Young |

(Continued)

FOREIGN PATENT DOCUMENTS

| CA | 2535467 A1 | 4/1993 |
|---|---|---|
| CN | 2460047 Y | 11/2001 |

(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Khadijeh A Vahdat

(57) ABSTRACT

A surgical instrument includes a handle assembly; a shaft assembly and an end effector. The shaft assembly includes an exterior shaft, a first clutch positioned within the exterior shaft to drive a first function of the surgical instrument when engaged. A second clutch within the exterior shaft to drive a second function when engaged. A rotary driver is positioned within the exterior shaft and configured to rotate within the exterior shaft. The rotary driver includes a first clutch engagement mechanism to engage the first clutch and a second clutch engagement mechanism configured to engage the second clutch independent of the first clutch engagement mechanism engaging the first clutch, such that, at different times both the first clutch and the second clutch (Continued)

are engaged simultaneously only the first clutch is engaged only the second clutch is engaged and neither the first clutch nor the second clutch is engaged simultaneously.

19 Claims, 56 Drawing Sheets

(51) Int. Cl.

| | | |
|---|---|---|
| *H01M 50/20* | (2021.01) | |
| *A61B 18/12* | (2006.01) | |
| *H01M 6/02* | (2006.01) | |
| *H01M 6/50* | (2006.01) | |
| *H01M 10/42* | (2006.01) | |
| *H01M 10/46* | (2006.01) | |
| *H01M 10/48* | (2006.01) | |
| *A61B 17/00* | (2006.01) | |
| *A61B 18/00* | (2006.01) | |
| *A61B 90/00* | (2016.01) | |
| *A61B 34/00* | (2016.01) | |

(52) U.S. Cl.
CPC ...... *A61B 18/1445* (2013.01); *A61B 18/1447* (2013.01); *H01M 6/02* (2013.01); *H01M 6/5044* (2013.01); *H01M 10/425* (2013.01); *H01M 10/46* (2013.01); *H01M 10/48* (2013.01); *H01M 50/20* (2021.01); *A61B 2017/003* (2013.01); *A61B 2017/00017* (2013.01); *A61B 2017/0023* (2013.01); *A61B 2017/00026* (2013.01); *A61B 2017/00039* (2013.01); *A61B 2017/0046* (2013.01); *A61B 2017/00084* (2013.01); *A61B 2017/00119* (2013.01); *A61B 2017/00123* (2013.01); *A61B 2017/00323* (2013.01); *A61B 2017/00398* (2013.01); *A61B 2017/00464* (2013.01); *A61B 2017/00477* (2013.01); *A61B 2017/00734* (2013.01); *A61B 2017/00876* (2013.01); *A61B 2017/320072* (2013.01); *A61B 2017/320073* (2017.08); *A61B 2017/320074* (2017.08); *A61B 2017/320078* (2017.08); *A61B 2017/320094* (2017.08); *A61B 2017/320095* (2017.08); *A61B 2018/0063* (2013.01); *A61B 2018/00297* (2013.01); *A61B 2018/00601* (2013.01); *A61B 2018/00607* (2013.01); *A61B 2018/00684* (2013.01); *A61B 2018/00767* (2013.01); *A61B 2018/00791* (2013.01); *A61B 2018/00827* (2013.01); *A61B 2018/00875* (2013.01); *A61B 2018/00898* (2013.01); *A61B 2018/00904* (2013.01); *A61B 2018/00946* (2013.01); *A61B 2018/00988* (2013.01); *A61B 2018/00994* (2013.01); *A61B 2018/1226* (2013.01); *A61B 2018/1455* (2013.01); *A61B 2034/252* (2016.02); *A61B 2090/061* (2016.02); *A61B 2560/0209* (2013.01); *A61B 2560/0475* (2013.01); *A61B 2562/0219* (2013.01); *H01M 2220/30* (2013.01)

(58) Field of Classification Search
CPC ........... A61B 2017/00017; A61B 2017/00026; A61B 2017/00039; A61B 2017/00084; A61B 2017/00119; A61B 2017/00123; A61B 2017/0023; A61B 2017/003; A61B 2017/00323; A61B 2017/00398; A61B 2017/0046; A61B 2017/00464; A61B 2017/00477; A61B 2017/00734; A61B 2017/00876; A61B 2017/320072; A61B 2017/320073; A61B 2017/320074; A61B 2017/320078; A61B 2017/320094; A61B 2017/320095; A61B 2018/00297; A61B 2018/00601; A61B 2018/00607; A61B 2018/0063; A61B 2018/00684; A61B 2018/00767; A61B 2018/00791; A61B 2018/00827; A61B 2018/1226; A61B 2018/1455; A61B 2034/252; A61B 2090/061; A61B 2560/0209; A61B 2560/0475; A61B 2562/0219; H01M 10/425; H01M 10/46; H01M 10/48; H01M 2220/30; H01M 2/1022; H01M 6/02; H01M 6/5044

USPC .................................................... 606/33–52
See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |

(56) References Cited

U.S. PATENT DOCUMENTS

| | | |
|---|---|---|
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |

(56) References Cited

U.S. PATENT DOCUMENTS

| | | |
|---|---|---|
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |

(56) References Cited

U.S. PATENT DOCUMENTS

| | | |
|---|---|---|
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |

(56) References Cited

U.S. PATENT DOCUMENTS

| | | |
|---|---|---|
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |

(56) References Cited

U.S. PATENT DOCUMENTS

| | | |
|---|---|---|
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |

(56) References Cited

U.S. PATENT DOCUMENTS

| | | |
|---|---|---|
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |

(56) References Cited

U.S. PATENT DOCUMENTS

| | | |
|---|---|---|
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |

(56) References Cited

U.S. PATENT DOCUMENTS

| | | |
|---|---|---|
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |

(56) References Cited

U.S. PATENT DOCUMENTS

| | | |
|---|---|---|
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |

(56) References Cited

U.S. PATENT DOCUMENTS

| | | |
|---|---|---|
| 8,357,149 B2 | 1/2013 | Govari et al. |
| 8,357,158 B2 | 1/2013 | McKenna et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Homer |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,521,331 B2 | 8/2013 | Itkowitz |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |

(56) References Cited

U.S. PATENT DOCUMENTS

| | | |
|---|---|---|
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,734,443 B2 | 5/2014 | Hixson et al. |
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |

(56) References Cited

U.S. PATENT DOCUMENTS

| | | |
|---|---|---|
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |

(56) References Cited

U.S. PATENT DOCUMENTS

| | | |
|---|---|---|
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,802,033 B2 | 10/2017 | Hibner et al. |
| 9,808,246 B2 | 11/2017 | Shelton, IV et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,878,184 B2 | 1/2018 | Beaupre |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,901,321 B2 | 2/2018 | Harks et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,656 B2 | 3/2018 | Stulen |
| 9,913,680 B2 | 3/2018 | Voegele et al. |
| 9,918,730 B2 | 3/2018 | Trees et al. |
| 9,925,003 B2 | 3/2018 | Parihar et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,974,539 B2 | 5/2018 | Yates et al. |
| 9,987,033 B2 | 6/2018 | Neurohr et al. |
| 10,004,526 B2 | 6/2018 | Dycus et al. |
| 10,004,527 B2 | 6/2018 | Gee et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,810 B2 | 8/2018 | Schall et al. |
| 10,045,819 B2 | 8/2018 | Jensen et al. |

(56) References Cited

U.S. PATENT DOCUMENTS

| | | |
|---|---|---|
| 10,070,916 B2 | 9/2018 | Artale |
| 10,080,609 B2 | 9/2018 | Hancock et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,699 B2 | 10/2018 | Boudreaux |
| 10,111,703 B2 | 10/2018 | Cosman, Jr. et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,410 B2 | 11/2018 | Strobl et al. |
| 10,130,412 B2 | 11/2018 | Wham |
| 10,154,848 B2 | 12/2018 | Chernov et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,179,022 B2 | 1/2019 | Yates et al. |
| 10,188,455 B2 | 1/2019 | Hancock et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,263,171 B2 | 4/2019 | Wiener et al. |
| 10,265,117 B2 | 4/2019 | Wiener et al. |
| 10,265,118 B2 | 4/2019 | Gerhardt |
| 10,271,840 B2 | 4/2019 | Sapre |
| 10,278,721 B2 | 5/2019 | Dietz et al. |
| 10,285,724 B2 | 5/2019 | Faller et al. |
| 10,285,750 B2 | 5/2019 | Coulson et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,602 B2 | 7/2019 | Strobl et al. |
| 10,342,606 B2 | 7/2019 | Cosman et al. |
| 10,349,999 B2 | 7/2019 | Yates et al. |
| 10,357,303 B2 | 7/2019 | Conlon et al. |
| 10,363,084 B2 | 7/2019 | Friedrichs |
| 10,376,305 B2 | 8/2019 | Yates et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,986 B2 | 10/2019 | Zikorus et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,485,607 B2 | 11/2019 | Strobl et al. |
| 10,492,849 B2 | 12/2019 | Juergens et al. |
| 10,507,033 B2 | 12/2019 | Dickerson et al. |
| 10,561,560 B2 | 2/2020 | Boutoussov et al. |
| 10,617,420 B2 | 4/2020 | Shelton, IV et al. |
| RE47,996 E | 5/2020 | Turner et al. |
| 10,677,764 B2 | 6/2020 | Ross et al. |
| 10,874,465 B2 | 12/2020 | Weir et al. |
| 10,966,747 B2 | 4/2021 | Worrell et al. |
| 10,993,763 B2 | 5/2021 | Batross et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0010485 A1* | 1/2002 | Griego ............ A61B 17/32056 606/167 |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177862 A1 | 11/2002 | Aranyi et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |

(56) References Cited

U.S. PATENT DOCUMENTS

| | | |
|---|---|---|
| 2004/0193153 A1 | 9/2004 | Sartor et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |

(56) References Cited

U.S. PATENT DOCUMENTS

| | | |
|---|---|---|
| 2009/0023985 A1 | 1/2009 | Ewers |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0177119 A1 | 7/2009 | Heidner et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0193567 A1* | 8/2010 | Scheib ............ A61B 17/07207 227/176.1 |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0015650 A1 | 1/2011 | Choi et al. |
| 2011/0028964 A1 | 2/2011 | Edwards |
| 2011/0071523 A1 | 3/2011 | Dickhans |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0160725 A1 | 6/2011 | Kabaya et al. |
| 2011/0238010 A1 | 9/2011 | Kirschenman et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136386 A1 | 5/2012 | Kishida et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0211542 A1 | 8/2012 | Racenet |
| 2012/0253328 A1 | 10/2012 | Cunningham et al. |
| 2012/0265241 A1 | 10/2012 | Hart et al. |
| 2012/0296325 A1 | 11/2012 | Takash I No |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0085510 A1 | 4/2013 | Stefanchik et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0277410 A1 | 10/2013 | Fernandez et al. |
| 2013/0296843 A1 | 11/2013 | Boudreaux et al. |
| 2013/0334989 A1 | 12/2013 | Kataoka |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0121569 A1 | 5/2014 | Schafer et al. |
| 2014/0135804 A1 | 5/2014 | Weisenburgh, II et al. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0246475 A1 | 9/2014 | Hall et al. |
| 2014/0263541 A1 | 9/2014 | Leimbach et al. |
| 2014/0263552 A1 | 9/2014 | Hall et al. |
| 2014/0276754 A1 | 9/2014 | Gilbert et al. |

(56) References Cited

U.S. PATENT DOCUMENTS

| | | |
|---|---|---|
| 2014/0276797 A1 | 9/2014 | Batchelor et al. |
| 2014/0276806 A1 | 9/2014 | Heim |
| 2015/0032150 A1 | 1/2015 | Ishida et al. |
| 2015/0080876 A1 | 3/2015 | Worrell et al. |
| 2015/0080887 A1 | 3/2015 | Sobajima et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0238260 A1 | 8/2015 | Nau, Jr. |
| 2015/0257780 A1 | 9/2015 | Houser |
| 2015/0272659 A1 | 10/2015 | Boudreaux et al. |
| 2015/0282879 A1 | 10/2015 | Ruelas |
| 2015/0313667 A1 | 11/2015 | Allen, IV |
| 2015/0320481 A1 | 11/2015 | Cosman, Jr. et al. |
| 2016/0045248 A1 | 2/2016 | Unger et al. |
| 2016/0051316 A1 | 2/2016 | Boudreaux |
| 2016/0074108 A1 | 3/2016 | Woodruff et al. |
| 2016/0157927 A1 | 6/2016 | Corbett et al. |
| 2016/0175029 A1 | 6/2016 | Witt et al. |
| 2016/0199125 A1 | 7/2016 | Jones |
| 2016/0206342 A1 | 7/2016 | Robertson et al. |
| 2016/0262786 A1 | 9/2016 | Madan et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0324537 A1 | 11/2016 | Green et al. |
| 2016/0346001 A1 | 12/2016 | Vakharia et al. |
| 2016/0367281 A1 | 12/2016 | Gee et al. |
| 2016/0374709 A1 | 12/2016 | Timm et al. |
| 2017/0000516 A1 | 1/2017 | Stulen et al. |
| 2017/0000541 A1 | 1/2017 | Yates et al. |
| 2017/0000542 A1 | 1/2017 | Yates et al. |
| 2017/0000553 A1 | 1/2017 | Wiener et al. |
| 2017/0000554 A1 | 1/2017 | Yates et al. |
| 2017/0056058 A1 | 3/2017 | Voegele et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0105757 A1 | 4/2017 | Weir et al. |
| 2017/0105782 A1 | 4/2017 | Scheib et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweiler et al. |
| 2017/0164994 A1 | 6/2017 | Smith |
| 2017/0164997 A1 | 6/2017 | Johnson et al. |
| 2017/0189095 A1 | 7/2017 | Danziger et al. |
| 2017/0189096 A1 | 7/2017 | Danziger et al. |
| 2017/0196586 A1 | 7/2017 | Witt et al. |
| 2017/0202571 A1 | 7/2017 | Shelton, IV et al. |
| 2017/0202591 A1 | 7/2017 | Shelton, IV et al. |
| 2017/0202592 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2017/0312014 A1 | 11/2017 | Strobl et al. |
| 2017/0312015 A1 | 11/2017 | Worrell et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0325874 A1 | 11/2017 | Noack et al. |
| 2017/0348064 A1 | 12/2017 | Stewart et al. |
| 2017/0360468 A1 | 12/2017 | Eichmann et al. |
| 2018/0014872 A1 | 1/2018 | Dickerson |
| 2018/0028257 A1 | 2/2018 | Yates et al. |
| 2018/0042658 A1 | 2/2018 | Shelton, IV et al. |
| 2018/0064961 A1 | 3/2018 | Wiener et al. |
| 2018/0078277 A1 | 3/2018 | Illizaliturri-Sanchez et al. |
| 2018/0098785 A1 | 4/2018 | Price et al. |
| 2018/0098808 A1 | 4/2018 | Yates et al. |
| 2018/0146976 A1 | 5/2018 | Clauda et al. |
| 2018/0177545 A1 | 6/2018 | Boudreaux et al. |
| 2018/0235691 A1 | 8/2018 | Voegele et al. |
| 2018/0280083 A1 | 10/2018 | Parihar et al. |
| 2019/0021783 A1 | 1/2019 | Asher et al. |
| 2019/0105067 A1 | 4/2019 | Boudreaux et al. |
| 2019/0201048 A1 | 7/2019 | Stulen et al. |
| 2019/0209201 A1 | 7/2019 | Boudreaux et al. |
| 2019/0262030 A1 | 8/2019 | Faller et al. |
| 2019/0274700 A1 | 9/2019 | Robertson et al. |
| 2019/0282288 A1 | 9/2019 | Boudreaux |
| 2019/0282292 A1 | 9/2019 | Wiener et al. |
| 2020/0030021 A1 | 1/2020 | Yates et al. |
| 2020/0054382 A1 | 2/2020 | Yates et al. |
| 2020/0078085 A1 | 3/2020 | Yates et al. |
| 2020/0078609 A1 | 3/2020 | Messerly et al. |
| 2020/0085465 A1 | 3/2020 | Timm et al. |
| 2020/0113624 A1 | 4/2020 | Worrell et al. |
| 2020/0138473 A1 | 5/2020 | Shelton, IV et al. |
| 2020/0222135 A1 | 7/2020 | Stulen et al. |
| 2020/0229833 A1 | 7/2020 | Vakharia et al. |
| 2020/0229834 A1 | 7/2020 | Olson et al. |
| 2020/0237434 A1 | 7/2020 | Scheib et al. |
| 2020/0261141 A1 | 8/2020 | Wiener et al. |
| 2020/0268433 A1 | 8/2020 | Wiener et al. |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 101474081 A | 7/2009 |
| CN | 101516285 A | 8/2009 |
| CN | 102100582 A | 6/2011 |
| CN | 102149312 A | 8/2011 |
| CN | 202027624 U | 11/2011 |
| CN | 103281982 A | 9/2013 |
| CN | 103379853 A | 10/2013 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |

(56) References Cited

FOREIGN PATENT DOCUMENTS

| | | |
|---|---|---|
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 2510891 B1 | 6/2016 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | 2000210299 A | 8/2000 |
| JP | 2000-271142 A | 10/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 20083364 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |
| WO | WO-2011060031 A1 | 5/2011 |
| WO | WO-2012044606 A2 | 4/2012 |
| WO | WO-2012088535 A1 | 6/2012 |
| WO | WO-2012/150567 A1 | 11/2012 |

OTHER PUBLICATIONS

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

(56) References Cited

OTHER PUBLICATIONS

Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Douglas, S.C. "Introduction to Adaptive Filter". Digital Signal Processing Handbook. Ed. Vijay K. Madisetti and Douglas B. Williams. Boca Raton: CRC Press LLC, 1999.
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, *Engineering Formulas* § Z.7 (7th ed. 1997).
Glaser and Subak-Sharpe, Integrated Circuit Engineering, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Jang, J. et al. "Neuro-fuzzy and Soft Computing." Prentice Hall, 1997, pp. 13-89, 199-293, 335-393, 453-496, 535-549.
Sullivan, "Optimal Choice for Number of Strands in a Litz-Wire Transformer Winding," IEEE Transactions on Power Electronics, vol. 14, No. 2, Mar. 1999, pp. 283-291.
Covidien Brochure, The LigaSure Precise™ Instrument, dated Mar. 2011 (2 pages).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Leonard I. Malis, M.D., "The Value of Irrigation During Bipolar Coagulation," 1989.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien 501(k) Summary Sonicision, dated Feb. 24, 2011 (7 pages).
Gerhard, Glen C., "Surgical Electrotechnology: Quo Vadis?," IEEE Transactions on Biomedical Engineering, vol. BME-31, No. 12, pp. 787-792, Dec. 1984.
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
Campbell et al, "Thermal Imaging in Surgery," p. 19-3, in Medical Infrared Imaging, N. A. Diakides and J. D. Bronzino, Eds. (2008).
Incropera et al., Fundamentals of Heat and Mass Transfer, Wiley, New York (1990). (Book—not attached).
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Moraleda et al., A Temperature Sensor Based on a Polymer Optical Fiber Macro-Bend, Sensors 2013, 13, 13076-13089, doi: 10.3390/s131013076, ISSN 1424-8220.

\* cited by examiner

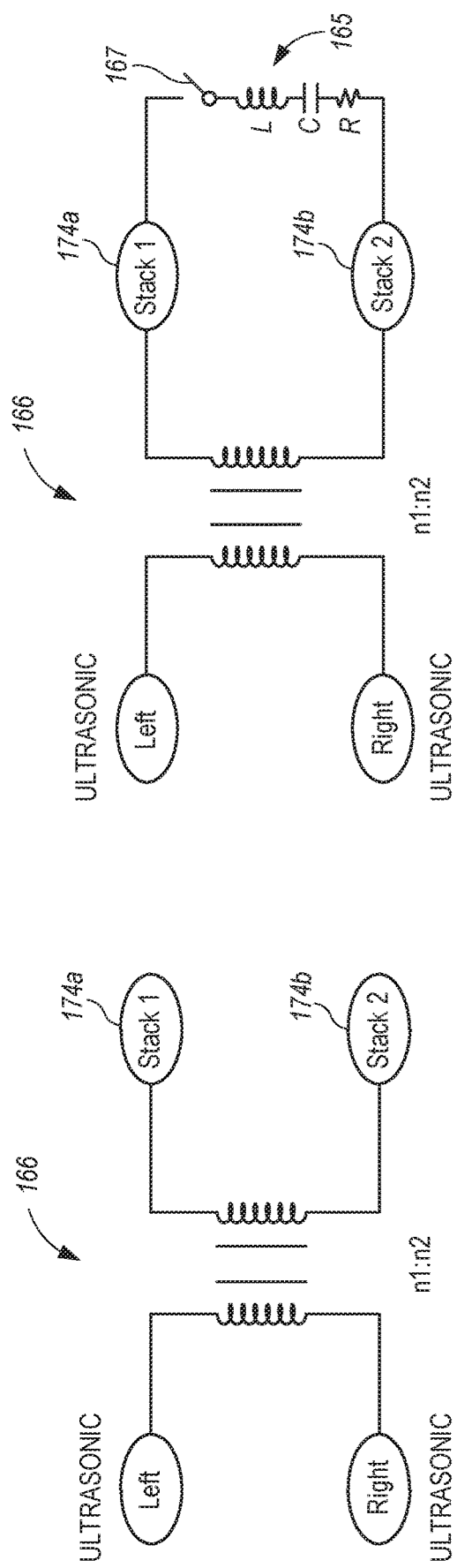

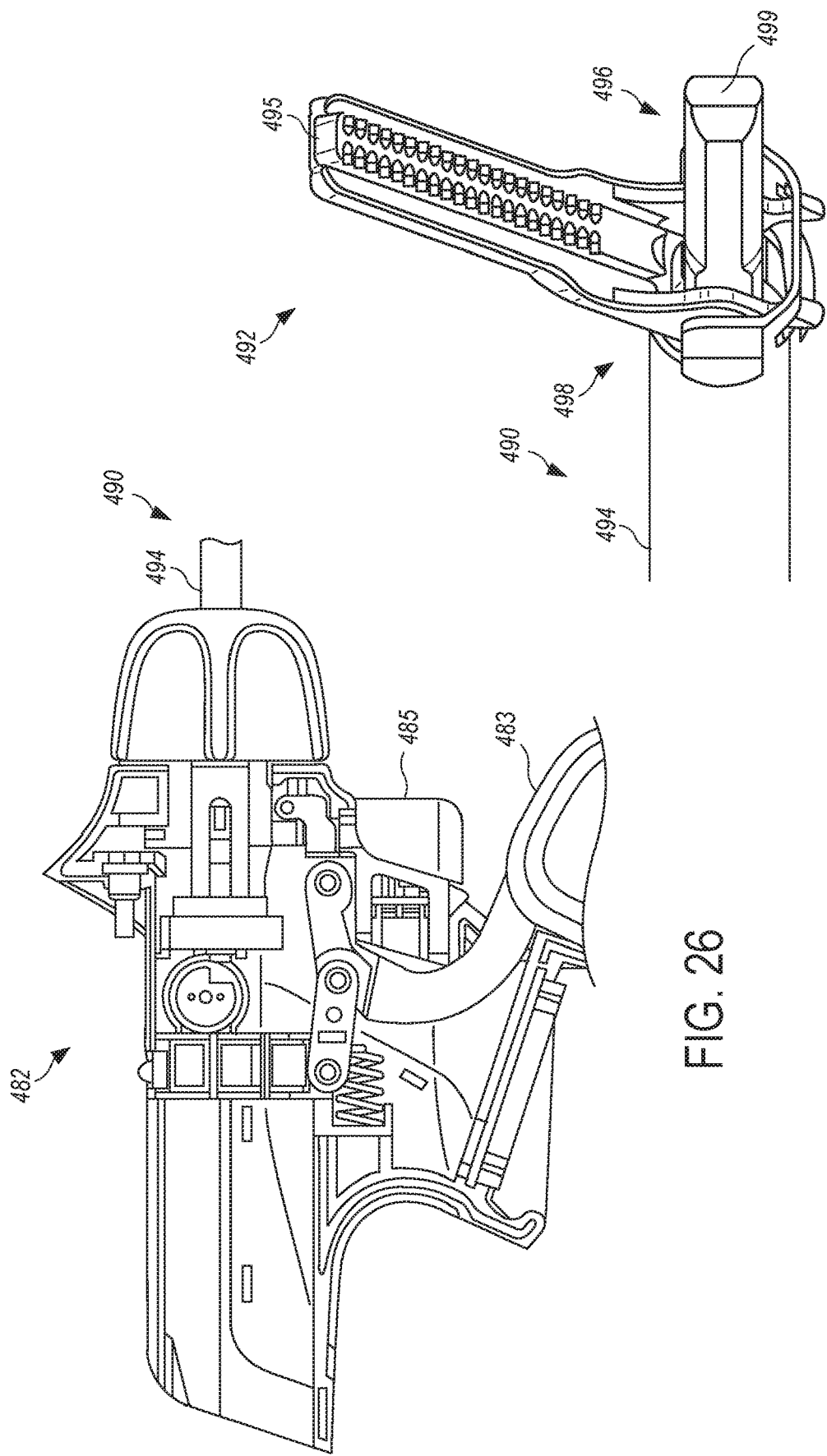

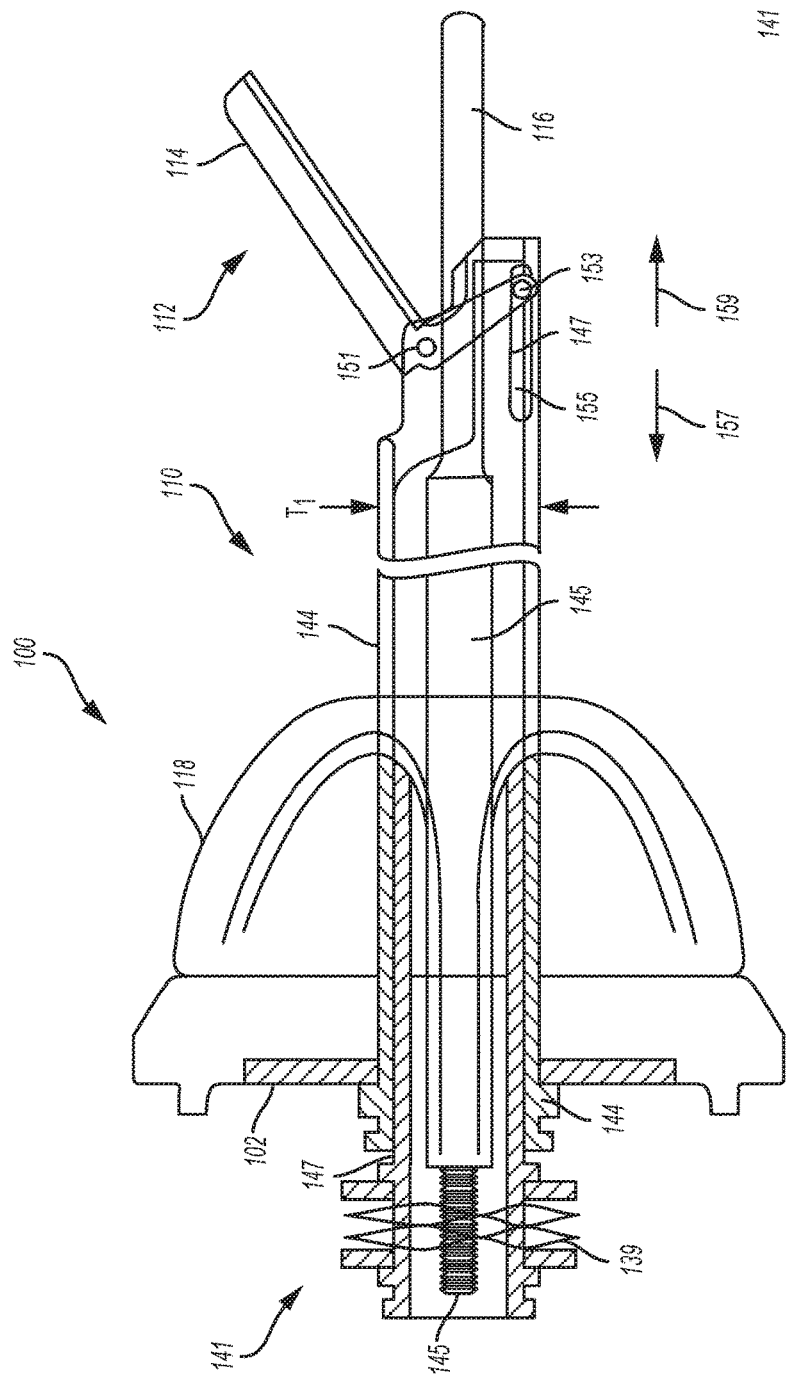
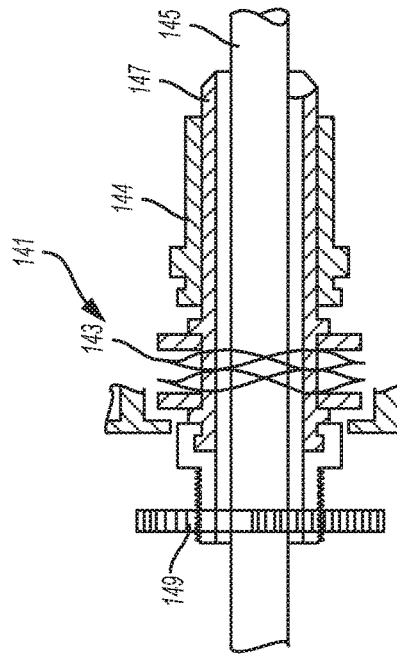
FIG. 28
FIG. 29

MODULAR BATTERY POWERED HANDHELD SURGICAL INSTRUMENT WITH MOTOR DRIVE

PRIORITY

This application claims the benefit of U.S. Provisional Application Ser. No. 62/279,635 filed Jan. 15, 2016 and U.S. Provisional Application Ser. No. 62/330,669, filed May 2, 2016, the contents of each of these provisional applications is incorporated herein by reference in their entirety.

BACKGROUND

The present disclosure is related generally to surgical instruments and associated surgical techniques. More particularly, the present disclosure is related to ultrasonic and electrosurgical systems that allow surgeons to perform cutting and coagulation and to adapt and customize such procedures based on the type of tissue being treated.

Ultrasonic surgical instruments are finding increasingly widespread applications in surgical procedures by virtue of the unique performance characteristics of such instruments. Depending upon specific instrument configurations and operational parameters, ultrasonic surgical instruments can provide simultaneous or near-simultaneous cutting of tissue and hemostasis by coagulation, desirably minimizing patient trauma. The cutting action is typically realized by an-end effector, or blade tip, at the distal end of the instrument, which transmits ultrasonic energy to tissue brought into contact with the end effector. Ultrasonic instruments of this nature can be configured for open surgical use, laparoscopic, or endoscopic surgical procedures including robotic-assisted procedures.

Some surgical instruments utilize ultrasonic energy for both precise cutting and controlled coagulation. Ultrasonic energy cuts and coagulates by vibrating a blade in contact with tissue. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

Electrosurgical instruments for applying electrical energy to tissue in order to treat and/or destroy the tissue are also finding increasingly widespread applications in surgical procedures. An electrosurgical instrument typically includes a hand piece, an instrument having a distally-mounted end effector (e.g., one or more electrodes). The end effector can be positioned against the tissue such that electrical current is introduced into the tissue. Electrosurgical instruments can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical instrument also may include a cutting member that is movable relative to the tissue and the electrodes to transect the tissue.

Electrical energy applied by an electrosurgical instrument can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical instrument can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

A challenge of using these medical devices is the inability to fully control and customize the functions of the surgical instruments. It would be desirable to provide a surgical instrument that overcomes some of the deficiencies of current instruments.

SUMMARY

In one aspect, the present disclosure provides A system comprising: a surgical instrument comprising: a handle assembly; a shaft assembly coupled to the handle assembly; and an end effector coupled to a distal end of the shaft assembly; the shaft assembly comprising: an exterior shaft; a first clutch positioned within the exterior shaft and configured to drive a first function of the surgical instrument when engaged; a second clutch positioned within the exterior shaft and configured to drive a second function of the surgical instrument when engaged; and a rotary driver positioned within the exterior shaft and configured to rotate within the exterior shaft, the rotary driver comprising: a first clutch engagement mechanism configured to engage the first clutch; and a second clutch engagement mechanism configured to engage the second clutch independent of the first clutch engagement mechanism engaging the first clutch, such that, at different times: both the first clutch and the second clutch are engaged simultaneously; only the first clutch is engaged; only the second clutch is engaged; and neither the first clutch nor the second clutch is engaged simultaneously.

In another aspect, the present disclosure provides a surgical instrument comprising: a handle assembly; a shaft assembly coupled to the handle assembly; and an end effector coupled to a distal end of the shaft; the shaft assembly comprising: an exterior frame; a first clutch positioned within the exterior frame and configured to drive a first function of the surgical instrument when engaged; a second clutch positioned within the exterior frame and configured to drive a second function of the surgical instrument when engaged; and a rotary driver having a portion positioned within the exterior frame and configured to rotate about a longitudinal axis and slide longitudinally within the exterior frame, the rotary driver comprising: a clutch engagement mechanism configured to: engage only the first clutch when the rotary driver is slid into the exterior frame at a first position; engage both the first and the second clutch simultaneously when the rotary driver is slid into the exterior frame at a second position; engage only the second clutch when the rotary driver is slid into the exterior frame at a third position; and engage neither the first nor the second clutch when the rotary driver is slid into the exterior frame at a fourth position.

In another aspect, the present disclosure provides a surgical instrument comprising a handle assembly; a shaft assembly coupled to the handle assembly; and an end effector coupled to a distal end of the shaft assembly; the shaft assembly comprising: an exterior shaft; a first clutch positioned within the exterior shaft and configured to drive a first function of the surgical instrument when engaged; a second clutch positioned within the exterior shaft and configured to drive a second function of the surgical instrument when engaged; and a rotary driver positioned within the exterior shaft and configured to rotate within the exterior shaft, the rotary driver comprising: a first clutch engagement mechanism configured to engage the first clutch; and a second clutch engagement mechanism configured to engage the second clutch independent of the first clutch engagement mechanism engaging the first clutch, such that, at different times: both the first clutch and the second clutch are engaged simultaneously; only the first clutch is engaged; only the second clutch is engaged; and neither the first clutch nor the second clutch is engaged simultaneously.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to affect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

Further, it is understood that any one or more of the following-described forms, expressions of forms, examples, can be combined with any one or more of the other following-described forms, expressions of forms, and examples.

The foregoing summary is illustrative only and is not intended to be in any way limiting. In addition to the illustrative aspects, and features described above, further aspects, and features will become apparent by reference to the drawings and the following detailed description.

FIGURES

The novel features of the various aspects described herein are set forth with particularity in the appended claims. The various aspects, however, both as to organization and methods of operation may be better understood by reference to the following description, taken in conjunction with the accompanying drawings as follows:

FIG. 12 is a schematic diagram of the transformer coupled to the ultrasonic drive circuit shown in FIG. 11, according to one aspect of the present disclosure.

FIG. 13 is a schematic diagram of the transformer shown in FIG. 12 coupled to a test circuit, according to one aspect of the present disclosure.

FIG. 26 is a detail view of a trigger portion and switch of the ultrasonic surgical instrument shown in FIG. 25, according to one aspect of the present disclosure.

FIG. 27 is a fragmentary, enlarged perspective view of an end effector from a distal end with a jaw member in an open position, according to one aspect of the present disclosure.

FIG. 28 illustrates a modular shaft assembly and end effector portions of the surgical instrument, according to one aspect of the present disclosure.

FIG. 29 is a detail view of an inner tube/spring assembly, according to one aspect of the present disclosure.

FIG. 63 is a diagram of one form of a direct digital synthesis circuit.

Figure 1:
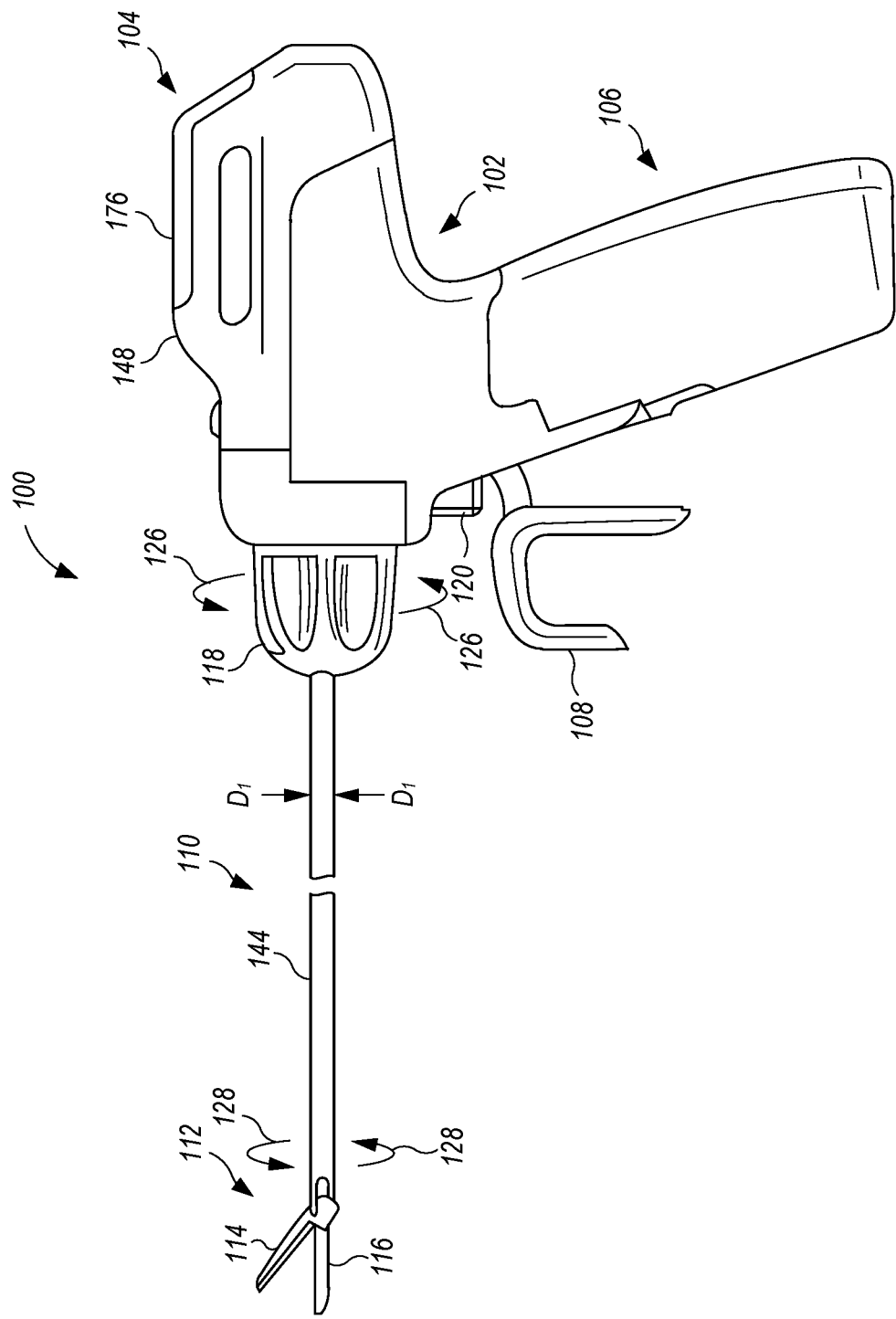
FIG. 1 is a diagram of a modular battery powered handheld ultrasonic surgical instrument, according to an aspect of the present disclosure.
Figure 61:
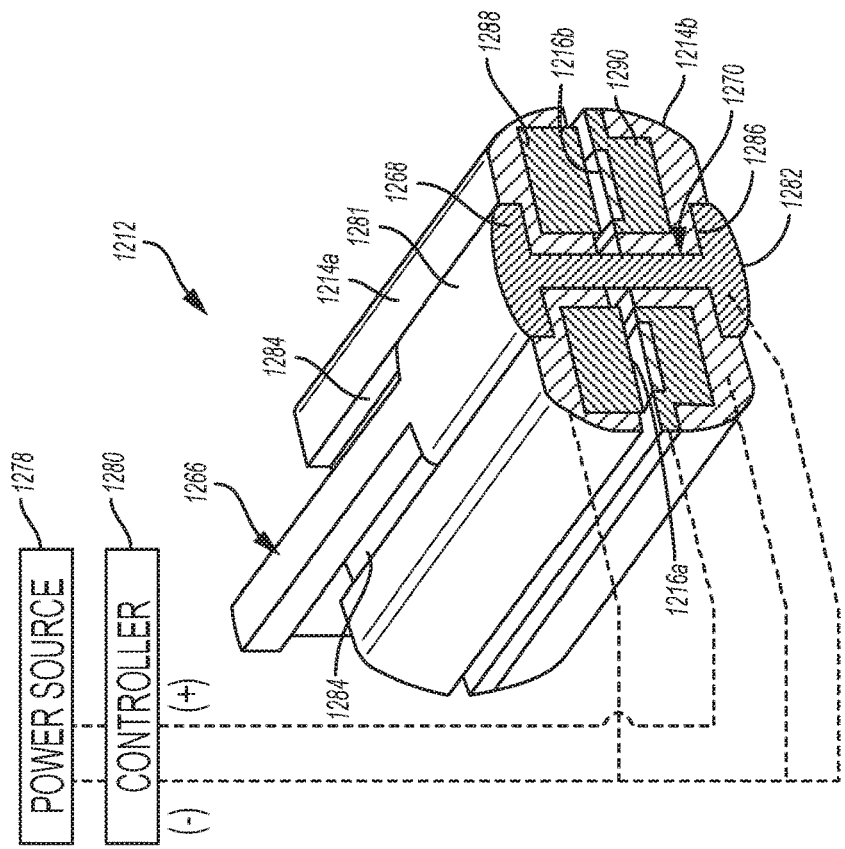
FIG. 61 illustrates a cross-sectional end view of the end effector of FIG. 60 in a closed configuration and with the blade in a distal position, according to one aspect to the present disclosure.
Figure 64:
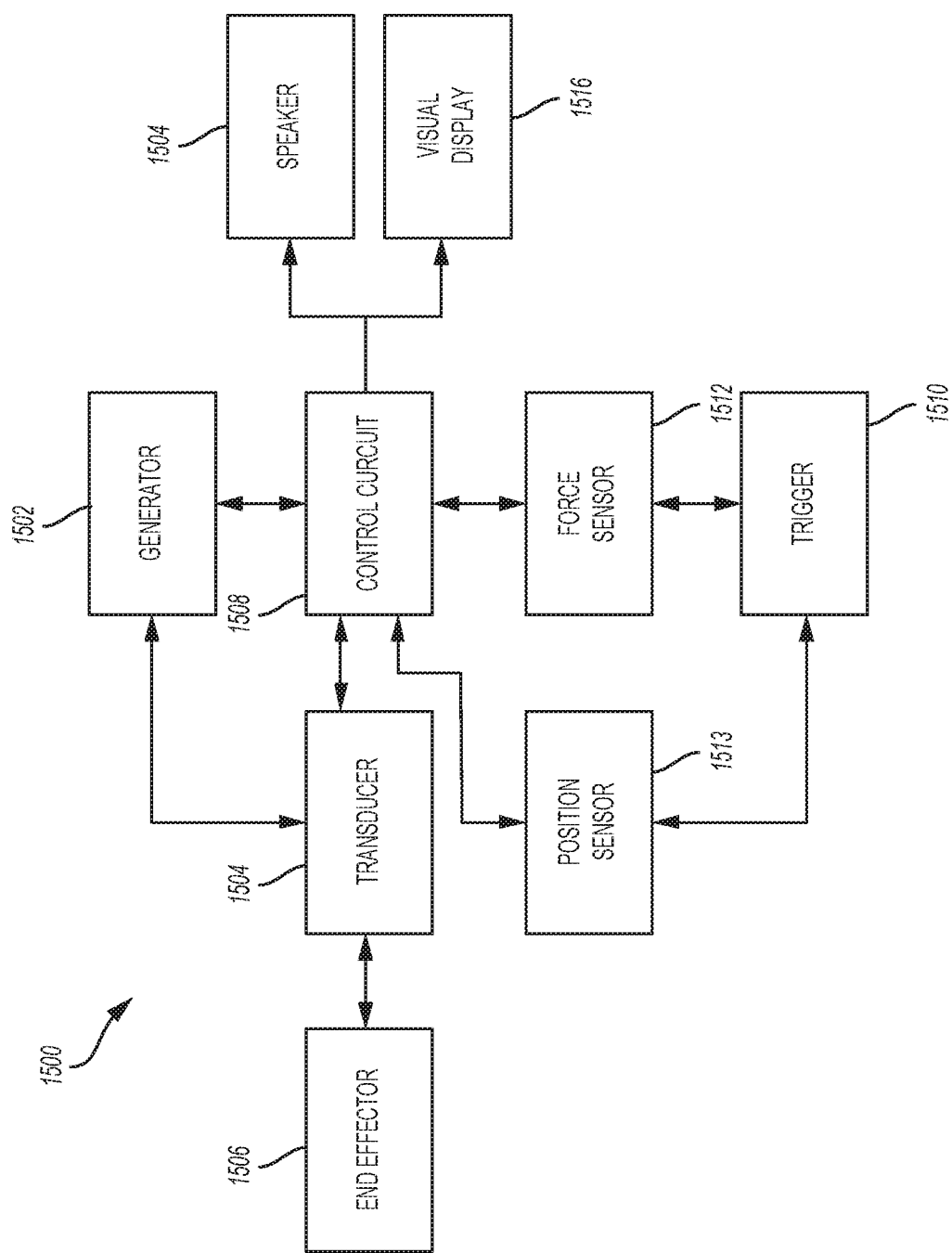
Figure 65:
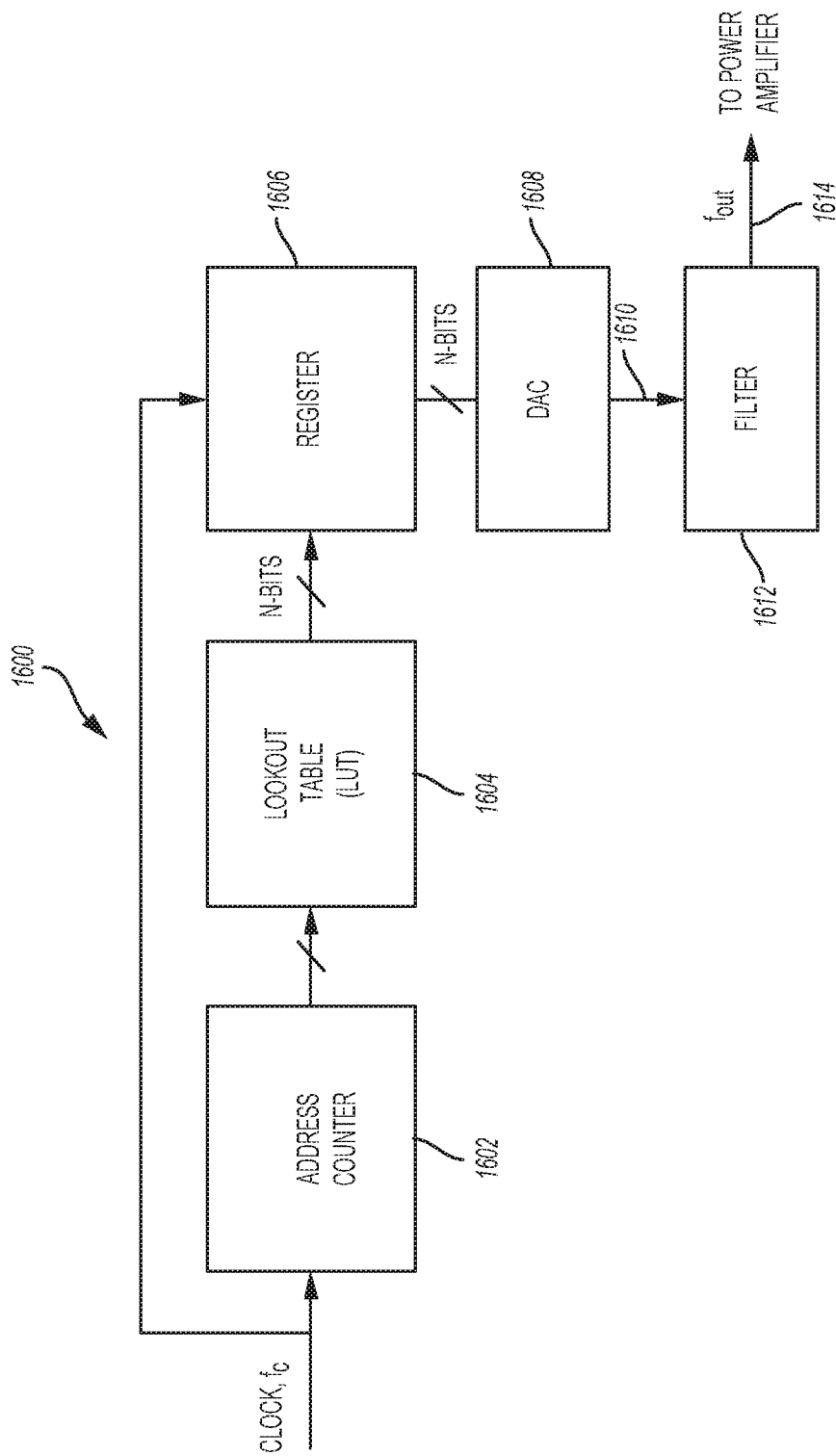

FIG. 64 illustrates a diagram of one aspect of a surgical instrument comprising a feedback system for use with any one of the surgical instruments described herein in connection with FIGS. 1-61, which may include or implement many of the features described herein FIG. 65 illustrates one aspect of a fundamental architecture for a digital synthesis circuit such as a direct digital synthesis (DDS) circuit configured to generate a plurality of wave shapes for the electrical signal waveform for use in any of the surgical instruments described herein in connection with FIGS. 1-61, according to one aspect of the present disclosure.

Figure 66:
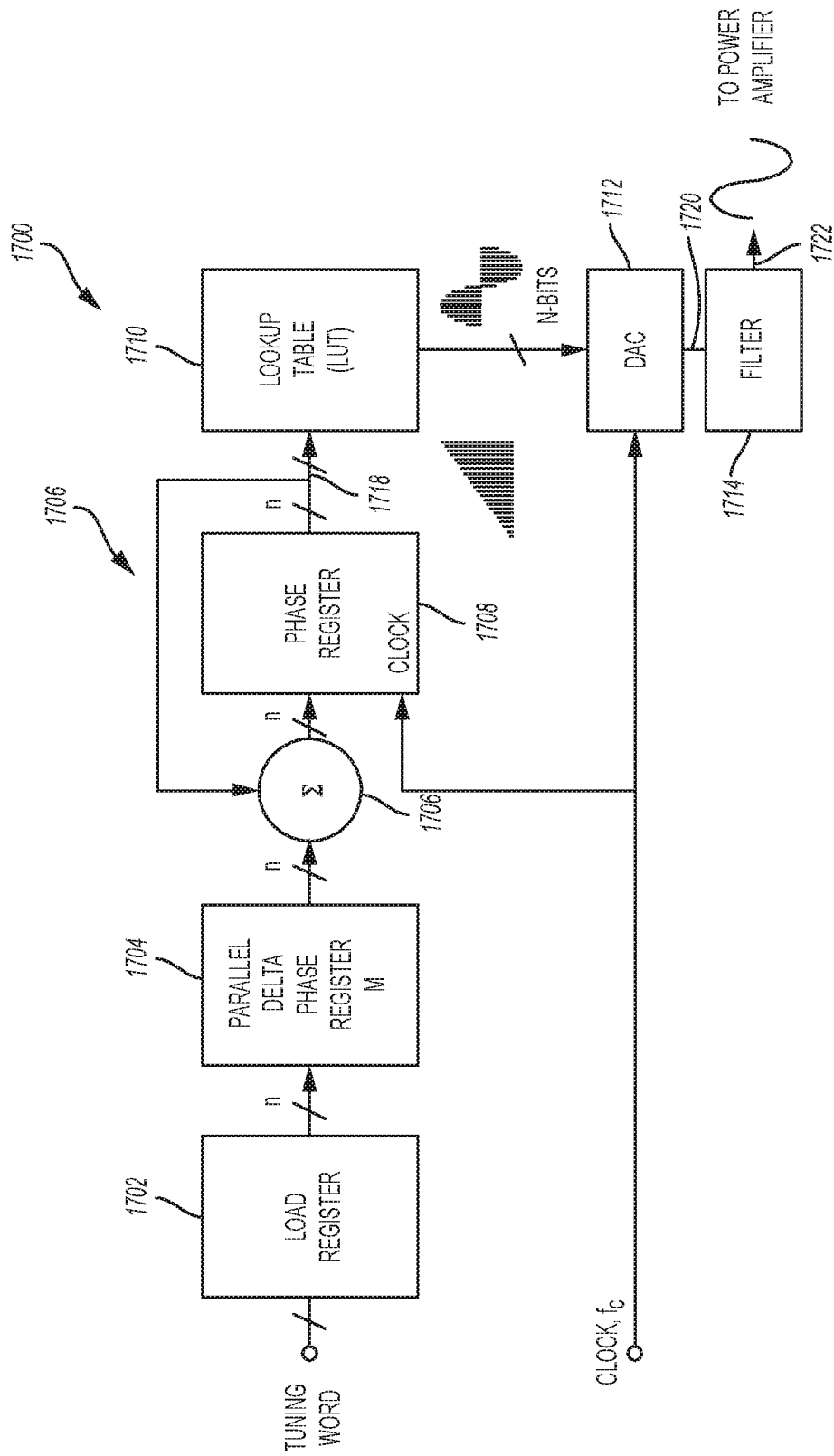

FIG. 66 illustrates one aspect of direct digital synthesis (DDS) circuit configured to generate a plurality of wave shapes for the electrical signal waveform for use in any of the surgical instruments described herein in connection with FIGS. 1-61, according to one aspect of the present disclosure.

Figure 67:
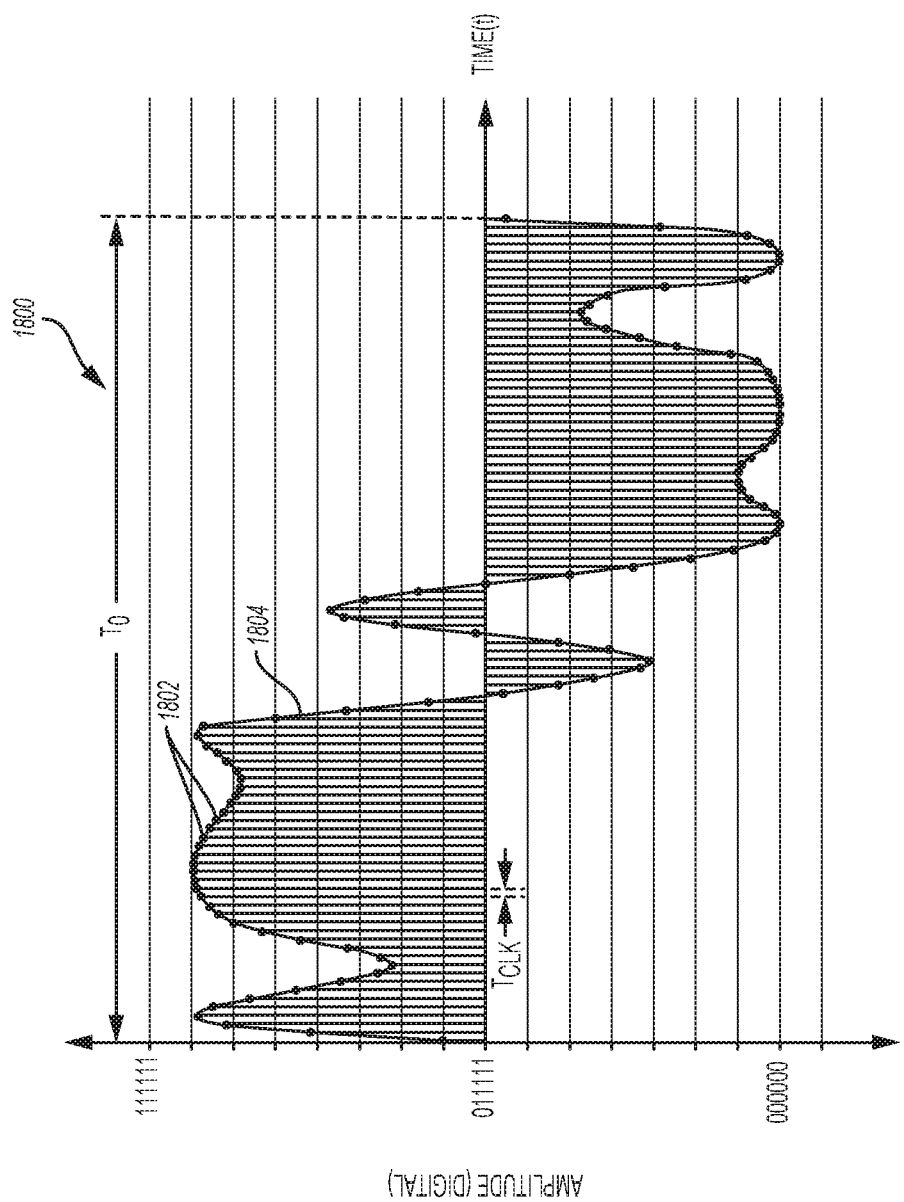

FIG. 67 illustrates one cycle of a discrete time digital electrical signal waveform, according to one aspect of the present disclosure of an analog waveform (shown superimposed over a discrete time digital electrical signal waveform for comparison purposes), according to one aspect of the present disclosure.

Figure 68A:
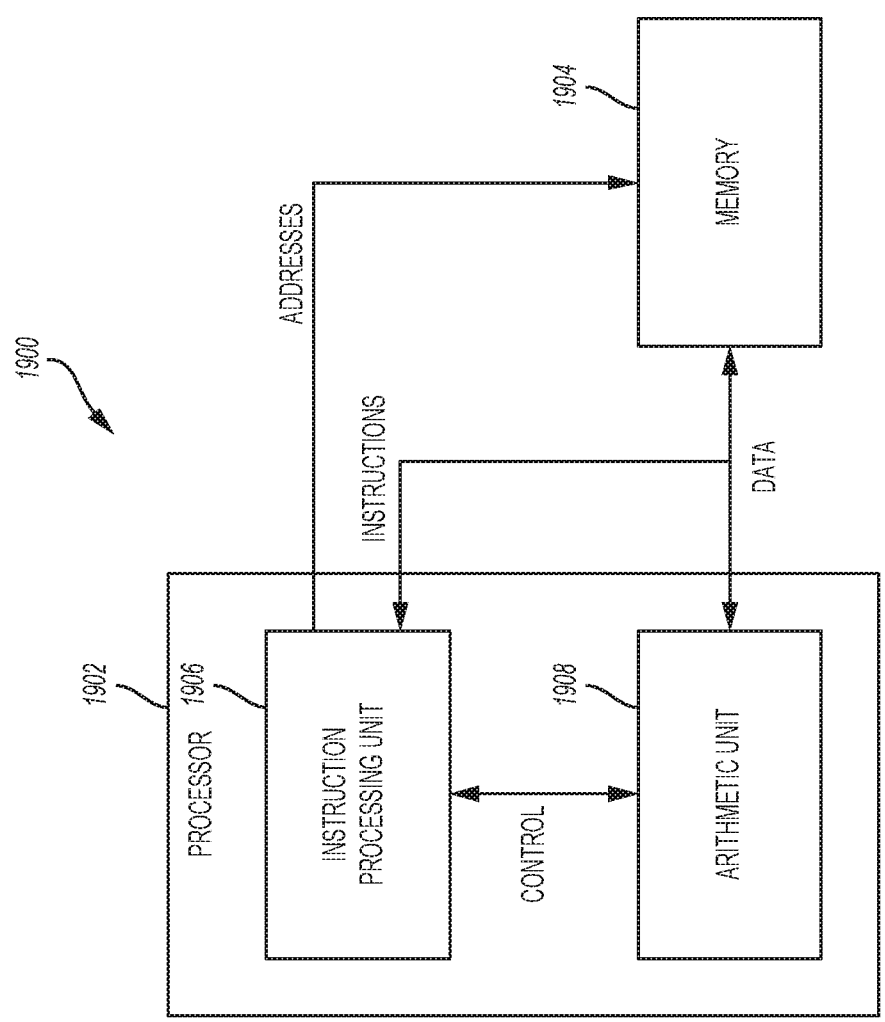

FIG. 68A illustrates a circuit comprising a controller comprising one or more processors coupled to at least one memory circuit for use in any of the surgical instruments described herein in connection with FIGS. 1-61, according to one aspect of the present disclosure.

Figure 68B:
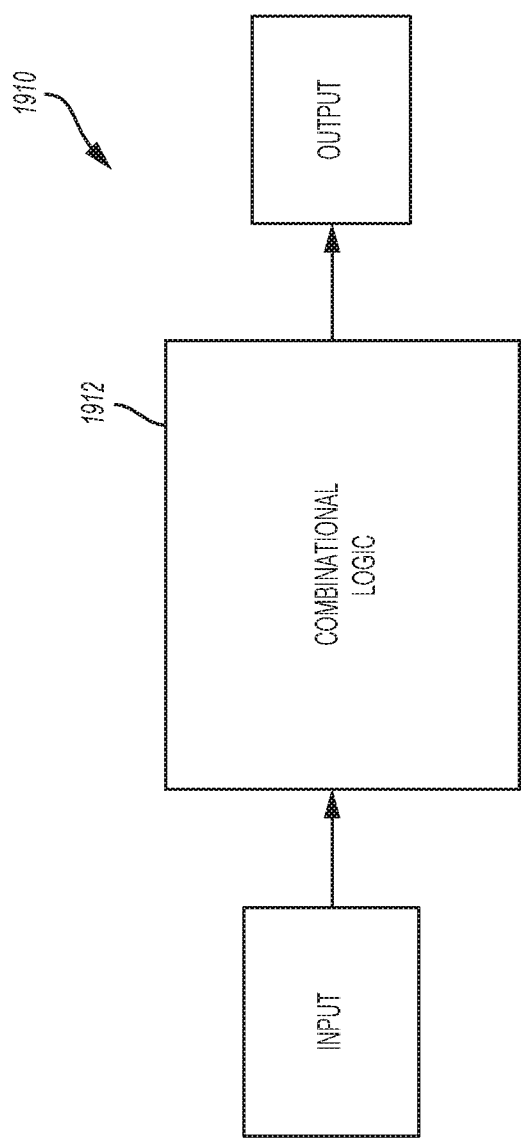

FIG. 68B illustrates a circuit comprising a finite state machine comprising a combinational logic circuit configured to implement any of the algorithms, processes, or techniques described herein, according to one aspect of the present disclosure.

Figure 68C:
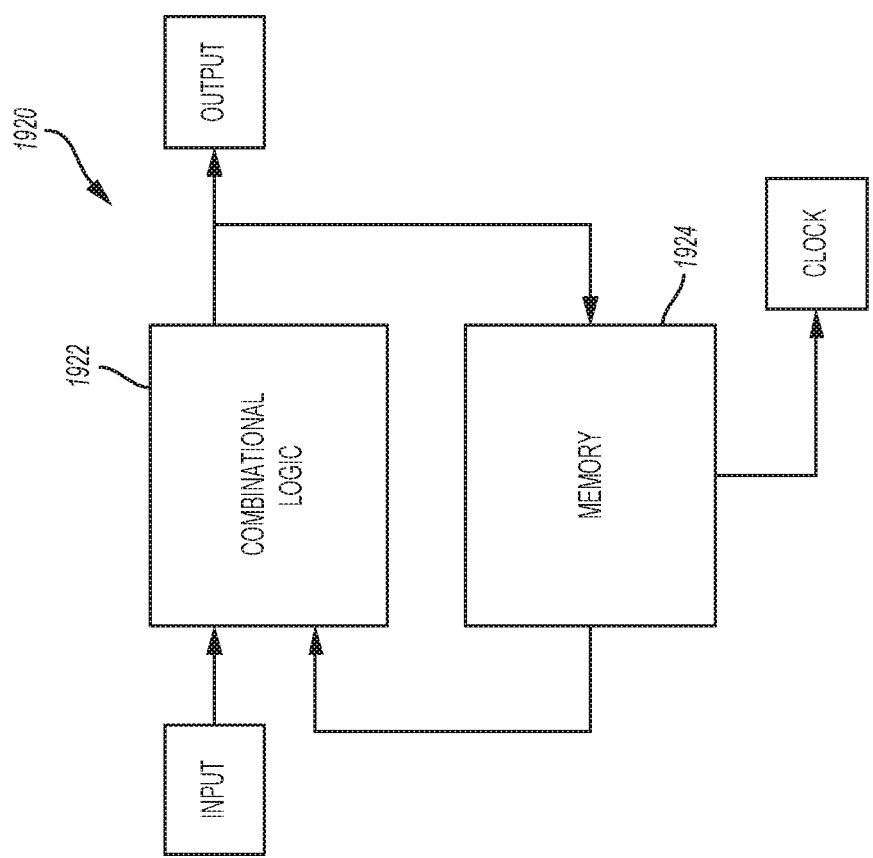

FIG. 68C illustrates a circuit comprising a finite state machine comprising a sequential logic circuit configured to implement any of the algorithms, processes, or techniques described herein, according to one aspect of the present disclosure.

Figure 69:
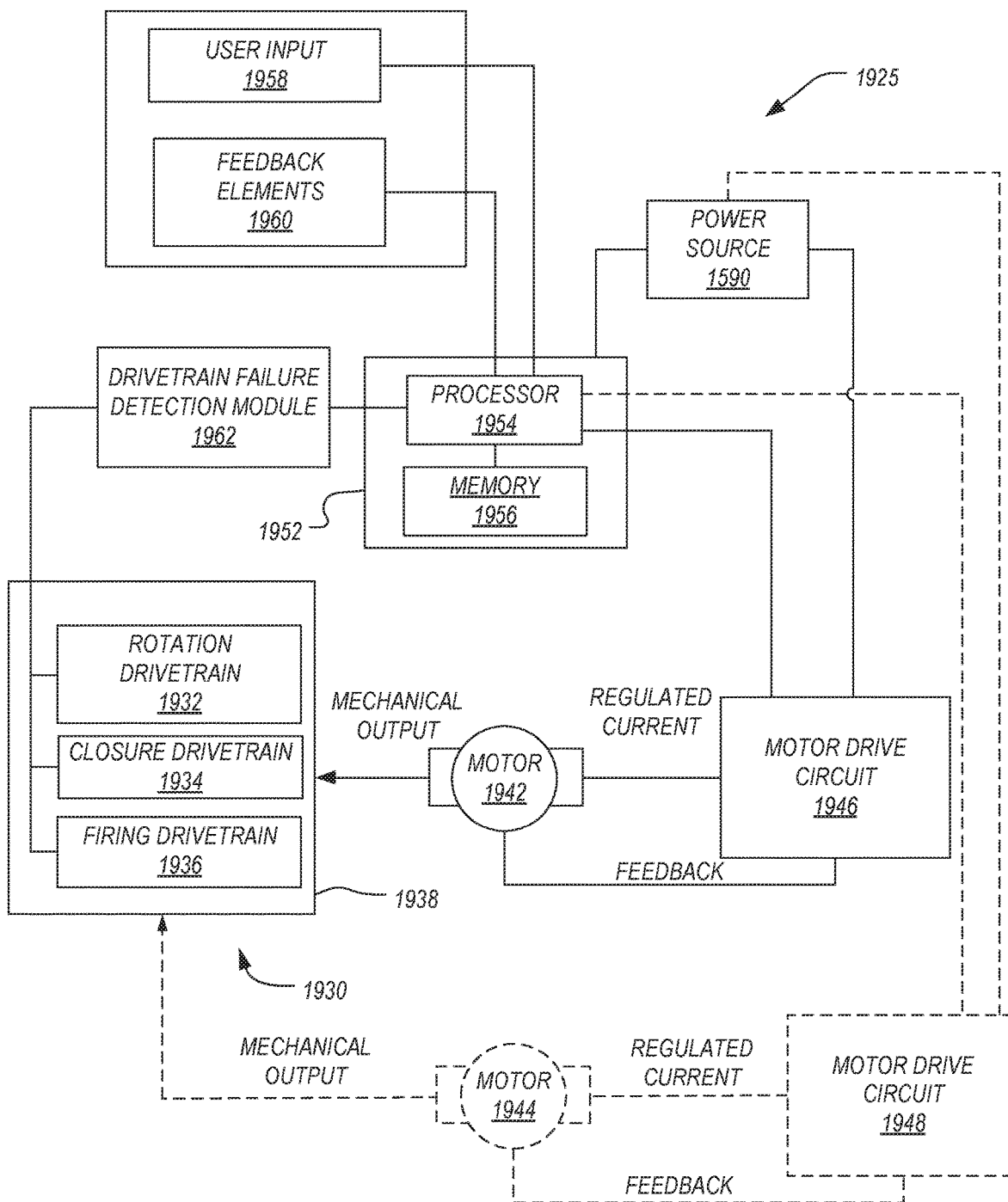

FIG. 69 is a circuit diagram of various components of a surgical instrument with motor control functions, according to one aspect of the present disclosure.

Figure 70:
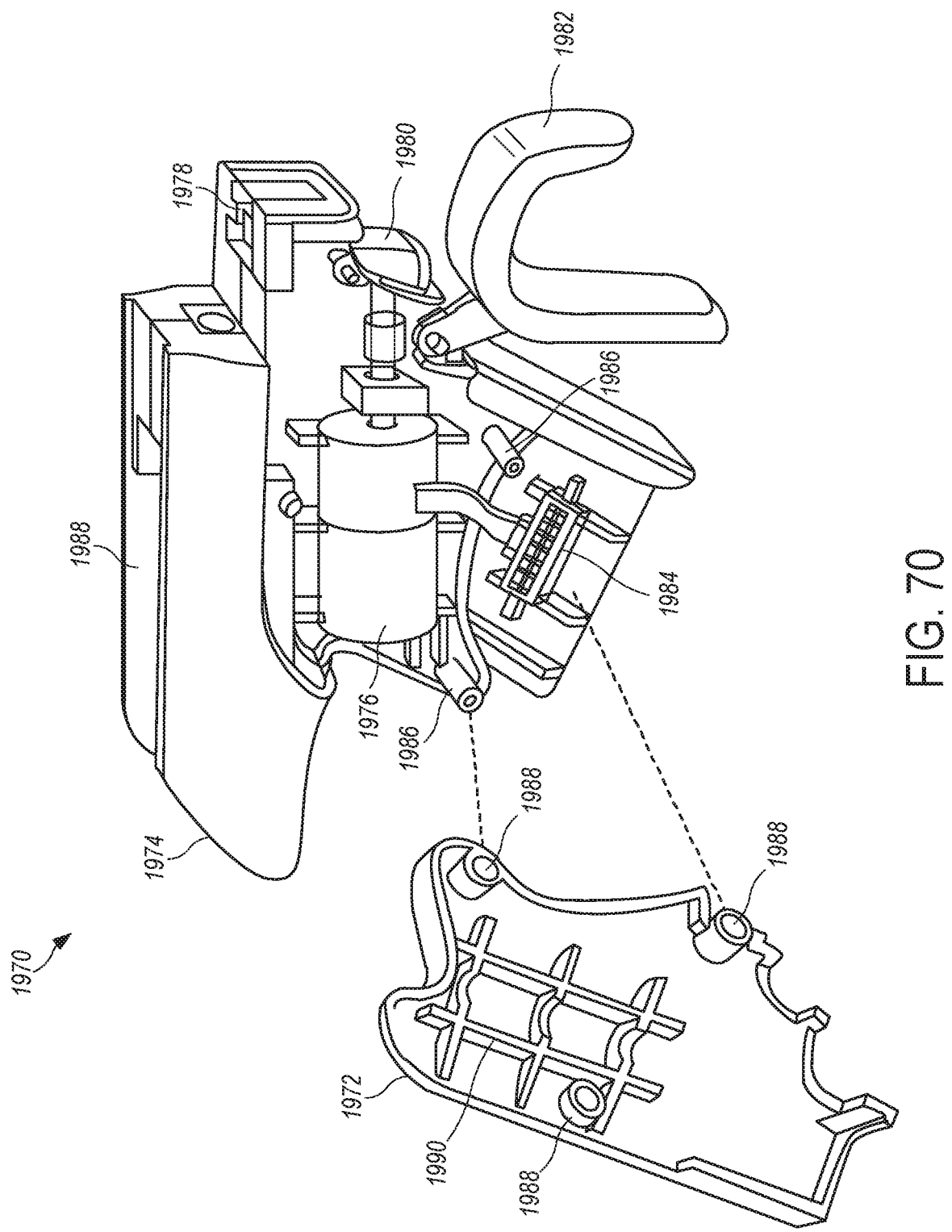

FIG. 70 illustrates a handle assembly with a removable service panel removed to shown internal components of the handle assembly, according to one aspect of the present disclosure.

Figure 71:
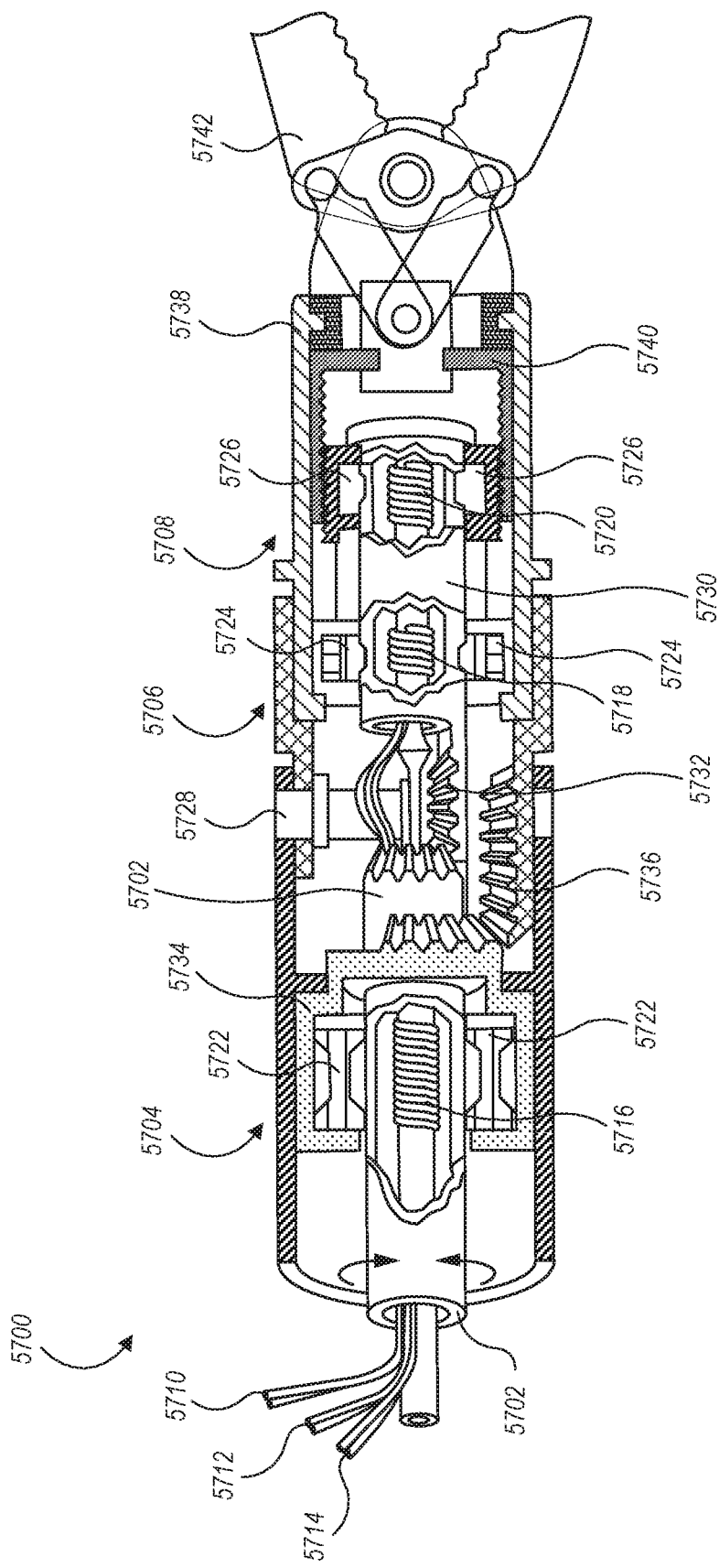

FIG. 71 shows the inner workings of a portion of a shaft assembly that is part of the surgical instrument and includes multiple clutch systems, according to one aspect of the present disclosure.

FIGS. 72A, 72B, 72C, 72D, 72E, and 72F show another variation for including multiple clutch systems, according to one aspect of the present disclosure.

Figure 73A:
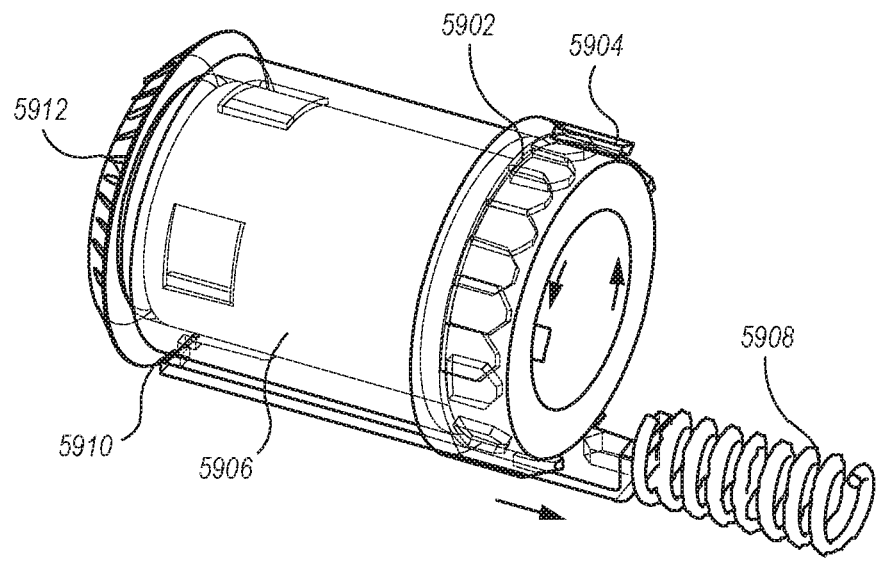
Figure 73B:
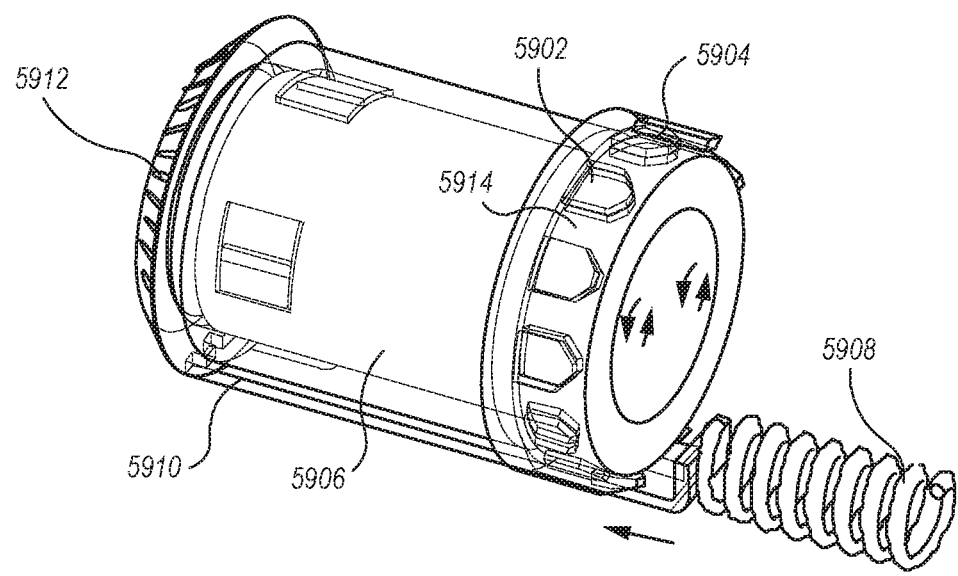

FIGS. 73A and 73B show a shaft assembly that may include a locking element to help stabilize engagement of the clutches, according to one aspect of the present disclosure.

Figure 74B:
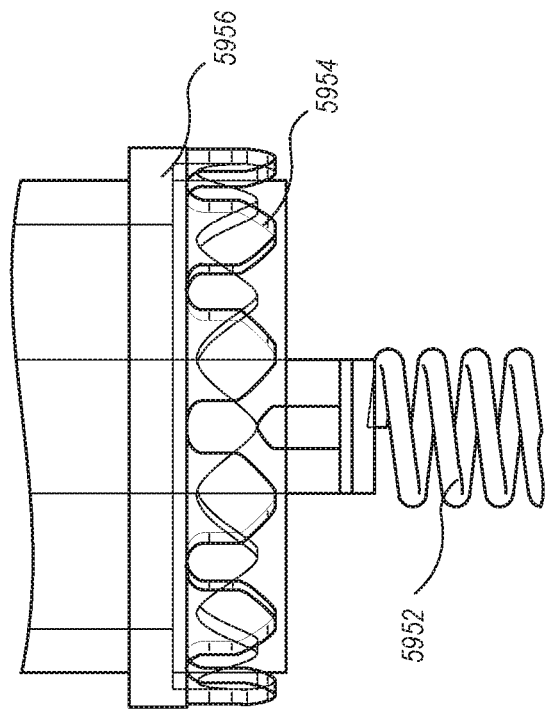
Figure 74A:
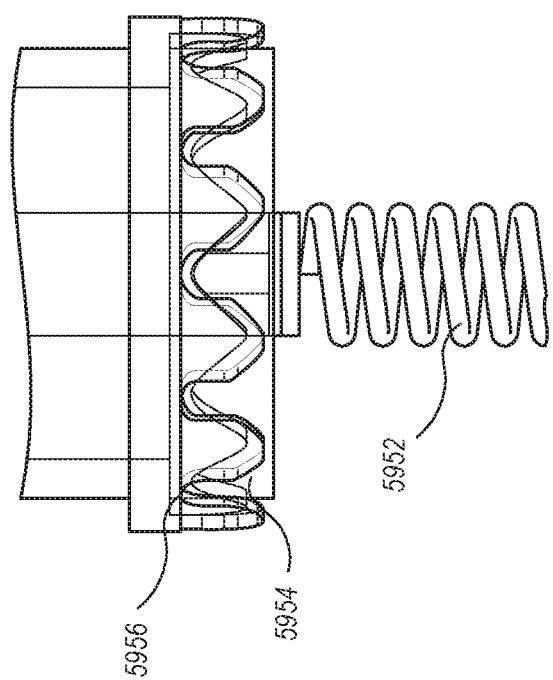

FIGS. 74A and 74B show side views of the locking element, according to one aspect of the present disclosure.

DESCRIPTION

This application is related to following commonly owned patent applications filed concurrently herewith, the content of each of which is incorporated herein by reference in its entirety:

This application is related to the following commonly owned patent applications filed Dec. 16, 2016, the content of each of which is incorporated herein by reference in its entirety:

U.S. patent application Ser. No. 15/382,515, titled MODULAR BATTERY POWERED HANDHELD SURGICAL INSTRUMENT AND METHODS THEREFOR, by inventors Frederick E. Shelton, I V, et al., filed Dec. 16, 2016, now U.S. Pat. No. 10,842,523.

U.S. patent application Ser. No. 15/382,238, titled MODULAR BATTERY POWERED HANDHELD SURGICAL INSTRUMENT WITH SELECTIVE APPLICATION OF ENERGY BASED ON TISSUE CHARACTERIZATION, by inventors Frederick E. Shelton, I V, et al., filed Dec. 16, 2016, now U.S. Patent Application Publication No. 2017/0202591.

U.S. patent application Ser. No. 15/382,246, titled MODULAR BATTERY POWERED HANDHELD SURGICAL INSTRUMENT WITH SELECTIVE APPLICATION OF ENERGY BASED ON BUTTON DISPLACEMENT, INTENSITY, OR LOCAL TISSUE CHARACTERIZATION, by inventors Frederick E. Shelton, I V, et al., filed Dec. 16, 2016, now U.S. Patent Application Publication No. 2017/0202607.

U.S. patent application Ser. No. 15/382,252, titled MODULAR BATTERY POWERED HANDHELD SURGICAL INSTRUMENT WITH VARIABLE MOTOR CONTROL LIMITS, by inventors Frederick E. Shelton, I V, et al., filed Dec. 16, 2016, now U.S. Pat. No. 10,537,351.

U.S. patent application Ser. No. 15/382,257, titled MODULAR BATTERY POWERED HANDHELD SURGICAL INSTRUMENT WITH MOTOR CONTROL LIMIT PROFILE, by inventors Frederick E. Shelton, I V, et al., filed Dec. 16, 2016, now U.S. Pat. No. 10,299,821.

U.S. patent application Ser. No. 15/382,265, titled MODULAR BATTERY POWERED HANDHELD SURGICAL INSTRUMENT WITH MOTOR CONTROL LIMITS BASED ON TISSUE CHARACTERIZATION, by inventors Frederick E. Shelton, I V, et al., filed Dec. 16, 2016, now U.S. Pat. No. 10,828,058.

U.S. patent application Ser. No. 15/382,274, titled MODULAR BATTERY POWERED HANDHELD SURGICAL INSTRUMENT WITH MULTI-FUNCTION MOTOR VIA SHIFTING GEAR ASSEMBLY, by inventors Frederick E. Shelton, I V, et al., filed Dec. 16, 2016, now U.S. Pat. No. 10,251,664.

U.S. patent application Ser. No. 15/382,281, titled MODULAR BATTERY POWERED HANDHELD SURGICAL INSTRUMENT WITH A PLURALITY OF CONTROL PROGRAMS, by inventor Frederick E. Shelton, IV, filed Dec. 16, 2016, now U.S. Patent Application Publication No. 2017/0202595.

U.S. patent application Ser. No. 15/382,283, titled MODULAR BATTERY POWERED HANDHELD SURGICAL INSTRUMENT WITH ENERGY CONSERVATION TECHNIQUES, by inventors Frederick E. Shelton, I V, et al., filed Dec. 16, 2016, now U.S. Pat. No. 10,709,469.

U.S. patent application Ser. No. 15/382,285, titled MODULAR BATTERY POWERED HANDHELD SURGICAL INSTRUMENT WITH VOLTAGE SAG RESISTANT BATTERY PACK, by inventors Frederick E. Shelton, I V, et al., filed Dec. 16, 2016, now U.S. Pat. No. 10,779,849.

U.S. patent application Ser. No. 15/382,287, titled MODULAR BATTERY POWERED HANDHELD SURGICAL INSTRUMENT WITH MULTISTAGE GENERATOR CIRCUITS, by inventors Frederick E. Shelton, I V, et al., filed Dec. 16, 2016, now U.S. Patent Application Publication No. 2017/0202597.

U.S. patent application Ser. No. 15/382,288, titled MODULAR BATTERY POWERED HANDHELD SURGICAL INSTRUMENT WITH MULTIPLE MAGNETIC POSITION SENSORS, by inventors Frederick E. Shelton, I V, et al., filed Dec. 16, 2016, now U.S. Patent Application Publication No. 2017/0202598.

U.S. patent application Ser. No. 15/382,290, titled MODULAR BATTERY POWERED HANDHELD SURGICAL INSTRUMENT CONTAINING ELONGATED MULTI-LAYERED SHAFT, by inventors Frederick E. Shelton, I V, et al., filed Dec. 16, 2016, now U.S. Pat. No. 10,835,307.

U.S. patent application Ser. No. 15/382,297, titled MODULAR BATTERY POWERED HANDHELD SURGICAL INSTRUMENT WITH SELF-DIAGNOSING CONTROL SWITCHES FOR REUSABLE HANDLE ASSEMBLY, by inventors Frederick E. Shelton, I V, et al., filed Dec. 16, 2016, now U.S. Patent Application Publication No. 2017/0202599.

U.S. patent application Ser. No. 15/382,306, titled MODULAR BATTERY POWERED HANDHELD SURGICAL INSTRUMENT WITH REUSABLE ASYMMETRIC HANDLE HOUSING, by inventors Frederick E. Shelton, I V, et al., filed Dec. 16, 2016, now U.S. Patent Application Publication No. 2017/0202571.

U.S. patent application Ser. No. 15/382,309, titled MODULAR BATTERY POWERED HANDHELD SURGICAL INSTRUMENT WITH CURVED END EFFECTORS HAVING ASYMMETRIC ENGAGEMENT BETWEEN JAW AND BLADE, by inventors Frederick E. Shelton, I V, et al., filed Dec. 16, 2016, now U.S. Pat. No. 10,716,615.

In the following detailed description, reference is made to the accompanying drawings, which form a part hereof. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the scope of the subject matter presented here.

Before explaining the various aspects of the present disclosure in detail, it should be noted that the various aspects disclosed herein are not limited in their application or use to the details of construction and arrangement of parts illustrated in the accompanying drawings and description. Rather, the disclosed aspects may be positioned or incorporated in other aspects, variations and modifications thereof, and may be practiced or carried out in various ways. Accordingly, aspects disclosed herein are illustrative in nature and are not meant to limit the scope or application thereof. Furthermore, unless otherwise indicated, the terms and expressions employed herein have been chosen for the purpose of describing the aspects for the convenience of the reader and are not to limit the scope thereof. In addition, it should be understood that any one or more of the disclosed aspects, expressions of aspects, and/or examples thereof, can be combined with any one or more of the other disclosed aspects, expressions of aspects, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings.

In various aspects, the present disclosure is directed to a mixed energy surgical instrument that utilizes both ultrasonic and RF energy modalities. The mixed energy surgical instrument my use modular shafts using that accomplish existing end-effector functions such as ultrasonic functions disclosed in U.S. Pat. No. 9,107,690, which is incorporated herein by reference in its entirety, combination device functions disclosed in U.S. Pat. Nos. 8,696,666 and 8,663,223, which are both incorporated herein by reference in their entireties, RF opposed electrode functions disclosed in U.S. Pat. Nos. 9,028,478 and 9,113,907, which are both incorporated herein by reference in their entireties, and RF I-blade offset electrode functions as disclosed in U.S. Patent Application Publication No. 2013/0023868, which is incorporated herein by reference in its entirety.

In various aspects, the present disclosure is directed to a modular battery powered handheld ultrasonic surgical instrument comprising a first generator, a second generator, and a control circuit for controlling the energy modality applied by the surgical instrument. The surgical instrument is configured to apply at least one energy modality that comprises an ultrasonic energy modality, a radio frequency (RF) energy modality, or a combination ultrasonic and RF energy modalities.

In another aspect, the present disclosure is directed to a modular battery powered handheld surgical instrument that can be configured for ultrasonic energy modality, RF modality, or a combination of ultrasonic and RF energy modalities. A mixed energy surgical instrument utilizes both ultrasonic and RF energy modalities. The mixed energy surgical instrument may use modular shafts that accomplish end effector functions. The energy modality may be selectable based on a measure of specific measured tissue and device parameters, such as, for example, electrical impedance, tissue impedance, electric motor current, jaw gap, tissue thickness, tissue compression, tissue type, temperature, among other parameters, or a combination thereof, to determine a suitable energy modality algorithm to employ ultrasonic vibration and/or electrosurgical high-frequency current to carry out surgical coagulation/cutting treatments on the living tissue based on the measured tissue parameters identified by the surgical instrument. Once the tissue parameters have been identified, the surgical instrument may be configured to control treatment energy applied to the tissue in a single or segmented RF electrode configuration or in an ultrasonic device, through the measurement of specific tissue/device parameters. Tissue treatment algorithms are described in commonly owned U.S. patent application Ser. No. 15/177,430, titled SURGICAL INSTRUMENT WITH USER ADAPTABLE TECHNIQUES, which is herein incorporated by reference in its entirety.

In another aspect, the present disclosure is directed to a modular battery powered handheld surgical instrument having a motor and a controller, where a first limiting threshold is used on the motor for the purpose of attaching a modular assembly and a second threshold is used on the motor and is associated with a second assembly step or functionality of the surgical instrument. The surgical instrument may comprise a motor driven actuation mechanism utilizing control of motor speed or torque through measurement of motor current or parameters related to motor current, wherein motor control is adjusted via a non-linear threshold to trigger motor adjustments at different magnitudes based on position, inertia, velocity, acceleration, or a combination thereof. Motor driven actuation of a moving mechanism and a motor controller may be employed to control the motor velocity or torque. A sensor associated with physical properties of the moving mechanism provides feedback to the motor controller. In one aspect, the sensor is employed to adjust a predefined threshold which triggers a change in the operation of the motor controller. A motor may be utilized to drive shaft functions such as shaft rotation and jaw closure and switching that motor to also provide a torque limited waveguide attachment to a transducer. A motor control algorithm may be utilized to generate tactile feedback to a user through a motor drive train for indication of device status and/or limits of the powered actuation. A motor powered modular advanced energy based surgical instrument may comprise a series of control programs or algorithms to operate a series of different shaft modules and transducers. In one aspect, the programs or algorithms reside in a module and are uploaded to a control handle when attached. The motor driven modular battery powered handheld surgical instrument may comprise a primary rotary drive capable of being selectably coupleable to at least two independent actuation functions (first, second, both, neither) and utilize a clutch mechanism located in a distal modular elongated tube.

In another aspect, the present disclosure is directed to modular battery powered handheld surgical instrument comprising energy conservation circuits and techniques using sleep mode de-energizing of a segmented circuit with short cuts to minimize non-use power drain and differing wake-up sequence order than the order of a sleep sequence. A disposable primary cell battery pack may be utilized with a battery powered modular handheld surgical instrument. The disposable primary cell may comprise power management circuits to compensate the battery output voltage with additional voltage to offset voltage sags under load and to prevent the battery pack output voltage from sagging below a predetermined level during operation under load. The circuitry of the surgical instrument comprises radiation tolerant components and amplification of electrical signals may be divided into multiple stages. An ultrasonic transducer housing or RF housing may contain the final amplification stage and may comprise different ratios depending on an energy modality associated with the ultrasonic transducer or RF module.

In another aspect, the present disclosure is directed to a modular battery powered handheld surgical instrument comprising multiple magnetic position sensors along a length of a shaft and paired in different configurations to allow multiple sensors to detect the same magnet in order to determine three dimensional position of actuation components of the shaft from a stationary reference plane and simultaneously diagnosing any error from external sources. Control and sensing electronics may be incorporated in the shaft. A portion of the shaft control electronics may be disposed along the inside of moving shaft components and are separated from other shaft control electronics that are disposed along the outside of the moving shaft components. Control and sensing electronics may be situated and designed such that they act as a shaft seal in the device.

In another aspect, the present disclosure is directed to a modular battery powered handheld surgical instrument comprising self diagnosing control switches within a battery powered, modular, reusable handle. The control switches are capable of adjusting their thresholds for triggering an event as well as being able to indicate external influences on the controls or predict time till replacement needed. The reusable handle housing is configured for use with modular disposable shafts and at least one control and wiring harness. The handle is configured to asymmetrically part when opened so that the switches, wiring harness, and/or control electronics can be supportably housed in one side such that the other side is removably attached to cover the primary housing.

Figure 2:
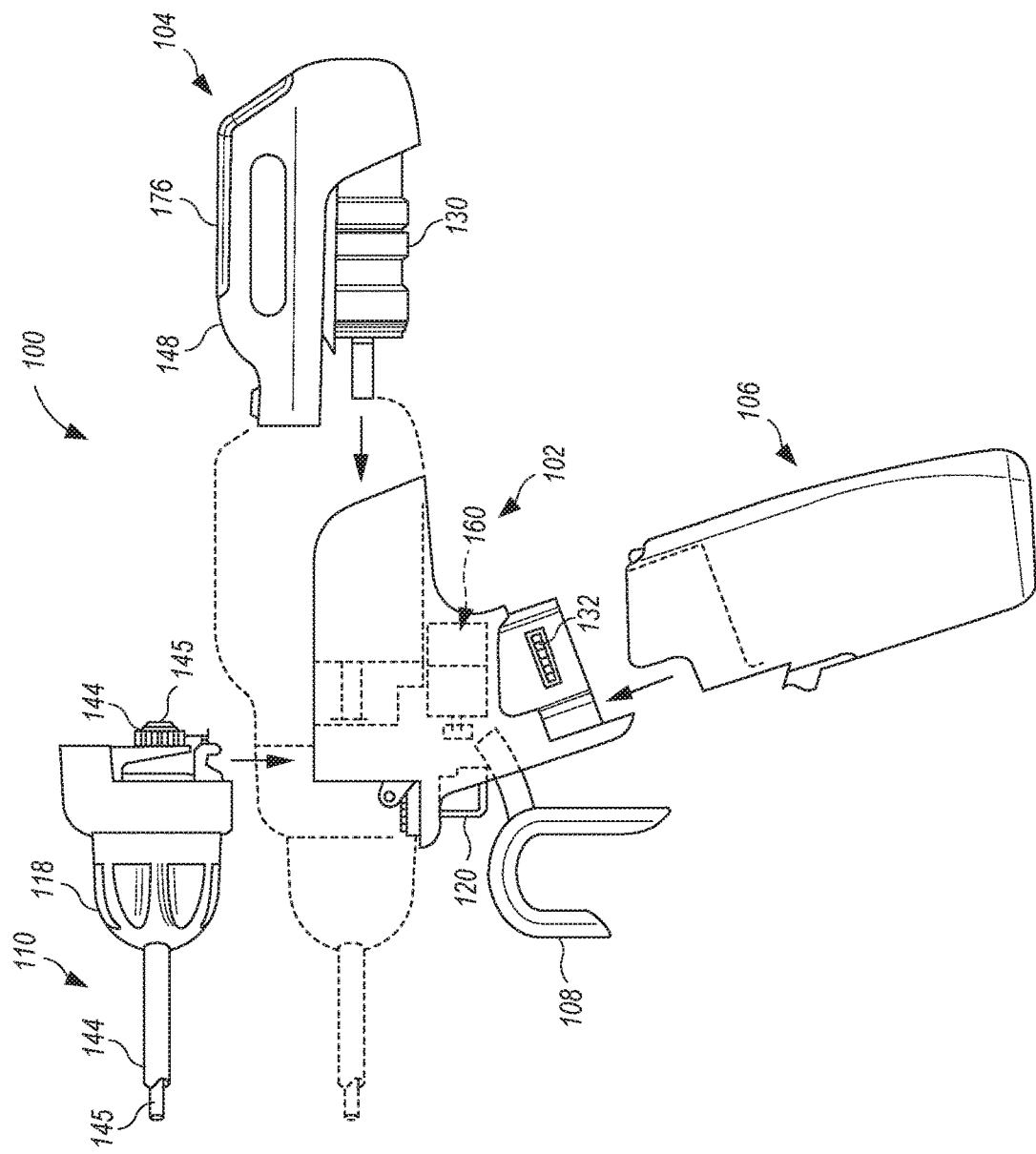
FIG. 2 is an exploded view of the surgical instrument shown in FIG. 1, according to an aspect of the present disclosure.

FIG. 1 is a diagram of a modular battery powered handheld ultrasonic surgical instrument 100, according to an aspect of the present disclosure. FIG. 2 is an exploded view of the surgical instrument 100 shown in FIG. 1, according to an aspect of the present disclosure. With reference now to FIGS. 1 and 2, the surgical instrument 100 comprises a handle assembly 102, an ultrasonic transducer/generator assembly 104, a battery assembly 106, a shaft assembly 110, and an end effector 112. The ultrasonic transducer/generator assembly 104, battery assembly 106, and shaft assembly 110 are modular components that are removably connectable to the handle assembly 102. The handle assembly 102 comprises a motor assembly 160. In addition, some aspects of the surgical instrument 100 include battery assemblies 106 that contain the ultrasonic generator and motor control circuits. The battery assembly 106 includes a first stage generator function with a final stage existing as part of the ultrasonic transducer/generator assembly 104 for driving 55 kHz and 33.1 Khz ultrasonic transducers. A different final stage generator for interchangeable use with the battery assembly 106, common generator components, and segmented circuits enable battery assembly 106 to power up sections of the drive circuits in a controlled manner and to enable checking of stages of the circuit before powering them up and enabling power management modes. In addition, general purpose controls may be provide in the handle assembly 102 with dedicated shaft assembly 110 controls located on the shafts that have those functions. For instance, an end effector 112 module may comprise distal rotation electronics, the shaft assembly 110 may comprise rotary shaft control along with articulation switches, and the handle assembly 102 may comprise energy activation controls and jaw member 114 trigger 108 controls to clamp and unclamp the end effector 112.

Figure 4:
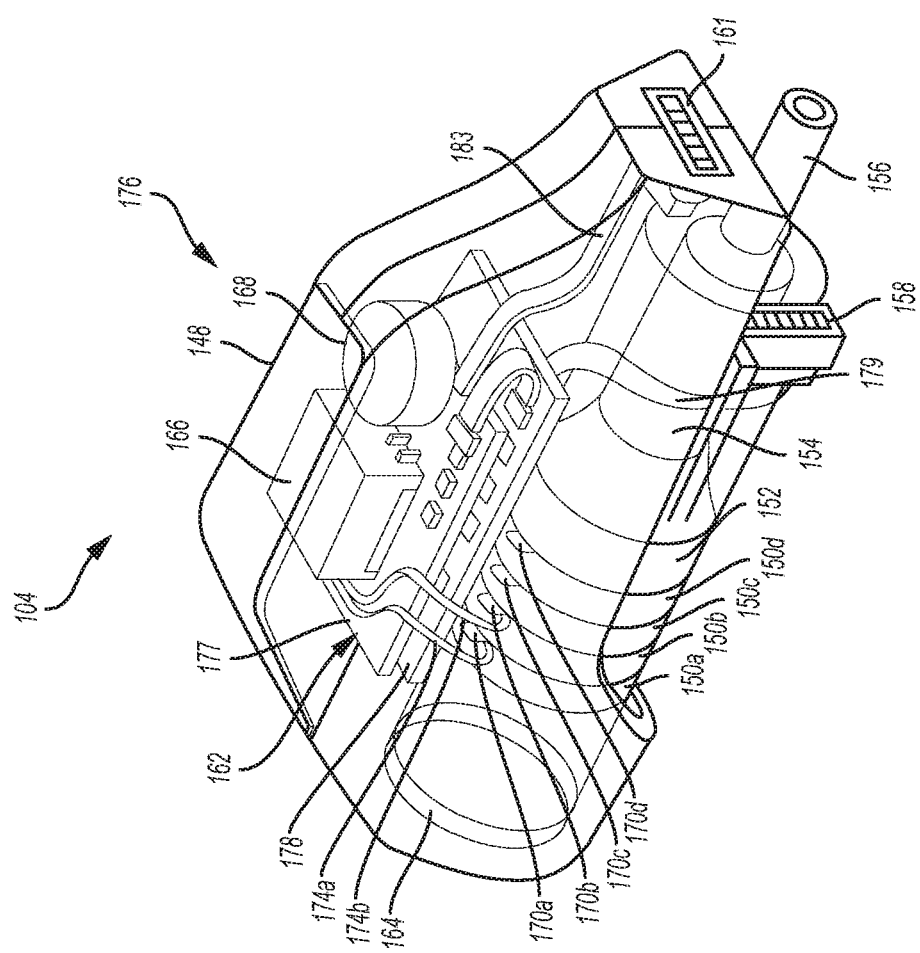
FIG. 4 is a perspective transparent view of the ultrasonic transducer/generator assembly of the surgical instrument shown in FIG. 1, according to aspect of the present disclosure.

The ultrasonic transducer/generator assembly 104 comprises a housing 148, a display 176, such as a liquid crystal display (LCD), for example, an ultrasonic transducer 130, and an ultrasonic generator 162 (FIG. 4). The shaft assembly 110 comprises an outer tube 144 an ultrasonic transmission waveguide 145, and an inner tube (not shown). The end effector 112 comprises a jaw member 114 and an ultrasonic blade 116. As described hereinbelow, a motor or other mechanism operated by the trigger 108 may be employed to close the jaw member 114. The ultrasonic blade 116 is the distal end of the ultrasonic transmission waveguide 145. The jaw member 114 is pivotally rotatable to grasp tissue between the jaw member and the ultrasonic blade 116. The jaw member 114 is operably coupled to a trigger 108 such that when the trigger 108 is squeezed the jaw member 114 closes to grasp tissue and when the trigger 108 is released the jaw member 114 opens to release tissue. In a one-stage trigger configuration, the trigger 108 functions to close the jaw member 114 when the trigger 108 is squeezed and to open the jaw member 114 when the trigger 108 is released. Once the jaw member 114 is closed, the switch 120 is activated to energize the ultrasonic generator to seal and cut the tissue. In a two-stage trigger configuration, during the first stage, the trigger 108 is squeezed part of the way to close the jaw member 114 and, during the second stage, the trigger 108 is squeezed the rest of the way to energize the ultrasonic generator to seal and cut the tissue. The jaw member 114a opens by releasing the trigger 108 to release the tissue. It will be appreciated that in other aspects, the ultrasonic transducer 103 may be activated without the jaw member 114 being closed.

The battery assembly 106 is electrically connected to the handle assembly 102 by an electrical connector 132. The handle assembly 102 is provided with a switch 120. The ultrasonic blade 116 is activated by energizing the ultrasonic transducer/generator circuit by actuating the switch 120. The battery assembly 106, according to one aspect, is a rechargeable, reusable battery pack with regulated output. In some cases, as is explained below, the battery assembly 106 facilitates user-interface functions. The handle assembly 102 is a disposable unit that has bays or docks for attachment to the battery assembly 106, the ultrasonic transducer/generator assembly 104, and the shaft assembly 110. The handle assembly 102 also houses various indicators including, for example, a speaker/buzzer and activation switches. In one aspect, the battery assembly is a separate component that is inserted into the housing of the handle assembly through a door or other opening defined by the housing of the handle assembly.

The ultrasonic transducer/generator assembly 104 is a reusable unit that produces high frequency mechanical motion at a distal output. The ultrasonic transducer/generator assembly 104 is mechanically coupled to the shaft assembly 110 and the ultrasonic blade 116 and, during operation of the device, produces movement at the distal output of the ultrasonic blade 116. In one aspect, the ultrasonic transducer/generator assembly 104 also provides a visual user interface, such as, through a red/green/blue (RGB) light-emitting diode (LED), LCD, or other display. As such, a visual indicator of the battery status is uniquely not located on the battery and is, therefore, remote from the battery.

In accordance with various aspects of the present disclosure, the three components of the surgical instrument 100, e.g., the ultrasonic transducer/generator assembly 104, the battery assembly 106, and the shaft assembly 110, are advantageously quickly disconnectable from one or more of the others. Each of the three components of the surgical instrument 100 is sterile and can be maintained wholly in a sterile field during use. Because the components of the surgical instrument 100 are separable, the surgical instrument 100 can be composed of one or more portions that are single-use items (e.g., disposable) and others that are multi-use items (e.g., sterilizable for use in multiple surgical procedures). Aspects of the components separate as part of the surgical instrument 100. In accordance with an additional aspect of the present disclosure, the handle assembly 102, battery assembly 106, and shaft assembly 110 components is equivalent in overall weight; each of the handle assembly 102, battery assembly 106, and shaft assembly 110 components is balanced so that they weigh the same or substantially the same. The handle assembly 102 overhangs the operator's hand for support, allowing the user's hand to more freely operate the controls of the surgical instrument 100 without bearing the weight. This overhang is set to be very close to the center of gravity. This combined with a triangular assembly configuration, makes the surgical instrument 100 advantageously provided with a center of balance that provides a very natural and comfortable feel to the user operating the device. That is, when held in the hand of the user, the surgical instrument 100 does not have a tendency to tip forward or backward or side-to-side, but remains relatively and dynamically balanced so that the waveguide is held parallel to the ground with very little effort from the user. Of course, the instrument can be placed in non-parallel angles to the ground just as easily.

A rotation knob 118 is operably coupled to the shaft assembly 110. Rotation of the rotation knob 118 ±360° in the direction indicated by the arrows 126 causes an outer tube 144 to rotate ±360° in the respective direction of the arrows 128. In one aspect, the rotation knob 118 may be configured to rotate the jaw member 114 while the ultrasonic blade 116 remains stationary and a separate shaft rotation knob may be provided to rotate the outer tube 144 ±360°. In various aspects, the ultrasonic blade 116 does not have to stop at ±360° and can rotate at an angle of rotation that is greater than ±360°. The outer tube 144 may have a diameter $D_1$ ranging from 5 mm to 10 mm, for example.

The ultrasonic blade 116 is coupled to an ultrasonic transducer 130 (FIG. 2) portion of the ultrasonic transducer/generator assembly 104 by an ultrasonic transmission waveguide located within the shaft assembly 110. The ultrasonic blade 116 and the ultrasonic transmission waveguide may be formed as a unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the ultrasonic blade 116 may be separable (and of differing composition) from the ultrasonic transmission waveguide, and coupled by, for example, a stud, weld, glue, quick connect, or other suitable known methods. The length of the ultrasonic transmission waveguide may be an integral number of one-half wavelengths (n$\lambda$/2), for example. The ultrasonic transmission waveguide may be preferably fabricated from a solid core shaft constructed out of material suitable to propagate ultrasonic energy efficiently, such as the titanium alloy discussed above (i.e., Ti6Al4V) or any suitable aluminum alloy, or other alloys, or other materials such as sapphire, for example.

The ultrasonic transducer/generator assembly 104 also comprises electronic circuitry for driving the ultrasonic transducer 130. The ultrasonic blade 116 may be operated at a suitable vibrational frequency range may be about 20 Hz to 120 kHz and a well-suited vibrational frequency range may be about 30-100 kHz. A suitable operational vibrational frequency may be approximately 55.5 kHz, for example. The ultrasonic transducer 130 is energized by the actuating the switch 120.

It will be appreciated that the terms "proximal" and "distal" are used herein with reference to a clinician gripping the handle assembly 102. Thus, the ultrasonic blade 116 is distal with respect to the handle assembly 102, which is more proximal. It will be further appreciated that, for convenience and clarity, spatial terms such as "top" and "bottom" also are used herein with respect to the clinician gripping the handle assembly 102. However, surgical instruments are used in many orientations and positions, and these terms are not intended to be limiting and absolute.

Figure 3:
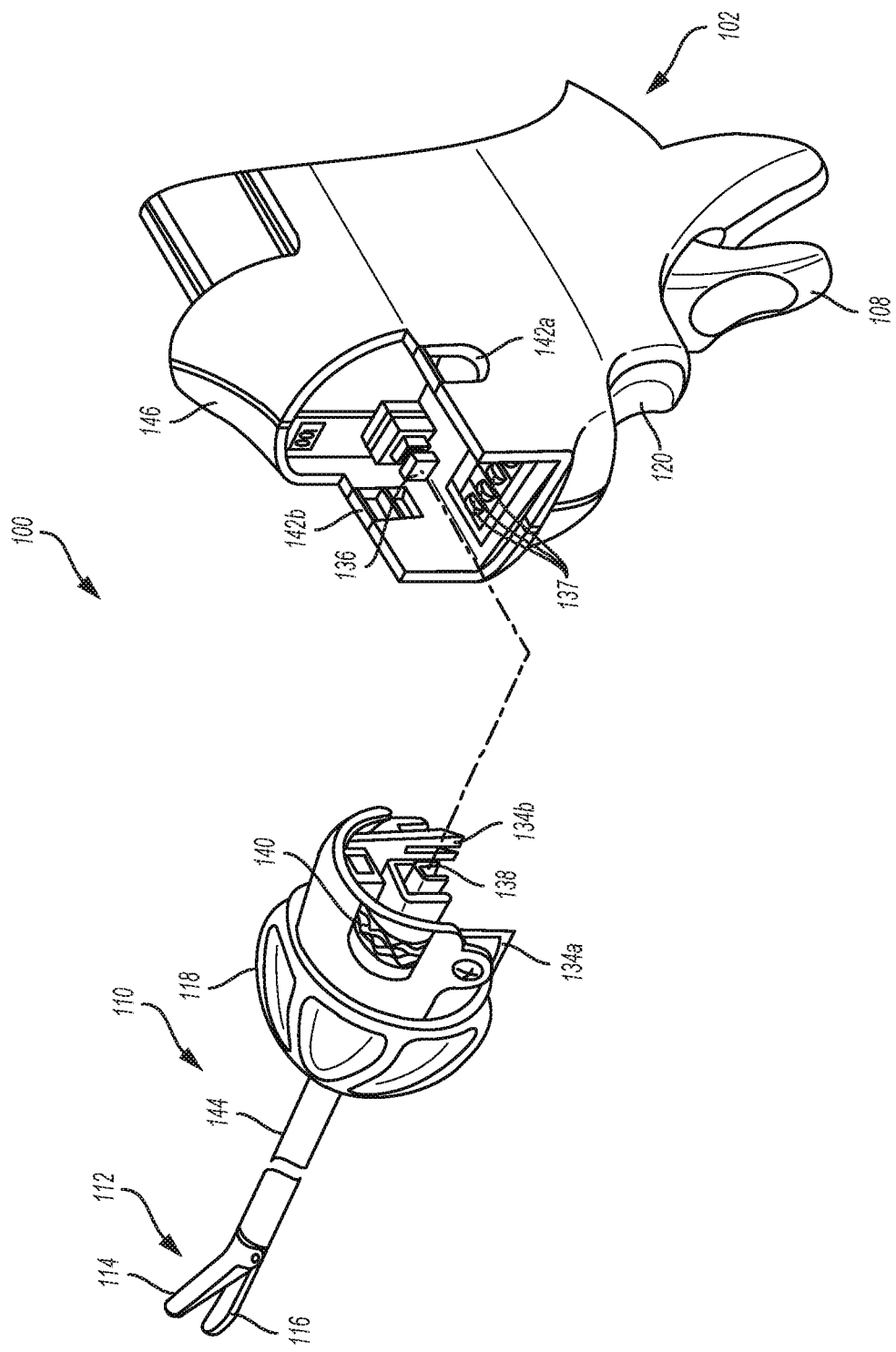
FIG. 3 is an exploded view of a modular shaft assembly of the surgical instrument shown in FIG. 1, according to aspect of the present disclosure.

FIG. 3 is an exploded view of a modular shaft assembly 110 of the surgical instrument 100 shown in FIG. 1, according to aspect of the present disclosure. The surgical instrument 100 uses ultrasonic vibration to carry out a surgical treatment on living tissue. The shaft assembly 110 couples to the handle assembly 102 via slots 142a, 142b formed on the handle assembly 102 and tabs 134a, 134b on the shaft assembly 110. The handle assembly 102 comprises a male coupling member 136 that is received in a corresponding female coupling member in the 138 shaft assembly 110. The male coupling member 136 is operably coupled to the trigger 108 such that when the trigger 108 is squeezed the male coupling member 136 translates distally to drive a closure tube mechanism 140 that translates an outer tube portion of the shaft assembly 110 to close the jaw member 114. As previously discussed, when the trigger 108 is released, the jaw member 114 opens. The male coupling member 136 also couples to the ultrasonic transmission waveguide 145 (FIG. 2) located within the outer tube 144 of the shaft assembly 110 and couples to the ultrasonic transducer 130 (FIG. 2), which is received within the nozzle 146 of the handle assembly 102. The shaft assembly 110 is electrically coupled to the handle assembly 102 via electrical contacts 137.

Figure 5:
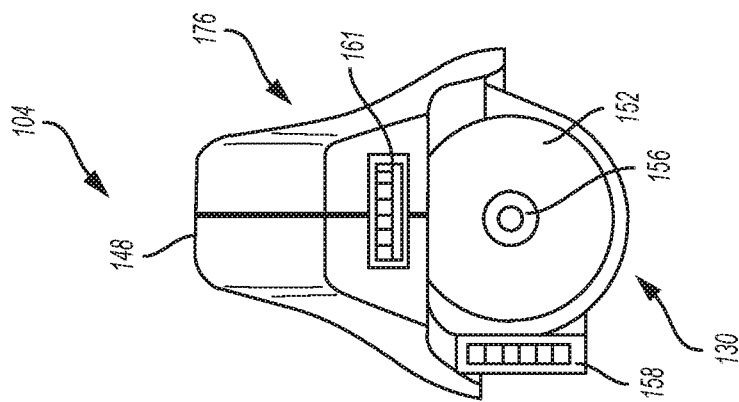
FIG. 5 is an end view of the ultrasonic transducer/generator assembly, according to aspect of the present disclosure.
Figure 6:
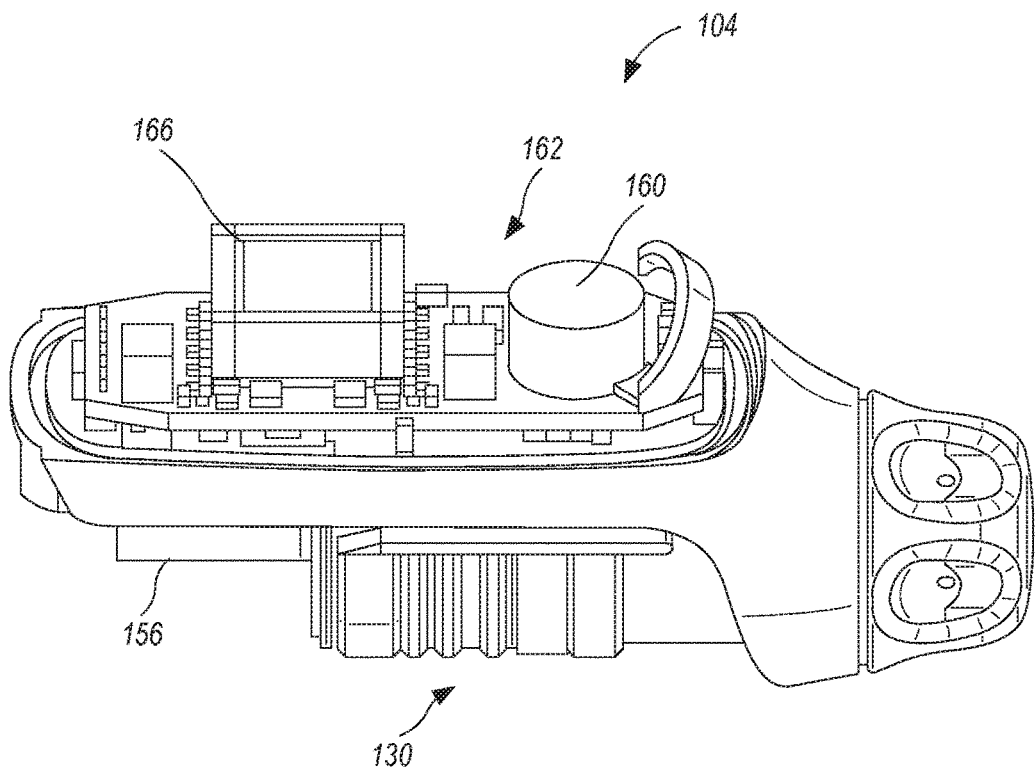
FIG. 6 is a perspective view of the ultrasonic transducer/generator assembly with the top housing portion removed to expose the ultrasonic generator, according to aspect of the present disclosure.
Figure 7:
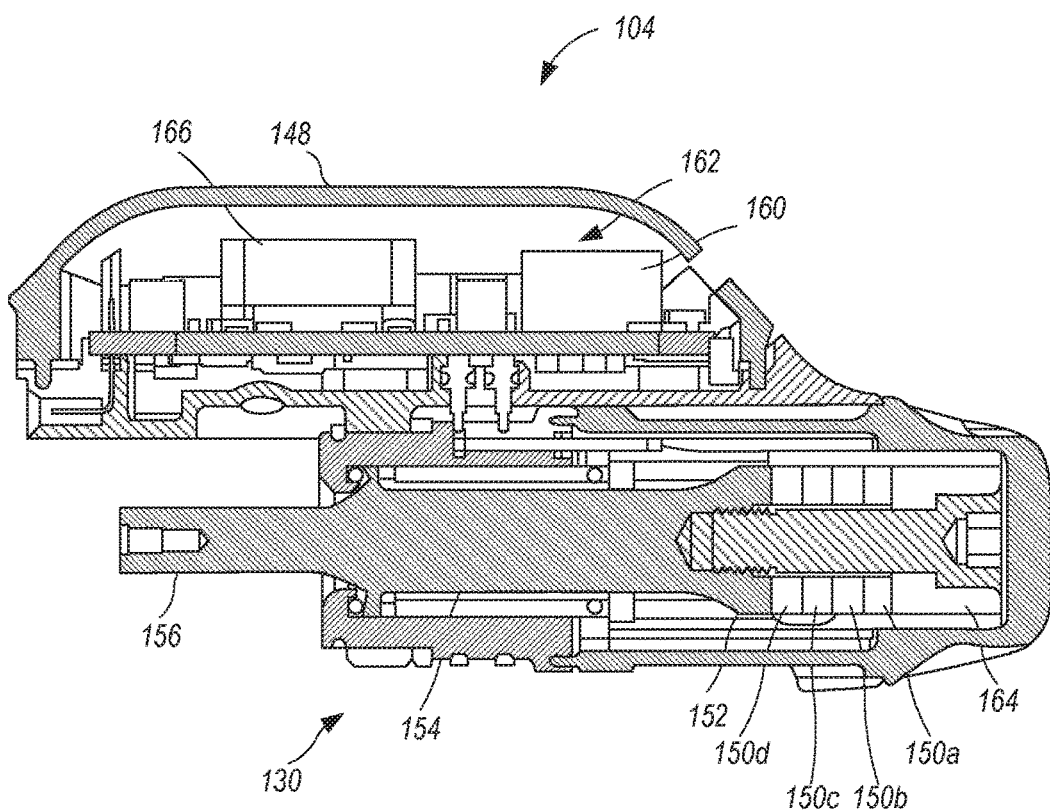
FIG. 7 is a sectional view of the of the ultrasonic transducer/generator assembly, according to aspect of the present disclosure.

FIG. 4 is a perspective transparent view of the ultrasonic transducer/generator assembly 104 of the surgical instrument 100 shown in FIG. 1, according to aspect of the present disclosure. FIG. 5 is an end view of the ultrasonic transducer/generator assembly 104, FIG. 6 is a perspective view of the ultrasonic transducer/generator assembly 104 with the top housing portion removed to expose the ultrasonic generator 162, and FIG. 7 is a sectional view of the of the ultrasonic transducer/generator assembly 104. With reference now to FIGS. 4-7, the ultrasonic transducer/generator assembly 104 comprises an ultrasonic transducer 130, an ultrasonic generator 162 to drive the ultrasonic transducer 130, and a housing 148. A first electrical connector 158 couples the ultrasonic generator 162 to the battery assembly 106 (FIGS. 1 and 2) and a second electrical connector 161 couples the ultrasonic generator 162 to the nozzle (FIG. 3). In one aspect, a display 176 may be provided on one side of the ultrasonic transducer/generator assembly 104 housing 148.

Figure 11:
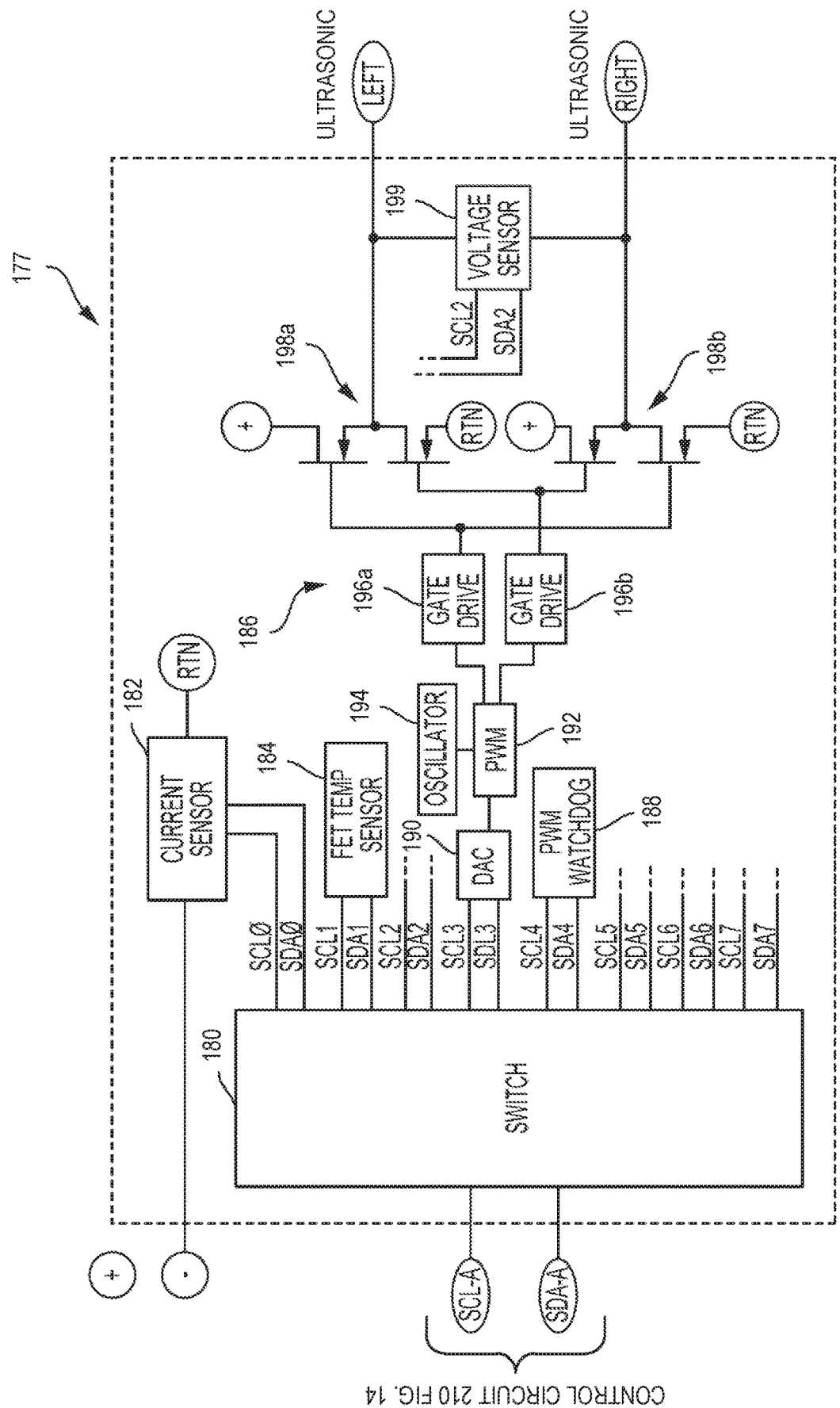
FIG. 11 is a schematic diagram of one aspect of an ultrasonic drive circuit shown in FIG. 4 suitable for driving an ultrasonic transducer, according to one aspect of the present disclosure.

The ultrasonic generator 162 comprises an ultrasonic driver circuit such as the electrical circuit 177 shown in FIG. 11 and, in some aspects, a second stage amplifier circuit 178. The electrical circuit 177 is configured for driving the ultrasonic transducer 130 and forms a portion of the ultrasonic generator circuit. The electrical circuit 177 comprises a transformer 166 and a blocking capacitor 168, among other components. The transformer 166 is electrically coupled to the piezoelectric elements 150a, 150b, 150c, 150d of the ultrasonic transducer 130. The electrical circuit 177 is electrically coupled to first electrical connector 158 via a first cable 179. The first electrical connector 158 is electrically coupled to the battery assembly 106 (FIGS. 1 and 2). The electrical circuit 177 is electrically coupled to second electrical connector 160 via a second cable 183. The second electrical connector 160 is electrically coupled to the nozzle 146 (FIG. 3). In one aspect, the second stage amplifier circuit 178 may be employed in a two stage amplification system.

The ultrasonic transducer 130, which is known as a "Langevin stack", generally includes a transduction portion comprising piezoelectric elements 150a-150d, a first resonator portion or end-bell 164, and a second resonator portion or fore-bell 152, and ancillary components. The total construction of these components is a resonator. There are other forms of transducers, such as magnetostrictive transducers, that could also be used. The ultrasonic transducer 130 is preferably an integral number of one-half system wavelengths (n$\lambda$/2; where "n" is any positive integer; e.g., n=1, 2, 3 . . . ) in length as will be described in more detail later. An acoustic assembly includes the end-bell 164, ultrasonic transducer 130, fore-bell 152, and a velocity transformer 154.

The distal end of the end-bell 164 is acoustically coupled to the proximal end of the piezoelectric element 150a, and the proximal end of the fore-bell 152 is acoustically coupled to the distal end of the piezoelectric element 150d. The fore-bell 152 and the end-bell 164 have a length determined by a number of variables, including the thickness of the transduction portion, the density and modulus of elasticity of the material used to manufacture the end-bell 164 and the fore-bell 152, and the resonant frequency of the ultrasonic transducer 130. The fore-bell 152 may be tapered inwardly from its proximal end to its distal end to amplify the ultrasonic vibration amplitude at the velocity transformer 154, or alternately may have no amplification. A suitable vibrational frequency range may be about 20 Hz to 120 kHz and a well-suited vibrational frequency range may be about 30-100 kHz. A suitable operational vibrational frequency may be approximately 55.5 kHz, for example.

The ultrasonic transducer 130 comprises several piezoelectric elements 150a-150d acoustically coupled or stacked to form the transduction portion. The piezoelectric elements 150a-150d may be fabricated from any suitable material, such as, for example, lead zirconate-titanate, lead metaniobate, lead titanate, barium titanate, or other piezoelectric ceramic material. Electrically conductive elements 170a, 170b, 170c, 170d are inserted between the piezoelectric elements 150a-150d to electrically couple the electrical circuit 177 to the piezoelectric elements 150a-150d. The electrically conductive element 170a located between piezoelectric elements 150a, 150b and the electrically conductive element 170d located between piezoelectric element 150d and the fore-bell 152 are electrically coupled to the positive electrode 174a of the electrical circuit 177. The electrically conductive element 170b located between piezoelectric elements 150b, 150c and the electrically conductive element 170c located between piezoelectric elements 150c, 150d are electrically coupled to the negative electrode 174b of the electrical circuit 177. The positive and negative electrodes 174a, 174b are electrically coupled to the electrical circuit 177 by electrical conductors.

The ultrasonic transducer 130 converts the electrical drive signal from the electrical circuit 177 into mechanical energy that results in primarily a standing acoustic wave of longitudinal vibratory motion of the ultrasonic transducer 130 and the ultrasonic blade 116 (FIGS. 1 and 3) at ultrasonic frequencies. In another aspect, the vibratory motion of the ultrasonic transducer 130 may act in a different direction. For example, the vibratory motion may comprise a local longitudinal component of a more complicated motion of the ultrasonic blade 116. When the acoustic assembly is energized, a vibratory motion in the form of a standing wave is generated through the ultrasonic transducer 130 to the ultrasonic blade 116 at a resonance and amplitude determined by various electrical and geometrical parameters. The amplitude of the vibratory motion at any point along the acoustic assembly depends upon the location along the acoustic assembly at which the vibratory motion is measured. A minimum or zero crossing in the vibratory motion standing wave is generally referred to as a node (i.e., where motion is minimal), and a local absolute value maximum or peak in the standing wave is generally referred to as an anti-node (i.e., where local motion is maximal). The distance between an anti-node and its nearest node is one-quarter wavelength (λ/4).

The wires transmit an electrical drive signal from the electrical circuit 177 to the positive electrode 170a and the negative electrode 170b. The piezoelectric elements 150a-150d are energized by the electrical signal supplied from the electrical circuit 177 in response to an actuator, such as the switch 120, for example, to produce an acoustic standing wave in the acoustic assembly. The electrical signal causes disturbances in the piezoelectric elements 150a-150d in the form of repeated small displacements resulting in large alternating compression and tension forces within the material. The repeated small displacements cause the piezoelectric elements 150a-150d to expand and contract in a continuous manner along the axis of the voltage gradient, producing longitudinal waves of ultrasonic energy. The ultrasonic energy is transmitted through the acoustic assembly to the ultrasonic blade 116 (FIGS. 1 and 3) via a transmission component or an ultrasonic transmission waveguide through the shaft assembly 110 (FIGS. 1-3).

Figure 10A:
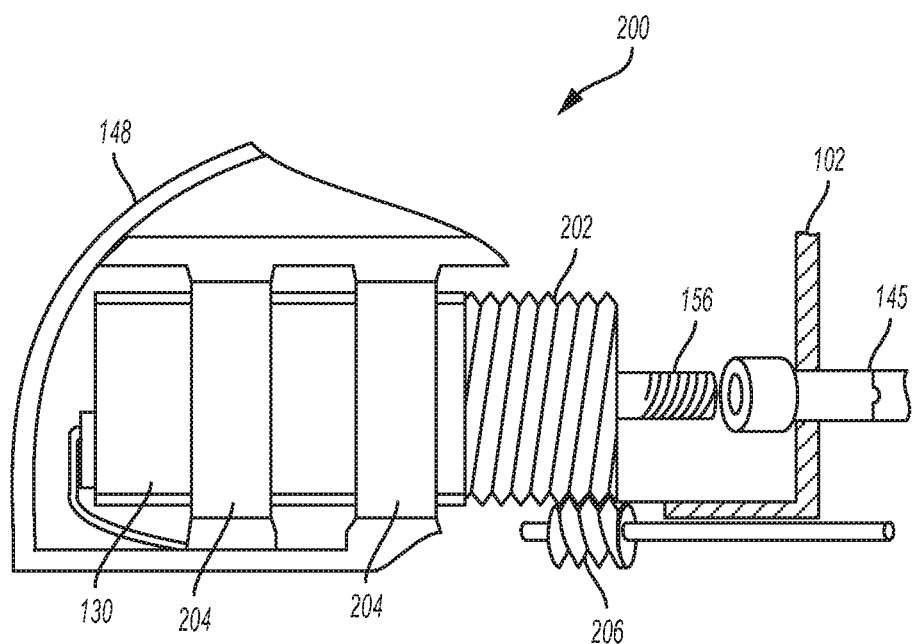
FIGS. 10A and 10B illustrate a shifting assembly that selectively rotates the ultrasonic transmission waveguide with respect to the ultrasonic transducer and urges them towards one another, according to one aspect of the present disclosure.
Figure 10B:
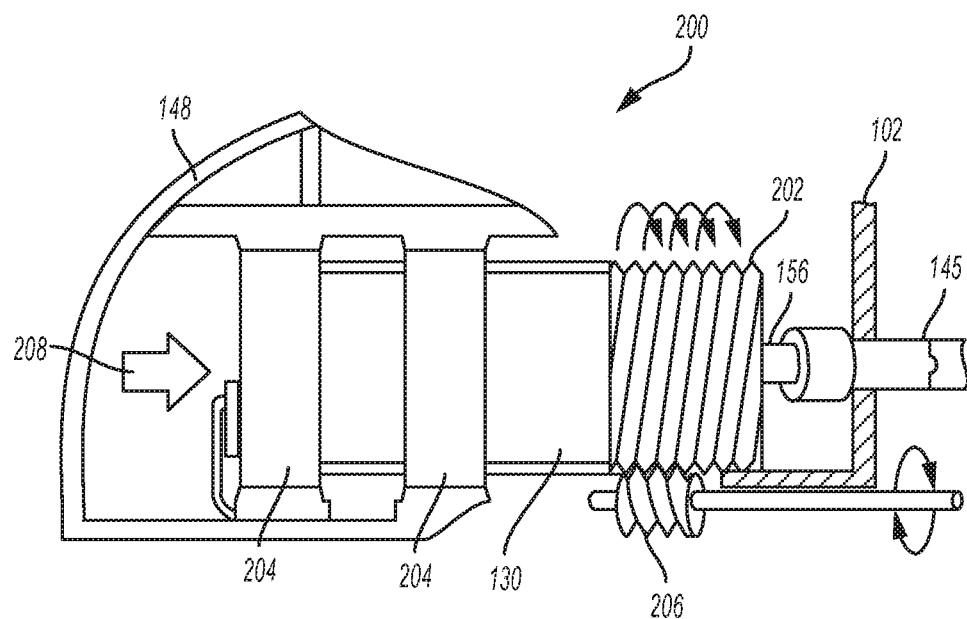

In order for the acoustic assembly to deliver energy to the ultrasonic blade 116 (FIGS. 1 and 3), components of the acoustic assembly are acoustically coupled to the ultrasonic blade 116. A coupling stud 156 of the ultrasonic transducer 130 is acoustically coupled to the ultrasonic transmission waveguide 145 by a threaded connection such as a stud. In one aspect, the ultrasonic transducer 130 may be acoustically coupled to the ultrasonic transmission waveguide 145 as shown in FIGS. 10A and 10B.

The components of the acoustic assembly are preferably acoustically tuned such that the length of any assembly is an integral number of one-half wavelengths (nλ/2), where the wavelength λ is the wavelength of a pre-selected or operating longitudinal vibration drive frequency $f_d$ of the acoustic assembly. It is also contemplated that the acoustic assembly may incorporate any suitable arrangement of acoustic elements.

The ultrasonic blade 116 (FIGS. 1 and 3) may have a length that is an integral multiple of one-half system wavelengths (nλ/2). A distal end of the ultrasonic blade 116 may be disposed near an antinode in order to provide the maximum longitudinal excursion of the distal end. When the ultrasonic transducer 130 is energized, the distal end of the ultrasonic blade 116 may be configured to move in the range of, for example, approximately 10 to 500 microns peak-to-peak, and preferably in the range of about 30 to 150 microns, and in some aspects closer to 100 microns, at a predetermined vibrational frequency of 55 kHz, for example.

Figure 8:
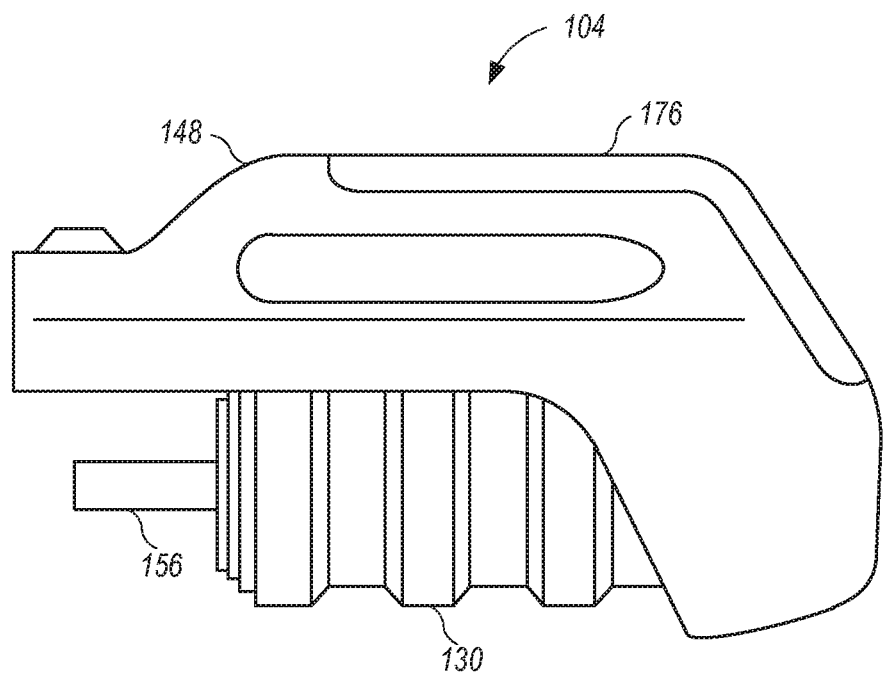
FIG. 8 is an elevation view of an ultrasonic transducer/generator assembly that is configured to operate at 31 kHz resonant frequency, according to one aspect of the present disclosure.
Figure 9:
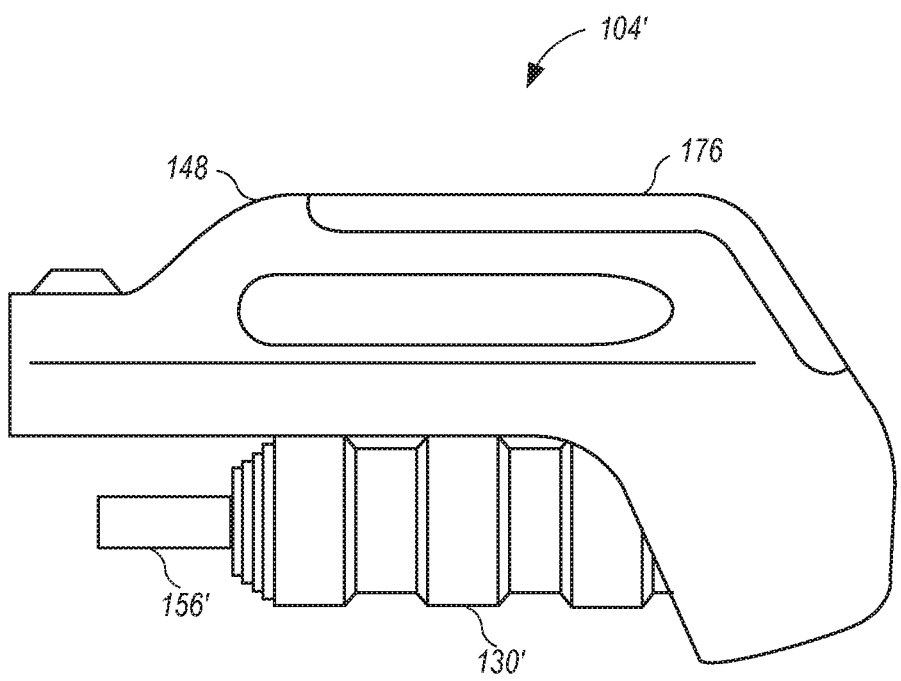
FIG. 9 is an elevation view of an ultrasonic transducer/generator assembly that is configured to operate at 55 kHz resonant frequency, according to one aspect of the present disclosure.

FIG. 8 is an elevation view of an ultrasonic transducer/generator assembly 104 that is configured to operate at 31 kHz resonant frequency, according to one aspect of the present disclosure. FIG. 9 is an elevation view of an ultrasonic transducer/generator assembly 104' that is configured to operate at 55 kHz resonant frequency, according to one aspect of the present disclosure. As can be seen, the ultrasonic transducer/generator assemblies 104, 104', the housings 148 are the same size in order to fit into the nozzle 146 of the surgical instrument 100 shown in FIG. 3. Nevertheless, the individual ultrasonic transducers 130, 130' will vary in size depending on the desired resonant frequency. For example, the ultrasonic transducer 130 shown in FIG. 8 is tuned at a resonant frequency of 31 kHz is physically larger than the ultrasonic transducer 130' shown in FIG. 9, which is tuned at a resonant frequency of 55 kHz. The coupling stud 156, 156' of the ultrasonic transducer 130, 130' may be acoustically coupled to the ultrasonic transmission waveguide 145 by a threaded connection such as a stud.

FIGS. 10A and 10B illustrate a shifting assembly 200 that selectively rotates the ultrasonic transmission waveguide 145 with respect to the ultrasonic transducer 130 and urges them towards one another, according to one aspect of the present disclosure. FIG. 10A illustrates the shifting assembly 200 with the ultrasonic transmission waveguide 145 and the ultrasonic transducer 130 in a disengaged configuration and FIG. 10B illustrates the shifting assembly 200 with the ultrasonic transmission waveguide 145 and the ultrasonic transducer 130 in an engaged configuration. With reference now to both FIGS. 10A and 10B, the shifting assembly 200 is located in the handle assembly 102 of the surgical instrument 100. One or more sleeves 204 hold the ultrasonic transducer 130 in place within the housing 148. The distal end of the ultrasonic transducer 130 includes threads 202 that are engaged by a worm gear 206. As the worm gear 206 rotates the ultrasonic transducer 130 is urged in the direction indicated by the arrow 208 to thread the threaded coupling stud 156 into a threaded end of the ultrasonic transmission waveguide 145. The worm gear 206 may be driven by a motor located within the handle assembly 102 of the surgical instrument 100.

In one aspect, the shifting assembly 200 may include a torque limited motor driven attachment of the ultrasonic transmission waveguide 145 via the motor located in the handle assembly 102 that controls shaft actuation of clamping, rotation, and articulation. The shifting assembly 200 in the handle assembly 102 applies the proper torque onto the ultrasonic transmission waveguide 145 into place with a predetermined minimum torque. For instance, the handle assembly 102 may include a transducer torqueing mechanism which shifts the primary motor longitudinally uncoupling the primary drive shaft spur gear and coupling the transducer torqueing gear which rotates the shaft and nozzle therefore screwing the wave guide into the transducer.

FIG. 11 is a schematic diagram of one aspect of a electrical circuit 177 shown in FIG. 4, suitable for driving an ultrasonic transducer 130, according to one aspect of the present disclosure. The electrical circuit 177 comprises an analog multiplexer 180. The analog multiplexer 180 multiplexes various signals from the upstream channels SCL-A/SDA-A such as ultrasonic, battery, and power control circuit. A current sensor 182 is coupled in series with the return or ground leg of the power supply circuit to measure the current supplied by the power supply. A field effect transistor (FET) temperature sensor 184 provides the ambient temperature. A pulse width modulation (PWM) watchdog timer 188 automatically generates a system reset if the main program neglects to periodically service it. It is provided to automatically reset the electrical circuit 177 when it hangs or freezes because of a software or hardware fault. It will be appreciated that the electrical circuit 177 may be configured as an RF driver circuit for driving the ultrasonic transducer 130 or for driving RF electrodes such as the electrical circuit 702 shown in FIG. 34, for example. Accordingly, with reference now back to FIG. 11, the electrical circuit 177 can be used to drive both ultrasonic transducers and RF electrodes interchangeably. If driven simultaneously, filter circuits may be provided in the corresponding first stage circuits 5504 to select either the ultrasonic waveform or the RF waveform. Such filtering techniques are described in commonly owned U.S. patent application Ser. No. 15/265, 293, titled TECHNIQUES FOR CIRCUIT TOPOLOGIES FOR COMBINED GENERATOR, which is herein incorporated by reference in its entirety.

Figure 14:
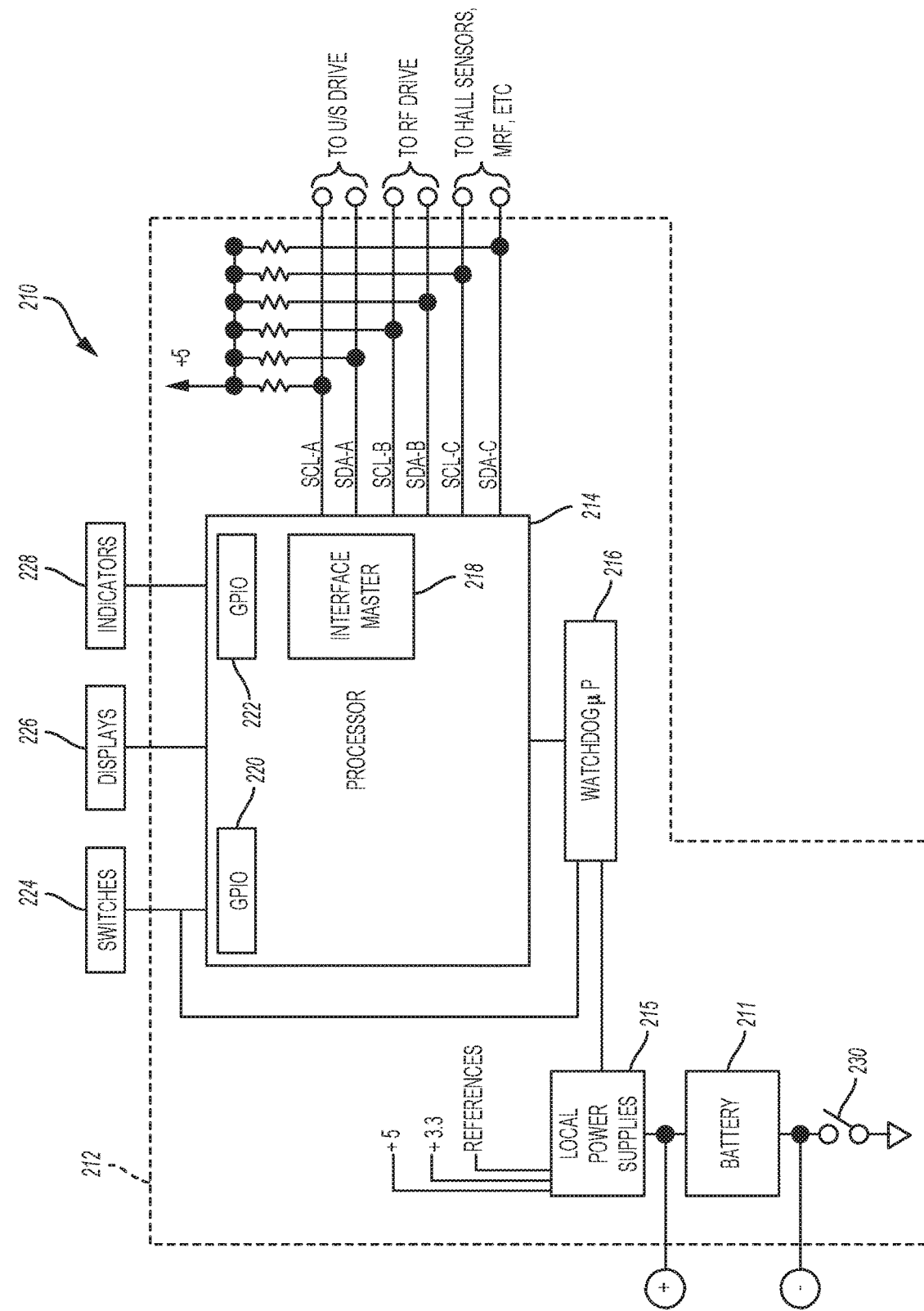
FIG. 14 is a schematic diagram of a control circuit, according to one aspect f the present disclosure.

A drive circuit 186 provides left and right ultrasonic energy outputs. A digital signal the represents the signal waveform is provided to the SCL-A/SDA-A inputs of the analog multiplexer 180 from a control circuit, such as the control circuit 210 (FIG. 14). A digital-to-analog converter 190 (DAC) converts the digital input to an analog output to drive a PWM circuit 192 coupled to an oscillator 194. The PWM circuit 192 provides a first signal to a first gate drive circuit 196a coupled to a first transistor output stage 198a to drive a first ultrasonic (Left) energy output. The PWM circuit 192 also provides a second signal to a second gate drive circuit 196b coupled to a second transistor output stage 198b to drive a second ultrasonic (Right) energy output. A voltage sensor 199 is coupled between the Ultrasonic Left/Right output terminals to measure the output voltage. The drive circuit 186, the first and second drive circuits 196a, 196b, and the first and second transistor output stages 198a, 198b define a first stage amplifier circuit. In operation, the control circuit 210 (FIG. 14) generates a digital waveform 1800 (FIG. 67) employing circuits such as direct digital synthesis (DDS) circuits 1500, 1600 (FIGS. 65 and 66). The DAC 190 receives the digital waveform 1800 and converts it into an analog waveform, which is received and amplified by the first stage amplifier circuit.

FIG. 12 is a schematic diagram of the transformer 166 coupled to the electrical circuit 177 shown in FIG. 11, according to one aspect of the present disclosure. The Ultrasonic Left/Right input terminals (primary winding) of the transformer 166 are electrically coupled to the Ultrasonic Left/Right output terminals of the electrical circuit 177. The secondary winding of the transformer 166 are coupled to the positive and negative electrodes 174a, 174b. The positive and negative electrodes 174a, 174b of the transformer 166 are coupled to the positive terminal 170a (Stack 1) and the negative terminal 170b (Stack 2) of the ultrasonic transducer 130 (FIG. 4). In one aspect, the transformer 166 has a turns-ratio of n1:n2 of 1:50.

FIG. 13 is a schematic diagram of the transformer 166 shown in FIG. 12 coupled to a test circuit 165, according to one aspect of the present disclosure. The test circuit 165 is coupled to the positive and negative electrodes 174a, 174b. A switch 167 is placed in series with an inductor/capacitor/resistor (LCR) load that simulates the load of an ultrasonic transducer.

FIG. 14 is a schematic diagram of a control circuit 210, according to one aspect f the present disclosure. The control circuit 210 is located within a housing of the battery assembly 106. The battery assembly 106 is the energy source for a variety of local power supplies 215. The control circuit comprises a main processor 214 coupled via an interface master 218 to various downstream circuits by way of outputs SCL-A/SDA-A, SCL-B/SDA-B, SCL-C/SDA-C, for example. In one aspect, the interface master 218 is a general purpose serial interface such as an I²C serial interface. The main processor 214 also is configured to drive switches 224 through general purposes input output 220 (GPIO), a display 226 (e.g., and LCD display), and various indicators 228 trough GPIO 222. A watchdog processor 216 is provided to control the main processor 214. A switch 230 is provided in series with the battery 211 to activate the control circuit 212 upon insertion of the battery assembly 106 into the handle assembly 102 (FIGS. 1-3).

In one aspect, the main processor 214 is coupled to the electrical circuit 177 (FIGS. 4 and 11) by way of output terminals SCL-A/SDA-A. The main processor 214 comprises a memory for storing tables of digitized drive signals or waveforms that are transmitted to the electrical circuit 177 for driving the ultrasonic transducer 130 (FIGS. 4-8), for example. In other aspects, the main processor 214 may generate a digital waveform and transmit it to the electrical circuit 177 or may store the digital waveform for later transmission to the electrical circuit 177. The main processor 214 also may provide RF drive by way of output terminals SCL-B/SDA-B and various sensors (e.g., Hall-effect sensors, magnetorheological fluid (MRF) sensors, etc.) by way of output terminals SCL-C/SDA-C. In one aspect, the main processor 214 is configured to sense the presence of ultrasonic drive circuitry and/or RF drive circuitry to enable appropriate software and user interface functionality.

In one aspect, the main processor 214 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QED analog, one or more 12-bit Analog-to-Digital Converters (ADC) with 12 analog input channels, among other features that are readily available for the product datasheet. Other processors may be readily substituted and, accordingly, the present disclosure should not be limited in this context.

Figure 15:
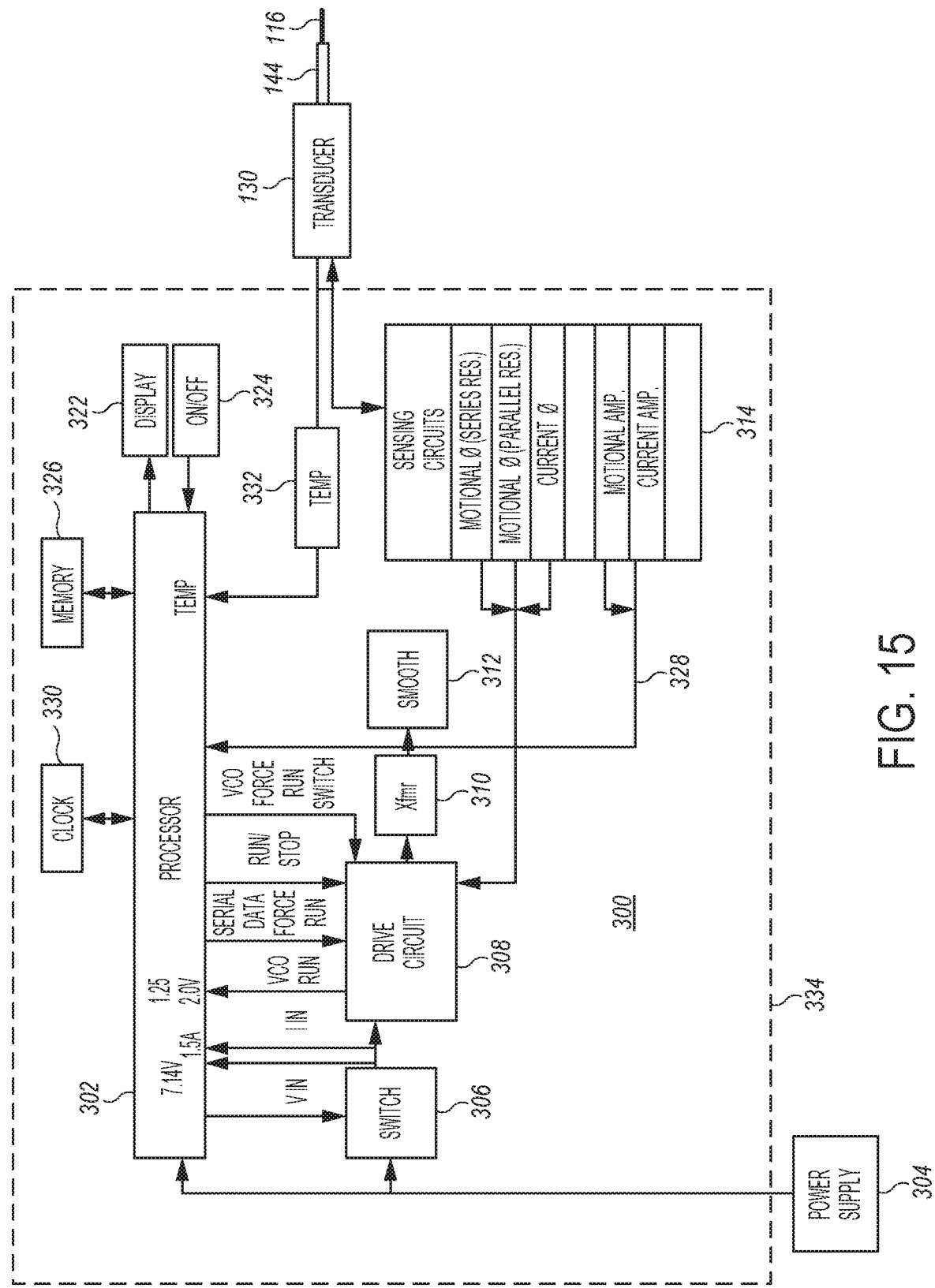
FIG. 15 shows a simplified block circuit diagram illustrating another electrical circuit contained within a modular ultrasonic surgical instrument, according to one aspect of the present disclosure.

FIG. 15 shows a simplified block circuit diagram illustrating another electrical circuit 300 contained within a modular ultrasonic surgical instrument 334, according to one aspect of the present disclosure. The electrical circuit 300 includes a processor 302, a clock 330, a memory 326, a power supply 304 (e.g., a battery), a switch 306, such as a metal-oxide semiconductor field effect transistor (MOSFET) power switch, a drive circuit 308 (PLL), a transformer 310, a signal smoothing circuit 312 (also referred to as a matching circuit and can be, e.g., a tank circuit), a sensing circuit 314, a transducer 130, and a shaft assembly 110 comprising an ultrasonic transmission waveguide that terminates at an ultrasonic blade 116, which may be referred to herein simply as the waveguide.

One feature of the present disclosure that severs dependency on high voltage (120 VAC) input power (a characteristic of general ultrasonic cutting devices) is the utilization of low-voltage switching throughout the wave-forming process and the amplification of the driving signal only directly before the transformer stage. For this reason, in one aspect of the present disclosure, power is derived from only a battery, or a group of batteries, small enough to fit either within the handle assembly 102 (FIGS. 1-3). State-of-the-art battery technology provides powerful batteries of a few centimeters in height and width and a few millimeters in depth. By combining the features of the present disclosure to provide a self-contained and self-powered ultrasonic device, a reduction in manufacturing cost may be achieved.

The output of the power supply 304 is fed to and powers the processor 302. The processor 302 receives and outputs signals and, as will be described below, functions according to custom logic or in accordance with computer programs that are executed by the processor 302. The electrical circuit 300 can also include a memory 326, preferably, random access memory (RAM), that stores computer-readable instructions and data.

The output of the power supply 304 also is directed to a switch 306 having a duty cycle controlled by the processor 302. By controlling the on-time for the switch 306, the processor 302 is able to dictate the total amount of power that is ultimately delivered to the transducer 316. In one aspect, the switch 306 is a MOSFET, although other switches and switching configurations are adaptable as well. The output of the switch 306 is fed to a drive circuit 308 that contains, for example, a phase detecting phase-locked loop (PLL) and/or a low-pass filter and/or a voltage-controlled oscillator. The output of the switch 306 is sampled by the processor 302 to determine the voltage and current of the output signal (V IN and I IN, respectively). These values are used in a feedback architecture to adjust the pulse width modulation of the switch 306. For instance, the duty cycle of the switch 306 can vary from about 20% to about 80%, depending on the desired and actual output from the switch 306.

The drive circuit 308, which receives the signal from the switch 306, includes an oscillatory circuit that turns the output of the switch 306 into an electrical signal having an ultrasonic frequency, e.g., 55 kHz (VCO). As explained above, a smoothed-out version of this ultrasonic waveform is ultimately fed to the ultrasonic transducer 130 to produce a resonant sine wave along the ultrasonic transmission waveguide 145 (FIG. 2).

At the output of the drive circuit 308 is a transformer 310 that is able to step up the low voltage signal(s) to a higher voltage. It is noted that upstream switching, prior to the transformer 310, is performed at low (e.g., battery driven) voltages, something that, to date, has not been possible for ultrasonic cutting and cautery devices. This is at least partially due to the fact that the device advantageously uses low on-resistance MOSFET switching devices. Low on-resistance MOSFET switches are advantageous, as they produce lower switching losses and less heat than a traditional MOSFET device and allow higher current to pass through. Therefore, the switching stage (pre-transformer) can be characterized as low voltage/high current. To ensure the lower on-resistance of the amplifier MOSFET(s), the MOSFET(s) are run, for example, at 10 V. In such a case, a separate 10 VDC power supply can be used to feed the MOSFET gate, which ensures that the MOSFET is fully on and a reasonably low on resistance is achieved. In one aspect of the present disclosure, the transformer 310 steps up the battery voltage to 120V root-mean-square (RMS). Transformers are known in the art and are, therefore, not explained here in detail.

In the circuit configurations described, circuit component degradation can negatively impact the circuit performance of the circuit. One factor that directly affects component performance is heat. Known circuits generally monitor switching temperatures (e.g., MOSFET temperatures). However, because of the technological advancements in MOSFET designs, and the corresponding reduction in size, MOSFET temperatures are no longer a valid indicator of circuit loads and heat. For this reason, according to one aspect of the present disclosure, a sensing circuit 314 senses the temperature of the transformer 310. This temperature sensing is advantageous as the transformer 310 is run at or very close to its maximum temperature during use of the device. Additional temperature will cause the core material, e.g., the ferrite, to break down and permanent damage can occur. The present disclosure can respond to a maximum temperature of the transformer 310 by, for example, reducing the driving power in the transformer 310, signaling the user, turning the power off, pulsing the power, or other appropriate responses.

In one aspect of the present disclosure, the processor 302 is communicatively coupled to the end effector 112, which is used to place material in physical contact with the ultrasonic blade 116, e.g., the clamping mechanism shown in FIG. 1. Sensors are provided that measure, at the end effector 112, a clamping force value (existing within a known range) and, based upon the received clamping force value, the processor 302 varies the motional voltage VM. Because high force values combined with a set motional rate can result in high blade temperatures, a temperature sensor 336 can be communicatively coupled to the processor 302, where the processor 302 is operable to receive and interpret a signal indicating a current temperature of the blade from the temperature sensor 336 and to determine a target frequency of blade movement based upon the received temperature. In another aspect, force sensors such as strain gages or pressure sensors may be coupled to the trigger 108 to measure the force applied to the trigger 108 by the user. In another aspect, force sensors such as strain gages or pressure sensors may be coupled to the switch 120 button such that displacement intensity corresponds to the force applied by the user to the switch 120 button.

According to one aspect of the present disclosure, the PLL portion of the drive circuit 308, which is coupled to the processor 302, is able to determine a frequency of waveguide movement and communicate that frequency to the processor 302. The processor 302 stores this frequency value in the memory 326 when the device is turned off. By reading the clock 330, the processor 302 is able to determine an elapsed time after the device is shut off and retrieve the last frequency of waveguide movement if the elapsed time is less than a predetermined value. The device can then start up at the last frequency, which, presumably, is the optimum frequency for the current load.

Figure 16:
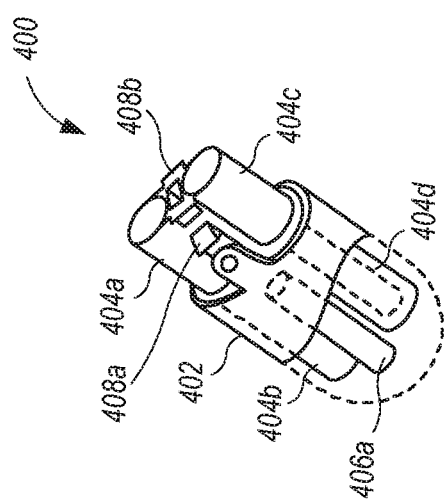
FIG. 16 shows a battery assembly for use with the surgical instrument, according to one aspect of the present disclosure.

FIG. 16 shows a battery assembly 400 for use with the surgical instrument 100, according to one aspect of the present disclosure. The battery assembly 400 comprises a housing 402 sized and configured to contain various energy cells. The energy cells may include rechargeable and non-rechargeable batteries. In one aspect, the battery assembly 400 includes four Li-ion non-rechargeable batteries 404a, 404b, 404c, 404d and two nickel metal hydride (NiMH) rechargeable batteries 406a (the second battery is not shown). The housing 402 comprises tabs 408a, 408b to removably connect the battery assembly 400 to the handle assembly 102 of the surgical instrument 100 (FIGS. 1 and 2).

Figure 17:
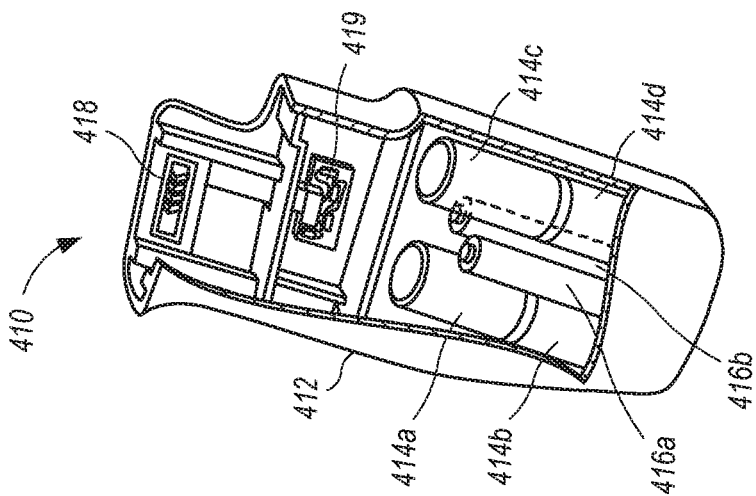
FIG. 17 shows a disposable battery assembly for use with the surgical instrument, according to one aspect of the present disclosure.

FIG. 17 shows a disposable battery assembly 410 for use with the surgical instrument 100, according to one aspect of the present disclosure. In one aspect, the disposable battery assembly 410 comprises a primary cell battery pack for use with a battery powered advanced energy instrument such as the surgical instrument 100 (FIGS. 1 and 2), comprising compensating electronics with additional voltage to offset a voltage sag from the disposable battery assembly 410 to prevent the output voltage from sagging below a predetermined level during operation under load. The disposable battery assembly 410 comprises a housing 412 sized and configured to contain various energy cells. The energy cells may include rechargeable and non-rechargeable batteries. In one aspect, the disposable battery assembly 410 includes four primary Lithium-ion (Li-ion) non-rechargeable batteries 414*a*, 414*b*, 414*c*, 414*d* and two secondary NiMH or Nickel Cadmium (NiCd) rechargeable batteries 416*a*, 416*b*. The housing 412 comprises electrical contact 418 to electrically couple the disposable battery assembly 410 to the handle assembly 102 of the surgical instrument 100. In the illustrated example the electrical contact 418 comprises four metal contacts. The disposable battery assembly 410 also includes electrical circuits 419 such as the control circuit 210 (FIG. 14) and/or the electrical circuit 300 (FIG. 15). The electrical circuits 419 are radiated hardened.

In one aspect, the disposable battery assembly 410 includes batteries 414*a-d*, electrical circuits 419, and other componentry that is resistant to gamma or other radiation sterilization. For instance, a switching mode power supply 460 (FIG. 22) or a linear power supply 470 (FIG. 24) and an optional charge circuit may be incorporated within the housing 412 of the disposable battery assembly 410 to reduce voltage sag of the primary Li-ion batteries 414*a-d* and to allow the secondary NiMH batteries 416*a*, 416*b* to be used to reduce voltage sag. This guarantees full charged cells at the beginning of each surgery that are easy to introduce into the sterile field. A dual type battery assembly including primary Li-ion batteries 414*a-d* and secondary NiMH batteries 416*a-b* can be used with dedicated energy cells 416*a-b* to control the electronics from dedicated energy cells 414*a-d* that run the generator and motor control circuits. In one aspect, the system pulls from the batteries involved in driving the electronics circuits in the case that batteries involved are dropping low. In one aspect, the system would include a one way diode system that would not allow for current to flow in the opposite direction, for example, from the batteries involved in driving the energy and/or motor control circuits to the batteries involved in driving the electronic circuits. In one additional aspect, the system may comprise a gamma friendly charge circuit and switch mode power supply using diodes and vacuum tube components that would minimize voltage sag at a predetermined level. The switch mode power supply may be eliminated by including a minimum sag voltage that is a division of the NiMH voltages (e.g., three NiMH cells). In another aspect, a modular system can be made wherein the radiation hardened components are located in a module, making this module sterilizable by radiation sterilization. Other non-radiation hardened components are included in other modular components and connections are made between the modular components such that the componentry operate together as if the components were located together on the same circuit board. If only two cells of the secondary NiMH batteries 416*a-b* are desired the switch mode power supply based on diodes and vacuum tubes allows for sterilizable electronics within the disposable primary Li-ion batteries 414*a-d*.

Figure 18:
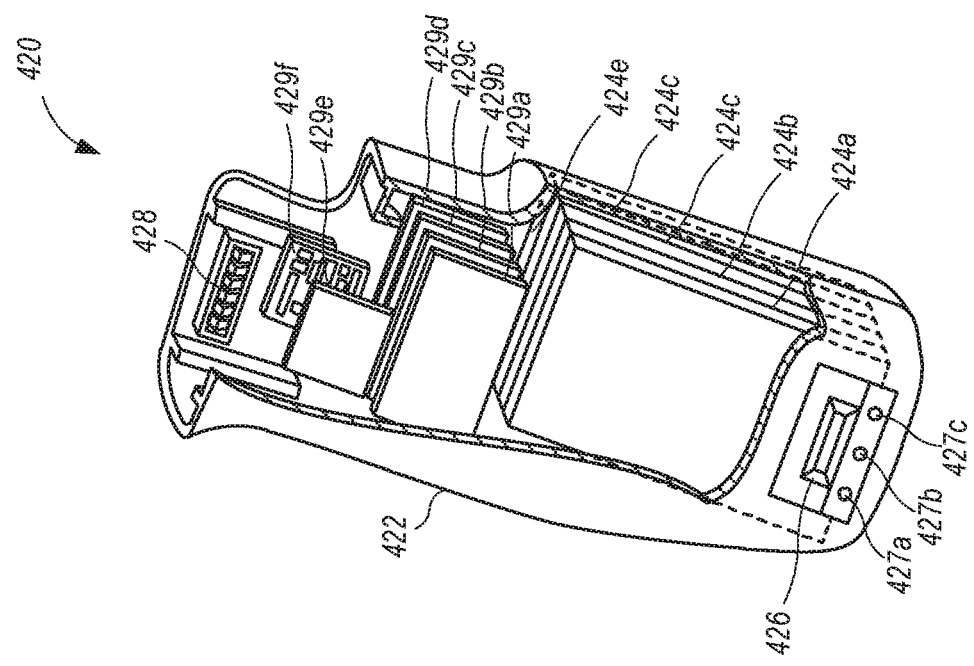
FIG. 18 shows a reusable battery assembly for use with the surgical instrument, according to one aspect of the present disclosure.

FIG. 18 shows a reusable battery assembly 420 for use with the surgical instrument 100, according to one aspect of the present disclosure. The reusable battery assembly 420 comprises a housing 422 sized and configured to contain various rechargeable energy cells. The energy cells may include rechargeable batteries. In one aspect, the reusable battery assembly 420 includes five laminated NiMH rechargeable batteries 424*a*, 424*b*, 424*c*, 424*d*, 424*e*. The housing 422 comprises electrical contact 428 to electrically couple the reusable battery assembly 420 to the handle assembly 102 of the surgical instrument 100 (FIGS. 1 and 2). In the illustrated example, the electrical contact 428 comprises six metal contacts. The reusable battery assembly 420 also includes up to six circuit boards 429*a*, 429*b*, 429*c*, 429*d*, 429*e*, 429*f* that may include electrical circuits such as the control circuit 210 (FIG. 14) and/or the electrical circuit 300 (FIG. 15). In one aspect, the reusable battery assembly 420 comprises drive FET transistors and associated circuitry 429*a-f* in the housing 422 for easy swap and no need to shut down the surgical instrument 100 (FIGS. 1 and 2) to replace the reusable battery assembly 420 with energy delivery.

The reusable battery assembly 420 comprises a battery test switch 426 and up to three LED indicators 427*a*, 427*b*, 427*c* to determine the health of the batteries 424*a-e* in the reusable battery assembly 420. The first LED indicator 427*a* may indicate fully charged batteries 424*a-e* that is ready to use. The second LED indicator 427*b* may indicate that the battery needs to be recharged. The third LED indicator 427*c* may indicate that battery is not good and to dispose. The reusable battery assembly 420 health indication to allow the user to determine the specific health and capabilities of the batteries 424*a-e* before it is inserted and used. For instance, charge status of the rechargeable secondary cells, sag voltage, primary cell voltage are checked by the activation of the battery test switch 426 which could measure these in an unload state or with a predefined resistive load placed on the system. The voltages could have at least one but more preferably three thresholds to compare the resulting voltages checks to. In the case of the first indicator 427*a*, the batteries 424*a-e* indicating whether or not they are suitable to use. With three levels the reusable battery assembly 420 could display full charge, minimum charge, and some marginal but limited charge status. This battery 424*a-e* health monitor would be useful for either the disposable battery assembly 410 (FIG. 17) or the reusable battery assembly 420. In the case of the disposable battery assembly 410 it is a ready/damaged indicator. In the case of the reusable battery assembly 420 it could indicate life remaining, recharge capacity, even age before failure in addition to ready/not ready.

Figure 19:
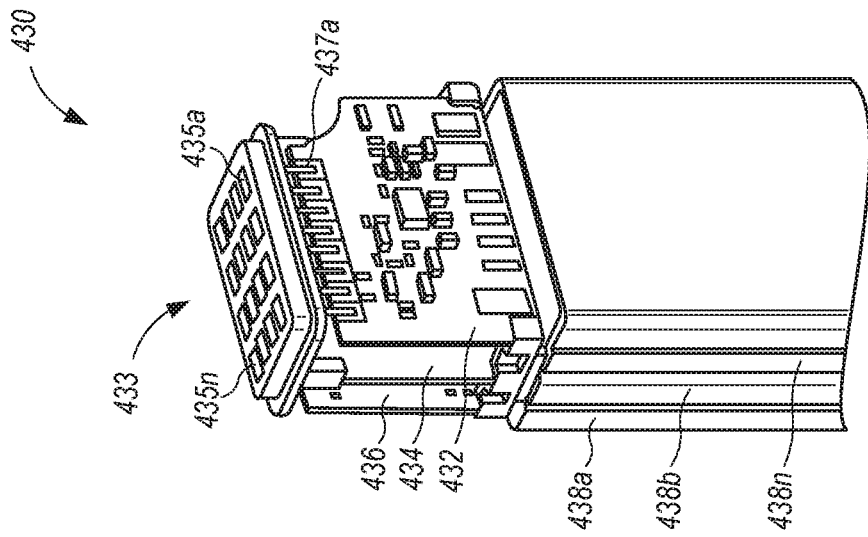
FIG. 19 is an elevated perspective view of a battery assembly with both halves of the housing shell removed exposing battery cells coupled to multiple circuit boards which are coupled to the multi-lead battery terminal in accordance with one aspect of the present disclosure.

FIG. 19 is an elevated perspective view of a removable battery assembly 430 with both halves of the housing shell removed exposing battery cells coupled to multiple circuit boards which are coupled to the multi-lead battery terminal in accordance with an aspect of the present disclosure. Further, more than or less than three circuit boards is possible to provide expanded or limited functionality. As shown in FIG. 19, the multiple circuit boards 432, 434, 436 may be positioned in a stacked architecture, which provides a number of advantages. For example, due to the smaller layout size, the circuit boards have a reduced footprint within the removable battery assembly 430, thereby allowing for a smaller battery. In addition, in this configuration, is possible to easily isolate power boards from digital boards to prevent any noise originating from the power boards to cause harm to the digital boards. Also, the stacked configuration allows for direct connect features between the boards, thereby reducing the presence of wires. Furthermore, the circuit boards can be configured as part of a rigid-flex-rigid circuit to allow the rigid parts to be "fanned" into a smaller volumetric area.

According to aspects of the present disclosure, the circuit board 432, 434, 436 provides a specific function. For instance, one circuit board 432 can provide the components for carrying out the battery protection circuitry. Similarly, another circuit board 434 can provide the components for carrying out the battery controller. Another circuit board 436 can, for example, provide high power buck controller components. Finally, the battery protection circuitry can provide connection paths for coupling the battery cells 438a-n. By placing the circuit boards in a stacked configuration and separating the boards by their respective functions, the boards may be strategically placed in a specific order that best handles their individual noise and heat generation. For example, the circuit board having the high-power buck controller components produces the most heat and, therefore, it can be isolated from the other boards and placed in the center of the stack. In this way, the heat can be kept away from the outer surface of the device in an effort to prevent the heat from being felt by the physician or operator of the device. In addition, the battery board grounds may be configured in a star topology with the center located at the buck controller board to reduce the noise created by ground loops.

The strategically stacked circuit boards, the low thermal conductivity path from the circuit boards to the multi-lead battery terminal assembly, and a flex circuit 3516 are features that assist in preventing heat from reaching the exterior surface of the device. The battery cells and buck components are thermally connected to a flex circuit within the handle assembly 102 (FIGS. 1 and 2) so that the heat generated by the cells and buck components enter a portion away from the physician's hand. The flex circuit presents a relatively high thermal mass, due to its broad area of exposure and the advantageous conduction characteristics of the copper, which redirects, absorbs, and/or dissipates heat across a broader area thereby slowing the concentration of heat and limiting high spot temperatures on the exterior surface of the device. Other techniques may be implemented as well, including, but not limited to, larger heat wells, sinks or insulators, a metal connector cap and heavier copper content in the flex circuit or the handle assembly 102 of the device.

Another advantage of the removable battery assembly 430 is realized when Li-ion batteries are used. As previously stated, Li-ion batteries should not be charged in a parallel configuration of multiple cells. This is because, as the voltage increases in a particular cell, it begins to accept additional charge faster than the other lower-voltage cells. Therefore, the cells are monitored so that a charge to that cell can be controlled individually. When a Li-ion battery is formed from a group of cells 438a-n, a multitude of wires extending from the exterior of the device to the batteries 438a-n is needed (at least one additional wire for each battery cell beyond the first). By having a removable battery assembly 430, a battery cell 438a-n can, in one aspect, have its own exposed set of contacts and, when the removable battery assembly 430 is not present inside the handle assembly 102 (FIGS. 1 and 2), a set of contacts can be coupled to a corresponding set of contacts in an external, non-sterile, battery-charging device. In another aspect, a battery cell 438a-n can be electrically connected to the battery protection circuitry to allow the battery protection circuitry to control and regulate recharging of a cell 438a-n. The removable battery assembly 430 is provided with circuitry to prevent use of the removable battery assembly 430 past an expected term-of-life. This term is not only dictated by the cells but is also dictated by the outer surfaces, including the battery casing or shell and the upper contact assembly. Such circuitry will be explained in further detail below and includes, for example, a use count, a recharge count, and an absolute time from manufacture count.

FIG. 19 also shows a multi-lead battery terminal assembly 433, which is an interface that electrically couples the components within the removable battery assembly 430 to an electrical interface of the handle assembly 102 (FIGS. 1 and 2). It is through the handle assembly 102 that the removable battery assembly 430 is able to electrically (and mechanically) couple with the ultrasonic transducer/generator assembly 104 (FIG. 4). As is explained above, the removable battery assembly 430, through the multi-lead battery terminal assembly 433, provides power to the surgical instrument 100 (FIGS. 1 and 2), as well as other functionality described herein. The multi-lead battery terminal assembly 433 includes a plurality of contacts pads 435a-n capable of separately electrically connecting a terminal within the removable battery assembly 430 to another terminal provided by a docking bay of the handle assembly 102. One example of such electrical connections coupled to the plurality of contact pads 435a-n as power and communication signal paths. In the aspect of the multi-lead battery terminal assembly 433, sixteen different contact pads 435a-n are shown. This number is merely illustrative. In an aspect, an interior side of the battery terminal assembly 433 has a well formed on the molded terminal holder that can be filled with potting materials to create a gas tight seal. The contact pads 435a-n are overmolded in the lid and extend through the potting well into the interior of the battery 430. Here a flex circuit can be used to rearrange the array of pins and provide an electrical connection to the circuit boards. In one example, a 4×4 array is converted to a 2×8 array. In one example the multi-lead battery terminal assembly 433, a plurality of contact pads 435a-n of the multi-lead battery terminal assembly 2804 include a corresponding plurality of interior contact pins 437a-n. A contact pin 437a provides a direct electrical coupling to a corresponding one of the contact pads 435a.

Figure 20:
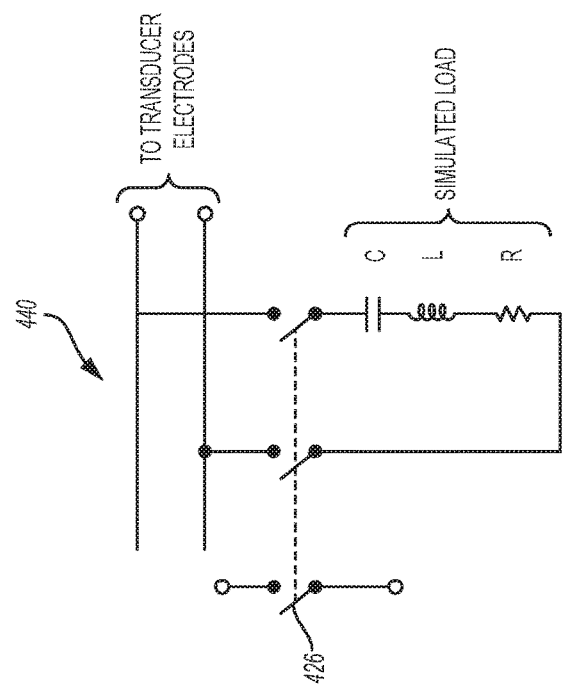
FIG. 20 illustrates a battery test circuit, according to one aspect of the present disclosure.

FIG. 20 illustrates a battery test circuit 440, according to one aspect of the present disclosure. The battery test circuit 440 includes the battery test switch 426 as described in FIG. 18. The battery test switch 426 is a switch that engages an LCR dummy load that simulates a transducer or shaft assembly electronics. As described in FIG. 18, additional indicator circuits may be coupled to the battery test circuit 440 to provide a suitable indication of the capacity of the batteries in the reusable battery assembly 420. The illustrated battery test circuit 440 may be employed in any of the battery assemblies 400, 410, 420, 430 described in connection with FIGS. 16-19, respectively.

Figure 21:
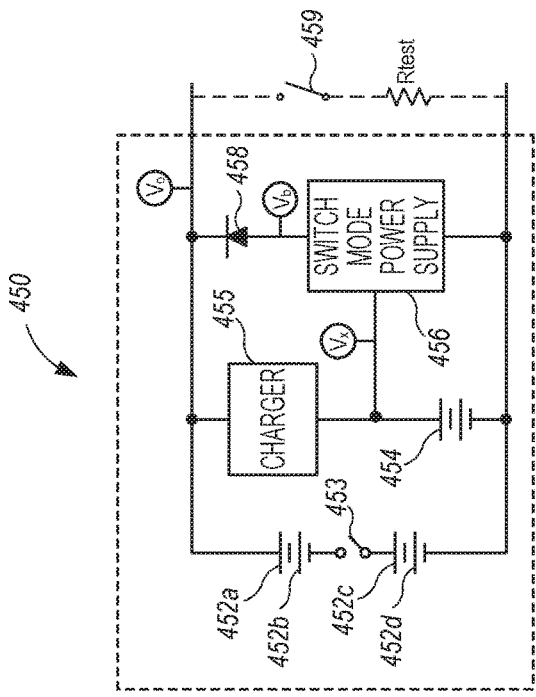
FIG. 21 illustrates a supplemental power source circuit to maintain a minimum output voltage, according to one aspect of the present disclosure.

FIG. 21 illustrates a supplemental power source circuit 450 to maintain a minimum output voltage, according to one aspect of the present disclosure. The supplemental power source circuit 450 may be included in any of the battery assemblies 400, 410, 420, 430 described in connection with FIGS. 16-19. The supplemental power source circuit 450 prevents the output voltage $V_o$ from sagging under high load conditions. The supplemental power source circuit 450 includes a set of four primary batteries 452a-b, 452c-d (up to n batteries may be used) that are activated when the switch 453 closes upon insertion of the battery assembly 400, 410, 420, 430 into the handle assembly 102 of the surgical instrument 100 (FIGS. 1 and 2). The primary batteries 452a-d may be Li-ion batteries such as CR123 A Li-ion batteries. Under load, the primary batteries 452a-d provide the output voltage $V_o$ while the secondary rechargeable battery 454 is charged by the battery charger 455. In one aspect, the secondary rechargeable battery 454 in a NiMH battery and the battery charger 455 is a suitable NiMH charger. When the output voltage $V_o$ sags or droops due to high load conditions the voltage $V_x$ operates the switch mode power supply 456 to restore the output voltage $V_o$ by supplying the additional current into the load. The diode 458 is provided to prevent current from flowing into the output of the switch mode power supply 456. Accordingly, the output voltage $V_b$ of the switch mode power supply 456 must exceed the voltage drop across the diode 458 (~0.7V) before the supplemental current can flow into the load. Optionally, a battery test switch 459 and test resistor $R_{Test}$ may be provided to test the supplemental power source circuit 450 under load conditions. In particular, in view of FIG. 21, the battery assemblies 400, 410, 420, 430 may comprise a test circuit 457a comprising a switch 457b and a resistor 457c such that when the switch 457b is closed (e.g., via the test button 426), the resistor 457c tests whether the primary batteries 452a-d are capable of delivering the output voltage $V_o$. Otherwise, the resistor 457 tests whether the secondary battery 454, via operation of the switch mode power supply 456, is capable of delivering a $V_b$ such that supplemental current passing through the diode 458 restores the output voltage $V_o$.

Figure 22:
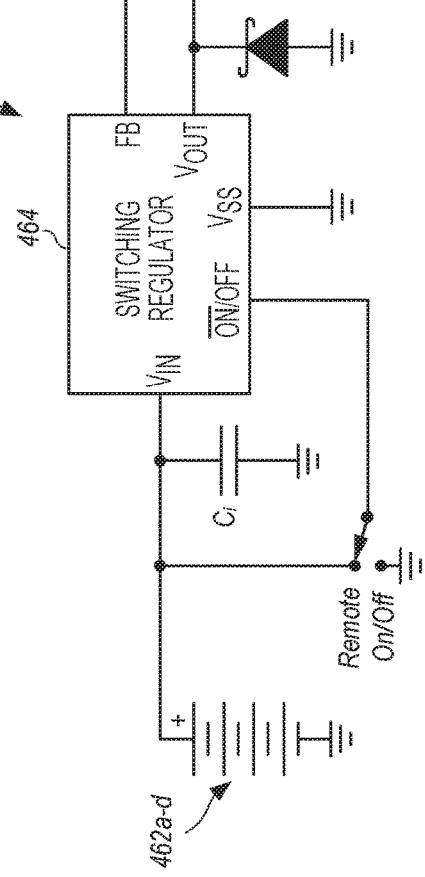
FIG. 22 illustrates a switch mode power supply circuit for supplying energy to the surgical instrument, according to one aspect of the present disclosure.

FIG. 22 illustrates a switch mode power supply circuit 460 for supplying energy to the surgical instrument 100, according to one aspect of the present disclosure. The switch mode power supply circuit 460 may be disposed within any one of the battery assemblies 400, 410, 430 described in connection with FIGS. 16, 17, and 19, respectively. In the illustrated example, the switch mode power supply circuit 460 comprises primary Li cell batteries 429a-d where the positive (+) output voltage is coupled to an input terminal $V_{IN}$ of a switching regulator 464. It will be appreciated that any suitable number of primary cells may be employed. The switch mode power supply circuit 460 includes a remote ON/OFF switch. The input $V_{IN}$ of the switching regulator 464 also includes an input filter represented by capacitor $C_i$. The output $V_{OUT}$ of the switching regulator 464 is coupled to an inductor L and an output filter represented by capacitor $C_o$. A catch diode D is disposed between $V_{OUT}$ and ground. A feedback signal is provided from the output filter $C_o$ to the FB input of the switching regulator 464. A load resistor $R_L$ represents a load. In one aspect, the minimum load is about 200 mA. In one aspect, the output voltage $V_{OUT}$ is 3.3 VDC at 800 mA.

Figure 23:
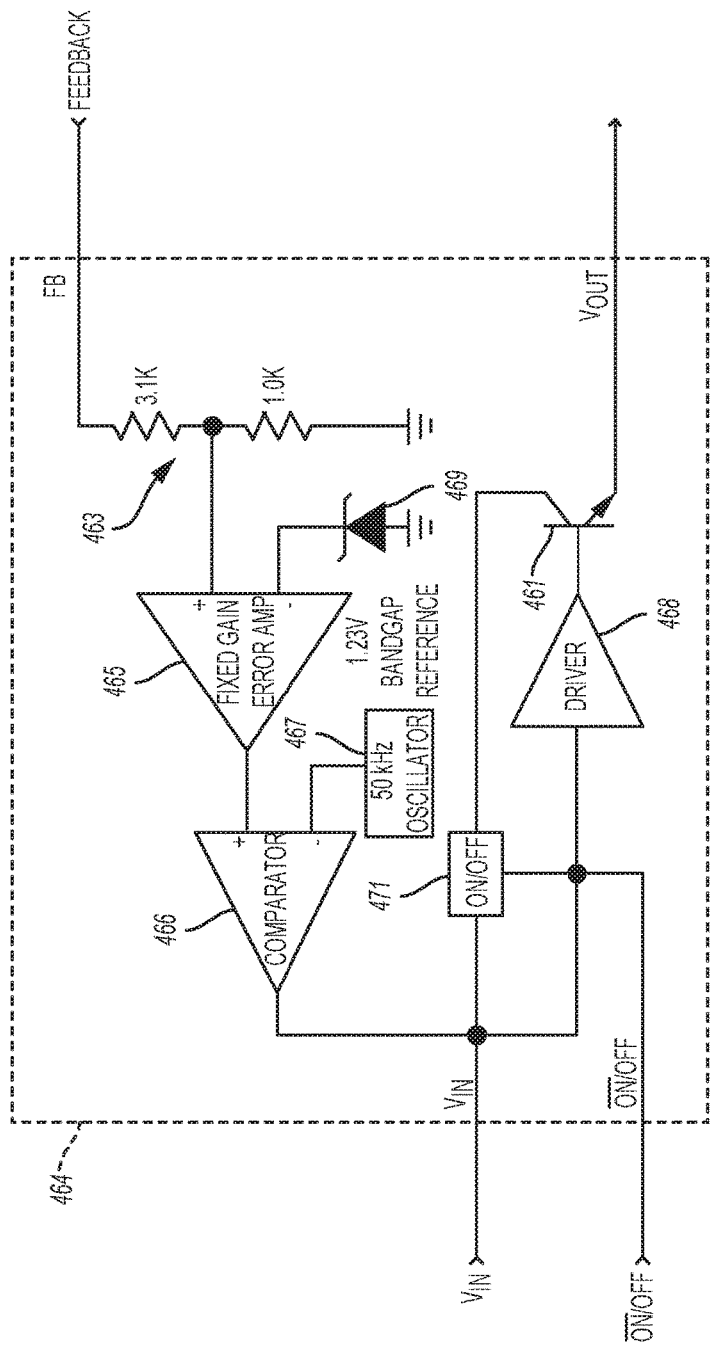
FIG. 23 illustrates a discrete version of the switching regulator shown in FIG. 22 for supplying energy to the surgical instrument, according to one aspect of the present disclosure.

FIG. 23 illustrates a discrete version of the switching regulator 464 shown in FIG. 22 for supplying energy to the surgical instrument 100, according to one aspect of the present disclosure. The switching regulator 464 receives the input voltage from a battery assembly 400, 410, 420, 430 at the $V_{IN}$ terminal. The signal at the ON/OFF input enables or disables the operation of the switching regulator 464 by controlling the state of the switch 471. A feedback signal is received from the load at the FB input where is divided by a voltage divider circuit 463. The voltage from the voltage divider 463 is applied to the positive input of a fixed gain amplifier 465. The negative input of the fixed gain amplifier 465 is coupled to a bandgap reference diode 469 (e.g., 1.23V). The amplified output of the fixed gain amplifier 465 is applied to the positive input of a comparator 466. The negative input of the comparator 466 receives a 50 kHz oscillator 467 input. The output of the comparator 466 is applied to a driver 468 which drives and output transistor 461. The output transistor 461 supplies voltage and current to the load via the $V_{OUT}$ terminal.

Figure 24:
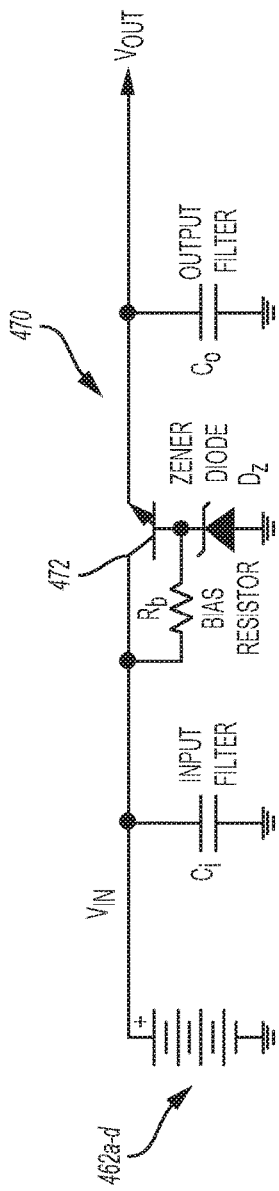
FIG. 24 illustrates a linear power supply circuit for supplying energy to the surgical instrument, according to one aspect of the present disclosure.

FIG. 24 illustrates a linear power supply circuit 470 for supplying energy to the surgical instrument 100, according to one aspect of the present disclosure. The linear power supply circuit 470 may be disposed within any one of the battery assemblies 400, 410, 420, 430 described in connection with FIGS. 16, 17, 18, and 19, respectively. In the illustrated example, the linear power supply circuit 470 comprises primary Li-ion cell batteries 462a-d where the positive (+) output voltage is coupled to the $V_{IN}$ terminal of transistor 472. The output of the transistor 472 supplies the current and voltage to the load via the $V_{OUT}$ terminal of the linear power supply circuit 470. An input filter $C_i$ is provided at the input side and an output filter $C_o$ is provided at an output side. A Zener diode $D_Z$ applies a regulated voltage to the base of the transistor 472. A bias resistor biases the Zener diode $D_Z$ and the transistor 472.

Figure 25:
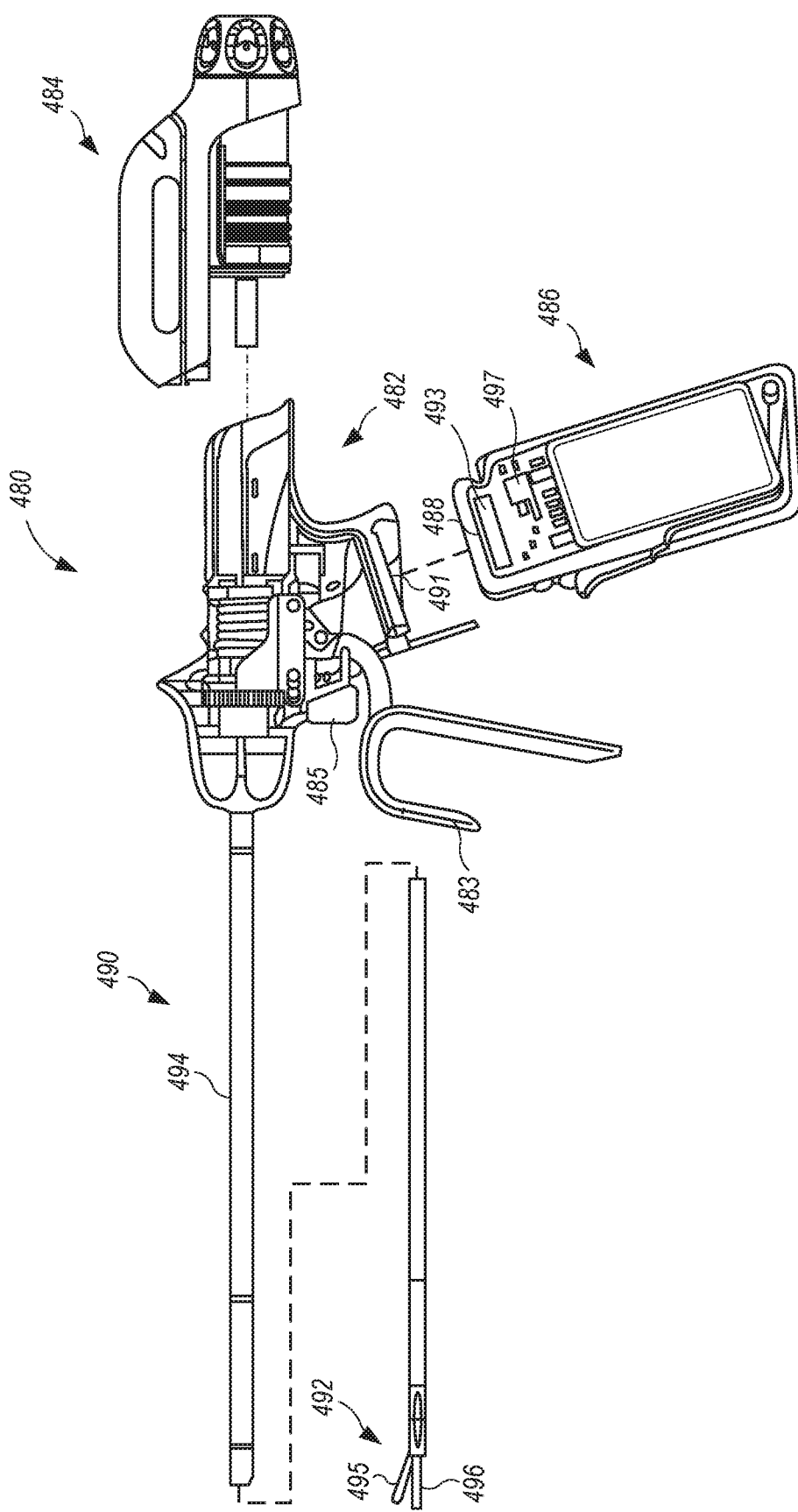
FIG. 25 is an elevational exploded view of modular handheld ultrasonic surgical instrument showing the left shell half removed from a handle assembly exposing a device identifier communicatively coupled to the multi-lead handle terminal assembly in accordance with one aspect of the present disclosure.

FIG. 25 is an elevational exploded view of modular handheld ultrasonic surgical instrument 480 showing the left shell half removed from a handle assembly 482 exposing a device identifier communicatively coupled to the multi-lead handle terminal assembly in accordance with one aspect of the present disclosure. In additional aspects of the present disclosure, an intelligent or smart battery is used to power the modular handheld ultrasonic surgical instrument 480. However, the smart battery is not limited to the modular handheld ultrasonic surgical instrument 480 and, as will be explained, can be used in a variety of devices, which may or may not have power requirements (e.g., current and voltage) that vary from one another. The smart battery assembly 486, in accordance with one aspect of the present disclosure, is advantageously able to identify the particular device to which it is electrically coupled. It does this through encrypted or unencrypted identification methods. For instance, a smart battery assembly 486 can have a connection portion, such as connection portion 488. The handle assembly 482 can also be provided with a device identifier communicatively coupled to the multi-lead handle terminal assembly 491 and operable to communicate at least one piece of information about the handle assembly 482. This information can pertain to the number of times the handle assembly 482 has been used, the number of times an ultrasonic transducer/generator assembly 484 (presently disconnected from the handle assembly 482) has been used, the number of times a waveguide shaft assembly 490 (presently connected to the handle assembly 482) has been used, the type of the waveguide shaft assembly 490 that is presently connected to the handle assembly 482, the type or identity of the ultrasonic transducer/generator assembly 484 that is presently connected to the handle assembly 482, and/or many other characteristics. When the smart battery assembly 486 is inserted in the handle assembly 482, the connection portion 488 within the smart battery assembly 486 makes communicating contact with the device identifier of the handle assembly 482. The handle assembly 482, through hardware, software, or a combination thereof, is able to transmit information to the smart battery assembly 486 (whether by self-initiation or in response to a request from the smart battery assembly 486). This communicated identifier is received by the connection portion 488 of the smart battery assembly 486. In one aspect, once the smart battery assembly 486 receives the information, the communication portion is operable to control the output of the smart battery assembly 486 to comply with the device's specific power requirements.

In one aspect, the communication portion includes a processor 493 and a memory 497, which may be separate or a single component. The processor 493, in combination with the memory, is able to provide intelligent power management for the modular handheld ultrasonic surgical instrument 480. This aspect is particularly advantageous because an ultrasonic device, such as the modular handheld ultrasonic surgical instrument 480, has a power requirement (frequency, current, and voltage) that may be unique to the modular handheld ultrasonic surgical instrument 480. In fact, the modular handheld ultrasonic surgical instrument 480 may have a particular power requirement or limitation for one dimension or type of outer tube 494 and a second different power requirement for a second type of waveguide having a different dimension, shape, and/or configuration.

A smart battery assembly 486, according to one aspect of the present disclosure, therefore, allows a battery assembly to be used amongst several surgical instruments. Because the smart battery assembly 486 is able to identify to which device it is attached and is able to alter its output accordingly, the operators of various different surgical instruments utilizing the smart battery assembly 486 no longer need be concerned about which power source they are attempting to install within the electronic device being used. This is particularly advantageous in an operating environment where a battery assembly needs to be replaced or interchanged with another surgical instrument in the middle of a complex surgical procedure.

In a further aspect of the present disclosure, the smart battery assembly 486 stores in a memory 497a record of each time a particular device is used. This record can be useful for assessing the end of a device's useful or permitted life. For instance, once a device is used 20 times, such batteries in the smart battery assembly 486 connected to the device will refuse to supply power thereto—because the device is defined as a "no longer reliable" surgical instrument. Reliability is determined based on a number of factors. One factor can be wear, which can be estimated in a number of ways including the number of times the device has been used or activated. After a certain number of uses, the parts of the device can become worn and tolerances between parts exceeded. For instance, the smart battery assembly 486 can sense the number of button pushes received by the handle assembly 482 and can determine when a maximum number of button pushes has been met or exceeded. The smart battery assembly 486 can also monitor an impedance of the button mechanism which can change, for instance, if the handle gets contaminated, for example, with saline.

This wear can lead to an unacceptable failure during a procedure. In some aspects, the smart battery assembly 486 can recognize which parts are combined together in a device and even how many uses a part has experienced. For instance, if the smart battery assembly 486 is a smart battery according to the present disclosure, it can identify the handle assembly 482, the waveguide shaft assembly 490, as well as the ultrasonic transducer/generator assembly 484, well before the user attempts use of the composite device. The memory 497 within the smart battery assembly 486 can, for example, record a time when the ultrasonic transducer/generator assembly 484 is operated, and how, when, and for how long it is operated. If the ultrasonic transducer/generator assembly 484 has an individual identifier, the smart battery assembly 486 can keep track of uses of the ultrasonic transducer/generator assembly 484 and refuse to supply power to that the ultrasonic transducer/generator assembly 484 once the handle assembly 482 or the ultrasonic transducer/generator assembly 484 exceeds its maximum number of uses. The ultrasonic transducer/generator assembly 484, the handle assembly 482, the waveguide shaft assembly 490, or other components can include a memory chip that records this information as well. In this way, any number of smart batteries in the smart battery assembly 486 can be used with any number of ultrasonic transducer/generator assemblies 484, staplers, vessel sealers, etc. and still be able to determine the total number of uses, or the total time of use (through use of the clock), or the total number of actuations, etc. of the ultrasonic transducer/generator assembly 484, the stapler, the vessel sealer, etc. or charge or discharge cycles.

Smart functionality may reside outside the battery assembly 486 and may reside in the handle assembly 482, the ultrasonic transducer/generator assembly 484, and/or the shaft assembly 490, for example.

When counting uses of the ultrasonic transducer/generator assembly 484, to intelligently terminate the life of the ultrasonic transducer/generator assembly 484, the surgical instrument accurately distinguishes between completion of an actual use of the ultrasonic transducer/generator assembly 484 in a surgical procedure and a momentary lapse in actuation of the ultrasonic transducer/generator assembly 484 due to, for example, a battery change or a temporary delay in the surgical procedure. Therefore, as an alternative to simply counting the number of activations of the ultrasonic transducer/generator assembly 484, a real-time clock (RTC) circuit can be implemented to keep track of the amount of time the ultrasonic transducer/generator assembly 484 actually is shut down. From the length of time measured, it can be determined through appropriate logic if the shutdown was significant enough to be considered the end of one actual use or if the shutdown was too short in time to be considered the end of one use. Thus, in some applications, this method may be a more accurate determination of the useful life of the ultrasonic transducer/generator assembly 484 than a simple "activations-based" algorithm, which for example, may provide that ten "activations" occur in a surgical procedure and, therefore, ten activations should indicate that the counter is incremented by one. Generally, this type and system of internal clocking will prevent misuse of the device that is designed to deceive a simple "activations-based" algorithm and will prevent incorrect logging of a complete use in instances when there was only a simple de-mating of the ultrasonic transducer/generator assembly 484 or the smart battery assembly 486 that was required for legitimate reasons.

Although the ultrasonic transducer/generator assemblies 484 of the surgical instrument 480 are reusable, in one aspect a finite number of uses may be set because the surgical instrument 480 is subjected to harsh conditions during cleaning and sterilization. More specifically, the battery pack is configured to be sterilized. Regardless of the material employed for the outer surfaces, there is a limited expected life for the actual materials used. This life is determined by various characteristics which could include, for example, the amount of times the pack has actually been sterilized, the time from which the pack was manufactured, and the number of times the pack has been recharged, to name a few. Also, the life of the battery cells themselves is limited. Software of the present disclosure incorporates inventive algorithms that verify the number of uses of the ultrasonic transducer/generator assembly 484 and smart battery assembly 486 and disables the device when this number of uses has been reached or exceeded. Analysis of the battery pack exterior in each of the possible sterilizing methods can be performed. Based on the harshest sterilization procedure, a maximum number of permitted sterilizations can be defined and that number can be stored in a memory of the smart battery assembly 486. If it is assumed that a charger is non-sterile and that the smart battery assembly 486 is to be used after it is charged, then the charge count can be defined as being equal to the number of sterilizations encountered by that particular pack.

In one aspect, the hardware in the battery pack may be to disabled to minimize or eliminate safety concerns due to continuous drain in from the battery cells after the pack has been disabled by software. A situation can exist where the battery's internal hardware is incapable of disabling the battery under certain low voltage conditions. In such a situation, in an aspect, the charger can be used to "kill" the battery. Due to the fact that the battery microcontroller is OFF while the battery is in its charger, a non-volatile, System Management Bus (SMB) based electrically erasable programmable read only memory (EEPROM) can be used to exchange information between the battery microcontroller and the charger. Thus, a serial EEPROM can be used to store information that can be written and read even when the battery microcontroller is OFF, which is very beneficial when trying to exchange information with the charger or other peripheral devices. This example EEPROM can be configured to contain enough memory registers to store at least (a) a use-count limit at which point the battery should be disabled (Battery Use Count), (b) the number of procedures the battery has undergone (Battery Procedure Count), and/or (c) a number of charges the battery has undergone (Charge Count), to name a few. Some of the information stored in the EEPROM, such as the Use Count Register and Charge Count Register are stored in write-protected sections of the EEPROM to prevent users from altering the information. In an aspect, the use and counters are stored with corresponding bit-inverted minor registers to detect data corruption.

Any residual voltage in the SMBus lines could damage the microcontroller and corrupt the SMBus signal. Therefore, to ensure that the SMBus lines of the battery controller 703 do not carry a voltage while the microcontroller is OFF, relays are provided between the external SMBus lines and the battery microcontroller board.

During charging of the smart battery assembly 486, an "end-of-charge" condition of the batteries within the smart battery assembly 486 is determined when, for example, the current flowing into the battery falls below a given threshold in a tapering manner when employing a constant-current/constant-voltage charging scheme. To accurately detect this "end-of-charge" condition, the battery microcontroller and buck boards are powered down and turned OFF during charging of the battery to reduce any current drain that may be caused by the boards and that may interfere with the tapering current detection. Additionally, the microcontroller and buck boards are powered down during charging to prevent any resulting corruption of the SMBus signal.

With regard to the charger, in one aspect the smart battery assembly 486 is prevented from being inserted into the charger in any way other than the correct insertion position. Accordingly, the exterior of the smart battery assembly 486 is provided with charger-holding features. A cup for holding the smart battery assembly 486 securely in the charger is configured with a contour-matching taper geometry to prevent the accidental insertion of the smart battery assembly 486 in any way other than the correct (intended) way. It is further contemplated that the presence of the smart battery assembly 486 may be detectable by the charger itself. For example, the charger may be configured to detect the presence of the SMBus transmission from the battery protection circuit, as well as resistors that are located in the protection board. In such case, the charger would be enabled to control the voltage that is exposed at the charger's pins until the smart battery assembly 486 is correctly seated or in place at the charger. This is because an exposed voltage at the charger's pins would present a hazard and a risk that an electrical short could occur across the pins and cause the charger to inadvertently begin charging.

In some aspects, the smart battery assembly 486 can communicate to the user through audio and/or visual feedback. For example, the smart battery assembly 486 can cause the LEDs to light in a pre-set way. In such a case, even though the microcontroller in the ultrasonic transducer/generator assembly 484 controls the LEDs, the microcontroller receives instructions to be carried out directly from the smart battery assembly 486.

In yet a further aspect of the present disclosure, the microcontroller in the ultrasonic transducer/generator assembly 484, when not in use for a predetermined period of time, goes into a sleep mode. Advantageously, when in the sleep mode, the clock speed of the microcontroller is reduced, cutting the current drain significantly. Some current continues to be consumed because the processor continues pinging waiting to sense an input. Advantageously, when the microcontroller is in this power-saving sleep mode, the microcontroller and the battery controller can directly control the LEDs. For example, a decoder circuit could be built into the ultrasonic transducer/generator assembly 484 and connected to the communication lines such that the LEDs can be controlled independently by the processor 493 while the ultrasonic transducer/generator assembly 484 microcontroller is "OFF" or in a "sleep mode." This is a power-saving feature that eliminates the need for waking up the microcontroller in the ultrasonic transducer/generator assembly 484. Power is conserved by allowing the generator to be turned off while still being able to actively control the user-interface indicators.

Another aspect slows down one or more of the microcontrollers to conserve power when not in use. For example, the clock frequencies of both microcontrollers can be reduced to save power. To maintain synchronized operation, the microcontrollers coordinate the changing of their respective clock frequencies to occur at about the same time, both the reduction and, then, the subsequent increase in frequency when full speed operation is required. For example, when entering the idle mode, the clock frequencies are decreased and, when exiting the idle mode, the frequencies are increased.

In an additional aspect, the smart battery assembly 486 is able to determine the amount of usable power left within its cells and is programmed to only operate the surgical instrument to which it is attached if it determines there is enough battery power remaining to predictably operate the device throughout the anticipated procedure. For example, the smart battery assembly 486 is able to remain in a non-operational state if there is not enough power within the cells to operate the surgical instrument for 20 seconds. According to one aspect, the smart battery assembly 486 determines the amount of power remaining within the cells at the end of its most recent preceding function, e.g., a surgical cutting. In this aspect, therefore, the smart battery assembly 486 would not allow a subsequent function to be carried out if, for example, during that procedure, it determines that the cells have insufficient power. Alternatively, if the smart battery assembly 486 determines that there is sufficient power for a subsequent procedure and goes below that threshold during the procedure, it would not interrupt the ongoing procedure and, instead, will allow it to finish and thereafter prevent additional procedures from occurring.

The following explains an advantage to maximizing use of the device with the smart battery assembly 486 of the present disclosure. In this example, a set of different devices have different ultrasonic transmission waveguides. By definition, the waveguides could have a respective maximum allowable power limit where exceeding that power limit overstresses the waveguide and eventually causes it to fracture. One waveguide from the set of waveguides will naturally have the smallest maximum power tolerance.

Because prior-art batteries lack intelligent battery power management, the output of prior-art batteries must be limited by a value of the smallest maximum allowable power input for the smallest/thinnest/most-frail waveguide in the set that is envisioned to be used with the device/battery. This would be true even though larger, thicker waveguides could later be attached to that handle and, by definition, allow a greater force to be applied. This limitation is also true for maximum battery power. For example, if one battery is designed to be used in multiple devices, its maximum output power will be limited to the lowest maximum power rating of any of the devices in which it is to be used. With such a configuration, one or more devices or device configurations would not be able to maximize use of the battery because the battery does not know the particular device's specific limits.

In one aspect, the smart battery assembly 486 may be employed to intelligently circumvent the above-mentioned ultrasonic device limitations. The smart battery assembly 486 can produce one output for one device or a particular device configuration and the same smart battery assembly 486 can later produce a different output for a second device or device configuration. This universal smart battery surgical system lends itself well to the modern operating room where space and time are at a premium. By having a smart battery pack operate many different devices, the nurses can easily manage the storage, retrieval, and inventory of these packs. Advantageously, in one aspect the smart battery system according to the present disclosure may employ one type of charging station, thus increasing ease and efficiency of use and decreasing cost of surgical room charging equipment.

In addition, other surgical instruments, such as an electric stapler, may have a different power requirement than that of the modular handheld ultrasonic surgical instrument 480. In accordance with various aspects of the present disclosure, a smart battery assembly 486 can be used with any one of a series of surgical instruments and can be made to tailor its own power output to the particular device in which it is installed. In one aspect, this power tailoring is performed by controlling the duty cycle of a switched mode power supply, such as buck, buck-boost, boost, or other configuration, integral with or otherwise coupled to and controlled by the smart battery assembly 486. In other aspects, the smart battery assembly 486 can dynamically change its power output during device operation. For instance, in vessel sealing devices, power management provides improved tissue sealing. In these devices, large constant current values are needed. The total power output needs to be adjusted dynamically because, as the tissue is sealed, its impedance changes. Aspects of the present disclosure provide the smart battery assembly 486 with a variable maximum current limit. The current limit can vary from one application (or device) to another, based on the requirements of the application or device.

FIG. 26 is a detail view of a trigger 483 portion and switch of the ultrasonic surgical instrument 480 shown in FIG. 25, according to one aspect of the present disclosure. The trigger 483 is operably coupled to the jaw member 495 of the end effector 492. The ultrasonic blade 496 is energized by the ultrasonic transducer/generator assembly 484 upon activating the activation switch 485. Continuing now with FIG. 25 and also looking to FIG. 26, the trigger 483 and the activation switch 485 are shown as components of the handle assembly 482. The trigger 483 activates the end effector 492, which has a cooperative association with the ultrasonic blade 496 of the waveguide shaft assembly 490 to enable various kinds of contact between the end effector jaw member 495 and the ultrasonic blade 496 with tissue and/or other substances. The jaw member 495 of the end effector 492 is usually a pivoting jaw that acts to grasp or clamp onto tissue disposed between the jaw and the ultrasonic blade 496. In one aspect, an audible feedback is provided in the trigger that clicks when the trigger is fully depressed. The noise can be generated by a thin metal part that the trigger snaps over while closing. This feature adds an audible component to user feedback that informs the user that the jaw is fully compressed against the waveguide and that sufficient clamping pressure is being applied to accomplish vessel sealing. In another aspect, force sensors such as strain gages or pressure sensors may be coupled to the trigger 483 to measure the force applied to the trigger 483 by the user. In another aspect, force sensors such as strain gages or pressure sensors may be coupled to the switch 485 button such that displacement intensity corresponds to the force applied by the user to the switch 485 button.

The activation switch 485, when depressed, places the modular handheld ultrasonic surgical instrument 480 into an ultrasonic operating mode, which causes ultrasonic motion at the waveguide shaft assembly 490. In one aspect, depression of the activation switch 485 causes electrical contacts within a switch to close, thereby completing a circuit between the smart battery assembly 486 and the ultrasonic transducer/generator assembly 484 so that electrical power is applied to the ultrasonic transducer, as previously described. In another aspect, depression of the activation switch 485 closes electrical contacts to the smart battery assembly 486. Of course, the description of closing electrical contacts in a circuit is, here, merely an example general description of switch operation. There are many alternative aspects that can include opening contacts or processor-controlled power delivery that receives information from the switch and directs a corresponding circuit reaction based on the information.

FIG. 27 is a fragmentary, enlarged perspective view of an end effector 492, according to one aspect of the present disclosure, from a distal end with a jaw member 495 in an open position. Referring to FIG. 27, a perspective partial view of the distal end 498 of the waveguide shaft assembly 490 is shown. The waveguide shaft assembly 490 includes an outer tube 494 surrounding a portion of the waveguide. The ultrasonic blade 496 portion of the waveguide 499 protrudes from the distal end 498 of the outer tube 494. It is the ultrasonic blade 496 portion that contacts the tissue during a medical procedure and transfers its ultrasonic energy to the tissue. The waveguide shaft assembly 490 also includes a jaw member 495 that is coupled to the outer tube 494 and an inner tube (not visible in this view). The jaw member 495, together with the inner and outer tubes and the ultrasonic blade 496 portion of the waveguide 499, can be referred to as an end effector 492. As will be explained below, the outer tube 494 and the non-illustrated inner tube slide longitudinally with respect to each other. As the relative movement between the outer tube 494 and the non-illustrated inner tube occurs, the jaw member 495 pivots upon a pivot point, thereby causing the jaw member 495 to open and close. When closed, the jaw member 495 imparts a pinching force on tissue located between the jaw member 495 and the ultrasonic blade 496, insuring positive and efficient blade-to-tissue contact.

FIG. 28 illustrates a modular shaft assembly 110 and end effector 112 portions of the surgical instrument 100, according to one aspect of the present disclosure. The shaft assembly 110 comprises an outer tube 144, an inner tube 147, and an ultrasonic transmission waveguide 145. The shaft assembly 110 is removably mounted to the handle assembly 102. The inner tube 147 is slidably received within the outer tube 144. The ultrasonic transmission waveguide 145 is positioned within the inner tube 147. The jaw member 114 of the end effector 112 is pivotally coupled to the outer tube 144 at a pivot point 151. The jaw member 114 also is coupled to inner tube 147 by a pin 153 such that as the inner tube 147 slides within the slot 155, the jaw member opens and closes. In the illustrated configuration, the inner tube 147 is in its distal position and the jaw member 114 is open. To close the jaw member 114, the inner tube 147 is retracted in the proximal direction 157 and to open the jaw member is advanced in the distal direction 159. The proximal end of the shaft assembly 110 comprises a jaw member tube (e.g., inner tube)/spring assembly 141. A spring 139 is provided to apply a constant force control mechanism for use with different shaft assemblies, motor closures to control constant force closures, two bar mechanism to drive closure systems, cam lobes to push and pull closure system, drive screw designs to drive closure or wave spring designs to control constant force.

FIG. 29 is a detail view of the inner tube/spring assembly 141. A closure mechanism 149 is operably coupled to the trigger 108 (FIGS. 1-3). Accordingly, as the trigger 108 is squeezed, the inner tube 143 is retracted in the proximal direction 157 to close the jaw member 114. Accordingly, as the trigger 108 is released, the inner tube 143 is advanced in the distal direction 159 to open the jaw member 114.

For a more detailed description of a combination ultrasonic/electrosurgical instrument, reference is made to U.S. Pat. No. 9,107,690, which is herein incorporated by reference.

Figure 30:
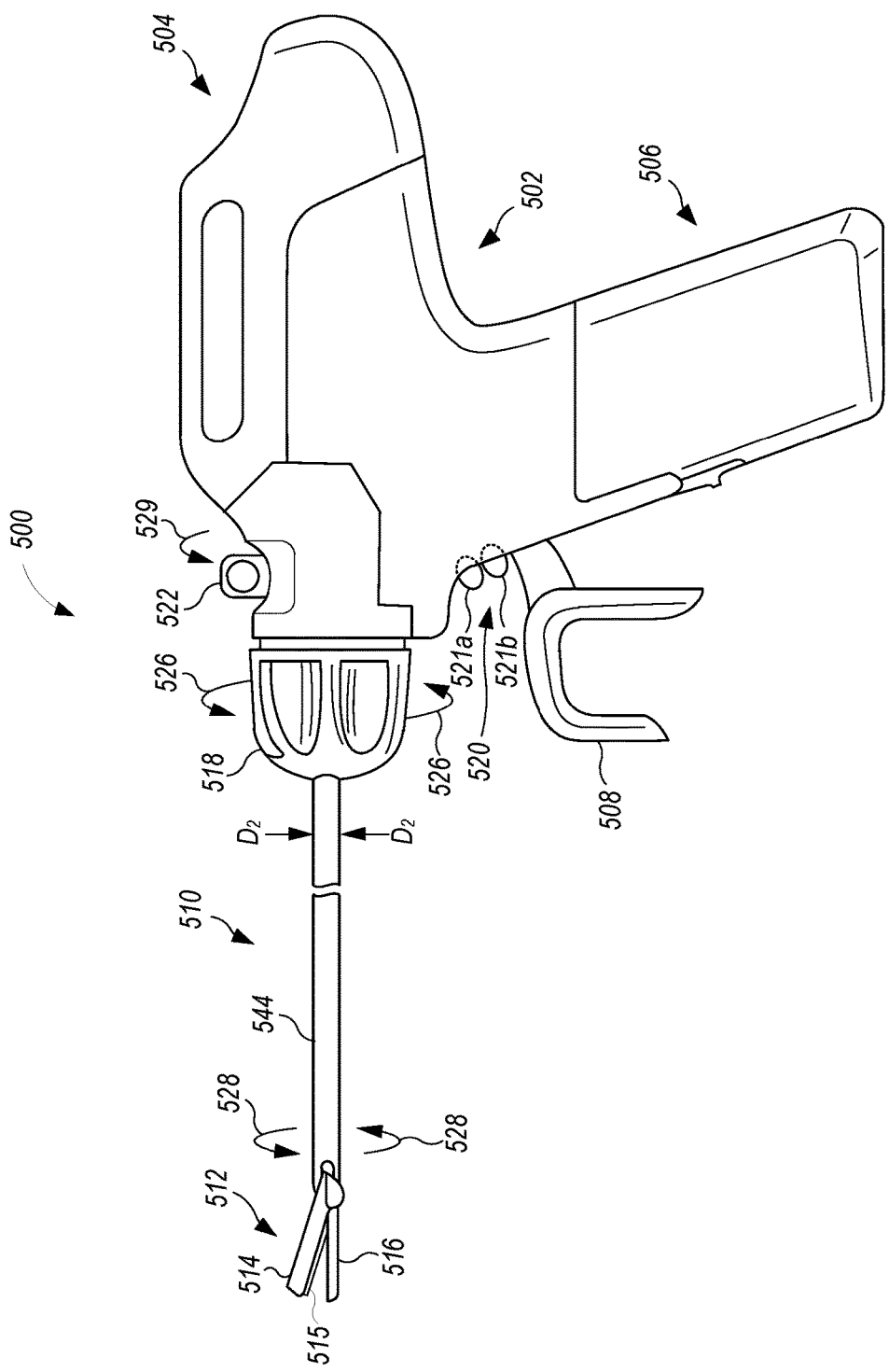
FIG. 30 illustrates a modular battery powered handheld combination ultrasonic/electrosurgical instrument, according to one aspect of the present disclosure.
Figure 31:
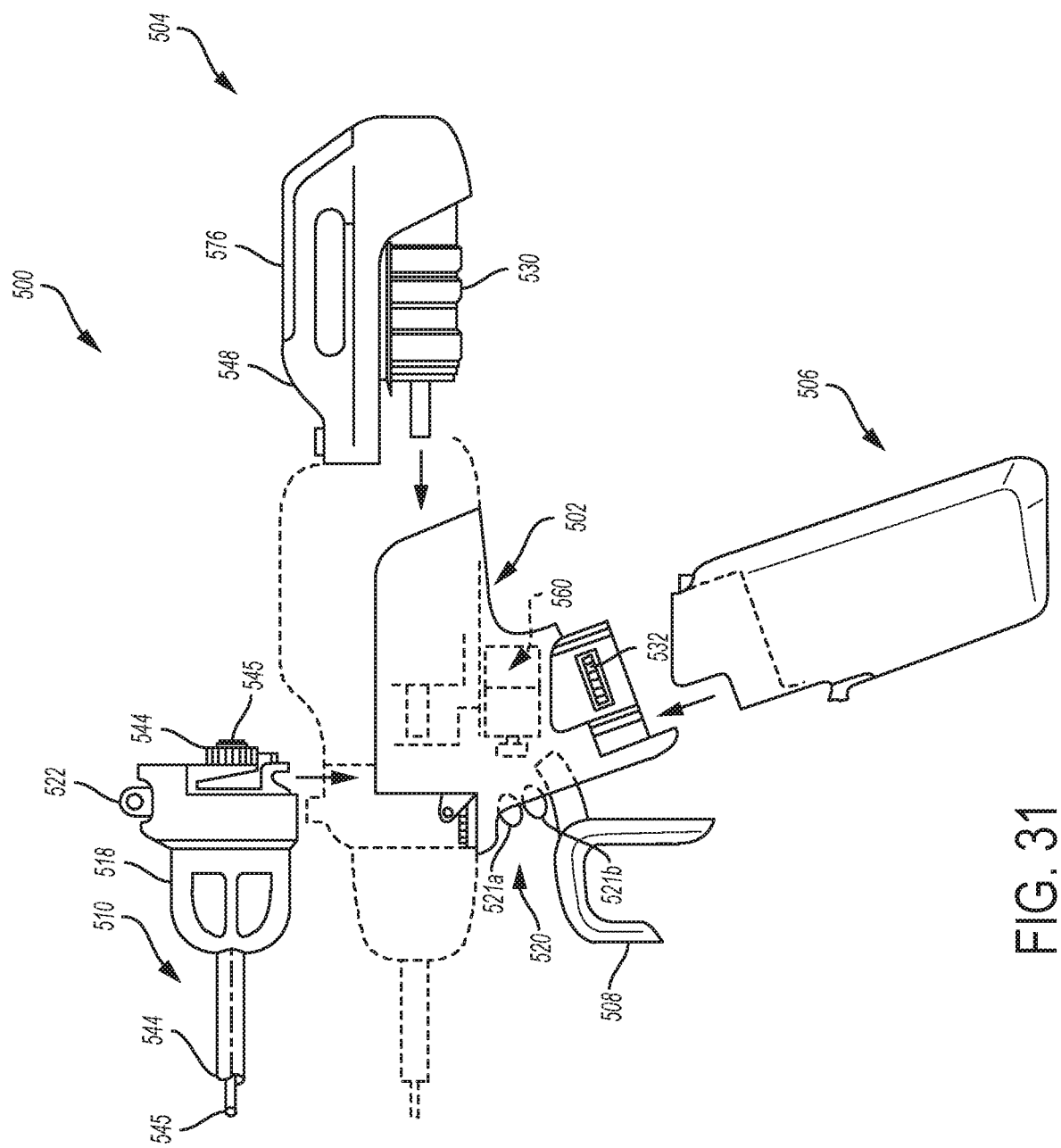
FIG. 31 is an exploded view of the surgical instrument shown in FIG. 30, according to one aspect of the present disclosure.

FIG. 30 illustrates a modular battery powered handheld combination ultrasonic/electrosurgical instrument 500, according to one aspect of the present disclosure. FIG. 31 is an exploded view of the surgical instrument 500 shown in FIG. 30, according to one aspect of the present disclosure. With reference now to FIGS. 30 and 31, the surgical instrument 500 comprises a handle assembly 502, an ultrasonic transducer/RF generator assembly 504, a battery assembly 506, a shaft assembly 510, and an end effector 512. The ultrasonic transducer/RF generator assembly 504, battery assembly 506, and shaft assembly 510 are modular components that are removably connectable to the handle assembly 502. The handle assembly 502 also comprises a motor assembly 560. The surgical instrument 500 is configured to use both ultrasonic vibration and electrosurgical high-frequency current to carry out surgical coagulation/cutting treatments on living tissue, and uses high-frequency current to carry out a surgical coagulation treatment on living tissue. The ultrasonic vibrations and the high-frequency (e.g., RF) current can be applied independently or in combination according to algorithms or user input control.

The ultrasonic transducer/RF generator assembly 504 comprises a housing 548, a display 576, such as an LCD display, for example, an ultrasonic transducer 530, an electrical circuit 177 (FIGS. 4, 10 and/or electrical circuit 300 in FIG. 14), and a electrical circuit 702 (FIG. 34) configured to drive an RF electrode and forms a portion of an RF generator circuit. The shaft assembly 510 comprises an outer tube 544 an ultrasonic transmission waveguide 545, and an inner tube (not shown). The end effector 512 comprises a jaw member 514 and an ultrasonic blade 516. The jaw member 514 comprises an electrode 515 that is coupled to an RF generator circuit. The ultrasonic blade 516 is the distal end of the ultrasonic transmission waveguide 545. The jaw member 514 is pivotally rotatable to grasp tissue between the jaw member 514 and the ultrasonic blade 516. The jaw member 514 is operably coupled to a trigger 508. The trigger 508 functions to close the jaw member 514 when the trigger 508 is squeezed and to open the jaw member 514 when the trigger 508 is released to release the tissue. In a one-stage trigger configuration, the trigger 508 is squeezed to close the jaw member 514 and, once the jaw member 514 is closed, a first switch 521a of a switch section is activated to energize the RF generator to seal the tissue. After the tissue is sealed, a second switch 521b of the switch section 520 is activated to energize the ultrasonic generator to cut the tissue. In various aspects, the trigger 508 may be a two-stage, or a multi-stage, trigger. In a two-stage trigger configuration, during the first stage, the trigger 508 is squeezed part of the way to close the jaw member 514 and, during the second stage, the trigger 508 is squeezed the rest of the way to energize the RF generator circuit to seal the tissue. After the tissue is sealed, one of the switches 521a, 521b can be activated to energize the ultrasonic generator to cut the tissue. After the tissue is cut, the jaw member 514 is opened by releasing the trigger 508 to release the tissue. In another aspect, force sensors such as strain gages or pressure sensors may be coupled to the trigger 508 to measure the force applied to the trigger 508 by the user. In another aspect, force sensors such as strain gages or pressure sensors may be coupled to the switch 520 button such that displacement intensity corresponds to the force applied by the user to the switch 520 button.

The battery assembly 506 is electrically connected to the handle assembly 502 by an electrical connector 532. The handle assembly 502 is provided with a switch section 520. A first switch 520a and a second switch 520b are provided in the switch section 520. The RF generator is activated by actuating the first switch 520a and the ultrasonic blade 516 is activated by actuating the second switch 520b. Accordingly, the first switch 520a energizes the RF circuit to drive high-frequency current through the tissue to form a seal and the second switch 520b energizes the ultrasonic transducer 530 to vibrate the ultrasonic blade 516 and cut the tissue.

A rotation knob 518 is operably coupled to the shaft assembly 510. Rotation of the rotation knob 518 ±360° in the direction indicated by the arrows 526 causes an outer tube 544 to rotate ±360° in the respective direction of the arrows 528. In one aspect, another rotation knob 522 may be configured to rotate the jaw member 514 while the ultrasonic blade 516 remains stationary and the rotation knob 518 rotates the outer tube 144 ±360°. The outer tube 144 may have a diameter $D_1$ ranging from 5 mm to 10 mm, for example.

Figure 32:
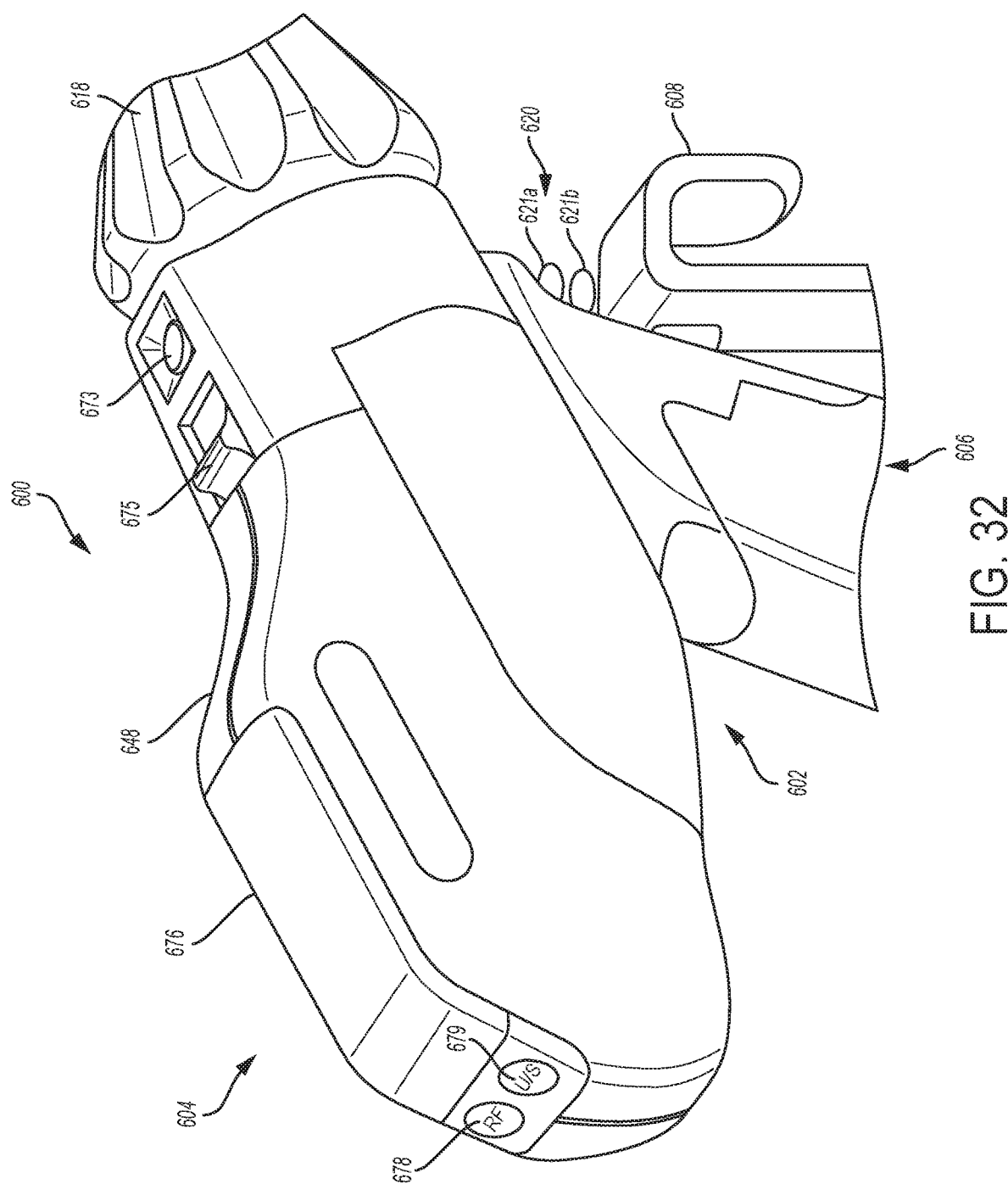
FIG. 32 is a partial perspective view of a modular battery powered handheld combination ultrasonic/RF surgical instrument, according to one aspect of the present disclosure.

FIG. 32 is a partial perspective view of a modular battery powered handheld combination ultrasonic/RF surgical instrument 600, according to one aspect of the present disclosure. The surgical instrument 600 is configured to use both ultrasonic vibration and high-frequency current to carry out surgical coagulation/cutting treatments on living tissue, and uses high-frequency current to carry out a surgical coagulation treatment on living tissue. The ultrasonic vibrations and the high-frequency (e.g., RF) current can be applied independently or in combination according to algorithms or user input control. The surgical instrument 600 comprises a handle assembly 602, an ultrasonic transducer/RF generator assembly 604, a battery assembly 606, a shaft assembly (not shown), and an end effector (not shown). The ultrasonic transducer/RF generator assembly 604, battery assembly 606, and shaft assembly are modular components that are removably connectable to the handle assembly 602.

A trigger 608 is operatively coupled to the handle assembly 602. As previously described, the trigger operates the end effector.

The ultrasonic transducer/RF generator assembly 604 comprises a housing 648, a display 676, such as an LCD display, for example. The display 676 provides a visual display of surgical procedure parameters such as tissue thickness, status of seal, status of cut, tissue thickness, tissue impedance, algorithm being executed, battery capacity, energy being applied (either ultrasonic vibration or RF current), among other parameters. The ultrasonic transducer/RF generator assembly 604 also comprises two visual feedback indicators 678, 679 to indicate the energy modality currently being applied in the surgical procedure. For example, one indicator 678 shows when RF energy is being used and another indicator 679 shows when ultrasonic energy is being used. It will be appreciated that when both energy modalities RF and ultrasonic are being applied, both indicators will show this condition. The surgical instrument 600 also comprises an ultrasonic transducer, an ultrasonic generator circuit and/or electrical circuit, a shaft assembly, and an end effector comprising a jaw member and an ultrasonic blade, the modular components being similar to those described in connection with FIGS. 30 and 31 and the description will not be repeated here for conciseness and clarity of disclosure.

The battery assembly 606 is electrically connected to the handle assembly 602 by an electrical connector. The handle assembly 602 is provided with a switch section 620. A first switch 620a and a second switch 620b are provided in the switch section 620. The ultrasonic blade is activated by actuating the first switch 620a and the RF generator is activated by actuating the second switch 620b. In another aspect, force sensors such as strain gages or pressure sensors may be coupled to the trigger 608 to measure the force applied to the trigger 608 by the user. In another aspect, force sensors such as strain gages or pressure sensors may be coupled to the switch 620 button such that displacement intensity corresponds to the force applied by the user to the switch 620 button.

A rotation knob 618 is operably coupled to the shaft assembly. Rotation of the rotation knob 618 ±360° causes an outer tube to rotate ±360° in the respective direction, as described herein in connection with FIGS. 30 and 31. In one aspect, another rotation knob may be configured to rotate the jaw member while the ultrasonic blade remains stationary and the rotation knob 618 rotates the outer tube ±360°. A button 673 is used to connect and retain the shaft assembly to the handle assembly 602. Another slide switch 675 is used to lock in and release the ultrasonic transducer/RF generator assembly 604.

In one aspect, the surgical instrument 500, 600 includes a battery powered advanced energy (ultrasonic vibration plus high-frequency current) with driver amplification broken into multiple stages. The different stages of amplification may reside in different modular components of the surgical instrument 500, 600 such as the handle assembly 502, 602 ultrasonic transducer/RF generator assembly 504, 604, battery assembly 506, 606, shaft assembly 510, and/or the end effector 112. In one aspect, the ultrasonic transducer/RF generator assembly 504, 604 may include an amplification stage in the ultrasonic transducer and/or RF electronic circuits within the housing 548, 648 and different ratios of amplification based on the energy modality associated with the particular energy mode. The final stage may be controlled via signals from the electronic system of the surgical instrument 100 located in the handle assembly 502, 602 and/or the battery assembly 506, 606 through a bus structure, such as I²C, as previously described. Final stage switches system may be employed to apply power to the transformer and blocking capacitors to form the RF waveform. Measurements of the RF output, such as voltage and current, are fed back to the electronic system over the bus. The handle assembly 502, 602 and/or battery assembly 506, 606 may contain the majority of the primary amplification circuits including any electrical isolation components, motor control, and waveform generator. The two differing ultrasonic transducers (e.g., ultrasonic transducer 130, 130' shown in FIGS. 8 and 9) and the RF transducer contain the electronics to utilize the preconditions generator signals and perform the final conditioning to power different frequency transducers of RF signals in the desired frequency ranges and amplitudes. This minimizes the weight size and cost of the electronics residing only in the transducers themselves. It also allows the primary processor boards to occupy the areas of the handle that have the most useful space which is rarely where the transducer is, due to its size. It also allows the electronics to be divided in such a way as the high wear high duty cycle elements could be only connectively attached to the primary electronics enabling it to be more serviceable and repairable since the system is designed for high repeated use before disposal.

The surgical instruments 500, 600 described in connection with FIGS. 30-32 are configured to use high-frequency current to carry out surgical coagulation/cutting treatments on living tissue, and uses high-frequency current to carry out a surgical coagulation treatment on living tissue. Accordingly, additional structural and functional components to carry out this additional functionality will be described hereinbelow in connection with FIGS. 33-44.

The structural and functional aspects of the battery assembly 506, 606 are similar to those of the battery assembly 106 for the surgical instrument 100 described in connection with FIGS. 1, 2, and 16-24, including the battery circuits described in connection with FIGS. 20-24. Accordingly, for conciseness and clarity of disclosure, such the structural and functional aspects of the battery assembly 106 are incorporated herein by reference and will not be repeated here. Similarly, unless otherwise noted, the structural and functional aspects of the shaft assembly 510 are similar to those of the shaft assembly 110 for the surgical instrument 100 described in connection with FIGS. 1-3. Accordingly, for conciseness and clarity of disclosure, such the structural and functional aspects of the shaft assembly 110 are incorporated herein by reference and will not be repeated here. Furthermore, the structural and functional aspects of the ultrasonic transducer 530 generator circuits are similar to those of the ultrasonic transducer 130 generator circuits for the surgical instrument 100 described in connection with FIGS. 1, 2, and 4-15. Accordingly, for conciseness and clarity of disclosure, such the structural and functional aspects of the ultrasonic transducer 130 and generator circuits are incorporated herein by reference and will not be repeated here. Furthermore, the surgical instruments 500, 600 include the circuits described in connection with FIGS. 12-15, including, for example, the control circuit 210 described in connection with FIG. 14 and the electrical circuit 300 described in connection withe FIG. 15. Accordingly, for conciseness and clarity of disclosure, the description of the circuits described in connection with FIGS. 12-15 is incorporated herein by reference and will not be repeated here.

Figure 33:
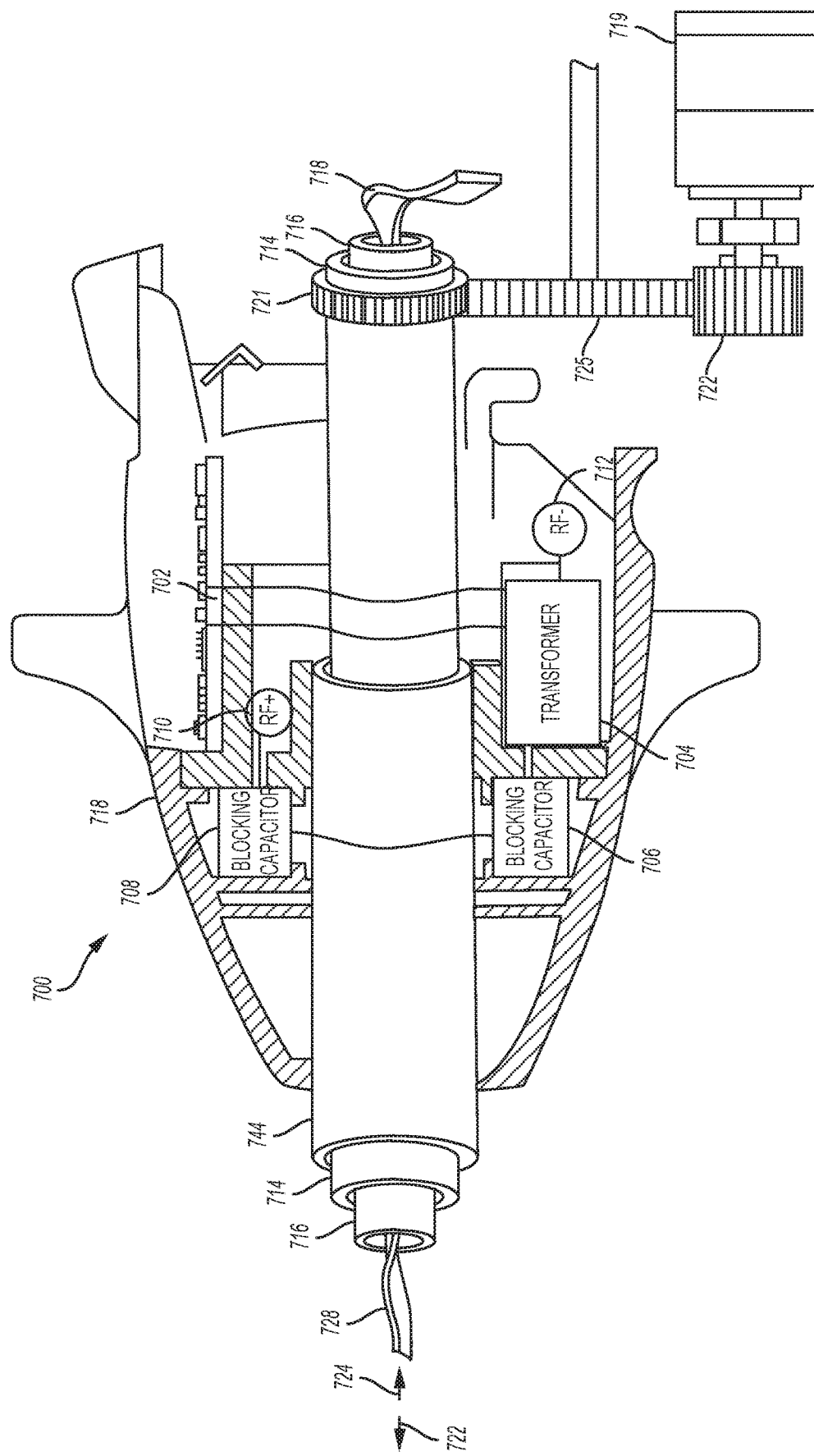
FIG. 33 illustrates a nozzle portion of the surgical instruments described in connection with FIGS. 30-32, according to one aspect of the present disclosure.

Turning now to FIG. 33, there is shown a nozzle 700 portion of the surgical instruments 500, 600 described in connection with FIGS. 30-32, according to one aspect of the present disclosure. The nozzle 700 contains an electrical circuit 702 configured to drive the high-frequency RF current to an electrode located in the end effector as described hereinbelow in connection with FIGS. 38-44. The electrical circuit 702 is coupled to the primary winding of a transformer 704. The positive side of the secondary winding of the transformer 704 is coupled to series connected first and second blocking capacitors 706, 708. The load side of the second blocking capacitor 708 is coupled to the positive RF(+) terminal which is coupled to the positive side of the end effector electrode. The negative side of the secondary winding of the transformer 704 is coupled to the negative RF(−) terminal, otherwise referred to as ground. It will be appreciated that the RF(−) or ground terminal of the RF energy circuit is coupled to an outer tube 744, which is formed of an electrically conductive metal. Accordingly, in use, high-frequency current is conducted from the end effector electrode RF(+), through the tissue, and returns through the negative electrode RF(−).

Wth reference now also to FIGS. 30, 31, in one aspect, the outer tube 744 is operably coupled to the jaw member 514 portion of the end effector 512 such that the jaw member 514 opens when the outer tube 744 is advanced in the distal direction 722 and the jaw member 514 closes when the outer tube 744 is retracted in the proximal direction 724. Although not shown in FIG. 33, the outer tube 744 is operably coupled to the trigger 508, which is used to open and close the jaw member 514 portion of the end effector 512. Examples of actuation mechanisms for use with ultrasonic surgical instruments as described herein are disclosed in U.S. Pub. No. 2006/0079879 and U.S. Pub. No. 2015/0164532, each of which is herein incorporated by reference.

Still with reference to FIGS. 30, 31, and 33, in one aspect, an inner tube 714 is slidably disposed within the outer tube 744. The inner tube 714 is operably coupled to the jaw member 514 to rotate the jaw member 514 while maintaining the ultrasonic blade 516 stationary. In the aspect shown in FIGS. 30 and 31 the inner tube 714 is rotated by the rotation knob 522. In the aspect shown in FIG. 33, a motor 719 may be provided within the handle assembly 502 to engage a gear 721 on the proximal end of the outer tube 744, optionally through an idler gear 725.

Still with reference to FIGS. 30, 31, and 33, in one aspect, an inner electrically insulative (e.g., rubber, plastic) tube 716 is slidably disposed within the inner tube 714. A flex circuit 728 may be disposed within the inner electrically insulative tube 716 to electrically couple energy and sensor circuits to the end effector 512. For example, the jaw member 514 may comprise an electrode coupled to conductors in the flex circuit 728. In other aspects, the end effector 512, jaw member 514, or the ultrasonic blade 516 may comprise various sensors or other electrical elements that can be interconnected to electrical circuits and components in the shaft assembly 510, the handle assembly 502, the ultrasonic transducer/RF generator assembly 504, and/or the battery assembly 506, for example.

Still with reference to FIGS. 30, 31, and 33, in one aspect, the ultrasonic transmission waveguide 545 (shown in FIG. 32 only; not shown in FIG. 33 for clarity) is disposed within the inner electrically insulative tube 716. In one aspect, the positive electrode RF(+) of the electrical circuit 702 is electrically coupled to the ultrasonic transmission waveguide 545 and the negative electrode RF(−) of the electrical circuit 702 is electrically coupled to an electrode disposed in the jaw member 514, which is electrically coupled to the outer tube 744. In operation, after tissue is grasped between the ultrasonic blade 516 and the jaw member 514, control circuits of the surgical instrument 500 can execute various algorithms to seal and the cut the tissue. The ultrasonic vibrations and high-frequency energy may be applied to the tissue in accordance with monitored tissue conditions such as tissue impedance, friction, and the like. In some situations, high-frequency current is applied to the tissue through the ultrasonic blade 516 and back to the outer tube 744 return path. The tissue impedance is monitored and when a tissue seal is formed, as may be determined by the tissue impedance, the ultrasonic blade 516 is mechanically energized to induce vibrational energy into the tissue to cut the tissue. In other aspects ultrasonic vibrations and high-frequency may be applied by pulsing these energy modalities, applying the energy modalities alternatively or simultaneously. In somewhat unique situations, an algorithm can detect when the tissue impedance is extremely low to deliver energy to the tissue. In response, the algorithm energizes the ultrasonic blade 516 mechanically to apply vibratory energy to the tissue until such time that the impedance rises above a threshold suitable for the application of the high-frequency current. Upon reaching this threshold, the algorithm switches energy delivery mode to high-frequency current to seal the tissue.

Figure 34:
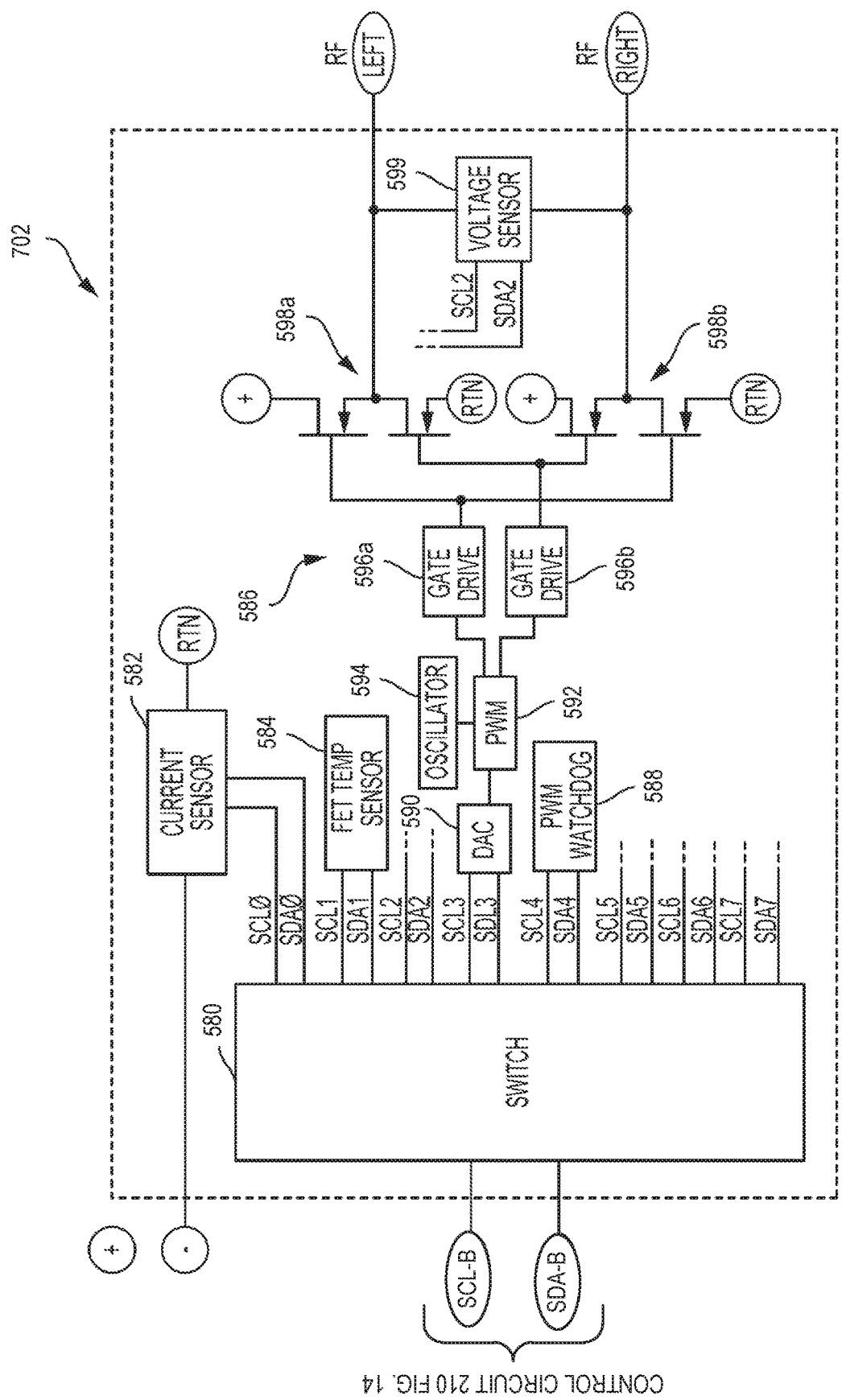
FIG. 34 is a schematic diagram of one aspect of a drive circuit configured for driving a high-frequency current (RF), according to one aspect of the present disclosure.

FIG. 34 is a schematic diagram of one aspect of an electrical circuit 702 configured to drive a high-frequency current (RF), according to one aspect of the present disclosure. The electrical circuit 702 comprises an analog multiplexer 580. The analog multiplexer 580 multiplexes various signals from the upstream channels SCL-A/SDA-A such as RF, battery, and power control circuit. A current sensor 582 is coupled in series with the return or ground leg of the power supply circuit to measure the current supplied by the power supply. A field effect transistor (FET) temperature sensor 584 provides the ambient temperature. A pulse width modulation (PWM) watchdog timer 588 automatically generates a system reset if the main program neglects to periodically service it. It is provided to automatically reset the electrical circuit 702 when it hangs or freezes because of a software or hardware fault. It will be appreciated that the electrical circuit 702 may be configured for driving RF electrodes or for driving the ultrasonic transducer 130 as described in connection with FIG. 11, for example. Accordingly, with reference now back to FIG. 34, the electrical circuit 702 can be used to drive both ultrasonic and RF electrodes interchangeably.

A drive circuit 586 provides left and right RF energy outputs. A digital signal that represents the signal waveform is provided to the SCL-A/SDA-A inputs of the analog multiplexer 580 from a control circuit, such as the control circuit 210 (FIG. 14). A digital-to-analog converter 590 (DAC) converts the digital input to an analog output to drive a PWM circuit 592 coupled to an oscillator 594. The PWM circuit 592 provides a first signal to a first gate drive circuit 596a coupled to a first transistor output stage 598a to drive a first RF+ (Left) energy output. The PWM circuit 592 also provides a second signal to a second gate drive circuit 596b coupled to a second transistor output stage 598b to drive a second RF− (Right) energy output. A voltage sensor 599 is coupled between the RF Left/RF output terminals to measure the output voltage. The drive circuit 586, the first and second drive circuits 596a, 596b, and the first and second transistor output stages 598a, 598b define a first stage amplifier circuit. In operation, the control circuit 210 (FIG. 14) generates a digital waveform 1800 (FIG. 67) employing circuits such as direct digital synthesis (DDS) circuits 1500, 1600 (FIGS. 65 and 66). The DAC 590 receives the digital waveform 1800 and converts it into an analog waveform, which is received and amplified by the first stage amplifier circuit.

Figure 35:
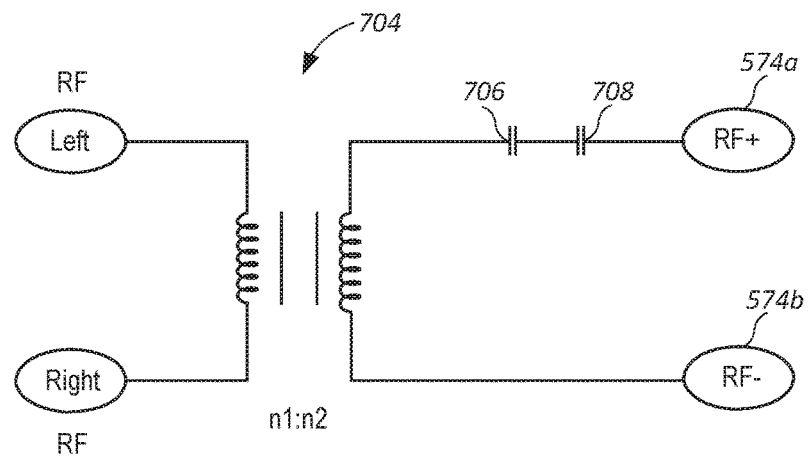
FIG. 35 is a schematic diagram of the transformer coupled to the RF drive circuit shown in FIG. 34, according to one aspect of the present disclosure.

FIG. 35 is a schematic diagram of the transformer 704 coupled to the electrical circuit 702 shown in FIG. 34, according to one aspect of the present disclosure. The RF Left/RF input terminals (primary winding) of the transformer 704 are electrically coupled to the RF Left/RF output terminals of the electrical circuit 702. One side of the secondary winding is coupled in series with first and second blocking capacitors 706, 708. The second blocking capacitor is coupled to the RF+ 574a terminal. The other side of the secondary winding is coupled to the RF− 574b terminal. As previously discussed, the RF+ 574a output is coupled to the ultrasonic blade 516 (FIG. 30) and the RF− 574b ground terminal is coupled to the outer tube 544 (FIG. 30). In one aspect, the transformer 166 has a turns-ratio of n1:n2 of 1:50.

Figure 36:
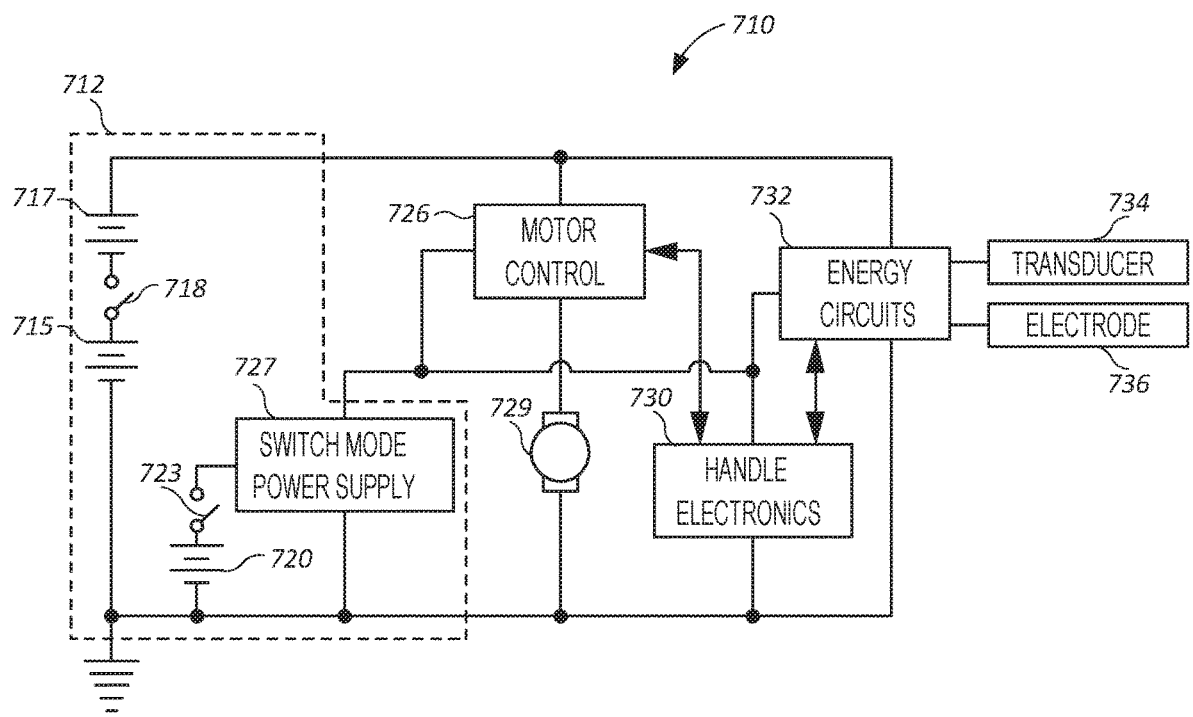
FIG. 36 is a schematic diagram of a circuit comprising separate power sources for high power energy/drive circuits and low power circuits, according to one aspect of the resent disclosure.

FIG. 36 is a schematic diagram of a circuit 710 comprising separate power sources for high power energy/drive circuits and low power circuits, according to one aspect of the present disclosure. A power supply 712 includes a primary battery pack comprising first and second primary batteries 715, 717 (e.g., Li-ion batteries) that are connected into the circuit 710 by a switch 718 and a secondary battery pack comprising a secondary battery 720 that is connected into the circuit by a switch 723 when the power supply 712 is inserted into the battery assembly. The secondary battery 720 is a sag preventing battery that has componentry resistant to gamma or other radiation sterilization. For instance, a switch mode power supply 727 and optional charge circuit within the battery assembly can be incorporated to allow the secondary battery 720 to reduce the voltage sag of the primary batteries 715, 717. This guarantees full charged cells at the beginning of a surgery that are easy to introduce into the sterile field. The primary batteries 715, 717 can be used to power the motor control circuits 726 and the energy circuits 732 directly. The power supply/battery pack 712 may comprise a dual type battery assembly including primary Li-ion batteries 715, 717 and secondary NiMH batteries 720 with dedicated energy cells 720 to control the handle electronics circuits 730 from dedicated energy cells 715, 717 to run the motor control circuits 726 and the energy circuits 732. In this case the circuit 710 pulls from the secondary batteries 720 involved in driving the handle electronics circuits 730 when the primary batteries 715, 717 involved in driving the energy circuits 732 and/or motor control circuits 726 are dropping low. In one various aspect, the circuit 710 may include a one way diode that would not allow for current to flow in the opposite direction (e.g., from the batteries involved in driving the energy and/or motor control circuits to the batteries involved in driving the electronics circuits).

Additionally, a gamma friendly charge circuit may be provided that includes a switch mode power supply 727 using diodes and vacuum tube components to minimize voltage sag at a predetermined level. With the inclusion of a minimum sag voltage that is a division of the NiMH voltages (3 NiMH cells) the switch mode power supply 727 could be eliminated. Additionally a modular system may be provided wherein the radiation hardened components are located in a module, making the module sterilizable by radiation sterilization. Other non-radiation hardened components may be included in other modular components and connections made between the modular components such that the componentry operates together as if the components were located together on the same circuit board. If only two NiMH cells are desired the switch mode power supply 727 based on diodes and vacuum tubes allows for sterilizable electronics within the disposable primary battery pack.

Figure 37:
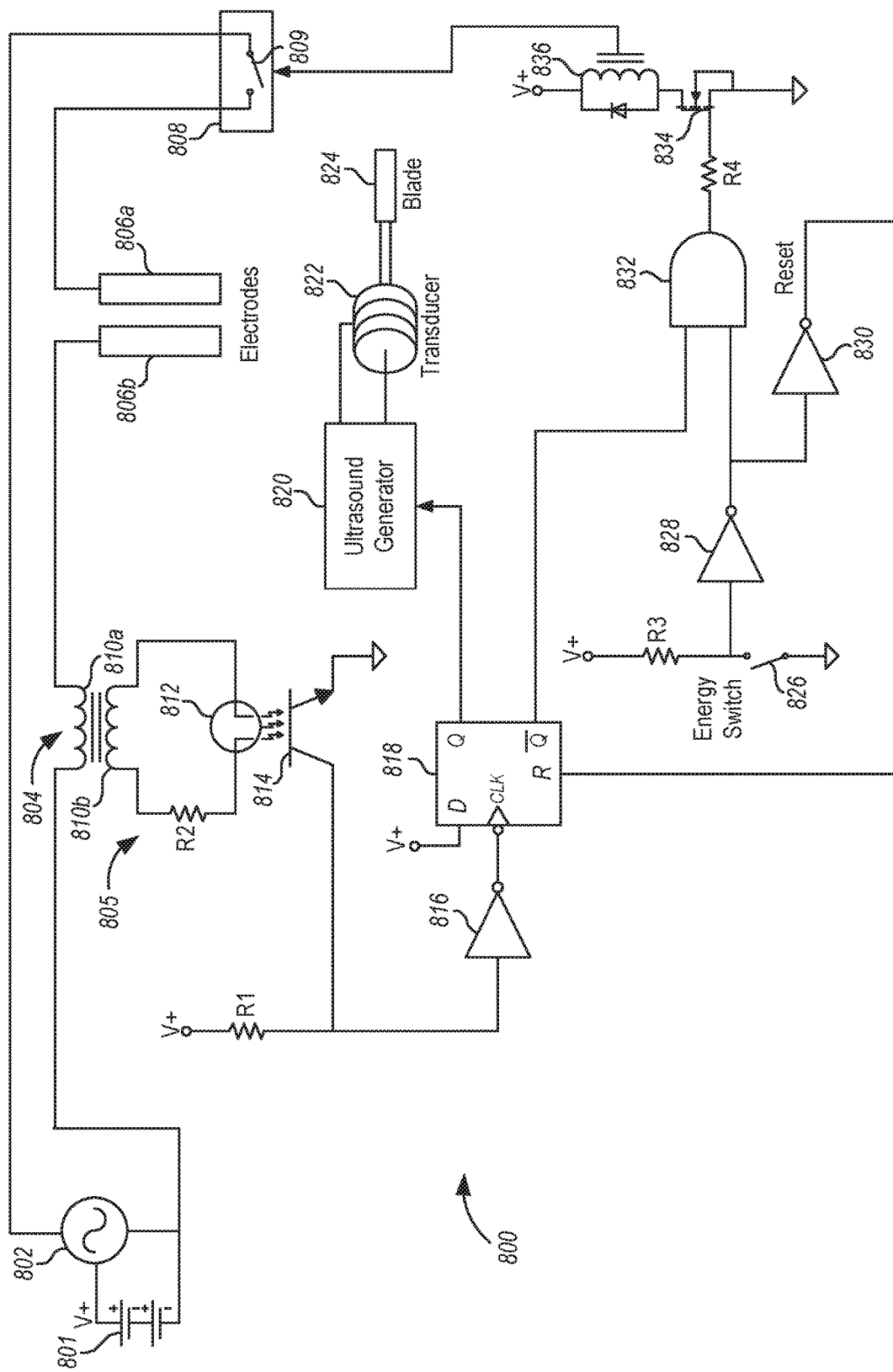
FIG. 37 illustrates a control circuit that allows a dual generator system to switch between the RF generator and the ultrasonic generator energy modalities for the surgical instrument shown in FIGS. 30 and 31.

Turning now to FIG. 37, there is shown a control circuit 800 for operating a battery 801 powered RF generator circuit 802 for use with the surgical instrument 500 shown in FIGS. 30 and 31, according to one aspect of the present disclosure. The surgical instrument 500 is configured to use both ultrasonic vibration and high-frequency current to carry out surgical coagulation/cutting treatments on living tissue, and uses high-frequency current to carry out a surgical coagulation treatment on living tissue.

FIG. 37 illustrates a control circuit 800 that allows a dual generator system to switch between the RF generator circuit 802 and the ultrasonic generator circuit 820 (similar to the electrical circuit 177 shown in FIGS. 11 and 12) energy modalities for the surgical instrument 500 shown in FIGS. 30 and 31. In one aspect, a current threshold in an RF signal is detected. When the impedance of the tissue is low the high-frequency current through tissue is high when RF energy is used as the treatment source for the tissue. According to one aspect, a visual indicator 812 or light located on the surgical instrument 500 may be configured to be in an on-state during this high current period. When the current falls below a threshold, the visual indicator 812 is in an off-state. Accordingly, a photo-transistor 814 may be configured to detect the transition from an on-state to an off-state and disengages the RF energy as shown in the control circuit 800 shown in FIG. 37. Therefore, when the energy button is released and the energy switch 826 is opened, the control circuit 800 is reset and both the RF and ultrasonic generator circuits 802, 820 are held off.

With reference to FIGS. 30-33 and 37, in one aspect, a method of managing an RF generator circuit 802 and ultrasound generator circuit 820 is provided. As previously described the RF generator circuit 802 and/or the ultrasound generator circuit 820 may be located in the handle assembly 502, the ultrasonic transducer/RF generator assembly 504, the battery assembly 506, the shaft assembly 510, and/or the nozzle 700. The control circuit 800 is held in a reset state if the energy switch 826 is off (e.g., open). Thus, when the energy switch 826 is opened, the control circuit 800 is reset and both the RF and ultrasonic generator circuits 802, 820 are turned off. When the energy switch 826 is squeezed and the energy switch 826 is engaged (e.g., closed), RF energy is delivered to the tissue and a visual indicator 812 operated by a current sensing step-up transformer 804 will be lit while the tissue impedance is low. The light from the visual indicator 812 provides a logic signal to keep the ultrasonic generator circuit 820 in the off state. Once the tissue impedance increases above a threshold and the high-frequency current through the tissue decreases below a threshold, the visual indicator 812 turns off and the light transitions to an off-state. A logic signal generated by this transition turns off the relay 808, whereby the RF generator circuit 802 is turned off and the ultrasonic generator circuit 820 is turned on, to complete the coagulation and cut cycle.

Still with reference to FIGS. 30-33 and 37, in one aspect, the dual generator circuit 802, 820 configuration employs an on-board RF generator circuit 802, which is battery 801 powered, for one modality and a second, on-board ultrasound generator circuit 820, which may be on-board in the handle assembly 502, battery assembly 506, shaft assembly 510, nozzle 700, and/or the ultrasonic transducer/RF generator assembly 504. The ultrasonic generator circuit 820 also is battery 801 operated. In various aspects, the RF generator circuit 802 and the ultrasonic generator circuit 820 may be an integrated or separable component of the handle assembly 502. According to various aspects, having the dual RF/ultrasonic generator circuits 802, 820 as part of the handle assembly 502 may eliminate the need for complicated wiring in an environment where the surgical instrument 500. The RF/ultrasonic generator circuits 802, 820 may be configured to provide the full capabilities of an existing generator while utilizing the capabilities of a cordless generator system simultaneously.

Either type of system can have separate controls for the modalities that are not communicating with each other. The surgeon activates the RF and Ultrasonic separately and at their discretion. Another approach would be to provide fully integrated communication schemes that share buttons, tissue status, instrument operating parameters (such as jaw closure, forces, etc.) and algorithms to manage tissue treatment. Various combinations of this integration can be implemented to provide the appropriate level of function and performance.

In one aspect, the control circuit 800 includes a battery 801 powered RF generator circuit 802 comprising a battery as an energy source. As shown, RF generator circuit 802 is coupled to two electrically conductive surfaces referred to herein as electrodes 806a, 806b and is configured to drive the electrodes 806a, 806b with RF energy (e.g., high-frequency current). A first winding 810a of a step-up transformer 804 is connected in series with one pole of the bipolar RF generator circuit 802 and the return electrode 806b. In one aspect, the first winding 810a and the return electrode 806b are connected to the negative pole of the bipolar RF generator circuit 802. The other pole of the bipolar RF generator circuit 802 is connected to the active electrode 806a through a switch contact 809 of a relay 808, or any suitable electromagnetic switching device comprising an armature which is moved by an electromagnet 836 to operate the switch contact 809. The switch contact 809 is closed when the electromagnet 836 is energized and the switch contact 809 is open when the electromagnet 836 is de-energized. When the switch contact is closed, RF current flows through conductive tissue (not shown) located between the electrodes 806a, 806b. It will be appreciated, that in one aspect, the active electrode 806a is connected to the positive pole of the bipolar RF generator circuit 802.

A visual indicator circuit 805 comprises a step-up transformer 804, a series resistor R2, and a visual indicator 812. The visual indicator 812 can be adapted for use with the surgical instrument 500 and other electrosurgical systems and tools, such as those described herein. The first winding 810a of the step-up transformer 804 is connected in series with the return electrode 806b and a second winding 810b of the step-up transformer 804 is connected in series with a resistor R2 and a visual indicator 812 comprising a type NE-2 neon bulb, for example.

In operation, when the switch contact 809 of the relay 808 is open, the active electrode 806a is disconnected from the positive pole of the bipolar RF generator circuit 802 and no current flows through the tissue, the return electrode 806b, and the first winding 810a of the step-up transformer 804. Accordingly, the visual indicator 812 is not energized and does not emit light. When the switch contact 809 of the relay 808 is closed, the active electrode 806a is connected to the positive pole of the bipolar RF generator circuit 802 enabling current to flow through tissue, the return electrode 806b, and the first winding 810a of the step-up transformer 804 to operate on tissue, for example cut and cauterize the tissue.

A first current flows through the first winding 810a as a function of the impedance of the tissue located between the active and return electrodes 806a, 806b providing a first voltage across the first winding 810a of the step-up transformer 804. A stepped up second voltage is induced across the second winding 810b of the step-up transformer 804. The secondary voltage appears across the resistor R2 and energizes the visual indicator 812 causing the neon bulb to light when the current through the tissue is greater than a predetermined threshold. It will be appreciated that the circuit and component values are illustrative and not limited thereto. When the switch contact 809 of the relay 808 is closed, current flows through the tissue and the visual indicator 812 is turned on.

Turning now to the energy switch 826 portion of the control circuit 800, when the energy switch 826 is open position, a logic high is applied to the input of a first inverter 828 and a logic low is applied of one of the two inputs of the AND gate 832. Thus, the output of the AND gate 832 is low and the transistor 834 is off to prevent current from flowing through the winding of the electromagnet 836. With the electromagnet 836 in the de-energized state, the switch contact 809 of the relay 808 remains open and prevents current from flowing through the electrodes 806a, 806b. The logic low output of the first inverter 828 also is applied to a second inverter 830 causing the output to go high and resetting a flip-flop 818 (e.g., a D-Type flip-flop). At which time, the Q output goes low to turn off the ultrasound generator circuit 820 circuit and the $\overline{Q}$ output goes high and is applied to the other input of the AND gate 832.

When the user presses the energy switch 826 on the instrument handle to apply energy to the tissue between the electrodes 806a, 806b, the energy switch 826 closes and applies a logic low at the input of the first inverter 828, which applies a logic high to other input of the AND gate 832 causing the output of the AND gate 832 to go high and turns on the transistor 834. In the on state, the transistor 834 conducts and sinks current through the winding of the electromagnet 836 to energize the electromagnet 836 and close the switch contact 809 of the relay 808. As discussed above, when the switch contact 809 is closed, current can flow through the electrodes 806a, 806b and the first winding 810a of the step-up transformer 804 when tissue is located between the electrodes 806a, 806b.

As discussed above, the magnitude of the current flowing through the electrodes 806a, 806b depends on the impedance of the tissue located between the electrodes 806a, 806b. Initially, the tissue impedance is low and the magnitude of the current high through the tissue and the first winding 810a. Consequently, the voltage impressed on the second winding 810b is high enough to turn on the visual indicator 812. The light emitted by the visual indicator 812 turns on the phototransistor 814, which pulls the input of the inverter 816 low and causes the output of the inverter 816 to go high. A high input applied to the CLK of the flip-flop 818 has no effect on the Q or the $\overline{Q}$ outputs of the flip-flop 818 and Q output remains low and the $\overline{Q}$ output remains high. Accordingly, while the visual indicator 812 remains energized, the ultrasound generator circuit 820 is turned OFF and the ultrasonic transducer 822 and ultrasonic blade 824 are not activated.

As the tissue between the electrodes 806a, 806b dries up, due to the heat generated by the current flowing through the tissue, the impedance of the tissue increases and the current therethrough decreases. When the current through the first winding 810a decreases, the voltage across the second winding 810b also decreases and when the voltage drops below a minimum threshold required to operate the visual indicator 812, the visual indicator 812 and the phototransistor 814 turn off. When the phototransistor 814 turns off, a logic high is applied to the input of the inverter 816 and a logic low is applied to the CLK input of the flip-flop 818 to clock a logic high to the Q output and a logic low to the $\overline{Q}$ output. The logic high at the Q output turns on the ultrasound generator circuit 820 to activate the ultrasonic transducer 822 and the ultrasonic blade 824 to initiate cutting the tissue located between the electrodes 806a, 806a. Simultaneously or near simultaneously with the ultrasound generator circuit 820 turning on, the $\overline{Q}$ output of the flip-flop 818 goes low and causes the output of the AND gate 832 to go low and turn off the transistor 834, thereby de-energizing the electromagnet 836 and opening the switch contact 809 of the relay 808 to cut off the flow of current through the electrodes 806a, 806b.

While the switch contact 809 of the relay 808 is open, no current flows through the electrodes 806a, 806b, tissue, and the first winding 810a of the step-up transformer 804. Therefore, no voltage is developed across the second winding 810b and no current flows through the visual indicator 812.

The state of the Q and the $\overline{Q}$ outputs of the flip-flop 818 remain the same while the user squeezes the energy switch 826 on the instrument handle to maintain the energy switch 826 closed. Thus, the ultrasonic blade 824 remains activated and continues cutting the tissue between the jaws of the end effector while no current flows through the electrodes 806a, 806b from the bipolar RF generator circuit 802. When the user releases the energy switch 826 on the instrument handle, the energy switch 826 opens and the output of the first inverter 828 goes low and the output of the second inverter 830 goes high to reset the flip-flop 818 causing the Q output to go low and turn off the ultrasound generator circuit 820. At the same time, the $\overline{Q}$ output goes high and the circuit is now in an off state and ready for the user to actuate the energy switch 826 on the instrument handle to close the energy switch 826, apply current to the tissue located between the electrodes 806a, 806b, and repeat the cycle of applying RF energy to the tissue and ultrasonic energy to the tissue as described above.

Figure 38:
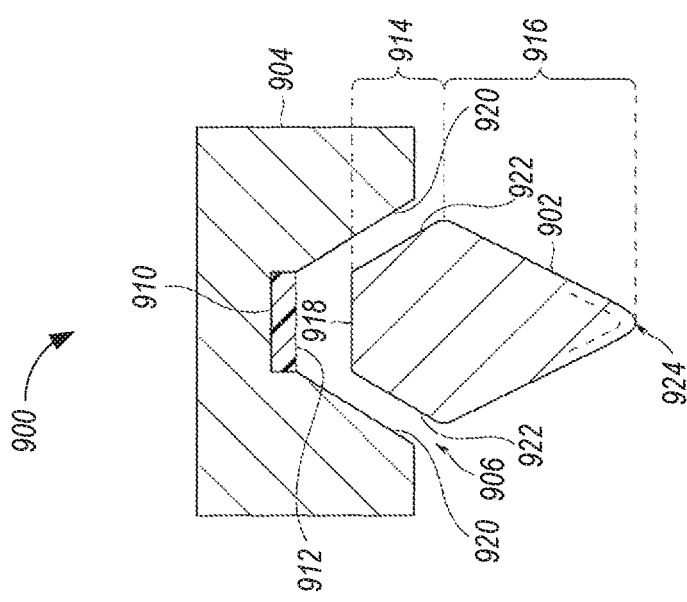
FIG. 38 is a sectional view of an end effector, according to one aspect of the present disclosure.
Figure 40:
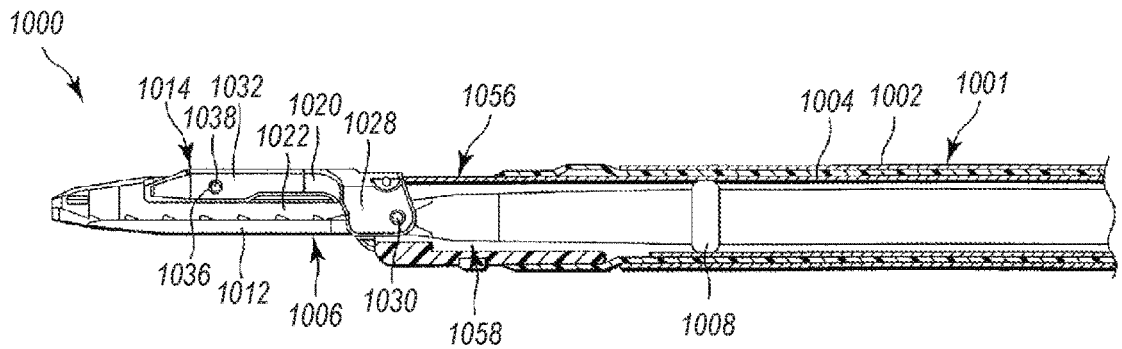
FIG. 40 is a partial longitudinal sectional side view showing a distal jaw section in a closed state, according to one aspect of the present disclosure.
Figure 41:
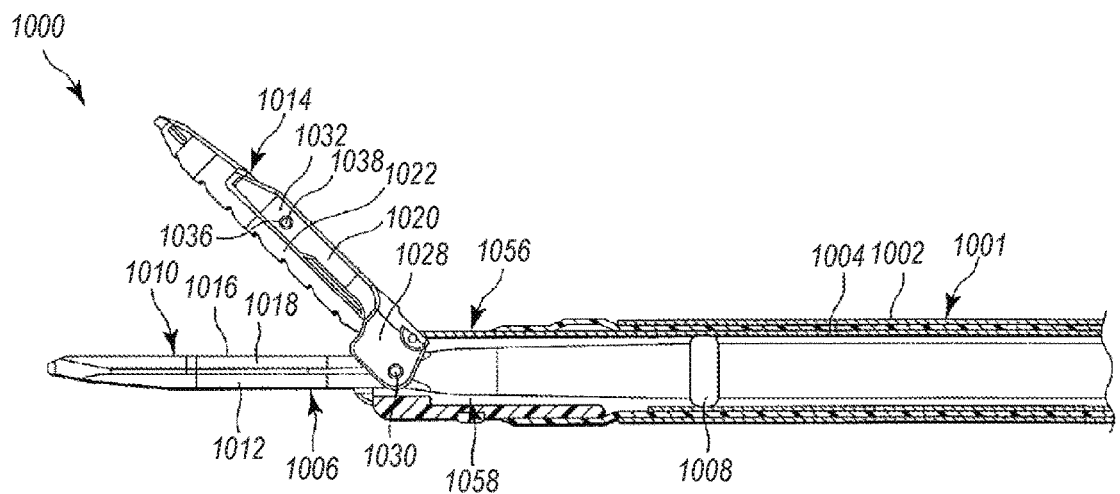
FIG. 41 is a partial longitudinal sectional side view showing the distal jaw section in an open state, according to one aspect of the present disclosure.
Figure 42:
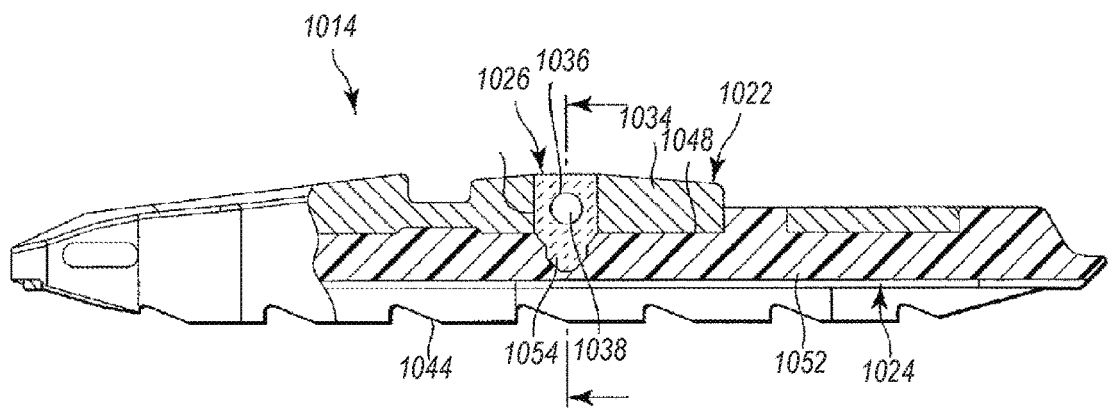
FIG. 42 is a partial longitudinal sectional side view showing a jaw member, according to one aspect of the present disclosure.

FIG. 38 is a sectional view of an end effector 900, according to one aspect of the present disclosure. The end effector 900 comprises an ultrasonic blade 902 and a jaw member 904. The jaw member 904 has a channel-shaped groove 906 in which part of the end effector 900 is engaged, along an axial direction. The channel-shaped groove 906 has a wide channel shape with a wide opening in a section orthogonal to an axis of the jaw member 904. The jaw member 904 is made of a conductive material, and an insulating member 910 is provided in a range where the ultrasonic blade 902 is in contact along the axial direction on a bottom surface portion 912 of the channel shape.

The ultrasonic blade 902 has a rhombic shape partially cut out in the section orthogonal to the axial direction. The sectional shape of the ultrasonic blade 902 is a shape which is cut out in the direction orthogonal to a longer diagonal line of the rhombic shape as shown in FIG. 38. The ultrasonic blade 902 with part of the rhombic shape cut out in the sectional shape has a trapezoidal portion 914 which is engaged in the channel-shaped groove 906 of the jaw member 904. A portion in which part of the rhombic shape is not cut out in the sectional shape is an isosceles triangle portion 916 of the ultrasonic blade 902.

When the trigger of the handle assembly is closed, the ultrasonic blade 902 and the jaw member 904 are fitted to each other. When they are fitted, the bottom surface portion 912 of the channel-shaped groove 906 abuts on a top surface portion 918 of the trapezoidal portion 914 of the ultrasonic blade 902, and two inner wall portions 920 of the channel-shaped groove 906 abut on inclined surface portions 922 of the trapezoidal portion 914.

Further, an apex portion 924 of the isosceles triangle portion 916 of the ultrasonic blade 902 is formed to be rounded, but the apex portion 924 has a slightly sharp angle.

When the surgical instrument is used as a spatulate ultrasound treatment instrument, the ultrasonic blade 902 acts as an ultrasound vibration treatment portion, and the apex portion 924 and its peripheral portion (shown by the dotted line) particularly act as a scalpel knife to the tissue of the treatment object.

Further, when the surgical instrument is used as a spatulate high-frequency treatment instrument, the apex portion 924 and its peripheral portion (shown by the dotted line) act as an electric scalpel knife to the tissue of the treatment object.

In one aspect, the bottom surface portion 912 and the inner wall portions 920, and the top surface portion 918 and the inclined surface portions 922 act as the working surfaces of an ultrasound vibration.

Further, in one aspect, the inner wall portions 920 and the inclined surface portions 922 act as the working surfaces of a bipolar high-frequency current.

In one aspect, the surgical instrument may be used as a spatulate treatment instrument of simultaneous output of ultrasound and high-frequency current, the ultrasonic blade 902 acts as the ultrasound vibration treatment portion, and the apex portion 924 and its peripheral portion (shown by the dotted line) particularly act as an electrical scalpel knife to the tissue of the treatment object.

Further, when the surgical instrument provides simultaneous output of ultrasound and high-frequency current, the bottom surface portion 912 and the top surface portion 918 act as the working surfaces of an ultrasound vibration, and the inner wall portions 920 and the inclined surface portions 922 act as the working surfaces of a bipolar high-frequency current.

Consequently, according to the configuration of the treatment portion shown in FIG. 37, excellent operability is provided not only in the case of use of the surgical instrument as an ultrasound treatment instrument or a high-frequency treatment instrument, but also in the case of use of the surgical instrument as an ultrasound treatment instrument or high-frequency current treatment instrument, and further in the case of use of the surgical instrument for the time of simultaneous output of ultrasound and high frequency.

When the surgical instrument performs high-frequency current output or simultaneous output of high-frequency current and ultrasound, monopolar output may be enabled instead of a bipolar output as the high-frequency output.

Figure 39:
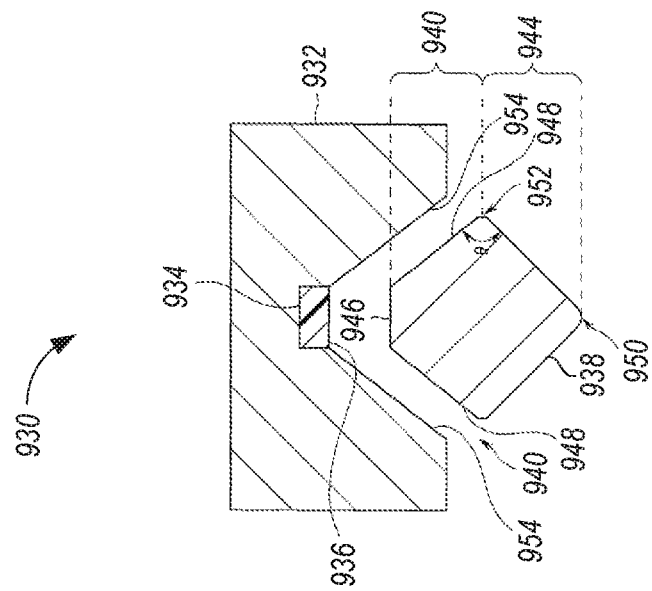
FIG. 39 is a sectional view of an end effector, according to one aspect of the present disclosure.

FIG. 39 is a sectional view of an end effector 930, according to one aspect of the present disclosure. The jaw member 932 is made of a conductive material, and an insulating member 934 is provided along the axial direction on a bottom surface portion 936 of the channel shape.

The ultrasonic blade 938 has a rhombic shape partially cut out in the section orthogonal to the axial direction. The sectional shape of the ultrasonic blade 938 is a shape in which part of the rhombic shape is cut out in the direction orthogonal to one diagonal line as shown in FIG. 39. The ultrasonic blade 938 with part of the rhombic shape cut out in the sectional shape has a trapezoidal portion 940 which is engaged in a channel-shaped groove 942 of the jaw member 932. A portion in which part of the rhombic shape is not cut out in the sectional shape is an isosceles triangle portion 944 of the end effector 900.

When the trigger of the handle assembly is closed, the ultrasonic blade 938 and the jaw member 906 are fitted to each other. When they are fitted, the bottom surface portion 936 of the channel-shaped groove 942 abuts on a top surface portion 946 of the trapezoidal portion 940 of the ultrasonic blade 938, and two inner wall portions 954 of the channel-shaped groove 932 abut on inclined surface portions 948 of the trapezoidal portion 940.

Further, an apex portion 950 of the isosceles triangle portion 944 of the ultrasonic blade 938 is formed to be rounded, but an apex portion 952 of the inner side of the hook shape has a slightly sharp angle. An angle θ of the apex portion 952 is preferably 45° to 100°. 45° is a strength limit of the ultrasonic blade 938. As above, the apex portion 952 of the ultrasonic blade 938 configures a protruding portion having a predetermined angle at the inner side of the hook-shaped portion, that is, an edge portion.

The treatment portion in the hook shape is often used for dissection. The apex portion 952 of the end effector 930 becomes a working portion at the time of dissection. Since the apex portion 952 has the slightly sharp angle θ, the apex portion 952 is effective for dissection treatment.

The ultrasonic blade 938 and the jaw member 932 shown in FIG. 39 perform the same operation as the ultrasonic blade 938 and the jaw member 932 shown in FIG. 38 at the time of ultrasound output, at the time of high-frequency output, and at the time of simultaneous output of ultrasound and high frequency respectively, except for the aforementioned operation at the time of dissection.

Referring now to FIGS. 40-43, there is shown and end effector 1000 operably coupled to an insertion sheath 1001, which is formed by an outer sheath 1002 and an inner sheath 1004. The end effector 1000 comprises an ultrasonic blade 1006 and a jaw member 1014. In the outer sheath 1002, the outside of a conductive metal pipe is covered with an insulating resin tube. The inner sheath 1004 is a conductive metal pipe. The inner sheath 1004 can be axially moved back and forth relative to the outer sheath 1002.

The ultrasonic blade 1006 is made of a conductive material having high acoustic effects and biocompatibility, for example, a titanium alloy such as a Ti-6Al-4V alloy. In the ultrasonic blade 1006, an insulating and elastic rubber lining 1008 is externally equipped in the position of nodes of the ultrasonic vibration. The rubber lining 1008 is disposed between the inner sheath 1004 and the ultrasonic blade 1006 in a compressed state. The ultrasonic blade 1006 is held to the inner sheath 1004 by the rubber lining 1008. A clearance is maintained between the inner sheath 1004 and the ultrasonic blade 1006.

An abutting portion 1010 is formed by the part of the ultrasonic blade 1012 facing the jaw member 1014 at the distal end portion of the ultrasonic blade 1006. Here, the ultrasonic blade 1012 is octagonal in its cross section perpendicular to the axial directions of the ultrasonic blade 1006. An abutting surface 1016 is formed by one surface of the abutting portion 1010 facing the jaw member 1014. A pair of electrode surfaces 1018 is formed by surfaces provided to the sides of the abutting surface 1016.

The jaw member 1014 is formed by a body member 1020, an electrode member 1022, a pad member 1024, and a regulating member 1026 as a regulating section.

The body member 1020 is made of a hard and conductive material. A proximal end portion of the body member 1020 constitutes a pivot connection portion 1028. The pivot connection portion 1028 is pivotally connected to a distal end portion of the outer sheath 1002 via a pivot connection shaft 1030. The pivot connection shaft 1030 extends in width directions perpendicular to the axial directions and the opening/closing directions. The body member 1020 can turn about the pivot connection shaft 1030 in the opening/closing directions relative to the outer sheath 1002. A distal end portion of the inner sheath 1004 is pivotally connected to the pivot connection portion 1028 of the body member 1020 at a position provided to the distal side and the opening-direction side of the pivot connection shaft 1030. If the movable handle is turned relative to the fixed handle in the handle unit, the inner sheath 1004 is moved back and forth relative to the outer sheath 1002, and the body member 1020 is driven by the inner sheath 1004 to turn about the pivot connection shaft 1030 in the opening/closing directions relative to the outer sheath 1002. In one aspect, a distal part of the body member 1020 constitutes a pair of pivot bearings 1032. The pair of pivot bearings 1032 are in the form of plates which extend in the axial directions and which are perpendicular to the width directions, and are disposed apart from each other in the width directions.

The electrode member 1022 is made of a hard and conductive material. The part of the electrode member 1022 provided on the opening-direction side constitutes a pivot support 1034. An insertion hole 1036 is formed through the pivot support 1034 in the width directions. A pivot support shaft 1038 is inserted through the insertion hole 1036 and extends in the width directions. The pivot support 1034 is disposed between the pair of pivot bearings 1032 of the body member 1020, and is pivotally supported on the pair of pivot bearings 1032 via the pivot support shaft 1038. The electrode member 1022 can oscillate about the pivot support shaft 1038 relative to the body member 1020. Further, the part of the electrode member 1022 provided on the closing-direction side constitutes an electrode section 1040. The electrode section 1040 extends in the axial directions and projects to the sides in the width directions. A recessed groove 1042 which is open toward the closing direction extends in the axial directions in the part of the electrode section 1040 provided on the closing-direction side. Teeth are axially provided in the parts of the groove 1042 provided in the closing direction side, thus forming a tooth portion 1044. The side surfaces that define the groove 1042 constitute a pair of electrode receiving surfaces 1046 that are inclined from the closing direction toward the sides in the width directions. A recessed mating receptacle 1048 which is open toward the closing direction axially extends in a bottom portion that defines the groove 1042. An embedding hole 1050 is formed through the pivot support 1034 of the electrode member 1022 in the opening/closing directions perpendicularly to the insertion hole 1036. The embedding hole 1050 is open to the mating receptacle 1048.

The pad member 1024 is softer than the ultrasonic blade 1006, and is made of an insulating material having biocompatibility such as polytetrafluoroethylene. The pad member 1024 is mated with the mating receptacle 1048 of the electrode member 1022. The part of the pad member 1024 provided on the closing-direction side protrudes from the electrode member 1022 to the closing direction, thus forming an abutting receptacle 1052. In the cross section perpendicular to the axial directions, the abutting receptacle 1052 is in a recessed shape corresponding to the projecting shape of the abutting portion 1010 of the ultrasonic blade 1012. When the jaw member 1014 is closed relative to the ultrasonic blade 1012, the abutting portion 1010 of the ultrasonic blade 1012 abuts onto and engages with the abutting receptacle 1052 of the pad member 1024. The pair of electrode surfaces 1018 of the ultrasonic blade 1012 are arranged parallel to the pair of electrode receiving surfaces 1046 of the electrode section 1040, and a clearance is maintained between the electrode section 1040 and the ultrasonic blade 1012.

The regulating member 1026 is harder than the ultrasonic blade 1006, and is made of an insulating high-strength material such as ceramics. The regulating pad member 1024 is pin-shaped. The regulating pad member 1024 is inserted into the embedding hole 1050 of the pivot support 1034 of the electrode member 1022, protrudes toward the mating receptacle 1048 of the electrode section 1040, and is embedded in the abutting receptacle 1052 of the pad member 1024 in the mating receptacle 1048. A closing-direction end of the regulating member 1026 constitutes a regulating end 1054. The regulating end 1054 does not protrude from the abutting receptacle 1052 to the closing direction, and is accommodated in the abutting receptacle 1052. The insertion hole 1036 is also formed through the regulating member 1026, and the pivot support shaft 1038 is inserted through the insertion hole 1036 of the regulating member 1026.

Here, the inner sheath 1004, the body member 1020, and the electrode member 1022 are electrically connected to one another, and constitute the first electrical path 1056 used in a high-frequency surgical treatment. The electrode section 1040 of the electrode member 1022 functions as one of bipolar electrodes used in a high-frequency surgical treatment. In one aspect, the ultrasonic blade 1006 constitutes the second electrical path 1058 used in the high-frequency treatment. The ultrasonic blade 1012 provided to the distal end portion of the ultrasonic blade 1006 functions as the other of the bipolar electrodes used in a high-frequency treatment. As described above, the ultrasonic blade 1006 is held to the inner sheath 1004 by the insulating rubber lining 1008, and the clearance is maintained between the inner sheath 1004 and the ultrasonic blade 1006. This prevents a short circuit between the inner sheath 1004 and the ultrasonic blade 1006. When the jaw member 1014 is closed relative to the ultrasonic blade 1012, the abutting portion 1010 of the ultrasonic blade 1012 abuts onto and engages with the abutting receptacle 1052 of the pad member 1024. Thus, the pair of electrode surfaces 1018 of the ultrasonic blade 1012 are arranged parallel to the pair of electrode receiving surfaces 1046 of the electrode section 1040, and the clearance is maintained between the electrode section 1040 and the ultrasonic blade 1012. This prevents a short circuit between the electrode section 1040 and the ultrasonic blade 1012.

Figure 44:
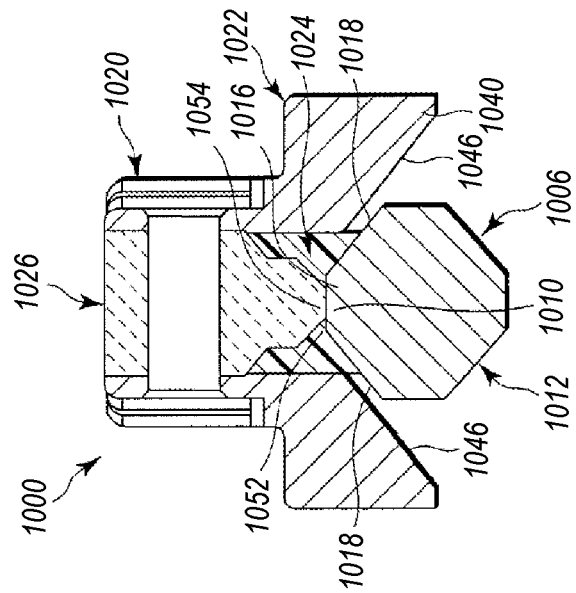
FIG. 44 is a cross-sectional view showing the distal jaw section in a worn state, according to one aspect of the present disclosure.
Figure 43:
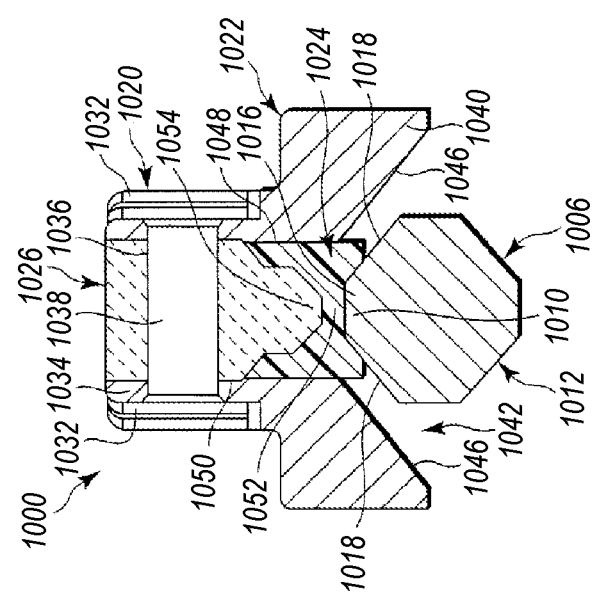
FIG. 43 is a cross-sectional view showing the distal jaw section in a normal state, according to one aspect of the present disclosure.

Referring to FIG. 44, the pad member 1024 is softer than the ultrasonic blade 1006. Therefore, the abutting receptacle 1052 is worn by the ultrasonic blade 1012 in the case where the ultrasonic blade 1012 is ultrasonically vibrated when the jaw member 1014 is closed relative to the ultrasonic blade 1012 and the abutting portion 1010 of the ultrasonic blade 1012 abuts onto and engages with the abutting receptacle 1052 of the pad member 1024. As the abutting receptacle 1052 is worn, the clearance between the electrode section 1040 and the ultrasonic blade 1012 is gradually reduced when the abutting portion 1010 is in a frictional engagement with the abutting receptacle 1052. When the abutting receptacle 1052 is worn more than a predetermined amount, the regulating end 1054 of the regulating member 1026 is exposed from the abutting receptacle 1052 in the closing direction. When the regulating end 1054 is exposed from the abutting receptacle 1052 in the closing direction, the regulating end 1054 contacts the ultrasonic blade 1012 before the electrode section 1040 contacts the ultrasonic blade 1012 if the jaw member 1014 is closed relative to the ultrasonic blade 1012. As a result, the contact between the ultrasonic blade 1012 and the electrode section 1040 is regulated. Here, the electrode section 1040 and the ultrasonic blade 1012 are hard. Therefore, when the ultrasonically vibrated ultrasonic blade 1012 contacts the electrode section 1040, the ultrasonic blade 1012 rapidly and repetitively comes in and out of contact with the electrode section 58. When a high-frequency voltage is applied between the electrode section 1040 and the ultrasonic blade 1012, sparking occurs between the ultrasonic blade 1012 and the electrode section 1040. In one aspect, the contact between the ultrasonic blade 1012 and the electrode section 1040 is regulated by the regulating end 1054 of the regulating member 1026, so that sparking is prevented. The regulating member 1026 is made of an insulating material, and is electrically insulated relative to the electrode member 1022. Thus, if the ultrasonically vibrated ultrasonic blade 1012 contacts the regulating end 1054 of the regulating member 1026, no sparking occurs between the regulating end 1054 and the ultrasonic blade 1012 even when the ultrasonic blade 1012 rapidly and repetitively comes in and out of contact with the regulating end 1054. This prevents sparking between the ultrasonic blade 1012 and the jaw member 1014.

The regulating member 1026 is made of a high-strength material harder than the ultrasonic blade 1006. Therefore, when the regulating end 1054 contacts the ultrasonically vibrated ultrasonic blade 1012, the regulating member 1026 is not worn, and the ultrasonic blade 1006 cracks. In the surgical treatment system according to one aspect, when the abutting receptacle 1052 is worn more than a predetermined amount, the regulating end 1054 contacts the ultrasonic blade 1012 to intentionally crack the ultrasonic blade 1006. By detecting this crack, the end of the life of the surgical treatment instrument is detected. Therefore, the position of the contact between the ultrasonic blade 1012 and the regulating end 1054 is set at the stress concentration region in the ultrasonic blade 1012 to ensure that the ultrasonic blade 1006 cracks when the regulating end 1054 contacts the ultrasonic blade 1012. In a linear ultrasonic blade 1006, stress concentrates in the positions of the nodes of the ultrasonic vibration, and a stress concentration region is located at the proximal end portion of the ultrasonic blade 1012.

For a more detailed description of a combination ultrasonic/electrosurgical instrument, reference is made to U.S. Pat. Nos. 8,696,666 and 8,663,223, each of which is herein incorporated by reference.

Figure 45:
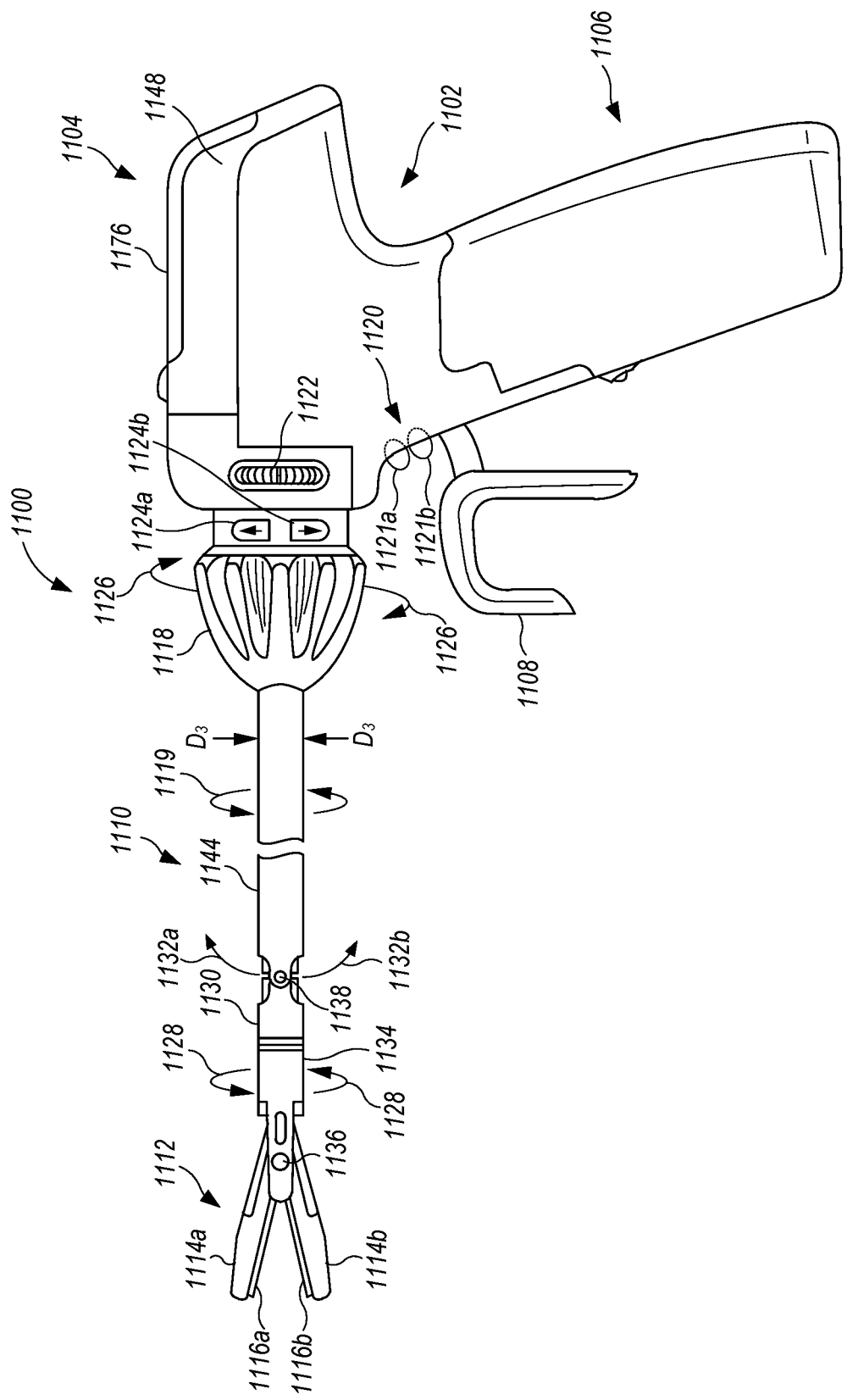
FIG. 45 illustrates a modular battery powered handheld electrosurgical instrument with distal articulation, according to one aspect of the present disclosure.
Figure 46:
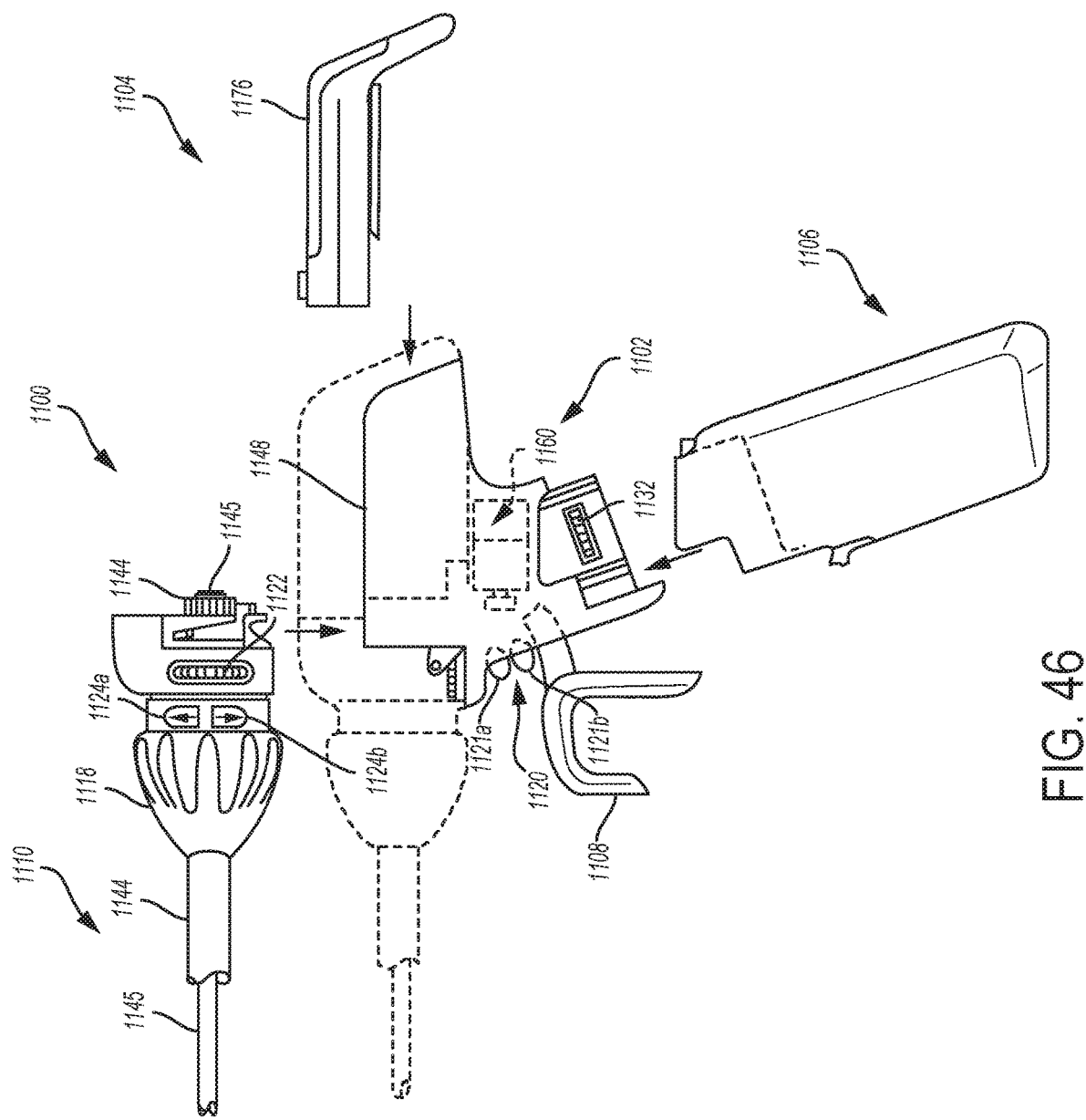
FIG. 46 is an exploded view of the surgical instrument shown in FIG. 45, according to one aspect of the present disclosure.

FIG. 45 illustrates a modular battery powered handheld electrosurgical instrument 1100 with distal articulation, according to one aspect of the present disclosure. The surgical instrument 1100 comprises having a handle assembly 1102, a knife drive assembly 1104, a battery assembly 1106, a shaft assembly 1110, and an end effector 1112. The end effector 1112 comprises a pair of jaw members 1114a, 1114b in opposing relationship affixed to a distal end thereof. The end effector 1112 is configured to articulate and rotate. FIG. 46 is an exploded view of the surgical instrument 1100 shown in FIG. 45, according to one aspect of the present disclosure. The end effector 1112 for use with the surgical instrument 1100 for sealing and cutting tissue includes a pair of jaw members 1114a, 1114b that in opposing relationship and movable relative to each other to grasp tissue therebetween. A jaw member 1114a, 1114b includes a jaw housing and an electrically conductive surface 1116a, 1116b, e.g., electrodes, adapted to connect to a source of electrosurgical energy (RF source) such that the electrically conductive surfaces are capable of conducting electrosurgical energy through tissue held therebetween to effect a tissue seal. One of the electrically conductive surfaces 1116b includes a channel defined therein and extending along a length thereof that communicates with a drive rod 1145 connected to a motor disposed in the knife drive assembly 1104. The knife is configured to translate and reciprocate along the channel to cut tissue grasped between the jaw members 1114a, 1114b.

Figure 47:
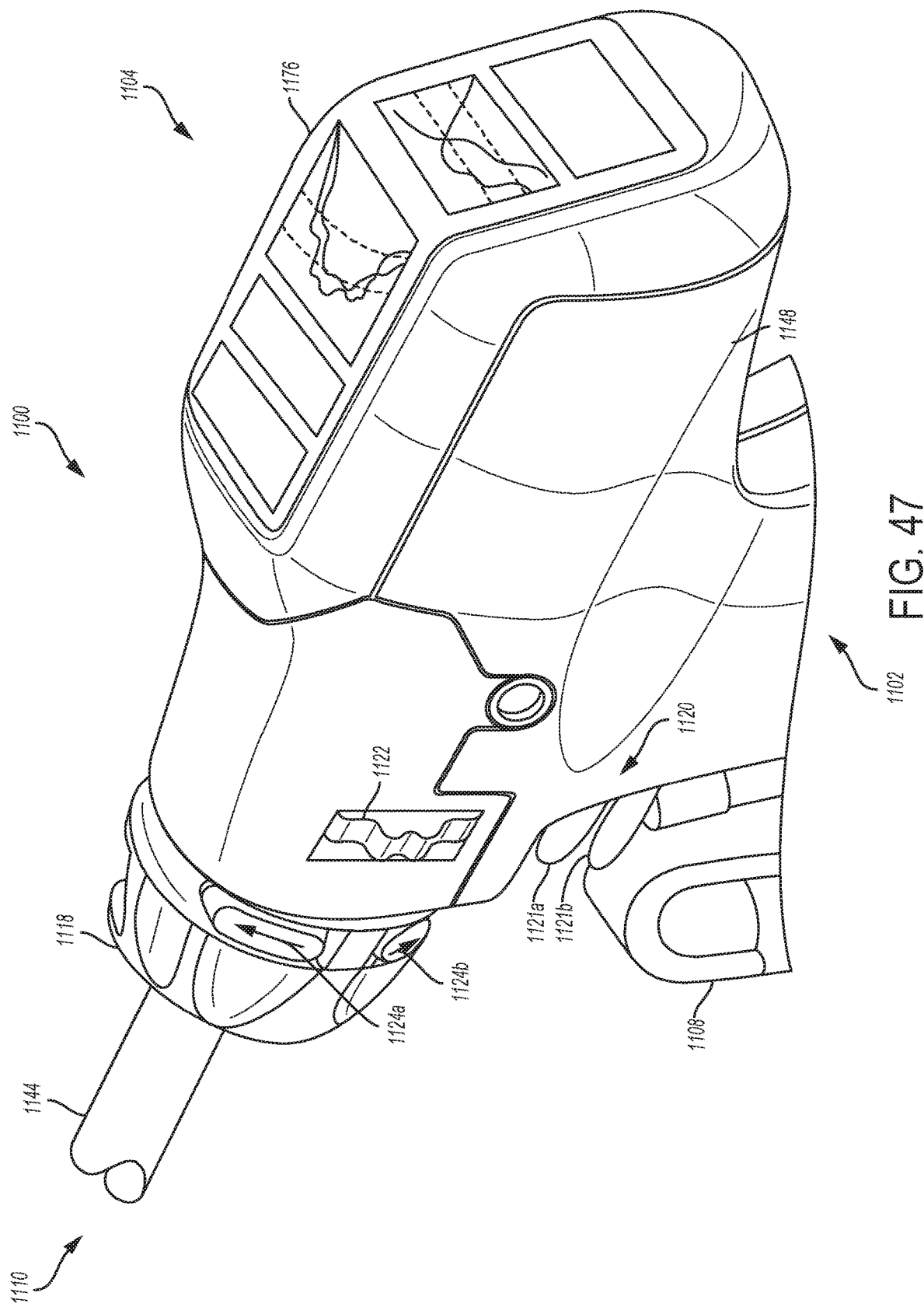
FIG. 47 is a perspective view of the surgical instrument shown in FIGS. 45 and 46 with a display located on the handle assembly, according to one aspect of the present disclosure.

FIG. 47 is a perspective view of the surgical instrument 1100 shown in FIGS. 45 and 46 with a display located on the handle assembly 1102, according to one aspect of the present disclosure. The handle assembly 1102 of the surgical instrument shown in FIGS. 45-47 comprises a motor assembly 1160 and a display assembly. The display assembly comprises a display 1176, such as an LCD display, for example, which is removably connectable to a housing 1148 portion of the handle assembly 1102. The display 1176 provides a visual display of surgical procedure parameters such as tissue thickness, status of seal, status of cut, tissue thickness, tissue impedance, algorithm being executed, battery capacity, among other parameters.

Figure 48:
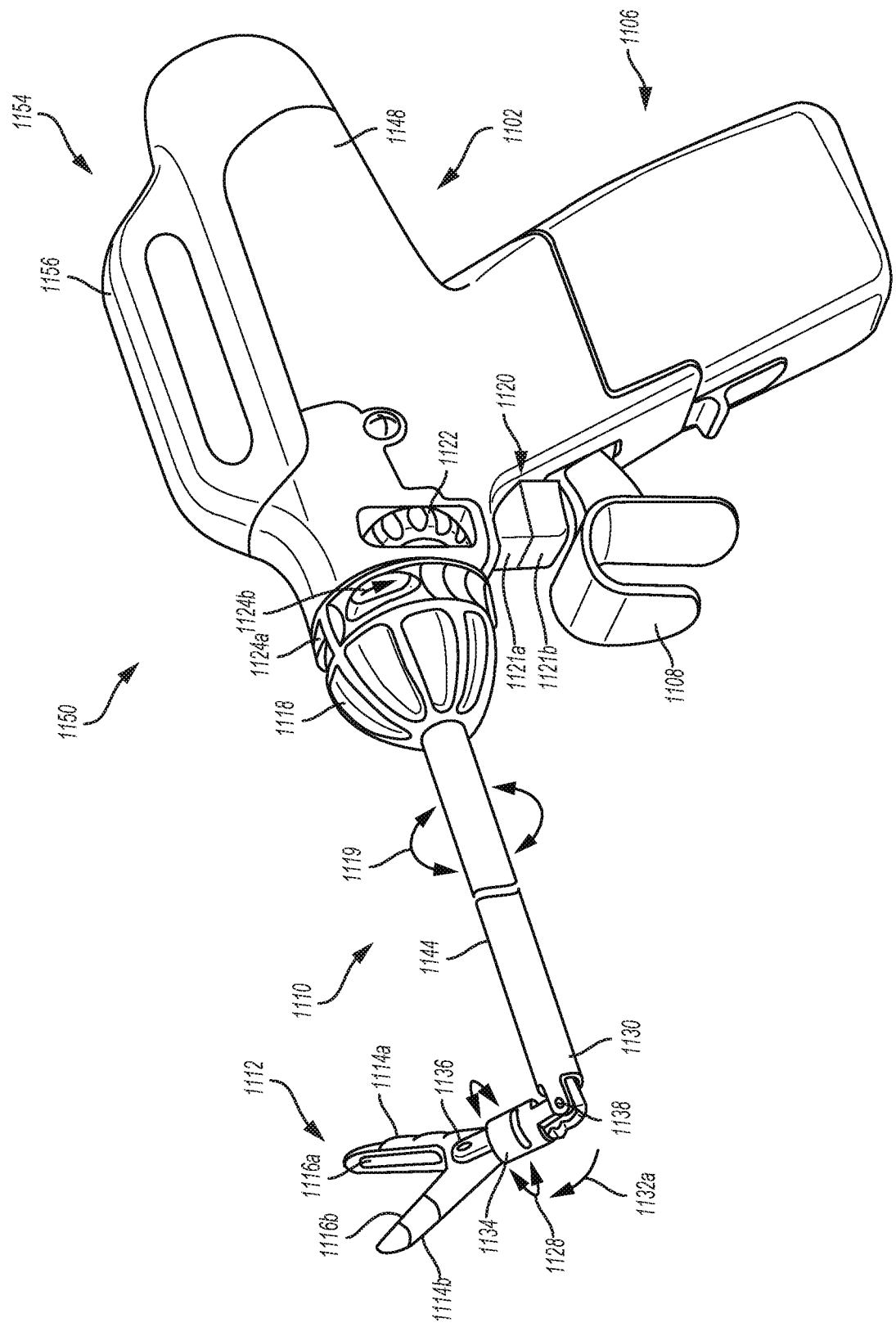
FIG. 48 is a perspective view of the instrument shown in FIGS. 45 and 46 without a display located on the handle assembly, according to one aspect of the present disclosure.

FIG. 48 is a perspective view of the instrument shown in FIGS. 45 and 46 without a display located on the handle assembly 1102, according to one aspect of the present disclosure. The handle assembly 1102 of the surgical instrument 1150 shown in FIG. 48 includes a different display assembly 1154 on a separate housing 1156. Wth reference now to FIGS. 45-48, the surgical instrument 1100, 1150 is configured to use high-frequency (RF) current and a knife to carry out surgical coagulation/cutting treatments on living tissue, and uses high-frequency current to carry out a surgical coagulation treatment on living tissue. The high-frequency (RF) current can be applied independently or in combination with algorithms or user input control. The display assembly, battery assembly 1106, and shaft assembly 1110 are modular components that are removably connectable to the handle assembly 1102. A motor 1140 is located within the handle assembly 1102. RF generator circuits and motor drive circuits are described herein in connection with FIGS. 34-37 and 50, for example, is located within the housing 1148.

The shaft assembly 1110 comprises an outer tube 1144, a knife drive rod 1145, and an inner tube (not shown). The shaft assembly 1110 comprises an articulation section 1130 and a distal rotation section 1134. The end effector 1112 comprises jaw members 1114a, 1114b in opposing relationship and a motor driven knife. The jaw member 1114a, 1114b comprises an electrically conductive surface 1116a, 1116b coupled to the RF generator circuit for delivering high-frequency current to tissue grasped between the opposed jaw members 1114a, 1114b. The jaw members 1114a, 1114b are pivotally rotatable about a pivot pin 1136 to grasp tissue between the jaw members 1114a, 1114b. The jaw members 1114a, 1114b are operably coupled to a trigger 1108 such that when the trigger 1108 is squeezed the jaw members 1114a, 1114b close to grasp tissue and when the trigger 1108 is released the jaw members 1114a, 1114b open to release tissue.

The jaw members 1114a, 1114b are operably coupled to a trigger 1108 such that when the trigger 1108 is squeezed the jaw members 1114a, 1114b close to grasp tissue and when the trigger 1108 is released the jaw members 1114a, 1114b open to release tissue. In a one-stage trigger configuration, the trigger 1108 is squeezed to close the jaw members 1114a, 1114b and, once the jaw members 1114a, 1114b are closed, a first switch 1121a of a switch section 1121 is activated to energize the RF generator to seal the tissue. After the tissue is sealed, a second switch 1121b of the switch section 1120 is activated to advance a knife to cut the tissue. In various aspects, the trigger 1108 may be a two-stage, or a multi-stage, trigger. In a two-stage trigger configuration, during the first stage, the trigger 1108 is squeezed part of the way to close the jaw members 1114a, 1114b and, during the second stage, the trigger 1108 is squeezed the rest of the way to energize the RF generator circuit to seal the tissue. After the tissue is sealed, one of the first and second switches 1121a, 1121b can be activated to advance the knife to cut the tissue. After the tissue is cut, the jaw members 1114a, 1114b are opened by releasing the trigger 1108 to release the tissue. In another aspect, force sensors such as strain gages or pressure sensors may be coupled to the trigger 1108 to measure the force applied to the trigger 1108 by the user. In another aspect, force sensors such as strain gages or pressure sensors may be coupled to the switch section 1120 first and second switch 1121a, 1121b buttons such that displacement intensity corresponds to the force applied by the user to the switch section 1120 first and second switch 1121a, 1121b buttons.

The battery assembly 1106 is electrically connected to the handle assembly 1102 by an electrical connector 1132. The handle assembly 1102 is provided with a switch section 1120. A first switch 1121a and a second switch 1121b are provided in the switch section 1120. The RF generator is energized by actuating the first switch 1121a and the knife is activated by energizing the motor 1140 by actuating the second switch 1121b. Accordingly, the first switch 1121a energizes the RF circuit to drive the high-frequency current through the tissue to form a seal and the second switch 1121b energizes the motor to drive the knife to cut the tissue. The structural and functional aspects of the battery assembly 1106 are similar to those of the battery assembly 106 for the surgical instrument 100 described in connection with FIGS. 1, 2, and 16-24. Accordingly, for conciseness and clarity of disclosure, such the structural and functional aspects of the battery assembly 106 are incorporated herein by reference and will not be repeated here.

A rotation knob 1118 is operably coupled to the shaft assembly 1110. Rotation of the rotation knob 1118 ±360° in the direction indicated by the arrows 1126 causes the outer tube 1144 to rotate ±360° in the respective direction of the arrows 1119. In one aspect, another rotation knob 1122 may be configured to rotate the end effector 1112 ±360° in the direction indicated by the arrows 1128 independently of the rotation of the outer tube 1144. The end effector 1112 may be articulated by way of first and second control switches 1124a, 1124b such that actuation of the first control switch 1124a articulates the end effector 1112 about a pivot 1138 in the direction indicated by the arrow 1132a and actuation of the second control switch 1124b articulates the end effector 1112 about the pivot 1138 in the direction indicated by the arrow 1132b. Further, the outer tube 1144 may have a diameter $D_3$ ranging from 5 mm to 10 mm, for example.

Figure 49:
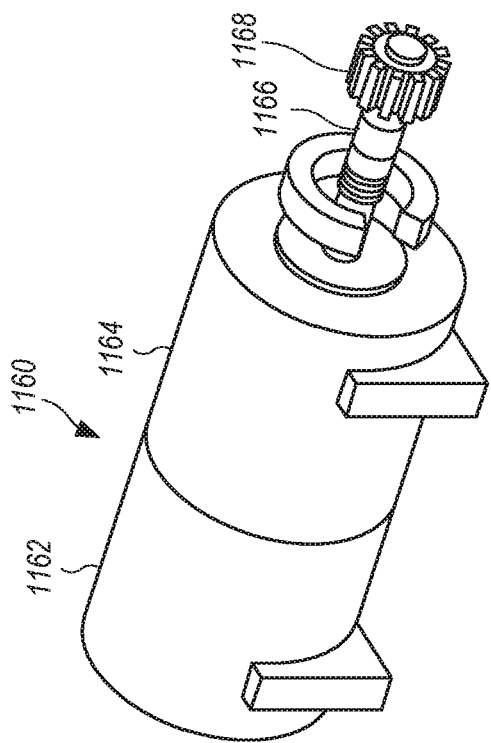
FIG. 49 is a motor assembly that can be used with the surgical instrument to drive the knife, according to one aspect of the present disclosure.

FIG. 49 is a motor assembly 1160 that can be used with the surgical instrument 1100, 1150 to drive the knife, according to one aspect of the present disclosure. The motor assembly 1160 comprises a motor 1162, a planetary gear 1164, a shaft 1166, and a drive gear 1168. The gear may be operably coupled to drive the knife bar 1145 (FIG. 46). In one aspect, the drive gear 1168 or the shaft 1166 is operably coupled to a rotary drive mechanism 1170 described in connection with FIG. 50 to drive distal head rotation, articulation, and jaw closure.

Figure 50:
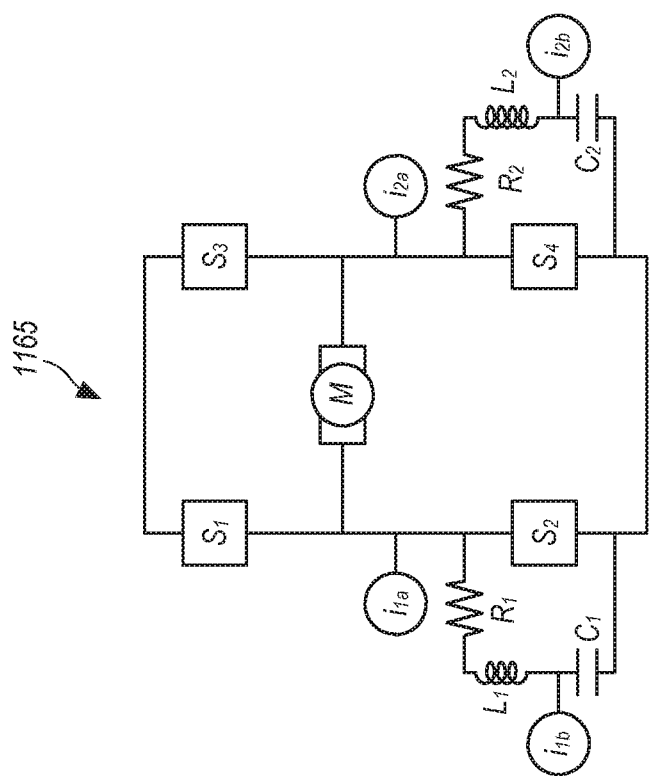
FIG. 50 is diagram of a motor drive circuit, according to one aspect of the present disclosure.

FIG. 50 is diagram of a motor drive circuit 1165, according to one aspect of the present disclosure. The motor drive circuit 1165 is suitable for driving the motor M, which may be employed in the surgical instruments 1100, 1150 described herein. The motor M is driven by an H-bridge comprising four switches $S_1$-$S_4$. The switches $S_1$-$S_4$ are generally solid state switches such as MOSFET switches. To turn the motor M in one direction, two switches $S_1$, $S_4$ are turned on and the other two switches $S_3$, $S_1$ are turned off. To reverse the direction of the motor M, the state of the switches $S_1$-$S_4$ is reversed such that the switches $S_1$, $S_4$ are turned off and the other two switches $S_3$, $S_1$ are turned on. Current sensing circuits can be placed in the motor drive circuit 1165 to sense motor currents $i_{1a}$, $i_{2a}$, $i_{1b}$, $i_{2b}$.

Figure 51:
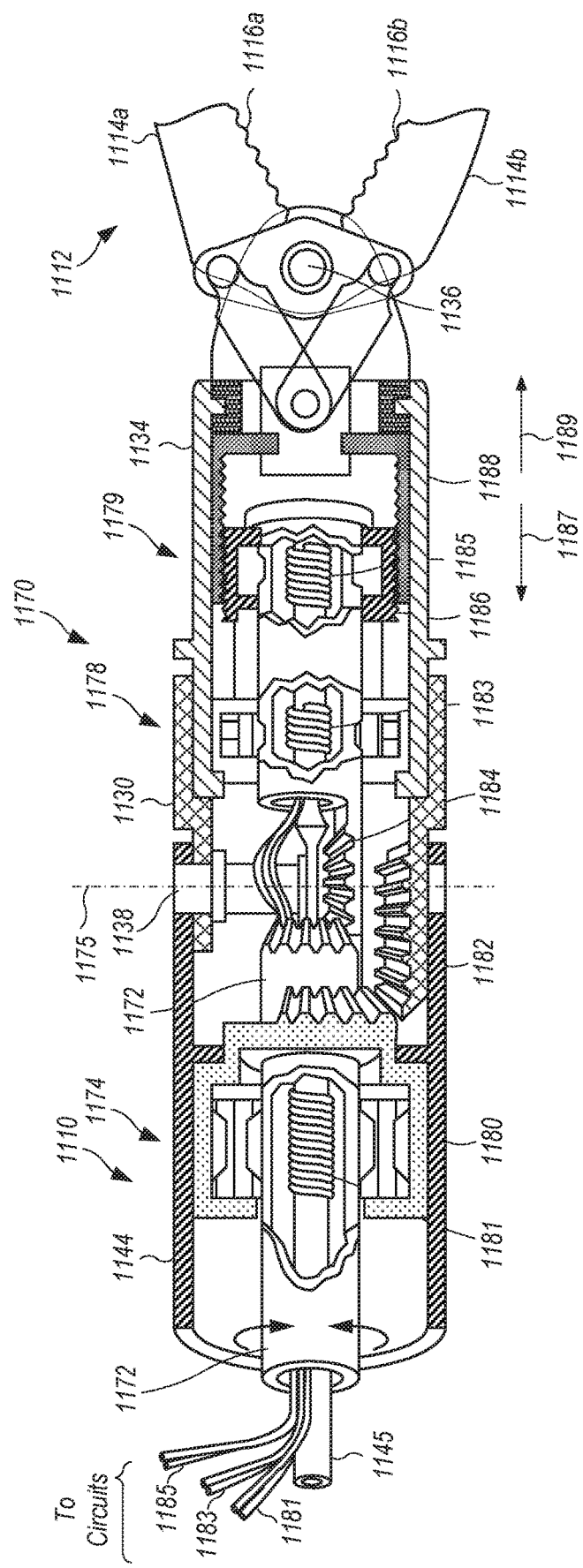
FIG. 51 illustrates a rotary drive mechanism to drive distal head rotation, articulation, and jaw closure, according to one aspect of the present disclosure.

FIG. 51 illustrates a rotary drive mechanism 1170 to drive distal head rotation, articulation, and jaw closure, according to one aspect of the present disclosure. The rotary drive mechanism 1170 has a primary rotary drive shaft 1172 that is operably coupled to the motor assembly 1160. The primary rotary drive shaft 1172 is capable of being selectively coupled to at least two independent actuation mechanisms (first, second, both, neither) with a clutch mechanism located within the outer tube 1144 of the shaft assembly 1110. The primary rotary drive shaft 1172 is coupled to independent clutches that allow the shaft functions to be independently coupled to the rotary drive shaft 1172. For example, the articulation clutch 1174 is engaged to articulate the shaft assembly 1110 about the articulation axis 1175 of the articulation section 1130. The distal head rotation clutch 1178 is engaged to rotate the distal rotation section 1134 and the jaw closure clutch 1179 is engaged to close the jaw members 1114a, 1114b of the end effector 1112. The knife is advanced and retracted by the knife drive rod 1145. All, none, or any combination of rotary mechanisms can be couple at any one time.

In one aspect, a micro-electrical clutching configuration enables rotation of the distal rotation section 1134 and articulation of the articulation section 1130 about pivot 1138 and articulation axis 1175. In one aspect, a ferro-fluid clutch couples the clutch to the primary rotary drive shaft 1172 via a fluid pump. The clutch ferro-fluid is activated by electrical coils 1181, 1183, 1185 which are wrapped around the knife drive rod 1145. The other ends of the coils 1181, 1183, 1185 are connected to three separate control circuits to independently actuate the clutches 1174, 1178, 1179. In operation, when the coils 1181, 1183, 1185 are not energized, the clutches 1174, 1178, 1179 are disengaged and there is no articulation, rotation, or jaw movements.

When the articulation clutch 1174 is engaged by energizing the coil 1181 and the distal head rotation clutch 1178 and the jaw closure clutch 1179 are disengaged by de-energizing the coils 1183, 1185, a gear 1180 is mechanically coupled to the primary rotary drive shaft 1172 to articulate the articulation section 1130. In the illustrated orientation, when the primary rotary drive shaft 1172 rotates clockwise, the gear 1180 rotates clockwise and the shaft articulates in the right direction about the articulation axis 1175 and when the primary rotary drive shaft 1172 rotates counter clockwise, the gear 1180 rotates counter clockwise and the shaft articulates in the left direction about the articulation axis 1175. It will be appreciated that left/right articulation depends on the orientation of the surgical instrument 1100, 1150.

When the articulation clutch 1174 and the jaw closure clutch 1179 are disengaged by de-energizing the coils 1181, 1185, and the distal head rotation clutch 1178 is engaged by energizing the coil 1183, the primary rotary drive shaft 1172 rotates the distal rotation section 1134 in the same direction of rotation. When the coil 1183 is energized, the distal head rotation clutch 1178 engages the primary rotary drive shaft 1172 with the distal rotation section 1134. Accordingly, the distal rotation section 1134 rotates with the primary rotary drive shaft 1172.

When the articulation clutch 1174 and the distal head rotation clutch 1178 are disengaged by de-energizing the coils 1181, 1183, and the jaw closure clutch 1179 is engaged by energizing the coil 1185, the jaw members 1114a, 114b can be opened or closed depending on the rotation of the primary rotary drive shaft 1172. When the coil 1185 is energized, the jaw closure clutch 1179 engages a captive inner threaded drive member 1186, which rotates in place in the direction of the primary rotary drive shaft 1172. The captive inner threaded drive member 1186 includes outer threads that are in threaded engagement with an outer threaded drive member 1188, which includes an inner threaded surface. As the primary rotary drive shaft 1172 rotates clockwise, the outer threaded drive member 1188 that is in threaded engagement with the captive inner threaded drive member 1186 will be driven in a proximal direction 1187 to close the jaw members 1114a, 1114b. As the primary rotary drive shaft 1172 rotates counterclockwise, the outer threaded drive member 1188 that is in threaded engagement with the captive inner threaded drive member 1186 will be driven in a distal direction 1189 to open the jaw members 1114a, 1114b.

Figure 52:
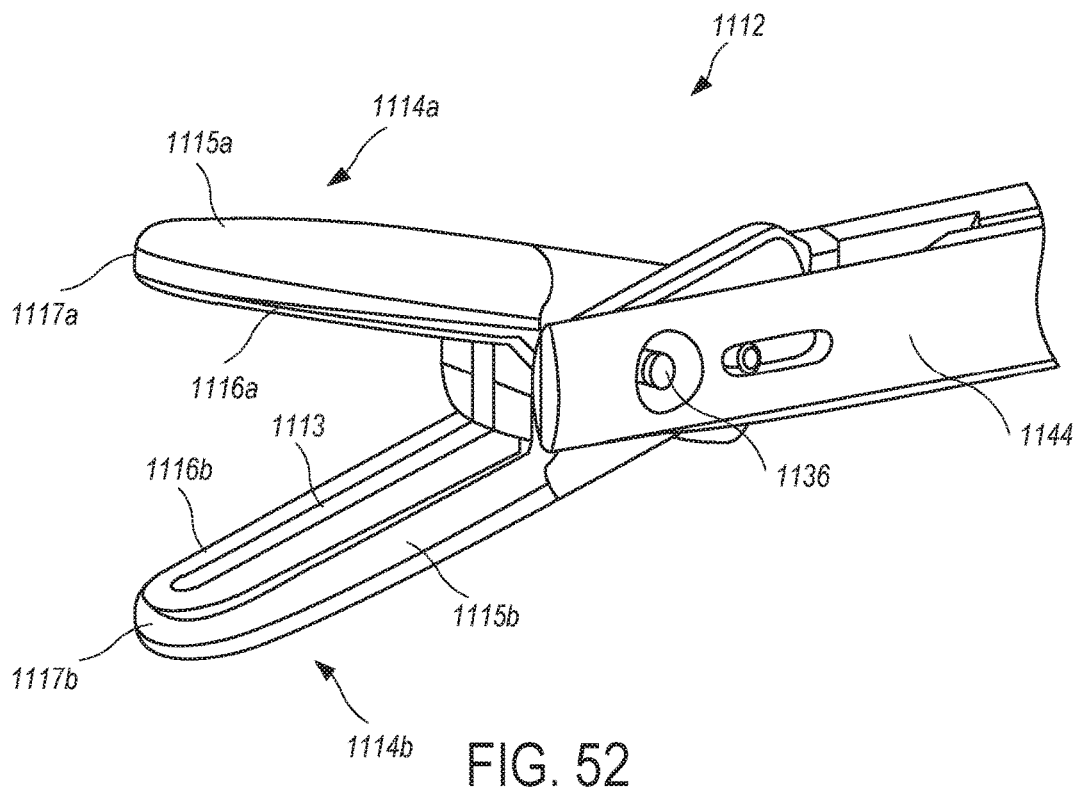
FIG. 52 is an enlarged, left perspective view of an end effector assembly with the jaw members shown in an open configuration, according to one aspect of the present disclosure.
Figure 53:
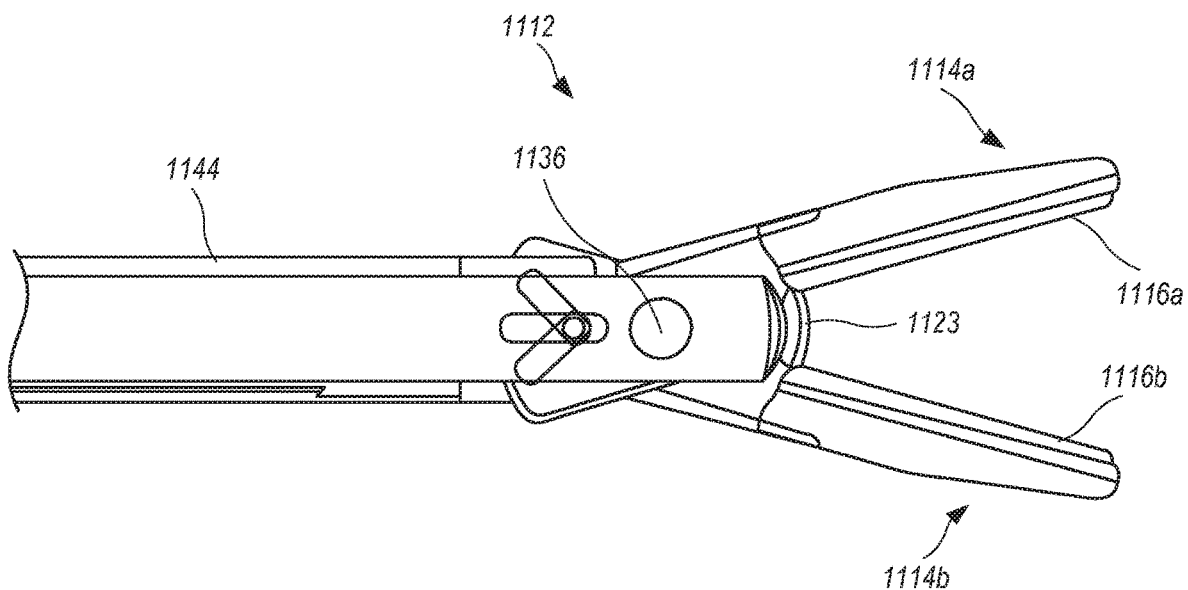
FIG. 53 is an enlarged, right side view of the end effector assembly of FIG. 52, according to one aspect of the present disclosure.

FIG. 52 is an enlarged, left perspective view of an end effector assembly with the jaw members shown in an open configuration, according to one aspect of the present disclosure. FIG. 53 is an enlarged, right side view of the end effector assembly of FIG. 52, according to one aspect of the present disclosure. Referring now to FIGS. 52 and 53, enlarged views of an end effector 1112 shown in an open position for approximating tissue. Jaw members 1114, 1114b are generally symmetrical and include similar component features which cooperate to permit facile rotation about pivot pin 1136 to effect the sealing and dividing of tissue. As a result and unless otherwise noted, only the jaw member 1114a and the operative features associated therewith are describe in detail herein but as can be appreciated, many of these features apply to the other jaw member 1114b as well.

The jaw member 1114a also includes a jaw housing 1115a, an insulative substrate or insulator 1117a and an electrically conductive surface 1116a. The insulator 1117a is configured to securely engage the electrically conductive sealing surface 1116a. This may be accomplished by stamping, by overmolding, by overmolding a stamped electrically conductive sealing plate and/or by overmolding a metal injection molded seal plate. These manufacturing techniques produce an electrode having an electrically conductive surface 1116a that is surrounded by an insulator 1117a.

As mentioned above, the jaw member 1114a includes similar elements which include: a jaw housing 1115b; insulator 1117b; and an electrically conductive surface 1116b that is dimensioned to securely engage the insulator 1117b. Electrically conductive surface 1116b and the insulator 1117b, when assembled, form a longitudinally-oriented knife channel 1113 defined therethrough for reciprocation of the knife blade 1123. The knife channel 1113 facilitates longitudinal reciprocation of the knife blade 1123 along a predetermined cutting plane to effectively and accurately separate the tissue along the formed tissue seal. Although not shown, the jaw member 1114a may also include a knife channel that cooperates with the knife channel 1113 to facilitate translation of the knife through tissue.

The jaw members 1114a, 1114b are electrically isolated from one another such that electrosurgical energy can be effectively transferred through the tissue to form a tissue seal. The electrically conductive surfaces 1116a, 1116b are also insolated from the remaining operative components of the end effector 1112 and the outer tube 1144. A plurality of stop members may be employed to regulate the gap distance between the electrically conductive surfaces 1116a, 1116b to insure accurate, consistent, and reliable tissue seals.

The structural and functional aspects of the battery assembly 1106 are similar to those of the battery assembly 106 for the surgical instrument 100 described in connection with FIGS. 1, 2, and 16-24, including the battery circuits described in connection with FIGS. 20-24. Accordingly, for conciseness and clarity of disclosure, such the structural and functional aspects of the battery assembly 106 are incorporated herein by reference and will not be repeated here. Furthermore, the structural and functional aspects of the RF generator circuits are similar to those of the RF generator circuits described in for the surgical instruments 500, 600 described in connection with FIGS. 34-37. Accordingly, for conciseness and clarity of disclosure, such the structural and functional aspects of the RF generator circuits are incorporated herein by reference and will not be repeated here. Furthermore, the surgical instrument 1100 includes the battery and control circuits described in connection with FIGS. 12-15, including, for example, the control circuit 210 described in connection with FIG. 14 and the electrical circuit 300 described in connection withe FIG. 15. Accordingly, for conciseness and clarity of disclosure, the description of the circuits described in connection with FIGS. 12-15 is incorporated herein by reference and will not be repeated here.

For a more detailed description of an electrosurgical instrument comprising a cutting mechanism and an articulation section that is operable to deflect the end effector away from the longitudinal axis of the shaft, reference is made to U.S. Pat. Nos. 9,028,478 and 9,113,907, each of which is herein incorporated by reference.

Figure 54:
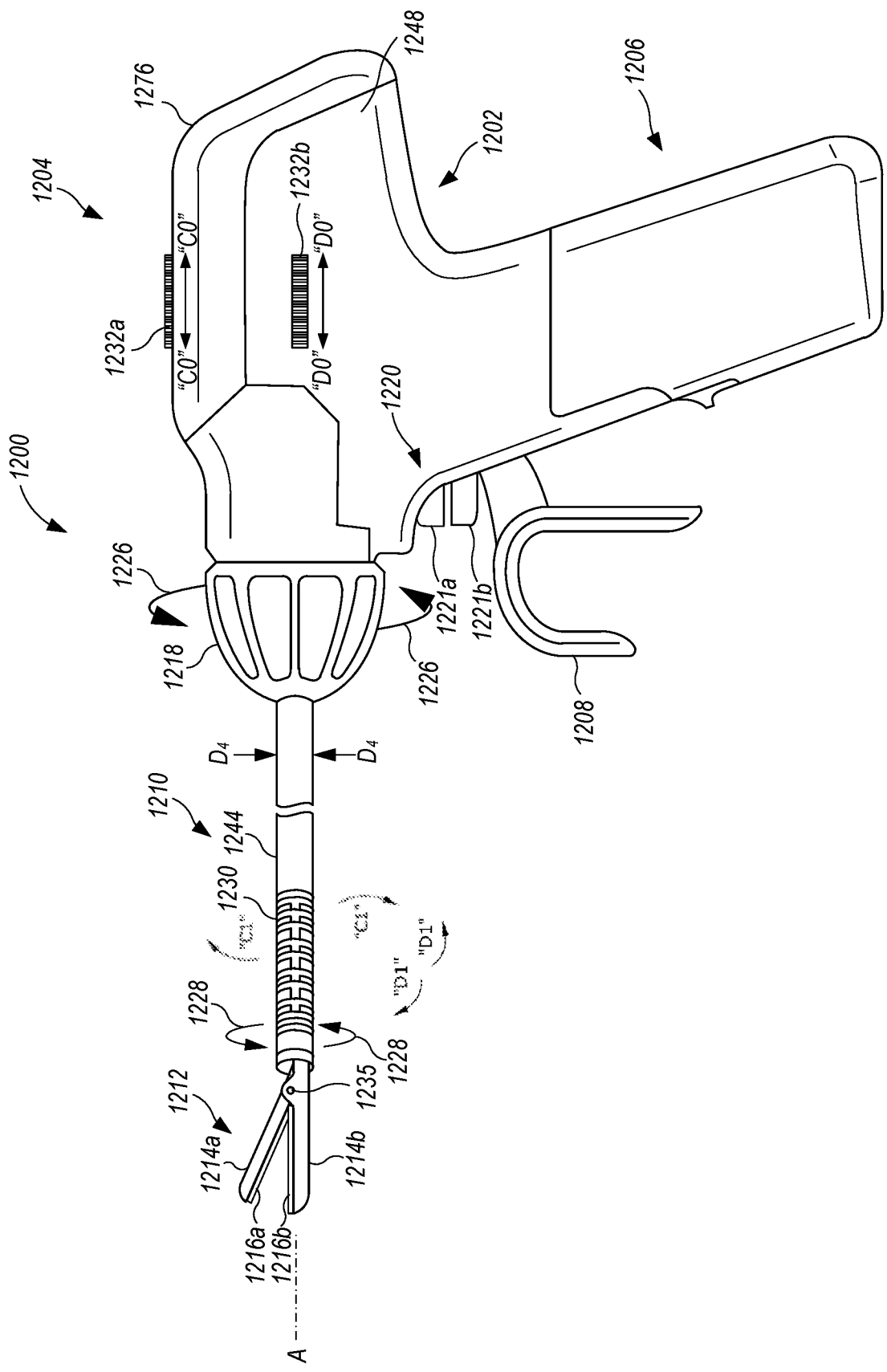
FIG. 54 illustrates a modular battery powered handheld electrosurgical instrument with distal articulation, according to one aspect of the present disclosure.
Figure 55:
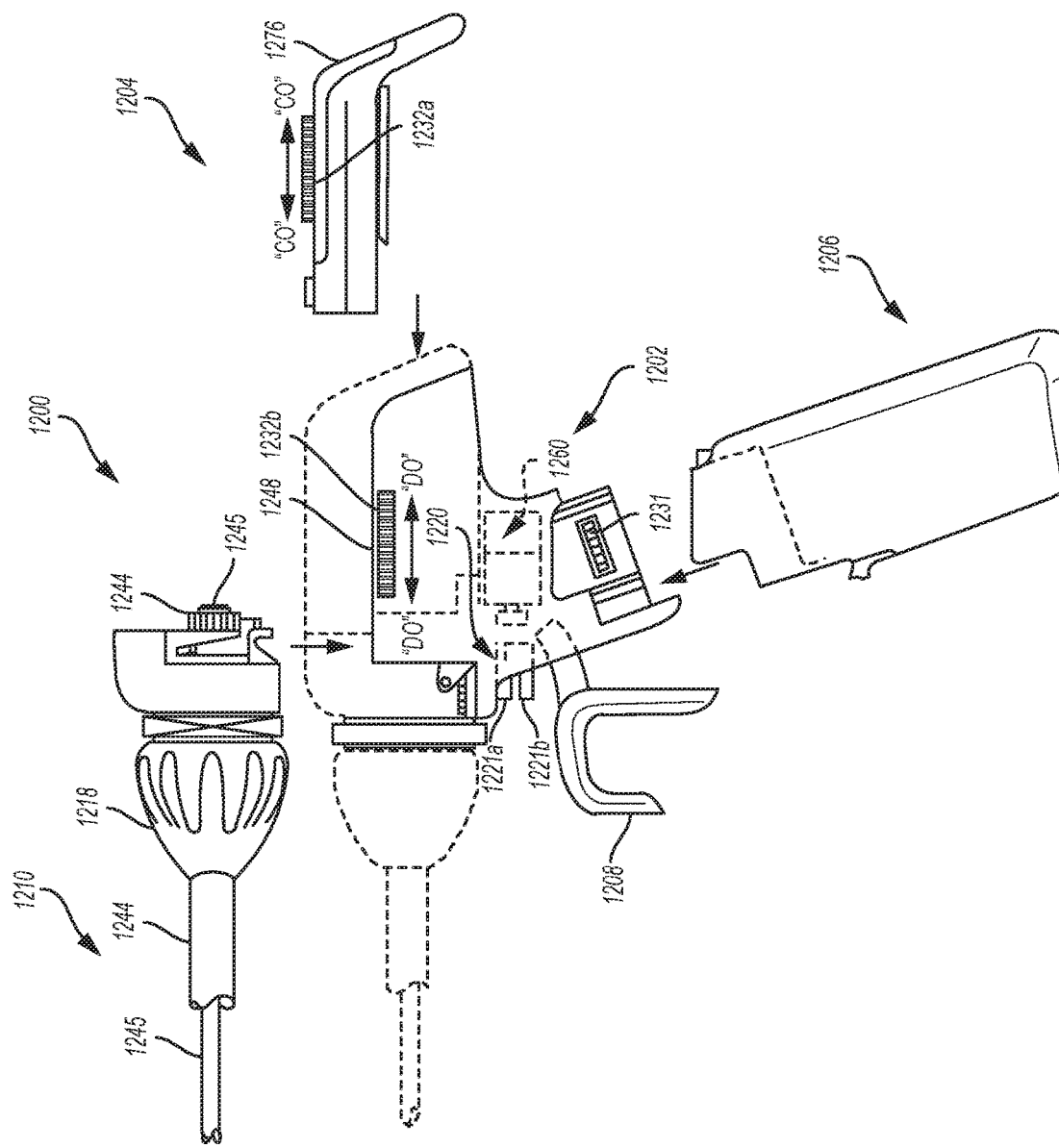
FIG. 55 is an exploded view of the surgical instrument shown in FIG. 54, according to one aspect of the present disclosure.

FIG. 54 illustrates a modular battery powered handheld electrosurgical instrument 1200 with distal articulation, according to one aspect of the present disclosure. The surgical instrument 1200 comprises a handle assembly 1202, a knife drive assembly 1204, a battery assembly 1206, a shaft assembly 1210, and an end effector 1212. The end effector 1212 comprises a pair of jaw members 1214a, 1214b in opposing relationship affixed to a distal end thereof. The end effector 1212 is configured to articulate and rotate. FIG. 55 is an exploded view of the surgical instrument 1200 shown in FIG. 54, according to one aspect of the present disclosure. The end effector 1212 for use with the surgical instrument 1200 for sealing and cutting tissue includes a pair of jaw members 1214a, 1214b in opposing relationship movable relative to each other to grasp tissue therebetween. Either jaw member 1214a, 1214b may include a jaw housing and an electrically conductive surface 1216a, 1216b, e.g., electrodes, adapted to connect to a source of electrosurgical energy (RF source) such that the electrically conductive surfaces are capable of conducting electrosurgical energy through tissue held therebetween to effect a tissue seal. The jaw members 1214a, 1214b and the electrically conductive surfaces 1216a, 1216b include a channel defined therein and extending along a length thereof that communicates with a knife drive rod 1245 connected to a knife drive assembly 1204. The knife 1274 (FIGS. 60-61) is configured to translate and reciprocate along the channels to cut tissue grasped between the jaw members 1214a, 1214b. The knife has an I-beam configuration such that the jaw members 1214a, 1214b are brought closer together as the knife 1274 advances through the channels. In one aspect, the electrically conductive surfaces 1216a, 1216b are offset relative to each other. The knife 1274 includes a sharp distal end.

The handle assembly 1202 of the surgical instrument shown in FIGS. 54-55 comprises a motor assembly 1260 and a knife drive assembly 1204. In one aspect, a display assembly may be provided on the housing 1248. The display assembly may comprise a display, such as an LCD display, for example, which is removably connectable to a housing 1248 portion of the handle assembly 1202. The LCD display provides a visual display of surgical procedure parameters such as tissue thickness, status of seal, status of cut, tissue thickness, tissue impedance, algorithm being executed, battery capacity, among other parameters. Wth reference now to FIGS. 54-55, the surgical instrument 1200 is configured to use high-frequency (RF) current and a knife 1274 (FIGS. 60-61) to carry out surgical coagulation/cutting treatments on living tissue, and uses high-frequency current to carry out a surgical coagulation treatment on living tissue. The high-frequency (RF) current can be applied independently or in combination with algorithms or user input control. The knife drive assembly 1204, battery assembly 1206, and shaft assembly 1210 are modular components that are removably connectable to the handle assembly 1202. A motor assembly 1240 may be located within the handle assembly 1202. The RF generator and motor drive circuits are described in connection with FIGS. 34-37 and 50, for example, are located within the housing 1248. The housing 1248 includes a removable cover plate 1276 to provide access to the circuits and mechanisms located within the housing 1248. The knife drive assembly 1204 includes gears and linkages operably coupled to the handle assembly 1202 and the switch section 1220 to activate and drive the knife 1274. As discussed in more detail hereinbelow, the knife 1274 has an I-beam configuration.

The shaft assembly 1210 comprises an outer tube 1244, a knife drive rod 1245, and an inner tube (not shown). The shaft assembly 1210 comprises an articulation section 1230. The end effector 1212 comprises a pair of jaw members 1214a, 1214b and a knife 1274 configured to reciprocate with channels formed in the jaw members 1214a, 1214b. In one aspect, the knife 1274 may be driven by a motor. The jaw member 1214a, 1214b comprises an electrically conductive surface 1216a, 1216b coupled to the RF generator circuit for delivering high-frequency current to tissue grasped between the jaw members 1214a, 1214b. The jaw members 1214a, 1214b are pivotally rotatable about a pivot pin 1235 to grasp tissue between the jaw members 1214a, 1214b. The jaw members 1214a, 1214b are operably coupled to a trigger 1208 such that when the trigger 1208 is squeezed one or both of the jaw members 1214a, 1214b close to grasp tissue and when the trigger 1208 is released the jaw members 1214a, 1214b open to release tissue. In the illustrated example, one jaw member 1214a is movable relative to the other jaw member 1214b. In other aspects, both jaw members 1214a, 1214b may be movable relative to each other. In another aspect, force sensors such as strain gages or pressure sensors may be coupled to the trigger 1208 to measure the force applied to the trigger 1208 by the user. In another aspect, force sensors such as strain gages or pressure sensors may be coupled to the switch section 1220 first and second switch 1221a, 1221b buttons such that displacement intensity corresponds to the force applied by the user to the switch section 1220 first and second switch 1221a, 1221b buttons.

The jaw member 1214a is operably coupled to a trigger 1208 such that when the trigger 1208 is squeezed the jaw member 1214a closes to grasp tissue and when the trigger 1208 is released the jaw member 1214a opens to release tissue. In a one-stage trigger configuration, the trigger 1208 is squeezed to close the jaw member 1214a and, once the jaw member 1214a is closed, a first switch 1221a of a switch section 1220 is activated to energize the RF generator to seal the tissue. After the tissue is sealed, a second switch 1221b of the switch section 1220 is activated to advance a knife to cut the tissue. In various aspects, the trigger 1208 may be a two-stage, or a multi-stage, trigger. In a two-stage trigger configuration, during the first stage, the trigger 1208 is squeezed part of the way to close the jaw member 1214a and during the second stage, the trigger 1208 is squeezed the rest of the way to energize the RF generator circuit to seal the tissue. After the tissue is sealed, one of the switches 1221a, 1221b can be activated to advance the knife to cut the tissue. After the tissue is cut, the jaw member 1214a is opened by releasing the trigger 1208 to release the tissue.

The shaft assembly 1210 includes an articulation section 1230 that is operable to deflect the end effector 1212 away from the longitudinal axis "A" of the shaft assembly 1210. The dials 1232a, 1232b are operable to pivot the articulation section 1230 at the distal end of the elongated shaft assembly 1210 to various articulated orientations with respect to the longitudinal axis A-A. More particularly, the articulation dials 1232a, 1232b operably couple to a plurality of cables or tendons that are in operative communication with the articulation section 1230 of the shaft assembly 1210, as described in greater detail below. One articulation dial 1232a may be rotated in the direction of arrows "C0" to induce pivotal movement in a first plane, e.g., a vertical plane, as indicated by arrows "C1". Similarly, another articulation dial 1232b may be rotated in the direction of arrows "D0" to induce pivotal movement in a second plane, e.g., a horizontal plane, as indicated by arrows "D1". Rotation of the articulation dials 1232a, 1232b in either direction of arrows "C0" or "D0" results in the tendons pivoting or articulating the shaft assembly 1210 about the articulation section 1230.

The battery assembly 1206 is electrically connected to the handle assembly 1202 by an electrical connector 1231. The handle assembly 1202 is provided with a switch section 1220. A first switch 1221a and a second switch 1221b are provided in the switch section 1220. The RF generator is energized by actuating the first switch 1221a and the knife 1274 may be activated by energizing the motor assembly 1240 by actuating the second switch 1221b. Accordingly, the first switch 1221a energizes the RF circuit to drive the high-frequency current through the tissue to form a seal and the second switch 1221b energizes the motor to drive the knife 1274 to cut the tissue. In other aspects, the knife 1274 may be fired manually using a two-stage trigger 1208 configuration. The structural and functional aspects of the battery assembly 1206 are similar to those of the battery assembly 106 for the surgical instrument 100 described in connection with FIGS. 1, 2, and 16-24. Accordingly, for conciseness and clarity of disclosure, such the structural and functional aspects of the battery assembly 106 are incorporated herein by reference and will not be repeated here.

A rotation knob 1218 is operably coupled to the shaft assembly 1210. Rotation of the rotation knob 1218 ±360° in the direction indicated by the arrows 1226 causes the outer tube 1244 to rotate ±360° in the respective direction of the arrows 1228. The end effector 1212 may be articulated by way of control buttons such that actuation of control buttons articulates the end effector 1212 in one direction indicated by arrows C1 and D1. Further, the outer tube 1244 may have a diameter $D_3$ ranging from 5 mm to 10 mm, for example.

Figure 56:
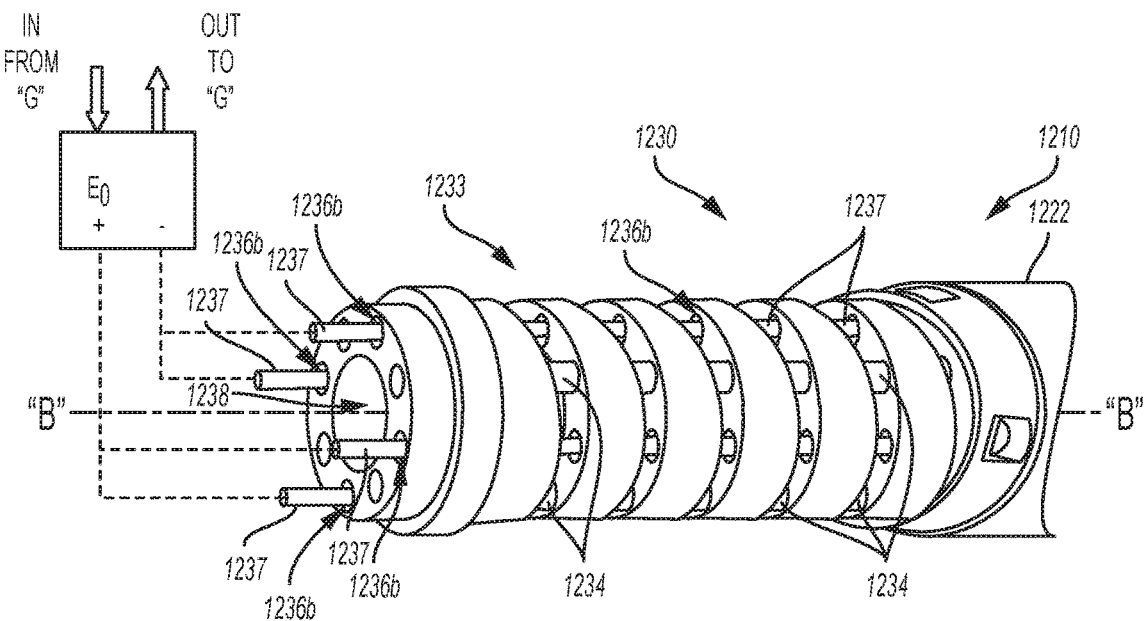
FIG. 56 is an enlarged area detail view of an articulation section illustrated in FIG. 54 including electrical connections, according to one aspect of the present disclosure.
Figure 57:
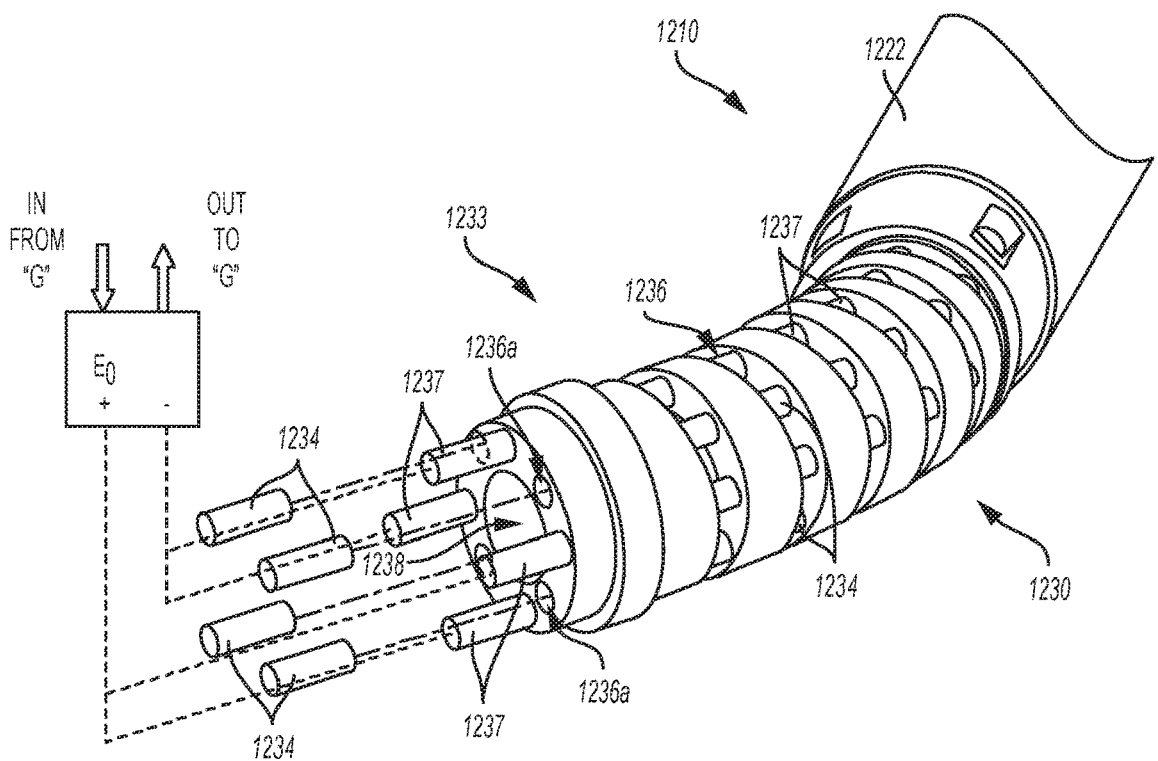
FIG. 57 is an enlarged area detail view articulation section illustrated in FIG. 56 including electrical connections, according to one aspect of the present disclosure.

FIG. 56 is an enlarged area detail view of an articulation section illustrated in FIG. 54 including electrical connections, according to one aspect of the present disclosure. FIG. 57 is an enlarged area detail view articulation section illustrated in FIG. 56 including electrical connections, according to one aspect of the present disclosure. With reference now to FIGS. 56-57, there is shown the articulation section 1230 is operably disposed on or coupled to the shaft assembly 1210 between the proximal end and the distal end 1222, respectively. In the aspect illustrated in FIGS. 56-57, the articulation section 1230 is defined by a plurality of articulating links 1233 (links 1233). The links 1233 are configured to articulate the shaft assembly 1210 transversely across the longitudinal axis "A-A" in either a horizontal or vertical plane, see FIG. 54. For illustrative purposes, the shaft assembly 1210 is shown articulated across the horizontal plane.

The links 1233 collectively define a central annulus 1238 therethrough that is configured to receive a drive mechanism, e.g., a drive rod, therethrough. As can be appreciated, the configuration of the central annulus 1238 provides adequate clearance for the drive rod therethrough. The central annulus 1238 defines an axis "B-B" therethrough that is parallel to the longitudinal axis "A-A" when the shaft assembly 1210 is in a non-articulated configuration, see FIG. 54.

Continuing with reference to FIGS. 56-57, the links 1233 are operably coupled to the articulation dials 1232a, 1232b via tendons 1234. For illustrative purposes, four (4) tendons 1234 are shown. The tendons 1234 may be constructed of stainless steel wire or other material suitable for transmitting tensile forces to a distal-most link of links 1233. Regardless of the construction materials, the tendons 1234 exhibit a spring rate that is amplified over the length of the tendons 1234 and thus, the tendons 1234 may tend to stretch when external loads are applied to the elongated shaft assembly 1210. This tendency to stretch may be associated with an unintended change in orientation of the distal end 1222 of the elongated shaft assembly 1210, e.g., without a corresponding movement of the articulation dials 1232a, 1232b initiated by the surgeon.

The tendons 1234 operably couple to the articulating dials 1232a, 1232b that are configured to actuate the tendons 1234, e.g., "pull" the tendons 1234, when the articulating dials 1232a, 1232b are rotated. The plurality of tendons 1234 operably couple to the links 1233 via one or more suitable coupling methods. More particularly, the link 1233 includes a corresponding plurality of first apertures or bores 1236a defined therein (four (4) bores 1236a are shown in the representative figures) that are radially disposed along the links 1233 and centrally aligned along a common axis, see FIG. 56. A bore of the plurality of bores 1236a is configured to receive a tendon 1234. A distal end of a tendon 1234 is operably coupled to a distal most link of the links 1233 by suitable methods, e.g., one or more of the coupling methods described above.

Continuing with reference to FIGS. 56-57 a link 1233 includes a second plurality of bores 1236b (four (4) bores 1236b are shown in the representative drawings, as best seen in FIG. 56). A bore 1236b is configured to receive a corresponding conductive lead of a plurality of conductive leads 1237 (four (4) conductive leads 1237 are shown in the representative drawings). The conductive leads 1237 are configured to transition between first and second states within the second plurality of bores 1236*b*. To facilitate transitioning of the conductive leads 1237, a bore 1236*b* includes a diameter that is greater than a diameter of the conductive leads 1237 when the conductive leads 1237 are in the first state.

The surgical instrument 1220 includes electrical circuitry that is configured to selectively induce a voltage and current flow to the plurality of conductive leads 1237 such that a conductive lead 1237 transitions from the first state to the second state. To this end, the generator G provides a voltage potential Eo of suitable proportion. A voltage is induced in a conductive lead 1237 and current flow therethrough. The current flowing through a conductive lead 1237 causes the conductive lead 1237 to transition from the first state (FIG. 56) to the second state (FIG. 57). In the second state, the conductive lead 1237 provides an interference fit between the conductive lead 1237 and the corresponding bores 1236*b*, as best seen in FIG. 57.

Figure 58:
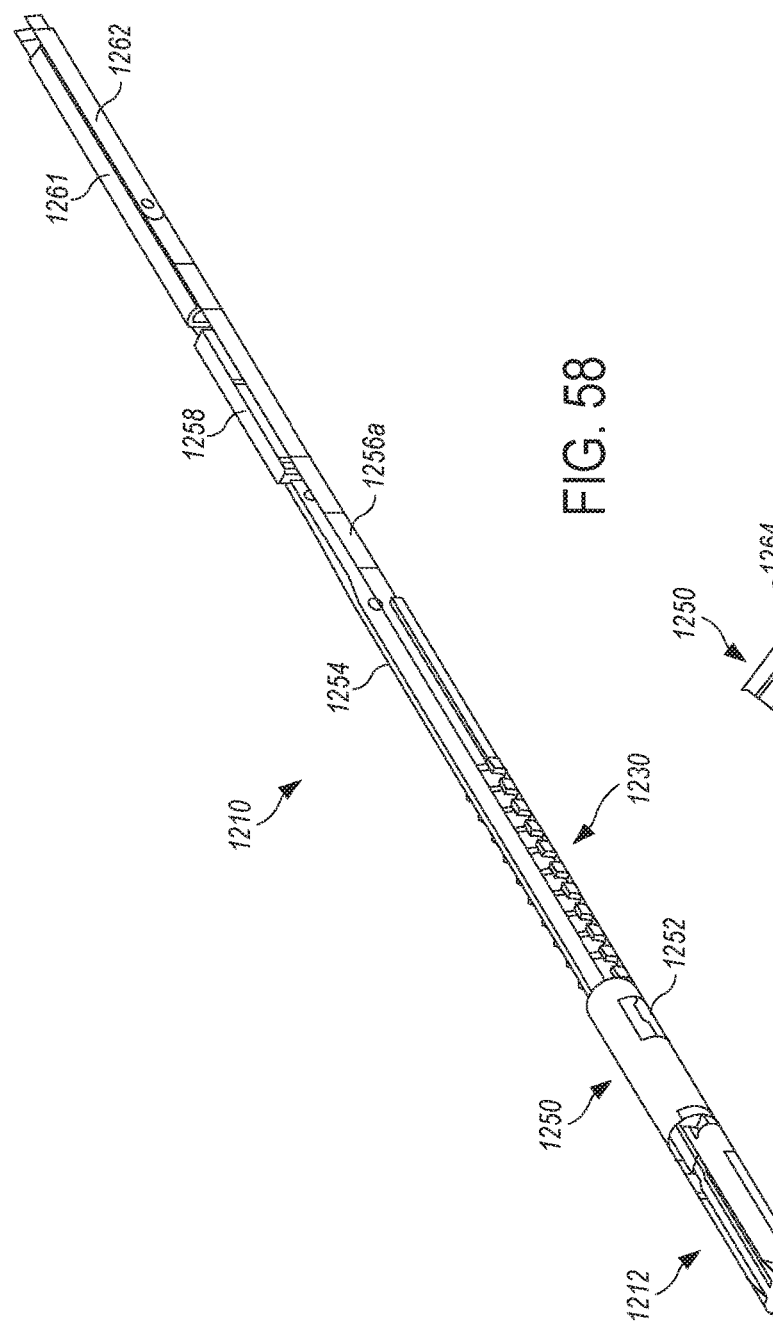
FIG. 58 illustrates a perspective view of components of the shaft assembly, end effector, and cutting member of the surgical instrument of FIG. 54, according to one aspect of the present disclosure.
Figure 59:
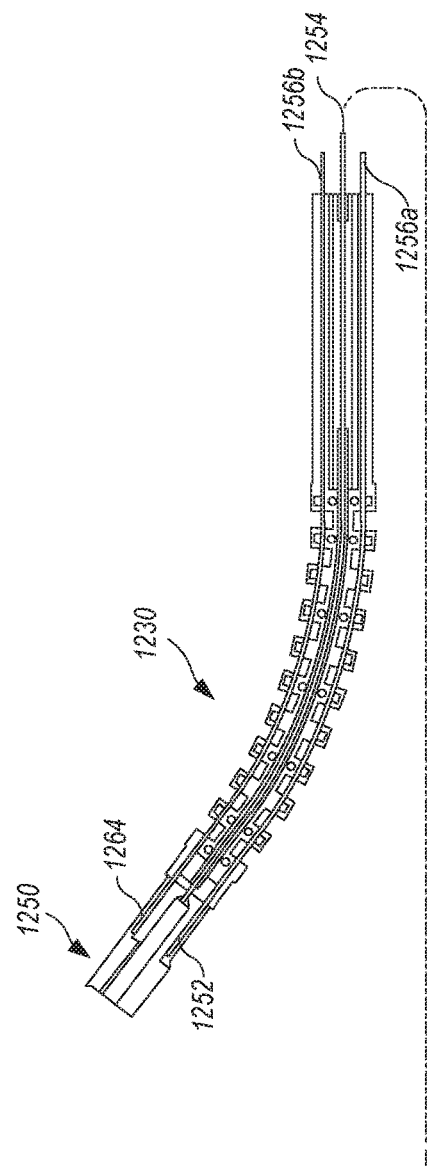
FIG. 59 illustrates the articulation section in a second stage of articulation, according to one aspect of the present disclosure.

FIG. 58 illustrates a perspective view of components of the shaft assembly 1210, end effector 1212, and cutting member 1254 of the surgical instrument 1200 of FIG. 54, according to one aspect of the present disclosure. FIG. 59 illustrates the articulation section in a second stage of articulation, according to one aspect of the present disclosure. With reference now to FIGS. 58-59, one articulation band 1256*a* is slidably disposed in one side recess of a separator 1261 while a second articulation band 1256*b* (FIG. 59) is slidably disposed in the other side recess of the separator 1261. A cutting member driver tube is movable longitudinally to drive a driver block 1258 longitudinally, to thereby move cutting member 1254 longitudinally. The side recesses include longitudinally extending grooves that are configured to reduce the contact surface area with articulation bands 1256*a*, 1256*b*, thereby reducing friction between separator 1261 and articulation bands 1256*a*, 1256*b*. The separator 1261 also may be formed of a low friction material and/or include a surface treatment to reduce friction. Articulation bands 1256*a*, 1256*b* extend longitudinally along the length of the shaft assembly 1210, including through the articulation section 1230. The distal end 1252 of one articulation band 1256*a* is secured to one side of the proximal portion 1250 of end effector 1212 at an anchor point. The distal end 1262 of the second articulation band 1256*b* is secured to the other side of proximal portion 1250 of end effector 1212 at an anchor point. A rotary articulation knob is operable to selectively advance the articulation band 1256*a* distally while simultaneously retracting the second articulation band 1256*b* proximally, and vice-versa. It should be understood that this opposing translation will cause articulation section 1230 to bend, thereby articulating end effector 1212. In particular, the end effector 1212 will deflect toward whichever articulation band 1256*a*, 1256*b* is being retracted proximally; and away from whichever articulation band 1256*a*, 1256*b* is being advanced distally.

With continued referenced to FIGS. 58-59, several of the above described components are shown interacting to bend the articulation section 1230 to articulate end effector 1212. In FIG. 58, articulation 1230 is in a straight configuration. Then, one of the articulation dials 1232*a*, 1232*b* (FIGS. 54-55) is rotated, which causes a lead screw to translate proximally and another lead screw to advance distally. This proximal translation of one lead screw pulls the articulation band 1256*b* proximally, which causes articulation section 1230 to start bending as shown in FIG. 59. This bending of articulation section 1230 pulls the other articulation band 1256*a* distally. The distal advancement of lead screw in response to rotation of the articulation dials 1232*a*, 1232*b* enables the articulation band 1256*a* and the drive member to advance distally. In some other versions, the distal advancement of the lead screw actively drives drive member and articulation band 1256*a* distally. As the user continues rotating one of the articulation dials 1232*a*, 1232*b*, the above described interactions continue in the same fashion, resulting in further bending of articulation section 1230 as shown in FIG. 59. It should be understand that rotating the articulation dials 1232*a*, 1232*b* in the opposite direction will cause articulation section 1230 to straighten, and further rotation in the opposite direction will cause articulation section 1230 to bend in the opposite direction.

Figure 60:
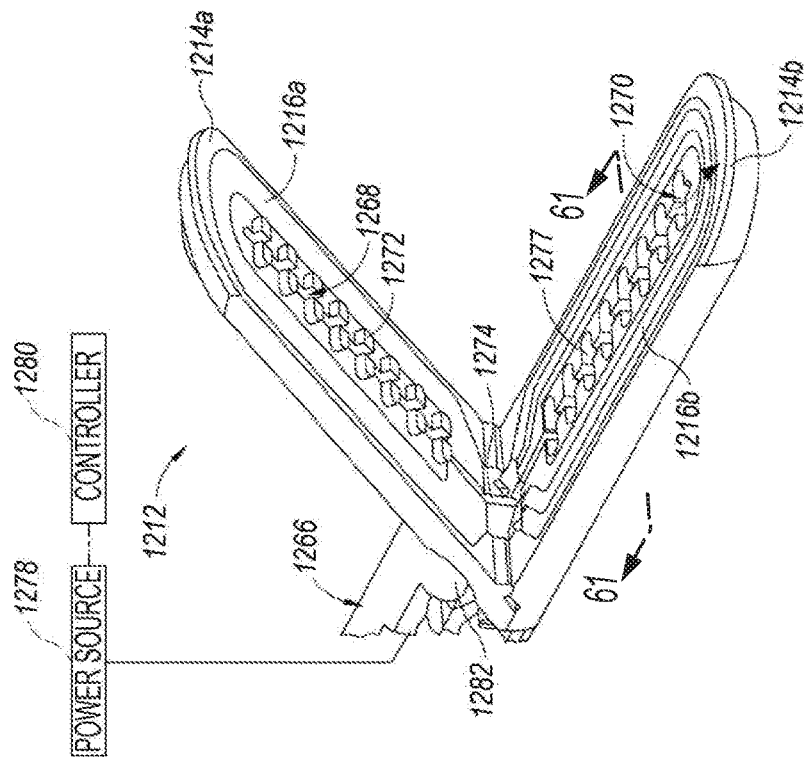
FIG. 60 illustrates a perspective view of the end effector of the device of FIGS. 54-59 in an open configuration, according to one aspect of the present disclosure.

FIG. 60 illustrates a perspective view of the end effector 1212 of the device of FIGS. 54-59 in an open configuration, according to one aspect of the present disclosure. The end effector 1212 of the present example comprises a pair of jaw members 1214*a*, 1214*b*. In the present example, one jaw member 1214*b* is fixed relative to shaft assembly; while the other jaw member 1214*a* pivots relative to shaft assembly, toward and away from the other jaw member 1214*b*. In some versions, actuators such as rods or cables, etc., may extend through a sheath and be joined with one jaw member 1214*a* at a pivotal coupling, such that longitudinal movement of the actuator rods/cables/etc. through the shaft assembly provides pivoting of the jaw member 1214*a* relative to shaft assembly and relative to the second jaw member 1214*b*. Of course, the jaw members 1214*a*, 1214*b* instead may have any other suitable kind of movement and may be actuated in any other suitable fashion. By way of example only, the jaw members 1214*a*, 1214*b* may be actuated and thus closed by longitudinal translation of a firing beam 1266, such that actuator rods/cables/etc. may simply be eliminated in some versions. The upper side of one jaw member 1214*a* including a plurality of teeth serrations 1272. It should be understood that the lower side of the other jaw member 1214*b* may include complementary serrations 1277 that nest with the serrations 1272, to enhance gripping of tissue captured between the jaw members 1214*a*, 1214*b* of the end effector 1212 without necessarily tearing the tissue.

FIG. 61 illustrates a cross-sectional end view of the end effector 1212 of FIG. 60 in a closed configuration and with the blade 1274 in a distal position, according to one aspect to the present disclosure. With reference now to FIGS. 60-61, one jaw member 1214*a* defines a longitudinally extending elongate slot 1268; while the other jaw member 1214*b* also defines a longitudinally extending elongate slot 1270. In addition, the underside of one jaw member 1214*a* presents an electrically conductive surface 1216*a*; while the top side of the other jaw member 1214*b* presents another electrically conductive surface 1216*b*. The electrically conductive surfaces 1216*a*, 1216*b* are in communication with an electrical source 1278 and a controller 1280 via one or more conductors (not shown) that extend along the length of shaft assembly. The electrical source 1278 is operable to deliver RF energy to first electrically conductive surface 1216*b* at a first polarity and to second electrically conductive surface 1216*a* at a second (opposite) polarity, such that RF current flows between electrically conductive surfaces 1216*a*, 1216*b* and thereby through tissue captured between the jaw members 1214*a*, 1214*b*. In some versions, firing beam 1266 serves as an electrical conductor that cooperates with the electrically conductive surfaces 1216*a*, 1216*b* (e.g., as a ground return) for delivery of bipolar RF energy captured between the jaw members 1214*a*, 1214*b*. The electrical source 1278 may be external to surgical instrument 1200 or may be integral with surgical instrument 1200 (e.g., in the handle assembly 1202, etc.), as described in one or more references cited herein or otherwise. A controller 1280 regulates delivery of power from electrical source 1278 to the electrically conductive surfaces 1216a, 1216b. The controller 1280 may also be external to surgical instrument 1200 or may be integral with surgical instrument 1200 (e.g., in handle assembly 1202, etc.), as described in one or more references cited herein or otherwise. It should also be understood that the electrically conductive surfaces 1216a, 1216b may be provided in a variety of alternative locations, configurations, and relationships.

Still with reference to FIGS. 60-61, the surgical instrument 1200 of the present example includes a firing beam 1266 that is longitudinally movable along part of the length of end effector 1212. The firing beam 1266 is coaxially positioned within the shaft assembly 1210, extends along the length of the shaft assembly 1210, and translates longitudinally within the shaft assembly 1210 (including the articulation section 1230 in the present example), though it should be understood that firing beam 12660 and the shaft assembly 1210 may have any other suitable relationship. The firing beam 1266 includes a knife 1274 with a sharp distal end, an upper flange 1281, and a lower flange 1282. As best seen in FIG. 61, the knife 1274 extends through slots 1268, 1270 of the jaw members 1214a, 1214b, with the upper flange 1281 being located above the jaw member 1214a in a recess 1284 and the lower flange 1282 being located below the jaw member 1214b in a recess 1286. The configuration of the knife 1274 and the flanges 1281, 1282 provides an "I-beam" type of cross section at the distal end of firing beam 1266. While the flanges 1281, 1282 extend longitudinally only along a small portion of the length of firing beam 1266 in the present example, it should be understood that the flanges 1281, 1282 may extend longitudinally along any suitable length of firing beam 1266. In addition, while the flanges 1281, 1282 are positioned along the exterior of the jaw members 1214a, 1214b, the flanges 1281, 1282 may alternatively be disposed in corresponding slots formed within jaw members 1214a, 1214b. For instance, the jaw members 1214a, 1214b may define a "T"-shaped slot, with parts of the knife 1274 being disposed in one vertical portion of a "T"-shaped slot and with the flanges 1281, 1282 being disposed in the horizontal portions of the "T"-shaped slots. Various other suitable configurations and relationships will be apparent to those of ordinary skill in the art in view of the teachings herein. By way of example only, the end effector 1212 may include one or more positive temperature coefficient (PTC) thermistor bodies 1288, 1290 (e.g., PTC polymer, etc.), located adjacent to the electrically conductive surfaces 1216a, 1216b and/or elsewhere.

The structural and functional aspects of the battery assembly 1206 are similar to those of the battery assembly 106 for the surgical instrument 100 described in connection with FIGS. 1, 2, and 16-24, including the battery circuits described in connection with FIGS. 20-24. Accordingly, for conciseness and clarity of disclosure, such the structural and functional aspects of the battery assembly 106 are incorporated herein by reference and will not be repeated here. Furthermore, the structural and functional aspects of the RF generator circuits are similar to those of the RF generator circuits described in for the surgical instruments 500, 600 described in connection with FIGS. 34-37. Accordingly, for conciseness and clarity of disclosure, such the structural and functional aspects of the RF generator circuits are incorporated herein by reference and will not be repeated here.

Furthermore, the surgical instrument 1200 includes the battery and control circuits described in connection with FIGS. 12-15, including, for example, the control circuit 210 described in connection with FIG. 14 and the electrical circuit 300 described in connection withe FIG. 15. Accordingly, for conciseness and clarity of disclosure, the description of the circuits described in connection with FIGS. 12-15 is incorporated herein by reference and will not be repeated here.

For a more detailed description of an electrosurgical instrument comprising a cutting mechanism and an articulation section that is operable to deflect the end effector away from the longitudinal axis of the shaft, reference is made to U.S. Pub. No. 2013/0023868, which is herein incorporated by reference.

It should also be understood that any of the surgical instruments 100, 480, 500, 600, 1100, 1150, 1200 described herein may be modified to include a motor or other electrically powered device to drive an otherwise manually moved component. Various examples of such modifications are described in U.S. Pub. No. 2012/0116379 and U.S. Pub. No. 2016/0256184, each of which is incorporated herein by reference. Various other suitable ways in which a motor or other electrically powered device may be incorporated into any of the devices herein will be apparent to those of ordinary skill in the art in view of the teachings herein.

It should also be understood that the circuits described in connection with FIGS. 11-15, 20-24, 34-37, and 50 may be configured to operate either alone or in combination with any of the surgical instruments 100, 480, 500, 600, 1100, 1150, 1200 described herein.

Figure 62:
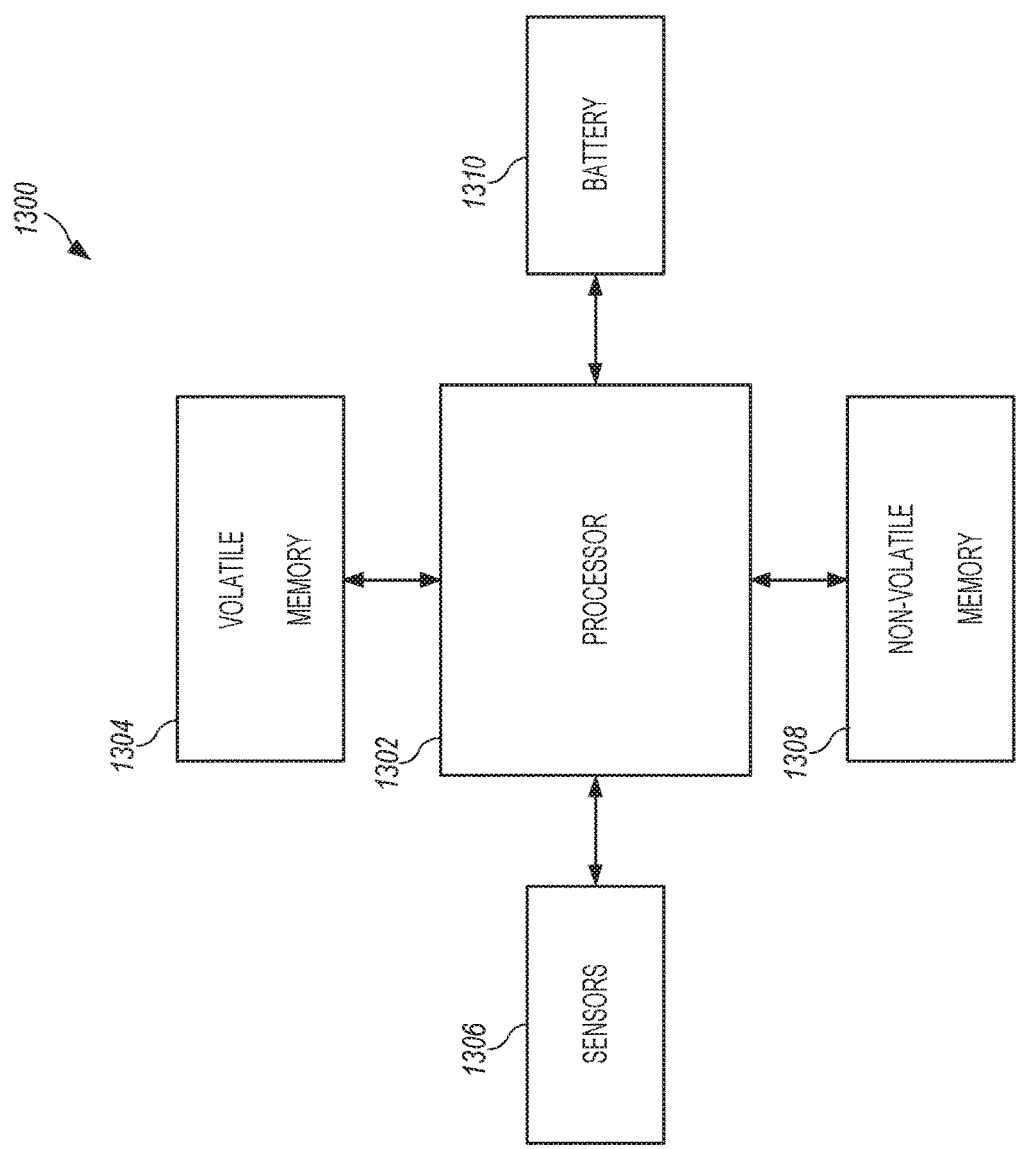
FIG. 62 illustrates the components of a control circuit of the surgical instrument, according to one aspect of the present disclosure.
Figure 63:
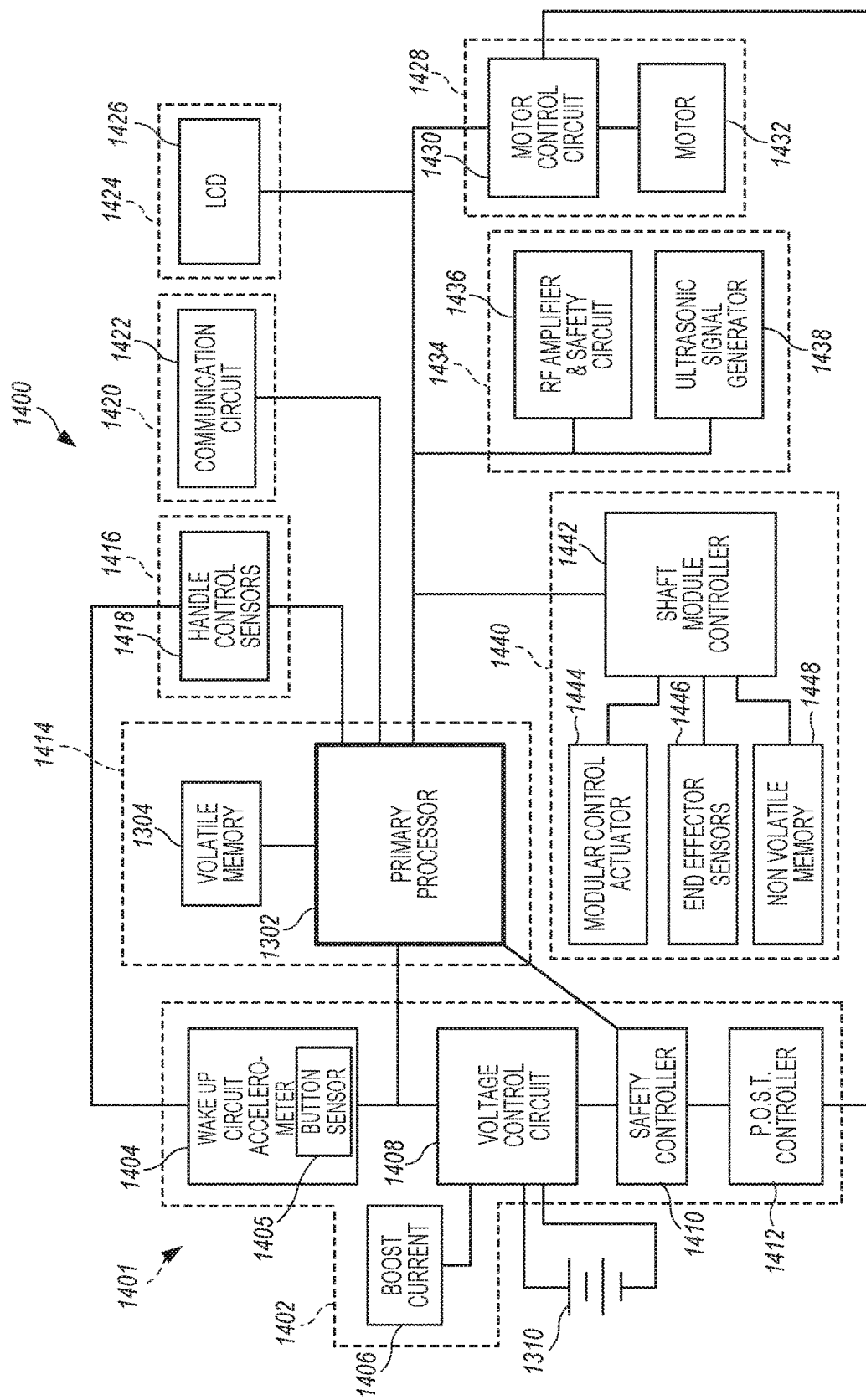
FIG. 63 is a system diagram of a segmented circuit comprising a plurality of independently operated circuit segments, according to one aspect of the present disclosure.

FIGS. 62-70 describe various circuits that are configured to operate with any one of the surgical instruments 100, 480, 500, 600, 1100, 1150, 1200 described in connections with FIGS. 1-61. Turning now to FIG. 62, there is shown the components of a control circuit 1300 of the surgical instrument, according to one aspect of the present disclosure. The control circuit 1300 comprises a processor 1302 coupled to a volatile memory 1304, one or more sensors 1306, a nonvolatile memory 1308 and a battery 1310. In one aspect, the surgical instrument may comprise a handle housing to house the control circuit 1300 and to contain general purpose controls to implement the power conservation mode. In some aspects, the processor 1302 may be a primary processor of the surgical instrument that includes one or more secondary processors. In some aspects, the processor 1302 may be stored within the battery 1310. The processor 1302 is configured to control various operations and functions of the surgical instrument by executing machine executable instructions, such as control programs or other software modules. For example, execution of an energy modality control program by the processor 1302 enables selection of a particular type of energy to be applied to patient tissue by a surgeon using the surgical instrument. The surgical instrument may comprise an energy modality actuator located on the handle of the surgical instrument. The actuator may be a slider, a toggle switch, a segmented momentary contact switch, or some other type of actuator. Actuation of the energy modality actuator causes the processor 1302 to activate an energy modality corresponding to a selected type of energy. The type of energy can be ultrasonic, RF, or a combination of ultrasonic and RF energy. In various aspects general, the processor 1302 is electrically coupled to the plurality of circuit segments of the surgical instrument as illustrated in FIG. 63 to activate or deactivate the circuit segments in accordance with energization and deenergization sequences.

The volatile memory 1304, such as a random-access memory (RAM), temporarily stores selected control programs or other software modules while the processor 1302 is in operation, such as when the processor 1302 executes a control program or software module. The one or more sensors 1306 may include force sensors, temperature sensors, current sensors or motion sensors. In some aspects, the one or more sensors 1306 may be located at the shaft, end effector, battery, or handle, or any combination or subcombination thereof. The one or more sensors 1306 transmit data associated with the operation of any one of the surgical instruments 100, 480, 500, 600, 1100, 1150, 1200 described in connection with FIGS. 1-61, such as the presence of tissue grasped by the jaws of the end effector or the force applied by the motor. In one aspect, the one or more sensors 1306 may include an accelerometer to verify the function or operation of the circuit segments, based on a safety check and a Power On Self Test (POST). Machine executable instructions such as control programs or other software modules are stored in the nonvolatile memory 1308. For example, the nonvolatile memory 1308 stores the Basic Input/Output System (BIOS) program. The nonvolatile memory 1308 may be a read-only memory, erasable programmable ROM (EPROM), an EEPROM, flash memory or some other type of nonvolatile memory device. Various examples of control programs are described in U.S. Pub. No. 2015/0272578, which is incorporated herein by reference in its entirety. The battery 1310 powers the surgical instrument by providing a source voltage that causes a current. The battery 1310 may comprise the motor control circuit segment 1428 illustrated in FIG. 63.

In one aspect, the processor 1302 may be any single core or multicore processor such as those known under the trade name ARM Cortex by Texas Instruments. In one aspect, the processor 1302 may be implemented as a safety processor comprising two microcontroller-based families such as TMS570 and RM4× known under the trade name Hercules ARM Cortex R4, also by Texas Instruments. Nevertheless, other suitable substitutes for microcontrollers and safety processor may be employed, without limitation. In one aspect, the safety processor may be configured specifically for IEC 61508 and ISO 26262 safety critical applications, among others, to provide advanced integrated safety features while delivering scalable performance, connectivity, and memory options.

In certain aspects, the processor 1302 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QED analog, one or more 12-bit Analog-to-Digital Converters (ADC) with 12 analog input channels, among other features that are readily available for the product datasheet. Other processors may be readily substituted and, accordingly, the present disclosure should not be limited in this context.

FIG. 63 is a system diagram 1400 of a segmented circuit 1401 comprising a plurality of independently operated circuit segments 1402, 1414, 1416, 1420, 1424, 1428, 1434, 1440, according to one aspect of the present disclosure. A circuit segment of the plurality of circuit segments of the segmented circuit 1401 comprises one or more circuits and one or more sets of machine executable instructions stored in one or more memory devices. The one or more circuits of a circuit segment are coupled to for electrical communication through one or more wired or wireless connection media. The plurality of circuit segments are configured to transition between three modes comprising a sleep mode, a standby mode and an operational mode.

In one aspect shown, the plurality of circuit segments 1402, 1414, 1416, 1420, 1424, 1428, 1434, 1440 start first in the standby mode, transition second to the sleep mode, and transition third to the operational mode. However, in other aspects, the plurality of circuit segments may transition from any one of the three modes to any other one of the three modes. For example, the plurality of circuit segments may transition directly from the standby mode to the operational mode. Individual circuit segments may be placed in a particular state by the voltage control circuit 1408 based on the execution by the processor 1302 of machine executable instructions. The states comprise a deenergized state, a low energy state, and an energized state. The deenergized state corresponds to the sleep mode, the low energy state corresponds to the standby mode, and the energized state corresponds to the operational mode. Transition to the low energy state may be achieved by, for example, the use of a potentiometer.

In one aspect, the plurality of circuit segments 1402, 1414, 1416, 1420, 1424, 1428, 1434, 1440 may transition from the sleep mode or the standby mode to the operational mode in accordance with an energization sequence. The plurality of circuit segments also may transition from the operational mode to the standby mode or the sleep mode in accordance with a deenergization sequence. The energization sequence and the deenergization sequence may be different. In some aspects, the energization sequence comprises energizing only a subset of circuit segments of the plurality of circuit segments. In some aspects, the deenergization sequence comprises deenergizing only a subset of circuit segments of the plurality of circuit segments.

Referring back to the system diagram 1400 in FIG. 63, the segmented circuit 1401 comprise a plurality of circuit segments comprising a transition circuit segment 1402, a processor circuit segment 1414, a handle circuit segment 1416, a communication circuit segment 1420, a display circuit segment 1424, a motor control circuit segment 1428, an energy treatment circuit segment 1434, and a shaft circuit segment 1440. The transition circuit segment comprises a wake up circuit 1404, a boost current circuit 1406, a voltage control circuit 1408, a safety controller 1410 and a POST controller 1412. The transition circuit segment 1402 is configured to implement a deenergization and an energization sequence, a safety detection protocol, and a POST.

In some aspects, the wake up circuit 1404 comprises an accelerometer button sensor 1405. In aspects, the transition circuit segment 1402 is configured to be in an energized state while other circuit segments of the plurality of circuit segments of the segmented circuit 1401 are configured to be in a low energy state, a deenergized state or an energized state. The accelerometer button sensor 1405 may monitor movement or acceleration of any one of the surgical instruments 100, 480, 500, 600, 1100, 1150, 1200 described herein in connection with FIGS. 1-61. For example, the movement may be a change in orientation or rotation of the surgical instrument. The surgical instrument may be moved in any direction relative to a three dimensional Euclidean space by for example, a user of the surgical instrument. When the accelerometer button sensor 1405 senses movement or acceleration, the accelerometer button sensor 1405 sends a signal to the voltage control circuit 1408 to cause the voltage control circuit 1408 to apply voltage to the processor circuit segment 1414 to transition the processor 1302 and the volatile memory 1304 to an energized state. In aspects, the processor 1302 and the volatile memory 1304 are in an energized state before the voltage control circuit 1409 applies voltage to the processor 1302 and the volatile memory 1304. In the operational mode, the processor 1302 may initiate an energization sequence or a deenergization sequence. In various aspects, the accelerometer button sensor 1405 may also send a signal to the processor 1302 to cause the processor 1302 to initiate an energization sequence or a deenergization sequence. In some aspects, the processor 1302 initiates an energization sequence when the majority of individual circuit segments are in a low energy state or a deenergized state. In other aspects, the processor 1302 initiates a deenergization sequence when the majority of individual circuit segments are in an energized state.

Additionally or alternatively, the accelerometer button sensor 1405 may sense external movement within a predetermined vicinity of the surgical instrument. For example, the accelerometer button sensor 1405 may sense a user of any one of the surgical instruments 100, 480, 500, 600, 1100, 1150, 1200 described herein in connection with FIGS. 1-61 moving a hand of the user within the predetermined vicinity. When the accelerometer button sensor 1405 senses this external movement, the accelerometer button sensor 1405 may send a signal to the voltage control circuit 1408 and a signal to the processor 1302, as previously described. After receiving the sent signal, the processor 1302 may initiate an energization sequence or a deenergization sequence to transition one or more circuit segments between the three modes. In aspects, the signal sent to the voltage control circuit 1408 is sent to verify that the processor 1302 is in operational mode. In some aspects, the accelerometer button sensor 1405 may sense when the surgical instrument has been dropped and send a signal to the processor 1302 based on the sensed drop. For example, the signal can indicate an error in the operation of an individual circuit segment. The one or more sensors 1306 may sense damage or malfunctioning of the affected individual circuit segments. Based on the sensed damage or malfunctioning, the POST controller 1412 may perform a POST of the corresponding individual circuit segments.

An energization sequence or a deenergization sequence may be defined based on the accelerometer button sensor 1405. For example, the accelerometer button sensor 1405 may sense a particular motion or a sequence of motions that indicates the selection of a particular circuit segment of the plurality of circuit segments. Based on the sensed motion or series of sensed motions, the accelerometer button sensor 1405 may transmit a signal comprising an indication of one or more circuit segments of the plurality of circuit segments to the processor 1302 when the processor 1302 is in an energized state. Based on the signal, the processor 1302 determines an energization sequence comprising the selected one or more circuit segments. Additionally or alternatively, a user of any one of the surgical instruments 100, 480, 500, 600, 1100, 1150, 1200 described herein in connection with FIGS. 1-61 may select a number and order of circuit segments to define an energization sequence or a deenergization sequence based on interaction with a graphical user interface (GUI) of the surgical instrument.

In various aspects, the accelerometer button sensor 1405 may send a signal to the voltage control circuit 1408 and a signal to the processor 1302 only when the accelerometer button sensor 1405 detects movement of any one the surgical instruments 100, 480, 500, 600, 1100, 1150, 1200 described herein in connection with FIGS. 1-61 or external movement within a predetermined vicinity above a predetermined threshold. For example, a signal may only be sent if movement is sensed for 5 or more seconds or if the surgical instrument is moved 5 or more inches. In other aspects, the accelerometer button sensor 1405 may send a signal to the voltage control circuit 1408 and a signal to the processor 1302 only when the accelerometer button sensor 1405 detects oscillating movement of the surgical instrument. A predetermined threshold reduces inadvertent transition of circuit segments of the surgical instrument. As previously described, the transition may comprise a transition to operational mode according to an energization sequence, a transition to low energy mode according to a deenergization sequence, or a transition to sleep mode according to a deenergization sequence. In some aspects, the surgical instrument comprises an actuator that may be actuated by a user of the surgical instrument. The actuation is sensed by the accelerometer button sensor 1405. The actuator may be a slider, a toggle switch, or a momentary contact switch. Based on the sensed actuation, the accelerometer button sensor 1405 may send a signal to the voltage control circuit 1408 and a signal to the processor 1302.

The boost current circuit 1406 is coupled to the battery 1310. The boost current circuit 1406 is a current amplifier, such as a relay or transistor, and is configured to amplify the magnitude of a current of an individual circuit segment. The initial magnitude of the current corresponds to the source voltage provided by the battery 1310 to the segmented circuit 1401. Suitable relays include solenoids. Suitable transistors include field-effect transistors (FET), MOSFET, and bipolar junction transistors (BJT). The boost current circuit 1406 may amplify the magnitude of the current corresponding to an individual circuit segment or circuit which requires more current draw during operation of any one of the surgical instruments 100, 480, 500, 600, 1100, 1150, 1200 described in connection with FIGS. 1-61. For example, an increase in current to the motor control circuit segment 1428 may be provided when a motor of the surgical instrument requires more input power. The increase in current provided to an individual circuit segment may cause a corresponding decrease in current of another circuit segment or circuit segments. Additionally or alternatively, the increase in current may correspond to voltage provided by an additional voltage source operating in conjunction with the battery 1310.

The voltage control circuit 1408 is coupled to the battery 1310. The voltage control circuit 1408 is configured to provide voltage to or remove voltage from the plurality of circuit segments. The voltage control circuit 1408 is also configured to increase or reduce voltage provided to the plurality of circuit segments of the segmented circuit 1401. In various aspects, the voltage control circuit 1408 comprises a combinational logic circuit such as a multiplexer (MUX) to select inputs, a plurality of electronic switches, and a plurality of voltage converters. An electronic switch of the plurality of electronic switches may be configured to switch between an open and closed configuration to disconnect or connect an individual circuit segment to or from the battery 1310. The plurality of electronic switches may be solid state devices such as transistors or other types of switches such as wireless switches, ultrasonic switches, accelerometers, inertial sensors, among others. The combinational logic circuit is configured to select an individual electronic switch for switching to an open configuration to enable application of voltage to the corresponding circuit segment. The combination logic circuit also is configured to select an individual electronic switch for switching to a closed configuration to enable removal of voltage from the corresponding circuit segment. By selecting a plurality of individual electronic switches, the combination logic circuit may implement a deenergization sequence or an energization sequence. The plurality of voltage converters may provide a stepped-up voltage or a stepped-down voltage to the plurality of circuit segments. The voltage control circuit 1408 may also comprise a microprocessor and memory device, as illustrated in FIG. 62.

The safety controller 1410 is configured to perform safety checks for the circuit segments. In some aspects, the safety controller 1410 performs the safety checks when one or more individual circuit segments are in the operational mode. The safety checks may be performed to determine whether there are any errors or defects in the functioning or operation of the circuit segments. The safety controller 1410 may monitor one or more parameters of the plurality of circuit segments. The safety controller 1410 may verify the identity and operation of the plurality of circuit segments by comparing the one or more parameters with predefined parameters. For example, if an RF energy modality is selected, the safety controller 1410 may verify that an articulation parameter of the shaft matches a predefined articulation parameter to verify the operation of the RF energy modality of any one of the surgical instruments 100, 480, 500, 600, 1100, 1150, 1200 described in connection with FIGS. 1-61. In some aspects, the safety controller 1410 may monitor, by the sensors 1306, a predetermined relationship between one or more properties of the surgical instrument to detect a fault. A fault may arise when the one or more properties are inconsistent with the predetermined relationship. When the safety controller 1410 determines that a fault exists, an error exists, or that some operation of the plurality of circuit segments was not verified, the safety controller 1410 prevents or disables operation of the particular circuit segment where the fault, error or verification failure originated.

The POST controller 1412 performs a POST to verify proper operation of the plurality of circuit segments. In some aspects, the POST is performed for an individual circuit segment of the plurality of circuit segments prior to the voltage control circuit 1408 applying a voltage to the individual circuit segment to transition the individual circuit segment from standby mode or sleep mode to operational mode. If the individual circuit segment does not pass the POST, the particular circuit segment does not transition from standby mode or sleep mode to operational mode. POST of the handle circuit segment 1416 may comprise, for example, testing whether the handle control sensors 1418 sense an actuation of a handle control of any one of the surgical instruments 100, 480, 500, 600, 1100, 1150, 1200 described in connection with FIGS. 1-61. In some aspects, the POST controller 1412 may transmit a signal to the accelerometer button sensor 1405 to verify the operation of the individual circuit segment as part of the POST. For example, after receiving the signal, the accelerometer button sensor 1405 may prompt a user of the surgical instrument to move the surgical instrument to a plurality of varying locations to confirm operation of the surgical instrument. The accelerometer button sensor 1405 may also monitor an output of a circuit segment or a circuit of a circuit segment as part of the POST. For example, the accelerometer button sensor 1405 can sense an incremental motor pulse generated by the motor 1432 to verify operation. A motor controller of the motor control circuit 1430 may be used to control the motor 1432 to generate the incremental motor pulse.

In various aspects, any one of the surgical instruments 100, 480, 500, 600, 1100, 1150, 1200 described in connection with FIGS. 1-61 may comprise additional accelerometer button sensors may be used. The POST controller 1412 may also execute a control program stored in the memory device of the voltage control circuit 1408. The control program may cause the POST controller 1412 to transmit a signal requesting a matching encrypted parameter from a plurality of circuit segments. Failure to receive a matching encrypted parameter from an individual circuit segment indicates to the POST controller 1412 that the corresponding circuit segment is damaged or malfunctioning. In some aspects, if the POST controller 1412 determines based on the POST that the processor 1302 is damaged or malfunctioning, the POST controller 1412 may send a signal to one or more secondary processors to cause one or more secondary processors to perform critical functions that the processor 1302 is unable to perform. In some aspects, if the POST controller 1412 determines based on the POST that one or more circuit segments do not operate properly, the POST controller 1412 may initiate a reduced performance mode of those circuit segments operating properly while locking out those circuit segments that fail POST or do not operate properly. A locked out circuit segment may function similarly to a circuit segment in standby mode or sleep mode.

The processor circuit segment 1414 comprises the processor 1302 and the volatile memory 1304 described with reference to FIG. 62. The processor 1302 is configured to initiate an energization or a deenergization sequence. To initiate the energization sequence, the processor 1302 transmits an energizing signal to the voltage control circuit 1408 to cause the voltage control circuit 1408 to apply voltage to the plurality or a subset of the plurality of circuit segments in accordance with the energization sequence. To initiate the deenergization sequence, the processor 1302 transmits a deenergizing signal to the voltage control circuit 1408 to cause the voltage control circuit 1408 to remove voltage from the plurality or a subset of the plurality of circuit segments in accordance with the deenergization sequence.

The handle circuit segment 1416 comprises handle control sensors 1418. The handle control sensors 1418 may sense an actuation of one or more handle controls of any one of the surgical instruments 100, 480, 500, 600, 1100, 1150, 1200 described herein in connection with FIGS. 1-61. In various aspects, the one or more handle controls comprise a clamp control, a release button, an articulation switch, an energy activation button, and/or any other suitable handle control. The user may activate the energy activation button to select between an RF energy mode, an ultrasonic energy mode or a combination RF and ultrasonic energy mode. The handle control sensors 1418 may also facilitate attaching a modular handle to the surgical instrument. For example, the handle control sensors 1418 may sense proper attachment of the modular handle to the surgical instrument and indicate the sensed attachment to a user of the surgical instrument. The LCD display 1426 may provide a graphical indication of the sensed attachment. In some aspects, the handle control sensors 1418 senses actuation of the one or more handle controls. Based on the sensed actuation, the processor 1302 may initiate either an energization sequence or a deenergization sequence.

The communication circuit segment 1420 comprises a communication circuit 1422. The communication circuit 1422 comprises a communication interface to facilitate signal communication between the individual circuit segments of the plurality of circuit segments. In some aspects, the communication circuit 1422 provides a path for the modular components of any one of the surgical instruments 100, 480, 500, 600, 1100, 1150, 1200 described herein in connection with FIGS. 1-61 to communicate electrically. For example, a modular shaft and a modular transducer, when attached together to the handle of the surgical instrument, can upload control programs to the handle through the communication circuit 1422.

The display circuit segment 1424 comprises a LCD display 1426. The LCD display 1426 may comprise a liquid crystal display screen, LED indicators, etc. In some aspects, the LCD display 1426 is an organic light-emitting diode (OLED) screen. The Display 226 may be placed on, embedded in, or located remotely from any one of the surgical instruments 100, 480, 500, 600, 1100, 1150, 1200 described herein in connection with FIGS. 1-61. For example, the Display 226 can be placed on the handle of the surgical instrument. The Display 226 is configured to provide sensory feedback to a user. In various aspects, the LCD display 1426 further comprises a backlight. In some aspects, the surgical instrument may also comprise audio feedback devices such as a speaker or a buzzer and tactile feedback devices such as a haptic actuator.

The motor control circuit segment 1428 comprises a motor control circuit 1430 coupled to a motor 1432. The motor 1432 is coupled to the processor 1302 by a driver and a transistor, such as a FET. In various aspects, the motor control circuit 1430 comprises a motor current sensor in signal communication with the processor 1302 to provide a signal indicative of a measurement of the current draw of the motor to the processor 1302. The processor transmits the signal to the Display 226. The Display 226 receives the signal and displays the measurement of the current draw of the motor 1432. The processor 1302 may use the signal, for example, to monitor that the current draw of the motor 1432 exists within an acceptable range, to compare the current draw to one or more parameters of the plurality of circuit segments, and to determine one or more parameters of a patient treatment site. In various aspects, the motor control circuit 1430 comprises a motor controller to control the operation of the motor. For example, the motor control circuit 1430 controls various motor parameters, such as by adjusting the velocity, torque and acceleration of the motor 1432. The adjusting is done based on the current through the motor 1432 measured by the motor current sensor.

In various aspects, the motor control circuit 1430 comprises a force sensor to measure the force and torque generated by the motor 1432. The motor 1432 is configured to actuate a mechanism of any one of the surgical instruments 100, 480, 500, 600, 1100, 1150, 1200 described herein in connection with FIGS. 1-61. For example, the motor 1432 is configured to control actuation of the shaft of the surgical instrument to realize clamping, rotation and articulation functionality. For example, the motor 1432 may actuate the shaft to realize a clamping motion with jaws of the surgical instrument. The motor controller may determine whether the material clamped by the jaws is tissue or metal. The motor controller may also determine the extent to which the jaws clamp the material. For example, the motor controller may determine how open or closed the jaws are based on the derivative of sensed motor current or motor voltage. In some aspects, the motor 1432 is configured to actuate the transducer to cause the transducer to apply torque to the handle or to control articulation of the surgical instrument. The motor current sensor may interact with the motor controller to set a motor current limit. When the current meets the predefined threshold limit, the motor controller initiates a corresponding change in a motor control operation. For example, exceeding the motor current limit causes the motor controller to reduce the current draw of the motor.

The energy treatment circuit segment 1434 comprises a RF amplifier and safety circuit 1436 and an ultrasonic signal generator circuit 1438 to implement the energy modular functionality of any one of the surgical instruments 100, 480, 500, 600, 1100, 1150, 1200 described in connection with FIGS. 1-61. In various aspects, the RF amplifier and safety circuit 1436 is configured to control the RF modality of the surgical instrument by generating an RF signal. The ultrasonic signal generator circuit 1438 is configured to control the ultrasonic energy modality by generating an ultrasonic signal. The RF amplifier and safety circuit 1436 and an ultrasonic signal generator circuit 1438 may operate in conjunction to control the combination RF and ultrasonic energy modality.

The shaft circuit segment 1440 comprises a shaft module controller 1442, a modular control actuator 1444, one or more end effector sensors 1446, and a non volatile memory 1448. The shaft module controller 1442 is configured to control a plurality of shaft modules comprising the control programs to be executed by the processor 1302. The plurality of shaft modules implements a shaft modality, such as ultrasonic, combination ultrasonic and RF, RF I-blade, and RF-opposable jaw. The shaft module controller 1442 can select shaft modality by selecting the corresponding shaft module for the processor 1302 to execute. The modular control actuator 1444 is configured to actuate the shaft according to the selected shaft modality. After actuation is initiated, the shaft articulates the end effector according to the one or more parameters, routines or programs specific to the selected shaft modality and the selected end effector modality. The one or more end effector sensors 1446 located at the end effector may include force sensors, temperature sensors, current sensors or motion sensors. The one or more end effector sensors 1446 transmit data about one or more operations of the end effector, based on the energy modality implemented by the end effector. In various aspects, the energy modalities include an ultrasonic energy modality, a RF energy modality, or a combination of the ultrasonic energy modality and the RF energy modality. The non volatile memory 1448 stores the shaft control programs. A control program comprises one or more parameters, routines or programs specific to the shaft. In various aspects, the non volatile memory 1448 may be an ROM, EPROM, EEPROM or flash memory. The non volatile memory 1448 stores the shaft modules corresponding to the selected shaft of nay one of the surgical instruments 100, 480, 500, 600, 1100, 1150, 1200 described herein in connection with FIGS. 1-61. The shaft modules may be changed or upgraded in the non volatile memory 1448 by the shaft module controller 1442, depending on the surgical instrument shaft to be used in operation.

FIG. 64 illustrates a diagram of one aspect of a surgical instrument 1500 comprising a feedback system for use with any one of the surgical instruments 100, 480, 500, 600, 1100, 1150, 1200 described herein in connection with FIGS. 1-61, which may include or implement many of the features described herein. For example, in one aspect, the surgical instrument 1500 may be similar to or representative of any one of the surgical instruments 100, 480, 500, 600, 1100, 1150, 1200. The surgical instrument 1500 may include a generator 1502. The surgical instrument 1500 also may include an end effector 1506, which may be activated when a clinician operates a trigger 1510. In various aspects, the end effector 1506 may include an ultrasonic blade to deliver ultrasonic vibration to carry out surgical coagulation/cutting treatments on living tissue. In other aspects the end effector 1506 may include electrically conductive elements coupled to an electrosurgical high-frequency current energy source to carry out surgical coagulation or cauterization treatments on living tissue and either a mechanical knife with a sharp edge or an ultrasonic blade to carry out cutting treatments on living tissue. When the trigger 1510 is actuated, a force sensor 1512 may generate a signal indicating the amount of force being applied to the trigger 1510. In addition to, or instead of a force sensor 1512, the surgical instrument 1500 may include a position sensor 1513, which may generate a signal indicating the position of the trigger 1510 (e.g., how far the trigger has been depressed or otherwise actuated). In one aspect, the position sensor 1513 may be a sensor positioned with the outer tubular sheath described above or reciprocating tubular actuating member located within the outer tubular sheath described above. In one aspect, the sensor may be a Hall-effect sensor or any suitable transducer that varies its output voltage in response to a magnetic field. The Hall-effect sensor may be used for proximity switching, positioning, speed detection, and current sensing applications. In one aspect, the Hall-effect sensor operates as an analog transducer, directly returning a voltage. With a known magnetic field, its distance from the Hall plate can be determined.

A control circuit 1508 may receive the signals from the sensors 1512 and/or 1513. The control circuit 1508 may include any suitable analog or digital circuit components. The control circuit 1508 also may communicate with the generator 1502 and/or the transducer 1504 to modulate the power delivered to the end effector 1506 and/or the generator level or ultrasonic blade amplitude of the end effector 1506 based on the force applied to the trigger 1510 and/or the position of the trigger 1510 and/or the position of the outer tubular sheath described above relative to the reciprocating tubular actuating member 58 located within the outer tubular sheath 56 described above (e.g., as measured by a Hall-effect sensor and magnet combination). For example, as more force is applied to the trigger 1510, more power and/or a higher ultrasonic blade amplitude may be delivered to the end effector 1506. According to various aspects, the force sensor 1512 may be replaced by a multi-position switch.

According to various aspects, the end effector 1506 may include a clamp or clamping mechanism, for example, such as that described above with respect to FIGS. 1-5. When the trigger 1510 is initially actuated, the clamping mechanism may close, clamping tissue between a clamp arm and the end effector 1506. As the force applied to the trigger increases (e.g., as sensed by force sensor 1512) the control circuit 1508 may increase the power delivered to the end effector 1506 by the transducer 1504 and/or the generator level or ultrasonic blade amplitude brought about in the end effector 1506. In one aspect, trigger position, as sensed by position sensor 1513 or clamp or clamp arm position, as sensed by position sensor 1513 (e.g., with a Hall-effect sensor), may be used by the control circuit 1508 to set the power and/or amplitude of the end effector 1506. For example, as the trigger is moved further towards a fully actuated position, or the clamp or clamp arm moves further towards the ultrasonic blade (or end effector 1506), the power and/or amplitude of the end effector 1506 may be increased.

According to various aspects, the surgical instrument 1500 also may include one or more feedback devices for indicating the amount of power delivered to the end effector 1506. For example, a speaker 1514 may emit a signal indicative of the end effector power. According to various aspects, the speaker 1514 may emit a series of pulse sounds, where the frequency of the sounds indicates power. In addition to, or instead of the speaker 1514, the surgical instrument 1500 may include a visual display 1516. The visual display 1516 may indicate end effector power according to any suitable method. For example, the visual display 1516 may include a series of LEDs, where end effector power is indicated by the number of illuminated LEDs. The speaker 1514 and/or visual display 1516 may be driven by the control circuit 1508. According to various aspects, the surgical instrument 1500 may include a ratcheting device (not shown) connected to the trigger 1510. The ratcheting device may generate an audible sound as more force is applied to the trigger 1510, providing an indirect indication of end effector power. The surgical instrument 1500 may include other features that may enhance safety. For example, the control circuit 1508 may be configured to prevent power from being delivered to the end effector 1506 in excess of a predetermined threshold. Also, the control circuit 1508 may implement a delay between the time when a change in end effector power is indicated (e.g., by speaker 1514 or visual display 1516), and the time when the change in end effector power is delivered. In this way, a clinician may have ample warning that the level of ultrasonic power that is to be delivered to the end effector 1506 is about to change.

In one aspect, the ultrasonic or high-frequency current generators of any one of the surgical instruments 100, 480, 500, 600, 1100, 1150, 1200 described herein in connection with FIGS. 1-61 may be configured to generate the electrical signal waveform digitally such that the desired using a predetermined number of phase points stored in a lookup table to digitize the wave shape. The phase points may be stored in a table defined in a memory, a field programmable gate array (FPGA), or any suitable non-volatile memory. FIG. 65 illustrates one aspect of a fundamental architecture for a digital synthesis circuit such as a direct digital synthesis (DDS) circuit 1600 configured to generate a plurality of wave shapes for the electrical signal waveform. The generator software and digital controls may command the FPGA to scan the addresses in the lookup table 1604 which in turn provides varying digital input values to a DAC circuit 1608 that feeds a power amplifier. The addresses may be scanned according to a frequency of interest. Using such a lookup table 1604 enables generating various types of wave shapes that can be fed into tissue or into a transducer, an RF electrode, multiple transducers simultaneously, multiple RF electrodes simultaneously, or a combination of RF and ultrasonic instruments. Furthermore, multiple lookup tables 1604 that represent multiple wave shapes can be created, stored, and applied to tissue from a generator.

The waveform signal may be configured to control at least one of an output current, an output voltage, or an output power of an ultrasonic transducer and/or an RF electrode, or multiples thereof (e.g. two or more ultrasonic transducers and/or two or more RF electrodes). Further, where the surgical instrument comprises an ultrasonic components, the waveform signal may be configured to drive at least two vibration modes of an ultrasonic transducer of the at least one surgical instrument. Accordingly, a generator may be configured to provide a waveform signal to at least one surgical instrument wherein the waveform signal corresponds to at least one wave shape of a plurality of wave shapes in a table. Further, the waveform signal provided to the two surgical instruments may comprise two or more wave shapes. The table may comprise information associated with a plurality of wave shapes and the table may be stored within the generator. In one aspect or example, the table may be a direct digital synthesis table, which may be stored in an FPGA of the generator. The table may be addressed by anyway that is convenient for categorizing wave shapes. According to one aspect, the table, which may be a direct digital synthesis table, is addressed according to a frequency of the waveform signal. Additionally, the information associated with the plurality of wave shapes may be stored as digital information in the table.

The analog electrical signal waveform may be configured to control at least one of an output current, an output voltage, or an output power of an ultrasonic transducer and/or an RF electrode, or multiples thereof (e.g., two or more ultrasonic transducers and/or two or more RF electrodes). Further, where the surgical instrument comprises ultrasonic components, the analog electrical signal waveform may be configured to drive at least two vibration modes of an ultrasonic transducer of the at least one surgical instrument. Accordingly, the generator circuit may be configured to provide an analog electrical signal waveform to at least one surgical instrument wherein the analog electrical signal waveform corresponds to at least one wave shape of a plurality of wave shapes stored in a lookup table 1604. Further, the analog electrical signal waveform provided to the two surgical instruments may comprise two or more wave shapes. The lookup table 1604 may comprise information associated with a plurality of wave shapes and the lookup table 1604 may be stored either within the generator circuit or the surgical instrument. In one aspect or example, the lookup table 1604 may be a direct digital synthesis table, which may be stored in an FPGA of the generator circuit or the surgical instrument. The lookup table 1604 may be addressed by anyway that is convenient for categorizing wave shapes. According to one aspect, the lookup table 1604, which may be a direct digital synthesis table, is addressed according to a frequency of the desired analog electrical signal waveform. Additionally, the information associated with the plurality of wave shapes may be stored as digital information in the lookup table 1604.

With the widespread use of digital techniques in instrumentation and communications systems, a digitally-controlled method of generating multiple frequencies from a reference frequency source has evolved and is referred to as direct digital synthesis. The basic architecture is shown in FIG. 65. In this simplified block diagram, a DDS circuit is coupled to a processor, controller, or a logic device of the generator circuit and to a memory circuit located either in the generator circuit of any one of the surgical instruments 100, 480, 500, 600, 1100, 1150, 1200 described herein in connection with FIGS. 1-61. The DDS circuit 1600 comprises an address counter 1602, lookup table 1604, a register 1606, a DAC circuit 1608, and a filter 1612. A stable clock $f_c$ is received by the address counter 1602 and the register 1606 drives a programmable-read-only-memory (PROM) which stores one or more integral number of cycles of a sinewave (or other arbitrary waveform) in a lookup table 1604. As the address counter 1602 steps through memory locations, values stored in the lookup table 1604 are written to a register 1606, which is coupled to a DAC circuit 1608. The corresponding digital amplitude of the signal at the memory location of the lookup table 1604 drives the DAC circuit 1608, which in turn generates an analog output signal 1610. The spectral purity of the analog output signal 1610 is determined primarily by the DAC circuit 1608. The phase noise is basically that of the reference clock $f_c$. The first analog output signal 1610 output from the DAC circuit 1608 is filtered by the filter 1612 and a second analog output signal 1614 output by the filter 1612 is provided to an amplifier having an output coupled to the output of the generator circuit. The second analog output signal has a frequency $f_{out}$.

Because the DDS circuit 1600 is a sampled data system, issues involved in sampling must be considered: quantization noise, aliasing, filtering, etc. For instance, the higher order harmonics of the DAC circuit 1608 output frequencies fold back into the Nyquist bandwidth, making them unfilterable, whereas, the higher order harmonics of the output of phase-locked-loop (PLL) based synthesizers can be filtered. The lookup table 1604 contains signal data for an integral number of cycles. The final output frequency $f_{out}$ can be changed changing the reference clock frequency $f_c$ or by reprogramming the PROM.

The DDS circuit 1600 may comprise multiple lookup tables 1604 where the lookup table 1604 stores a waveform represented by a predetermined number of samples, wherein the samples define a predetermined shape of the waveform. Thus multiple waveforms having a unique shape can be stored in multiple lookup tables 1604 to provide different tissue treatments based on instrument settings or tissue feedback. Examples of waveforms include high crest factor RF electrical signal waveforms for surface tissue coagulation, low crest factor RF electrical signal waveform for deeper tissue penetration, and electrical signal waveforms that promote efficient touch-up coagulation. In one aspect, the DDS circuit 1600 can create multiple wave shape lookup tables 1604 and during a tissue treatment procedure (e.g., "on-the-fly" or in virtual real time based on user or sensor inputs) switch between different wave shapes stored in separate lookup tables 1604 based on the tissue effect desired and/or tissue feedback. Accordingly, switching between wave shapes can be based on tissue impedance and other factors, for example. In other aspects, the lookup tables 1604 can store electrical signal waveforms shaped to maximize the power delivered into the tissue per cycle (i.e., trapezoidal or square wave). In other aspects, the lookup tables 1604 can store wave shapes synchronized in such way that they make maximizing power delivery by the multifunction surgical instrument any one of the surgical instruments 100, 480, 500, 600, 1100, 1150, 1200 described herein in connection with FIGS. 1-61 while delivering RF and ultrasonic drive signals. In yet other aspects, the lookup tables 1604 can store electrical signal waveforms to drive ultrasonic and RF therapeutic, and/or sub-therapeutic, energy simultaneously while maintaining ultrasonic frequency lock. Custom wave shapes specific to different instruments and their tissue effects can be stored in the non-volatile memory of the generator circuit or in the non-volatile memory (e.g., EEPROM) of any one of the surgical instruments 100, 480, 500, 600, 1100, 1150, 1200 described herein in connection with FIGS. 1-61 and be fetched upon connecting the multifunction surgical instrument to the generator circuit. An example of an exponentially damped sinusoid, as used in many high crest factor "coagulation" waveforms is shown in FIG. 67.

A more flexible and efficient implementation of the DDS circuit 1600 employs a digital circuit called a Numerically Controlled Oscillator (NCO). A block diagram of a more flexible and efficient digital synthesis circuit such as a DDS circuit 1700 is shown in FIG. 66. In this simplified block diagram, a DDS circuit 1700 is coupled to a processor, controller, or a logic device of the generator and to a memory circuit located either in the generator or in any of the surgical instruments 100, 480, 500, 600, 1100, 1150, 1200 described herein in connection with FIGS. 1-61. The DDS circuit 1700 comprises a load register 1702, a parallel delta phase register 1704, an adder circuit 1716, a phase register 1708, a lookup table 1710 (phase-to-amplitude converter), a DAC circuit 1712, and a filter 1714. The adder circuit 1716 and the phase register 1708a form part of a phase accumulator 1706. A clock signal $f_c$ is applied to the phase register 1708 and the DAC circuit 1712. The load register 1702 receives a tuning word that specifies output frequency as a fraction of the reference clock frequency $f_c$. The output of the load register 1702 is provided to a parallel delta phase register 1704 with a tuning word M.

The DDS circuit 1700 includes a sample clock that generates a clock frequency $f_c$, a phase accumulator 1706, and a lookup table 1710 (e.g., phase to amplitude converter). The content of the phase accumulator 1706 is updated once per clock cycle $f_c$. When time the phase accumulator 1706 is updated, the digital number, M, stored in the parallel delta phase register 1704 is added to the number in the phase register 1708 by an adder circuit 1716. Assuming that the number in the parallel delta phase register 1704 is 00 . . . 01 and that the initial contents of the phase accumulator 1706 is 00 . . . 00. The phase accumulator 1706 is updated by 00 . . . 01 per clock cycle. If the phase accumulator 1706 is 32-bits wide, 232 clock cycles (over 4 billion) are required before the phase accumulator 1706 returns to 00 . . . 00, and the cycle repeats.

The truncated output 1718 of the phase accumulator 1706 is provided to a phase-to amplitude converter lookup table 1710 and the output of the lookup table 1710 is coupled to a DAC circuit 1712. The truncated output 1718 of the phase accumulator 1706 serves as the address to a sine (or cosine) lookup table. An address in the lookup table corresponds to a phase point on the sinewave from 0° to 360°. The lookup table 1710 contains the corresponding digital amplitude information for one complete cycle of a sinewave. The lookup table 1710 therefore maps the phase information from the phase accumulator 1706 into a digital amplitude word, which in turn drives the DAC circuit 1712. The output of the DAC circuit is a first analog signal 1720 and is filtered by a filter 1714. The output of the filter 1714 is a second analog signal 1722, which is provided to a power amplifier coupled to the output of the generator circuit.

In one aspect, the electrical signal waveform may be digitized into 1024 (210) phase points, although the wave shape may be digitized is any suitable number of 2n phase points ranging from 256 (28) to 281,474,976,710,656 (248), where n is a positive integer, as shown in TABLE 1. The electrical signal waveform may be expressed as An(θn), where a normalized amplitude An at a point n is represented by a phase angle θn is referred to as a phase point at point n. The number of discrete phase points n determines the tuning resolution of the DDS circuit 1700 (as well as the DDS circuit 1600 shown in FIG. 65).

TABLE 1

| N | Number of Phase Points $2^n$ |
|---|---|
| 24 | 16,777,216 |
| 26 | 67,108,864 |
| 28 | 268,435,456 |
| ... | ... |
| 32 | 4,294,967,296 |
| ... | ... |
| 48 | 281,474,976,710,656 |
| ... | ... |

The generator circuit algorithms and digital control circuits scan the addresses in the lookup table 1710, which in turn provides varying digital input values to the DAC circuit 1712 that feeds the filter 1714 and the power amplifier. The addresses may be scanned according to a frequency of interest. Using the lookup table enables generating various types of shapes that can be converted into an analog output signal by the DAC circuit 1712, filtered by the filter 1714, amplified by the power amplifier coupled to the output of the generator circuit, and fed to the tissue in the form of RF energy or fed to an ultrasonic transducer and applied to the tissue in the form of ultrasonic vibrations which deliver energy to the tissue in the form of heat. The output of the amplifier can be applied to an RF electrode, multiple RF electrodes simultaneously, an ultrasonic transducer, multiple ultrasonic transducers simultaneously, or a combination of RF and ultrasonic transducers, for example. Furthermore, multiple wave shape tables can be created, stored, and applied to tissue from a generator circuit.

With reference back to FIG. 65, for n=32, and M=1, the phase accumulator 1706 steps through 232 possible outputs before it overflows and restarts. The corresponding output wave frequency is equal to the input clock frequency divided by 232. If M=2, then the phase register 1708 "rolls over" twice as fast, and the output frequency is doubled. This can be generalized as follows.

For a phase accumulator 1706 configured to accumulate n-bits (n generally ranges from 24 to 32 in most DDS systems, but as previously discussed n may be selected from a wide range of options), there are $2^n$ possible phase points. The digital word in the delta phase register, M, represents the amount the phase accumulator is incremented per clock cycle. If fc is the clock frequency, then the frequency of the output sinewave is equal to:

$$f_o = \frac{M \cdot fc}{2^n} \qquad \text{Eq. 1}$$

Equation 1 is known as the DDS "tuning equation." Note that the frequency resolution of the system is equal $$\frac{f_o}{2^n}.$$

For n=32, the resolution is greater than one part in four billion. In one aspect of the DDS circuit 1700, not all of the bits out of the phase accumulator 1706 are passed on to the lookup table 1710, but are truncated, leaving only the first 13 to 15 most significant bits (MSBs), for example. This reduces the size of the lookup table 1710 and does not affect the frequency resolution. The phase truncation only adds a small but acceptable amount of phase noise to the final output.

The electrical signal waveform may be characterized by a current, voltage, or power at a predetermined frequency. Further, where any one of the surgical instruments 100, 480, 500, 600, 1100, 1150, 1200 described herein in connection with FIGS. 1-61 comprises ultrasonic components, the electrical signal waveform may be configured to drive at least two vibration modes of an ultrasonic transducer of the at least one surgical instrument. Accordingly, the generator circuit may be configured to provide an electrical signal waveform to at least one surgical instrument wherein the electrical signal waveform is characterized by a predetermined wave shape stored in the lookup table 1710 (or lookup table 1604 FIG. 65). Further, the electrical signal waveform may be a combination of two or more wave shapes. The lookup table 1710 may comprise information associated with a plurality of wave shapes. In one aspect or example, the lookup table 1710 may be generated by the DDS circuit 1700 and may be referred to as a direct digital synthesis table. DDS works by first storing a large repetitive waveform in onboard memory. A cycle of a waveform (sine, triangle, square, arbitrary) can be represented by a predetermined number of phase points as shown in TABLE 1 and stored into memory. Once the waveform is stored into memory, it can be generated at very precise frequencies. The direct digital synthesis table may be stored in a non-volatile memory of the generator circuit and/or may be implemented with a FPGA circuit in the generator circuit. The lookup table 1710 may be addressed by any suitable technique that is convenient for categorizing wave shapes. According to one aspect, the lookup table 1710 is addressed according to a frequency of the electrical signal waveform. Additionally, the information associated with the plurality of wave shapes may be stored as digital information in a memory or as part of the lookup table 1710.

In one aspect, the generator circuit may be configured to provide electrical signal waveforms to at least two surgical instruments simultaneously. The generator circuit also may be configured to provide the electrical signal waveform, which may be characterized two or more wave shapes, via an output channel of the generator circuit to the two surgical instruments simultaneously. For example, in one aspect the electrical signal waveform comprises a first electrical signal to drive an ultrasonic transducer (e.g., ultrasonic drive signal), a second RF drive signal, and/or a combination thereof. In addition, an electrical signal waveform may comprise a plurality of ultrasonic drive signals, a plurality of RF drive signals, and/or a combination of a plurality of ultrasonic and RF drive signals.

In addition, a method of operating the generator circuit according to the present disclosure comprises generating an electrical signal waveform and providing the generated electrical signal waveform to any one of the surgical instruments 100, 480, 500, 600, 1100, 1150, 1200 described herein in connection with FIGS. 1-61, where generating the electrical signal waveform comprises receiving information associated with the electrical signal waveform from a memory. The generated electrical signal waveform comprises at least one wave shape. Furthermore, providing the generated electrical signal waveform to the at least one surgical instrument comprises providing the electrical signal waveform to at least two surgical instruments simultaneously.

The generator circuit as described herein may allow for the generation of various types of direct digital synthesis tables. Examples of wave shapes for RF/Electrosurgery signals suitable for treating a variety of tissue generated by the generator circuit include RF signals with a high crest factor (which may be used for surface coagulation in RF mode), a low crest factor RF signals (which may be used for deeper tissue penetration), and waveforms that promote efficient touch-up coagulation. The generator circuit also may generate multiple wave shapes employing a direct digital synthesis lookup table 1710 and, on the fly, can switch between particular wave shapes based on the desired tissue effect. Switching may be based on tissue impedance and/or other factors.

In addition to traditional sine/cosine wave shapes, the generator circuit may be configured to generate wave shape(s) that maximize the power into tissue per cycle (i.e., trapezoidal or square wave). The generator circuit may provide wave shape(s) that are synchronized to maximize the power delivered to the load when driving RF and ultrasonic signals simultaneously and to maintain ultrasonic frequency lock, provided that the generator circuit includes a circuit topology that enables simultaneously driving RF and ultrasonic signals. Further, custom wave shapes specific to instruments and their tissue effects can be stored in a non-volatile memory (NVM) or an instrument EEPROM and can be fetched upon connecting any one of the surgical instruments 100, 480, 500, 600, 1100, 1150, 1200 described herein in connection with FIGS. 1-61 to the generator circuit.

The DDS circuit 1700 may comprise multiple lookup tables 1604 where the lookup table 1710 stores a waveform represented by a predetermined number of phase points (also may be referred to as samples), wherein the phase points define a predetermined shape of the waveform. Thus multiple waveforms having a unique shape can be stored in multiple lookup tables 1710 to provide different tissue treatments based on instrument settings or tissue feedback. Examples of waveforms include high crest factor RF electrical signal waveforms for surface tissue coagulation, low crest factor RF electrical signal waveform for deeper tissue penetration, and electrical signal waveforms that promote efficient touch-up coagulation. In one aspect, the DDS circuit 1700 can create multiple wave shape lookup tables 1710 and during a tissue treatment procedure (e.g., "on-the-fly" or in virtual real time based on user or sensor inputs) switch between different wave shapes stored in different lookup tables 1710 based on the tissue effect desired and/or tissue feedback. Accordingly, switching between wave shapes can be based on tissue impedance and other factors, for example. In other aspects, the lookup tables 1710 can store electrical signal waveforms shaped to maximize the power delivered into the tissue per cycle (i.e., trapezoidal or square wave). In other aspects, the lookup tables 1710 can store wave shapes synchronized in such way that they make maximizing power delivery by any one of the surgical instruments 100, 480, 500, 600, 1100, 1150, 1200 described herein in connection with FIGS. 1-61 when delivering RF and ultrasonic drive signals. In yet other aspects, the lookup tables 1710 can store electrical signal waveforms to drive ultrasonic and RF therapeutic, and/or sub-therapeutic, energy simultaneously while maintaining ultrasonic frequency lock. Generally, the output wave shape may be in the form of a sine wave, cosine wave, pulse wave, square wave, and the like. Nevertheless, the more complex and custom wave shapes specific to different instruments and their tissue effects can be stored in the non-volatile memory of the generator circuit or in the non-volatile memory (e.g., EEPROM) of the surgical instrument and be fetched upon connecting the surgical instrument to the generator circuit. One example of a custom wave shape is an exponentially damped sinusoid as used in many high crest factor "coagulation" waveforms, as shown in FIG. 67.

FIG. 67 illustrates one cycle of a discrete time digital electrical signal waveform 1800, according to one aspect of the present disclosure of an analog waveform 1804 (shown superimposed over the discrete time digital electrical signal waveform 1800 for comparison purposes). The horizontal axis represents Time (t) and the vertical axis represents digital phase points. The digital electrical signal waveform 1800 is a digital discrete time version of the desired analog waveform 1804, for example. The digital electrical signal waveform 1800 is generated by storing an amplitude phase point 1802 that represents the amplitude per clock cycle $T_{clk}$ over one cycle or period $T_o$. The digital electrical signal waveform 1800 is generated over one period $T_o$ by any suitable digital processing circuit. The amplitude phase points are digital words stored in a memory circuit. In the example illustrated in FIGS. 65, 66, the digital word is a six-bit word that is capable of storing the amplitude phase points with a resolution of 26 or 64 bits. It will be appreciated that the examples shown in FIGS. 65, 66 is for illustrative purposes and in actual implementations the resolution can be much higher. The digital amplitude phase points 1802 over one cycle $T_o$ are stored in the memory as a string of string words in a lookup table 1604, 1710 as described in connection with FIGS. 65, 66, for example. To generate the analog version of the analog waveform 1804, the amplitude phase points 1802 are read sequentially from the memory from 0 to $T_o$ per clock cycle $T_{clk}$ and are converted by a DAC circuit 1608, 1712, also described in connection with FIGS. 65, 66. Additional cycles can be generated by repeatedly reading the amplitude phase points 1802 of the digital electrical signal waveform 1800 the from 0 to $T_o$ for as many cycles or periods as may be desired. The smooth analog version of the analog waveform 1804 is achieved by filtering the output of the DAC circuit 1608, 1712 by a filter 1612, 1714 (FIGS. 65 and 66). The filtered analog output signal 1614, 1722 (FIGS. 65 and 66) is applied to the input of a power amplifier.

In one aspect, as illustrated in FIG. 68A, a circuit 1900 may comprise a controller comprising one or more processors 1902 (e.g., microprocessor, microcontroller) coupled to at least one memory circuit 1904. The at least one memory circuit 1904 stores machine executable instructions that when executed by the processor 1902, cause the processor 1902 to execute machine instructions to implement any of the algorithms, processes, or techniques described herein.

The processor 1902 may be any one of a number of single or multi-core processors known in the art. The memory circuit 1904 may comprise volatile and non-volatile storage media. In one aspect, as illustrated in FIG. 68A, the processor 1902 may include an instruction processing unit 1906 and an arithmetic unit 1908. The instruction processing unit may be configured to receive instructions from the one memory circuit 1904.

In one aspect, a circuit 1910 may comprise a finite state machine comprising a combinational logic circuit 1912, as illustrated in FIG. 68B, configured to implement any of the algorithms, processes, or techniques described herein. In one aspect, a circuit 1920 may comprise a finite state machine comprising a sequential logic circuit, as illustrated in FIG. 68C. The sequential logic circuit 1920 may comprise the combinational logic circuit 1912 and at least one memory circuit 1914, for example. The at least one memory circuit 1914 can store a current state of the finite state machine, as illustrated in FIG. 68C. The sequential logic circuit 1920 or the combinational logic circuit 1912 can be configured to implement any of the algorithms, processes, or techniques described herein. In certain instances, the sequential logic circuit 1920 may be synchronous or asynchronous.

In other aspects, the circuit may comprise a combination of the processor 1902 and the finite state machine to implement any of the algorithms, processes, or techniques described herein. In other aspects, the finite state machine may comprise a combination of the combinational logic circuit 1910 and the sequential logic circuit 1920.

FIG. 69 is a schematic diagram of a circuit 1925 of various components of a surgical instrument with motor control functions, according to one aspect of the present disclosure. In various aspects, the surgical instruments 100, 480, 500, 600, 1100, 1150, 1200 described herein in connection with FIGS. 1-68C may include a drive mechanism 1930 which is configured to drive shafts and/or gear components in order to perform the various operations associated with the surgical instruments 100, 480, 500, 600, 1100, 1150, 1200. In one aspect, the drive mechanism 1930 160 includes a rotation drivetrain 1932 configured to rotate end effector 112, 512, 1000, 1112, 1212 as described in connection with FIGS. 1, 20, 40, 41, 45, 54, for example, about a longitudinal axis relative to handle housing. The drive mechanism 1930 further includes a closure drivetrain 1934 configured to close a jaw member to grasp tissue with the end effector. In addition, the drive mechanism 1930 includes a firing drive train 1936 configured to fire an I-beam knife of the end effector to cut tissue grasped by the end effector.

The drive mechanism 1930 includes a selector gearbox assembly 1938 that can be located in the handle assembly of the surgical instrument. Proximal to the selector gearbox assembly 1938 is a function selection module which includes a first motor 1942 that functions to selectively move gear elements within the selector gearbox assembly 1938 to selectively position one of the drivetrains 1932, 1934, 1936 into engagement with an input drive component of an optional second motor 1944 and motor drive circuit 1946 (shown in dashed line to indicate that the second motor 1944 and motor drive circuit 1946 are optional components).

Still referring to FIG. 69, the motors 1942, 1944 are coupled to motor control circuits 1946, 1948, respectively, which are configured to control the operation of the motors 1942, 1944 including the flow of electrical energy from a power source 1950 to the motors 1942, 1944. The power source 1950 may be a DC battery (e.g., rechargeable lead-based, nickel-based, lithium-ion based, battery etc.) or any other power source suitable for providing electrical energy to the surgical instrument.

The surgical instrument further includes a microcontroller 1952 ("controller"). In certain instances, the controller 1952 may include a microprocessor 1954 ("processor") and one or more computer readable mediums or memory units 1956 ("memory"). In certain instances, the memory 1956 may store various program instructions, which when executed may cause the processor 1954 to perform a plurality of functions and/or calculations described herein. The power source 1950 can be configured to supply power to the controller 1952, for example.

The processor 1954 be in communication with the motor control circuit 1946. In addition, the memory 1956 may store program instructions, which when executed by the processor 1954 in response to a user input 1958 or feedback elements 1960, may cause the motor control circuit 1946 to motivate the motor 1942 to generate at least one rotational motion to selectively move gear elements within the selector gearbox assembly 1938 to selectively position one of the drivetrains 1932, 1934, 1936 into engagement with the input drive component of the second motor 1944. Furthermore, the processor 1954 can be in communication with the motor control circuit 1948. The memory 1956 also may store program instructions, which when executed by the processor 1954 in response to a user input 1958, may cause the motor control circuit 1948 to motivate the motor 1944 to generate at least one rotational motion to drive the drivetrain engaged with the input drive component of the second motor 1948, for example.

The controller 1952 and/or other controllers of the present disclosure may be implemented using integrated and/or discrete hardware elements, software elements, and/or a combination of both. Examples of integrated hardware elements may include processors, microprocessors, microcontrollers, integrated circuits, ASICs, PLDs, DSPs, FPGAs, logic gates, registers, semiconductor devices, chips, microchips, chip sets, microcontrollers, system on a chip (SoC), and/or single in-line package (SIP). Examples of discrete hardware elements may include circuits and/or circuit elements such as logic gates, field effect transistors, bipolar transistors, resistors, capacitors, inductors, and/or relays. In certain instances, the controller 1952 may include a hybrid circuit comprising discrete and integrated circuit elements or components on one or more substrates, for example.

In certain instances, the controller 1952 and/or other controllers of the present disclosure may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, one or more 12-bit ADC with 12 analog input channels, among other features that are readily available. Other microcontrollers may be readily substituted for use with the present disclosure. Accordingly, the present disclosure should not be limited in this context.

In various instances, one or more of the various steps described herein can be performed by a finite state machine comprising either a combinational logic circuit or a sequential logic circuit, where either the combinational logic circuit or the sequential logic circuit is coupled to at least one memory circuit. The at least one memory circuit stores a current state of the finite state machine. The combinational or sequential logic circuit is configured to cause the finite state machine to the steps. The sequential logic circuit may be synchronous or asynchronous. In other instances, one or more of the various steps described herein can be performed by a circuit that includes a combination of the processor 1958 and the finite state machine, for example.

In various instances, it can be advantageous to be able to assess the state of the functionality of a surgical instrument to ensure its proper function. It is possible, for example, for the drive mechanism, as explained above, which is configured to include various motors, drivetrains, and/or gear components in order to perform the various operations of the surgical instrument, to wear out over time. This can occur through normal use, and in some instances the drive mechanism can wear out faster due to abuse conditions. In certain instances, a surgical instrument can be configured to perform self-assessments to determine the state, e.g. health, of the drive mechanism and it various components.

For example, the self-assessment can be used to determine when the surgical instrument is capable of performing its function before a re-sterilization or when some of the components should be replaced and/or repaired. Assessment of the drive mechanism and its components, including but not limited to the rotation drivetrain 1932, the closure drivetrain 1934, and/or the firing drivetrain 1936, can be accomplished in a variety of ways. The magnitude of deviation from a predicted performance can be used to determine the likelihood of a sensed failure and the severity of such failure. Several metrics can be used including: Periodic analysis of repeatably predictable events, Peaks or drops that exceed an expected threshold, and width of the failure.

In various instances, a signature waveform of a properly functioning drive mechanism or one or more of its components can be employed to assess the state of the drive mechanism or the one or more of its components. One or more vibration sensors can be arranged with respect to a properly functioning drive mechanism or one or more of its components to record various vibrations that occur during operation of the properly functioning drive mechanism or the one or more of its components. The recorded vibrations can be employed to create the signature waveform. Future waveforms can be compared against the signature waveform to assess the state of the drive mechanism and its components.

Still referring to FIG. 69, the surgical instrument 1930 includes a drivetrain failure detection module 1962 configured to record and analyze one or more acoustic outputs of one or more of the drivetrains 1932, 1934, 1936. The processor 1954 can be in communication with or otherwise control the module 1962. As described below in greater detail, the module 1962 can be embodied as various means, such as circuitry, hardware, a computer program product comprising a computer readable medium (for example, the memory 1956) storing computer readable program instructions that are executable by a processing device (for example, the processor 1954), or some combination thereof. In some aspects, the processor 36 can include, or otherwise control the module 1962.

FIG. 70 illustrates a handle assembly 1970 with a removable service panel 1972 removed to shown internal components of the handle assembly, according to one aspect of the present disclosure. The removable service panel 1972, or removable service cover, also includes reinforcing ribs 1990 for strength. The removable service panel 1972 comprises a plurality of fasteners 1988 that mate with a plurality of fasteners 1986 on the handle housing 1974 to removably attach the removable service panel 1972 to the handle housing 1974. In one aspect, the fasteners 1988 in the removable service panel 1972 comprise a first set of magnets and the handle housing 1974 comprises a second set of magnets that magnetically latch the service panel 1972 to the handle housing 1974. In one aspect, the first and second set of magnets 6112a, 6112b are rare-earth permanent magnets.

In FIG. 70, the removable service panel 1972 is shown removed from the handle housing 1974 to show the location of electrical and mechanical components of the surgical instrument such as the motor 1976 and electrical contacts 1984 to electrically couple the battery assembly or flexible circuits to the handle housing 1974. The motor 1976 and the electrical contacts 1984 are also removable from the handle housing 1974. The handle assembly 1970 also comprises a trigger 1982 and an actuation switch 1980, each of which is removable from the handle housing 1974. As previously described, the removable trigger 1982 may have multiple stages of operation to close the jaw member, fire the knife, activate the ultrasonic transducer, activate the high-frequency current, and/or open the jaw member. The actuation switch 1980 may be replaced with multiple switches to activate different functions such as, for example, close the jaw member, fire the knife, activate the ultrasonic transducer, activate the high-frequency current, and/or open the jaw member. As shown in FIG. 70, the handle assembly 1970 includes electrical contacts 1978 to electrically couple the handle assembly 1970 to the shaft assembly, where the electrical contacts 1978 are removable from the handle housing 1974. The handle housing 1974 also defines a space to receive a removable ultrasonic transducer assembly, ultrasonic transducer, ultrasonic transducer drive circuits, high-frequency current drive circuits, and/or display assembly, as previously discussed herein.

With reference ow to FIGS. 71-74B, in various aspects, the present disclosure provides a modular battery powered handheld surgical instrument with motor drive comprising a primary rotary drive configured to be selectably coupleable to at least two independent actuations (first, second, both, neither) and utilizing a clutch mechanism that is located entirely in the distal modular elongated tube of the shaft assembly. The motor drive may be adapted for use with any of the surgical instruments 100, 480, 500, 600, 1100, 1150, 1200 described herein in connection with FIGS. 1-70.

Aspects of the present disclosure are presented for a system and surgical instrument comprising a handle assembly and shaft assembly, with the shaft assembly including two or more distinct clutches configured to move various parts of the surgical instrument when engaged. The shaft assembly also includes an interior mechanism, such as a rotary drive, capable of selectively coupling to the clutches using independent actuation mechanisms. Each of the clutches may be engaged independently through the independent actuation mechanisms, such that the first clutch may be engaged only, the second clutch may be engaged only, both clutches may be engaged simultaneously, or neither of the clutches may be engaged at the same time. In some aspects, more clutches are included in the shaft assembly and may be engaged independently in similar manners. Example actions engaged by the clutches include engaging a clutch for articulating a portion of the shaft assembly, engaging another clutch to cause distal head rotation of the shaft assembly that includes an end effector, and engaging a third clutch to cause jaw closure and opening of the end effector.

In some aspects, the clutches are comprised of a micro electrical clutching design, whereby an actuation mechanism inside the shaft assembly engages the clutch by activating an electric coil that creates a magnetic field. The clutch itself may include a ferrofluid that reacts in the presence of magnetism. Thus, when the actuation mechanism creates the magnetic field in close proximity to the clutch, the actuation mechanism attaches to the clutch via the magnetic field. Rotation of the rotary drive may then cause rotation of a component within the shaft assembly coupled to the clutch. The other clutches within the shaft assembly may be engaged in a similar manner.

In some aspects, the rotary drive may be slidable within the shaft assembly, allowing for a single actuation mechanism to slide to different positions in order to engage multiple clutches at different times.

In some aspects, the surgical instrument may include one or more locking mechanisms configured to maintain the actuation mechanism in its deactivated state until it may be unambiguously determine that one or more of the clutches is desired to be engaged. The locking mechanism may be biased in a locked state and may be automatically deactivated within the first few degrees of clutch drive motion to ensure that system is placed in a specific articulated or actuated state.

Referring to FIG. 71, illustration 5700 shows the inner workings of a portion of a shaft assembly that is part of the surgical instrument, according to some aspects. This shaft assembly includes a rotary drive 5702 that may interact with three clutch systems, 5704, 5706, and 5708 through actuation mechanisms 5716, 5718, 5720, respectively, coupled to a rotary drive 5702. In this case, each of the actuation mechanisms include electrically conductive coils wrapped around the rotary drive 5702. Each of the coils may receive power through electrically conductive wires, such as wires 5710, 5712, and 5714, respectively. These wires may be coupled to in electrical power source.

Each of the clutches may comprise a material or mechanism that can be activated to attach to or engage with the actuation mechanisms. For example, the clutch systems 5704, 5706, and 5708 each include a cylindrical cavity, 5722, 5724, and 5726, respectively, positioned cylindrically around the rotary drive 5702. These cylindrical cavities may be filled with a ferrofluid, such as a magnetorheological fluid. The ferrofluid may be resting in a deactivated state that is semi-viscous. When in the presence of magnetism, such as a magnetic field, the ferrofluid may activate, harden, and align with the magnetic field such that the ferrofluid attaches to the magnetic source. Thus, electricity flowing to each of the electrically conductive coils, causing a magnetic field, may be used to engage the clutch in its local proximity. Because each of the coils 5716, 5718, 5720, may receive power independently, any and all combinations of clutches may be engaged at any particular time.

In some aspects, the shaft assembly may include other components, such as an articulation joint 5728, and an end effector comprising jaws 5742, for example. Certain portions of the shaft assembly may also be configured to rotate longitudinally along with rotary drive, such as rotating distal portion 5738. Each of these components may be activated and manipulated using the clutch systems described herein.

For example, the clutch system 5704 may be configured to control movement about the actuation joint 5728, according to some aspects. The clutch cavity 5722 that includes the ferrofluid may be coupled to a first articulation component 5734. Towards the distal end of the articulation component 134 is a gear, that is coupled to a second gear of a second articulation component 5736. When the clutch system 5704 is engaged, such as in the manner described above, the rotary drive 5702, when rotated, may also cause the first articulation component 5734 to correspondingly rotate. The distal gear then causes the rotation of the second articulation component 5736 which causes articulation about the articulation joint 5728. As shown in this example, because of the articulation joint 5728, the rotary drive 5702 is actually broken up into two main parts, including a distal rotary drive component 5730 that is coupled to the proximal rotary drive component 5702 via a system of gears 5732 and other connectors, as shown.

As another example, the clutch system 5706 may be configured to control rotation of the distal end of the shaft assembly, according to some aspects. The clutch cavity 5724 that includes the ferrofluid may be coupled to the rotatable distal portion 5738, as shown. Thus, when the clutch system 5706 is engaged, such as in the manner described above, the rotary drive 5702, when rotated, may cause rotatable distal portion 5738 to correspondingly rotate.

As another example, the clutch system 5708 may be configured to control jaw movement of the jaws 5742 of the end effector, according to some aspects. The clutch cavity 5726 that includes the ferrofluid may be coupled to a connector 5740 via a series of angled threads, similar to threads of a screw. Thus, when the clutch system 5708 is engaged, rotation by the rotary driver 5702 causes the connector 5740 to move proximally and distally, along with some rotation. The longitudinal motion of the connector 5740 may pull or push a fulcrum of the jaws, causing them to open and close. In other cases, rotation of the rotary drive 5702 may cause the connector 5740 to only rotate, wherein some other mechanism may be designed to cause the jaws to open and close. Examples may include a rotating gear system that converts the rotation into translation movement, a pair of electrical contacts coupled to the distal end of the connector 5740 that activates jaw movement, and other mechanisms apparent to those with skill in the art.

The example design in illustration 5700 shows that the different clutch systems may be engaged independently, meaning any combination of them may be engaged simultaneously, or separately, as desired by a user. This is achievable by the independent activations of the coils 5716, 5718, 5720, via the independent wires 5710, 5712, 5714. Therefore, the example design as shown allows for the shaft assembly to simultaneously articulate, rotate, and open and close the jaws, or any sub combination thereof, and aspects are not so limited. Similarly, additional clutch systems configured to perform or manipulate different actions of the shaft assembly may be further included, and are consistent with the teachings of this disclosure.

Figure 72C:
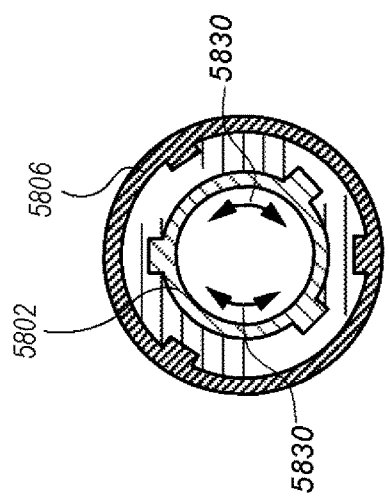
Figure 72D:
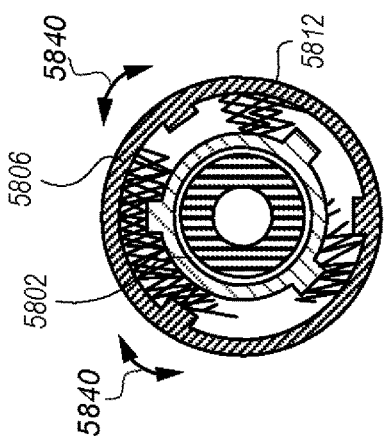
Figure 72A:
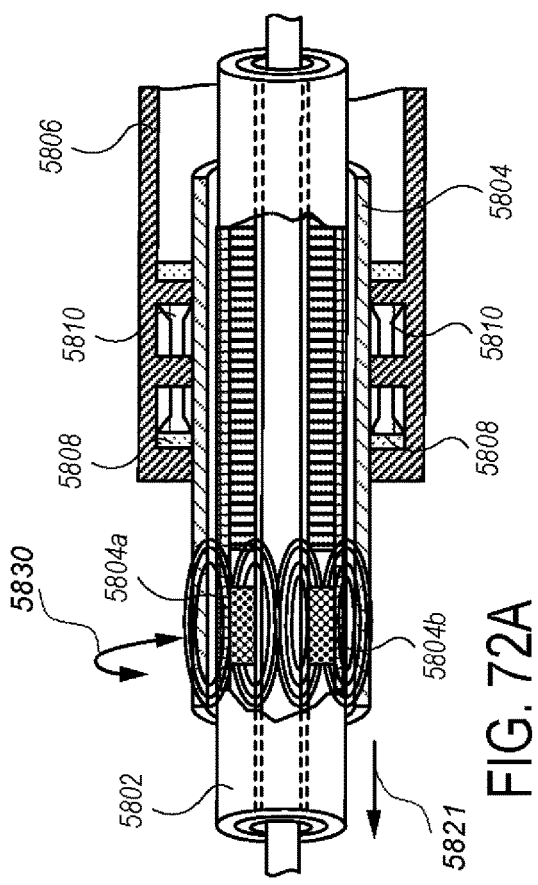

Referring to FIGS. 72A, 72B, 72C, 72D, 72E, and 72F another variation for including multiple clutch systems is shown, according to some aspects. Referring to FIG. 72A, in this case, the rotary drive 5802 includes a pair of permanent magnets 5804 *a*, 5804 *b*. In other cases, more than two permanent magnets may be used. The rotary drive 5802 is configured to slide back 5821 and forth 5822, within the remaining exterior shaft portion of the shaft assembly.

The rotary drive 5802 is also configured to rotate in the direction of the arrows 5830, as shown. In some aspects, the rotary drive 5802 may be contained in a rotating primary shaft 5804 that does not slide back and forth within the exterior shaft. The rotating primary shaft 5804 may be configured to rotate when engaged with one or more clutches. The outer, exterior frame of the shaft assembly 5806 is configured to not move initially and includes a pair of cylindrical clutch cavities 5808, 5810. These cavities may again be filled with magnetorheological fluid that remains in a highly viscous state outside the presence of a magnetic field. The clutch cavities 5808, 5810 may be positioned in close proximity to each other, such that the length of the magnets 5804 *a*, 5804 *b* may influence both ferrofluids within both cavities at the same time when the magnets are slid into a particular position.

Figure 72B:
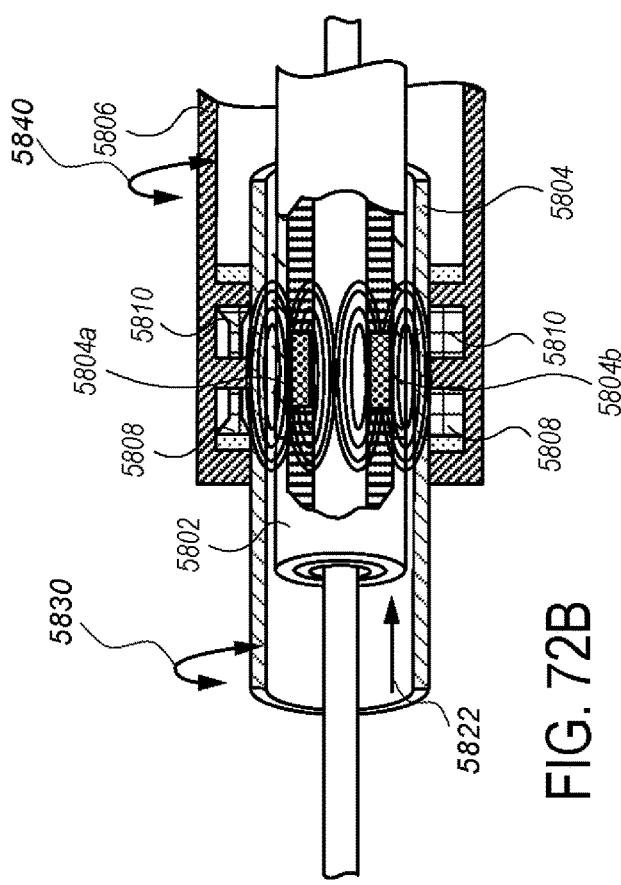

Referring to FIG. 72B, the rotary drive 5802 has been slid into a place such that magnets 5804 *a*, 5804 *b* can influence both ferrofluids found in the clutch cavities 5808, 5810 via their magnetic fields. That is, the rotary drive 5802 is slid into a position where the magnets 5804 *a*, 5804 *b* are roughly both in between the clutch cavities 5808, 5810. This may cause the ferrofluids to align and attach to the rotating primary shaft 5804. When this occurs, rotation of the rotary drive 5802 causes rotation of the rotating primary shaft 5804, along with rotation 5840 of the exterior frame 5806. The rotation of the exterior frame 5806 may cause one of the actions described in FIG. 71 to occur. In general, shown herein is another example of how a rotary drive may be configured to engage one or more clutch mechanisms of the shaft assembly. Once a clutch is engaged, rotation of the rotary drive may cause an action to occur consistent with any of the methods for connecting a clutch to an action, described herein.

Referring to FIG. 72C, shown is a cross-sectional view of the shaft assembly when the rotary drive is not engaged with a clutch, according to some aspects. Here, the rotary drive 5802 is configured to move freely, independent of the exterior shaft portion 5806. Because the rotary drive 5802 is not engaged with a clutch, only the rotary drive 5802 rotates, while the exterior shaft 5806 stays in place.

Referring to FIG. 72D, shown is a cross-sectional view of the shaft assembly when the rotary drive is engaged with a clutch, according to some aspects. Here, the shaded regions 5812 signify that a clutch is engaged by the ferrofluid being aligned and attaching to the rotary drive 5802, due to the near proximity of the magnets. Thus, when the rotary drive 5802 is rotated, a component coupled to the clutch, such as the exterior shaft 5806 in this case, will similarly rotate 5840, as shown.

Figure 72E:
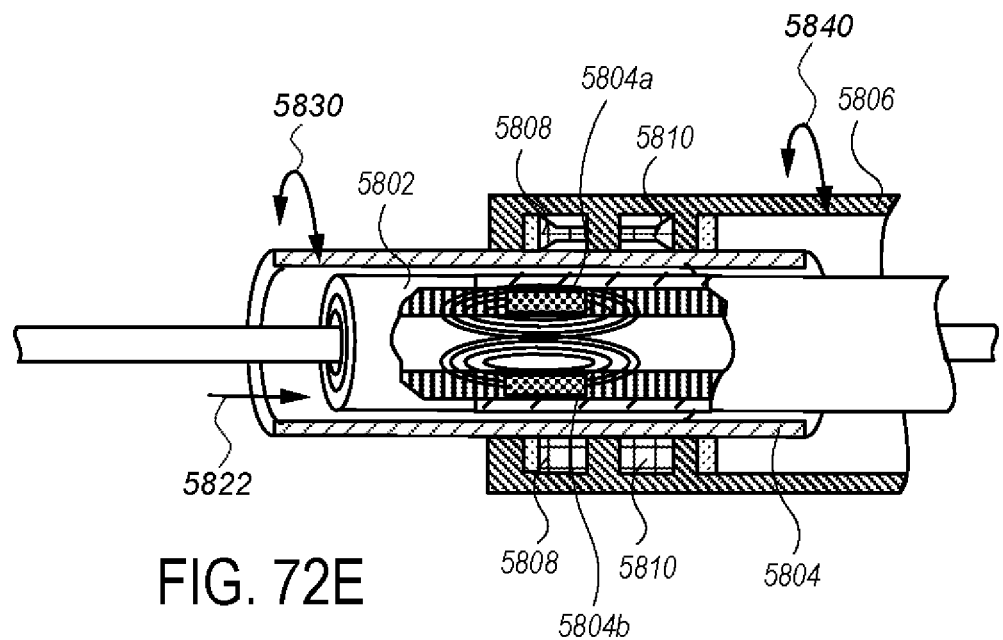

Referring to FIG. 72E, in some aspects, the sliding design of the rotary drive with magnets may also allow for different combinations of clutch mechanisms to be engaged. For example, rather than having the rotary drive 5802 slid into a position that simultaneously engages both clutch cavities 5808, 5810, the rotary drive 5802 may be slid into place to engage only clutch cavity 5808, as shown. In this position, the magnets 5804*a*, 5804*b* are able to only influence the ferrofluid in the clutch 5808. Thus, assuming that the clutch 5808 is coupled to a separate action component that is different than what the clutch 5810 is coupled to, then rotation of the rotary drive 5802 causes only the action component of the clutch 5808 to be engaged, while the action component of the clutch 5810 remains inert.

Figure 72F:
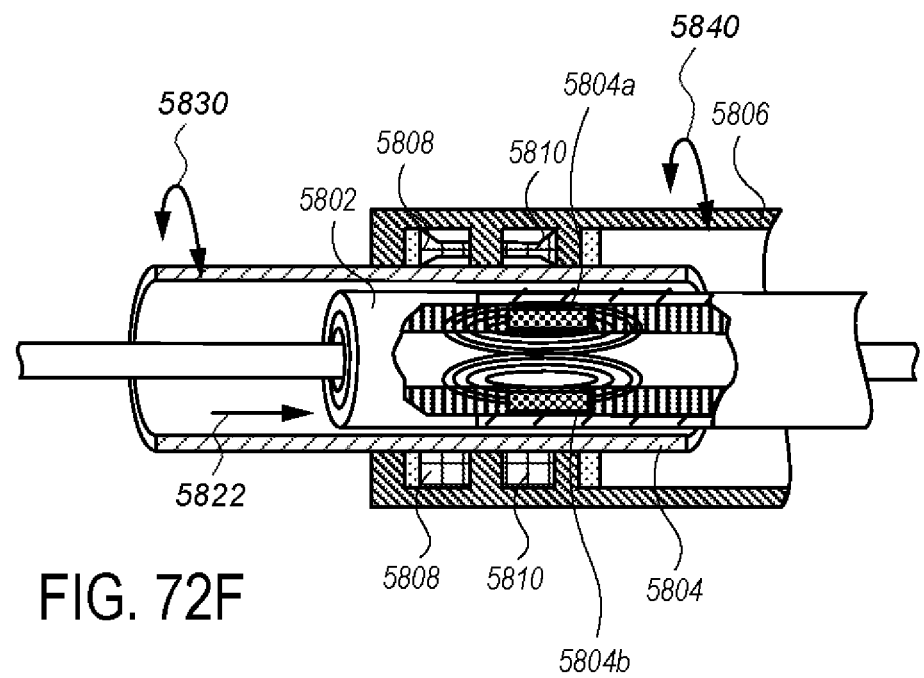

Referring to FIG. 72F, similarly, the rotary drive 5802 may be slid into a third position to allow engagement only of the second clutch 5810. As shown, the magnets 5804*a*, 5804*b* are able to only influence the ferrofluid in the clutch 5810. Thus, assuming that the clutch 5808 and the clutch 5810 have different action components or functions attached to them, then rotation of the rotary drive 5802 in this position causes only the action component of the clutch 5810 to be engaged, while the action component or function of the clutch 5808 remains inert. In general, because of the design of the shaft assembly that includes the two clutch cavities spaced near each other, and with the magnets in the rotary drive 5802 sufficiently long enough, it is possible for the rotary drive 5802 to engage both clutches simultaneously, either clutch only, or neither clutches at the same time.

Referring to FIG. 73A, in some aspects, the shaft assembly may include a locking element to help stabilize engagement of the clutches. The locking element may be biased into a locked state to hold the clutch engagement mechanism in a non-energize state but is automatically deactivated within a first few degrees of clutch drive motion. In this example, the locking element includes a set of ridges or teeth 5902 on the outer side of an interior shaft 5906. An outer shaft may include a set of ridges or grooves 5904 to allow the teeth 5902 to rotate into place. If these teeth 5902 and grooves 5904 are out of alignment, then the shaft assembly may be considered in an unlocked state. Furthermore, the rotational alignment of the teeth 5902 may be controlled by a spring mechanism 5908. The spring mechanism 5908 may be manually biased such that the distal end of the locking mechanism 5910 is retracted away from the distal gear 5912. In some aspects, when the distal end of the locking mechanism 5910 does not engaged the distal gear 5912, the clutch mechanism may be considered in an unlocked state.

Referring to FIG. 73B, shown is an example of when the locking element is in the locked state, according to some aspects. Here, the spring mechanism 5908 is relaxed or allowed to enter its naturally biased state. In its naturally biased state the spring mechanism 5908 causes the interior shaft 5906 to rotate, thereby causing the teeth 5902 to rotate and align with the grooves 5904, as shown. This creates a notable space 5914 that shows the components are in alignment. In addition, the teeth at the distal end of the locking element 5910 is now pushed to engage with the gear

5912. The distal end 5910 engages the distal gear 5912, preventing it from moving so that the gears 5912 are unable to rotate.

Referring to FIGS. 74A and 74B, shown are side views of the locking element, according to some aspects. In FIG. 74A, the spring mechanism 5952 is naturally biased to push against the other locking mechanism components. This causes the teeth 5954 of the interior shaft to align with the grooves of the outer shaft 5956. In contrast, a force pushing out towards the spring mechanism 5952 causes the spring mechanism 5952 to compress, and allows for a rotation of the teeth of the interior shaft 5954. This shows that the teeth 5954 are out of alignment with the grooves 5956, representing the locking element in an unlocked state.

In some aspects, this locking element may be positioned just below the rotary drive and may be manipulated by a separate switch in the shaft assembly or the handle assembly of a surgical instrument. A single locking mechanism may be used to prevent rotation of the rotary drive unless and until the locking mechanism is placed in an unlocked state. In other cases, multiple but smaller spring mechanisms may be positioned just on the inside of the exterior shaft of the shaft assembly, and may be spring biased to press against a component that would normally be rotated by an engaged clutch. That is, the locking mechanism would be designed to resist rotation of a component of a clutch system, even when the clutch is engaged, unless the locking mechanism is placed in an unlocked state. In some aspects, multiple locking mechanisms may be installed in the shaft assembly, with each locking mechanism coupled to each of the different clutch systems.

Aspects of the devices disclosed herein can be designed to be disposed of after a single use, or they can be designed to be used multiple times. Various aspects may, in either or both cases, be reconditioned for reuse after at least one use. Reconditioning may include any combination of the steps of disassembly of the device, followed by cleaning or replacement of particular pieces, and subsequent reassembly. In particular, aspects of the device may be disassembled, and any number of the particular pieces or parts of the device may be selectively replaced or removed in any combination. Upon cleaning and/or replacement of particular parts, aspects of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

While various details have been set forth in the foregoing description, it will be appreciated that the various aspects of the techniques for operating a generator for digitally generating electrical signal waveforms and surgical instruments may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices (e.g. floppy disk, hard disk drive, Compact Disc (CD), Digital Video Disk (DVD), or digital tape). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components, and/or electrically interacting components, and/or electrically interactable components, and/or optically interacting components, and/or optically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered clauses:

1. A system comprising: a surgical instrument comprising: a handle assembly; a shaft assembly coupled to the handle assembly; and an end effector coupled to a distal end of the shaft assembly; the shaft assembly comprising: an exterior shaft; a first clutch positioned within the exterior shaft and configured to drive a first function of the surgical instrument when engaged; a second clutch positioned within the exterior shaft and configured to drive a second function of the surgical instrument when engaged; and a rotary driver positioned within the exterior shaft and configured to rotate within the exterior shaft, the rotary driver comprising: a first clutch engagement mechanism configured to engage the first clutch; and a second clutch engagement mechanism configured to engage the second clutch independent of the first clutch engagement mechanism engaging the first clutch, such that, at different times: both the first clutch and the second clutch are engaged simultaneously; only the first clutch is engaged; only the second clutch is engaged; and neither the first clutch nor the second clutch is engaged simultaneously.

2. The system of clause 1, wherein the first clutch comprises a cavity containing a magnetorheological fluid configured to be magnetized in the presence of an electric current.

3. The system of clause 2, wherein the first clutch engagement mechanism comprises an electrical conduit configured to cause the first clutch engagement mechanism to engage the first clutch by generating an electrical current near the magnetorheological fluid that causes a magnetic attraction between the first clutch and the first clutch engagement mechanism.

4. The system of clause 3, wherein: the second clutch comprises a cavity containing the magnetorheological fluid configured to be magnetized in the presence of an electric current; and the second clutch engagement mechanism comprises a second electrical conduit configured to cause the second clutch engagement mechanism to engage the second clutch by generating a second electrical current that causes a magnetic attraction between the second clutch and the second clutch engagement mechanism.

5. The system of any one of clauses 1-4, wherein the first function comprises a rotation of a distal end of the shaft assembly.

6. The system of any one of clauses 1-5, wherein the second function comprises a closure of a pair of jaws of the end effector.

7. The system of any one of clauses 1-6, wherein the shaft assembly further comprises: an articulation joint; a proximal shaft component coupled to the handle assembly; and a distal shaft component coupled to the proximal component and configured to articulate about the articulation joint.

8. The system of clause 7, wherein the rotary shaft further comprises a proximal rotary shaft component coupled to the handle assembly and a distal rotary shaft component coupled to the proximal rotary shaft component and configured to articulate about the articulation joint as the distal shaft component articulates.

9. The system of clause 8, wherein the distal rotary shaft component comprises the first clutch engagement mechanism and the second clutch engagement mechanism.

10. The system of clause 9, wherein: the proximal shaft component comprises a third clutch positioned within the exterior shaft and configured to drive a third function of the surgical instrument when engaged; and the proximal rotary shaft component comprises a third clutch engagement mechanism configured to engage the third clutch independent of the first and second clutch engagement mechanisms engaging the first clutch and the second clutch, respectively.

11. The system of clause 10, wherein the third function comprises an articulation of the shaft about the articulation joint.

12. The system of any one of clauses 1-11, wherein the surgical instrument further comprises a locking mechanism.

13. A surgical instrument comprising: a handle assembly; a shaft assembly coupled to the handle assembly; and an end effector coupled to a distal end of the shaft; the shaft assembly comprising: an exterior frame; a first clutch positioned within the exterior frame and configured to drive a first function of the surgical instrument when engaged; a second clutch positioned within the exterior frame and configured to drive a second function of the surgical instrument when engaged; and a rotary driver having a portion positioned within the exterior frame and configured to rotate about a longitudinal axis and slide longitudinally within the exterior frame, the rotary driver comprising: a clutch engagement mechanism configured to: engage only the first clutch when the rotary driver is slid into the exterior frame at a first position; engage both the first and the second clutch simultaneously when the rotary driver is slid into the exterior frame at a second position; engage only the second clutch when the rotary driver is slid into the exterior frame at a third position; and engage neither the first nor the second clutch when the rotary driver is slid into the exterior frame at a fourth position.

15. A surgical instrument according to any of clauses 1-12.

The invention claimed is:

1. A system comprising:
a surgical instrument comprising:
    a handle assembly;
    a shaft assembly coupled to the handle assembly; and
    an end effector coupled to a distal end of the shaft assembly;
    the shaft assembly comprising:
        an exterior shaft;
        a first clutch positioned within the exterior shaft and configured to drive a first function of the surgical instrument when engaged with a first clutch engagement mechanism;
        a second clutch positioned within the exterior shaft and configured to drive a second function of the surgical instrument when engaged with a second clutch engagement mechanism; and
        a rotary driver positioned within the exterior shaft and configured to rotate within the exterior shaft, the rotary driver comprising:
            the first clutch engagement mechanism configured to engage the first clutch; and
            the second clutch engagement mechanism configured to engage the second clutch independent of the first clutch engagement mechanism engaging the first clutch, such that, at different times:
                the first clutch is engaged with the first clutch engagement mechanism and the second clutch is engaged with the second clutch engagement mechanism simultaneously;
                only the first clutch is engaged with the first clutch engagement mechanism without the second clutch being engaged with the second clutch engagement mechanism;
                only the second clutch is engaged with the second clutch engagement mechanism without the first clutch being engaged with the first clutch engagement mechanism; and
                neither the first clutch nor the second clutch is engaged with the first clutch engagement mechanism or the second clutch engagement mechanism.

2. The system of claim 1, wherein the first clutch comprises a cavity containing a first magnetorheological fluid configured to be magnetized in the presence of an electric current.

3. The system of claim 2, wherein the first clutch engagement mechanism comprises an electrical conduit configured to cause the first clutch engagement mechanism to engage the first clutch by generating an electrical current near the first magnetorheological fluid that causes a magnetic attraction between the first clutch and the first clutch engagement mechanism.

4. The system of claim 3, wherein:
the second clutch comprises a cavity containing a second magnetorheological fluid configured to be magnetized in the presence of an electric current; and the second clutch engagement mechanism comprises a second electrical conduit configured to cause the second clutch engagement mechanism to engage the second clutch by generating a second electrical current that causes a magnetic attraction between the second clutch and the second clutch engagement mechanism.

5. The system of claim 1, wherein the first function comprises a rotation of the distal end of the shaft assembly.

6. The system of claim 1, wherein the second function comprises a closure of a pair of jaws of the end effector.

7. The system of claim 1, wherein the shaft assembly further comprises:
an articulation joint;
a proximal shaft component coupled to the handle assembly; and
a distal shaft component coupled to the proximal shaft component and configured to articulate about the articulation joint.

8. The system of claim 7, wherein the rotary driver further comprises a proximal rotary shaft component coupled to the handle assembly and a distal rotary shaft component coupled to the proximal rotary shaft component and configured to articulate about the articulation joint as the distal shaft component articulates.

9. The system of claim 8, wherein the distal rotary shaft component comprises the first clutch engagement mechanism and the second clutch engagement mechanism.

10. The system of claim 9, wherein:
the proximal shaft component comprises a third clutch positioned within the exterior shaft and configured to drive a third function of the surgical instrument when engaged; and
the proximal rotary shaft component comprises a third clutch engagement mechanism configured to engage the third clutch independent of the first and second clutch engagement mechanisms engaging the first clutch and the second clutch, respectively.

11. The system of claim 10, wherein the third function comprises an articulation of the distal shaft component about the articulation joint.

12. The system of claim 1, wherein the surgical instrument further comprises a locking mechanism.

13. A surgical instrument comprising:
a handle assembly;
a generator assembly;
a shaft assembly coupled to the handle assembly; and
an end effector coupled to a distal end of the shaft assembly;
the shaft assembly comprising:
an exterior shaft;
a first clutch positioned within the exterior shaft and configured to drive a first function of the surgical instrument when engaged with a first clutch engagement mechanism;
a second clutch positioned within the exterior shaft and configured to drive a second function of the surgical instrument when engaged with a second clutch engagement mechanism; and
a rotary driver positioned within the exterior shaft and configured to rotate within the exterior shaft, the rotary driver comprising:
the first clutch engagement mechanism configured to engage the first clutch; and
the second clutch engagement mechanism configured to engage the second clutch independent of the first clutch engagement mechanism engaging the first clutch, such that, at different times:

the first clutch is engaged with the first clutch engagement mechanism and the second clutch is engaged with the second clutch engagement mechanism simultaneously;
only the first clutch is engaged with the first clutch engagement mechanism without the second clutch being engaged with the second clutch engagement mechanism;
only the second clutch is engaged with the second clutch engagement mechanism without the first clutch being engaged with the first clutch engagement mechanism; and
neither the first clutch nor the second clutch is engaged with the first clutch engagement mechanism or the second clutch engagement mechanism.

14. The surgical instrument of claim 13, wherein:
the first clutch comprises a cavity containing a first magnetorheological fluid configured to be magnetized in the presence of an electric current;
the first clutch engagement mechanism comprises an electrical conduit configured to cause the first clutch engagement mechanism to engage the first clutch by generating an electrical current near the first magnetorheological fluid that causes a magnetic attraction between the first clutch and the first clutch engagement mechanism;
the second clutch comprises a cavity containing a second magnetorheological fluid configured to be magnetized in the presence of an electric current; and
the second clutch engagement mechanism comprises a second electrical conduit configured to cause the second clutch engagement mechanism to engage the second clutch by generating a second electrical current that causes a magnetic attraction between the second clutch and the second clutch engagement mechanism.

15. The surgical instrument of claim 13, wherein the first function comprises a rotation of the distal end of the shaft assembly.

16. The surgical instrument of claim 13, wherein the second function comprises a closure of a pair of jaws of the end effector.

17. The surgical instrument of claim 13, wherein the shaft assembly further comprises:
an articulation joint;
a proximal shaft component coupled to the handle assembly; and
a distal shaft component coupled to the proximal shaft component and configured to articulate about the articulation joint.

18. The surgical instrument of claim 17, wherein the rotary driver further comprises a proximal rotary shaft component coupled to the handle assembly and a distal rotary shaft component coupled to the proximal rotary shaft component and configured to articulate about the articulation joint as the distal shaft component articulates.

19. The surgical instrument of claim 18, wherein:
the distal rotary shaft component comprises the first clutch engagement mechanism and the second clutch engagement mechanism;
the proximal shaft component comprises a third clutch positioned within the exterior shaft and configured to drive a third function of the surgical instrument when engaged;
the proximal rotary shaft component comprises a third clutch engagement mechanism configured to engage the third clutch independent of the first and second clutch engagement mechanisms engaging the first clutch and the second clutch, respectively; and the third function comprises an articulation of the distal shaft component about the articulation joint.

\* \* \* \* \*